(12) United States Patent
Yoo et al.

(10) Patent No.: US 9,353,120 B2
(45) Date of Patent: May 31, 2016

(54) TETRAAZA MACROCYCLIC COMPOUND, PREPARATION METHOD THEREOF AND USE THEREOF

(71) Applicant: Kyungpook National University Industry-Academic Cooperation Foundation, Daegu (KR)

(72) Inventors: Jeong Soo Yoo, Daegu (KR); Darpan Pandya, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 0 days.

(21) Appl. No.: 14/645,967

(22) Filed: Mar. 12, 2015

(65) Prior Publication Data

US 2015/0291608 A1    Oct. 15, 2015

Related U.S. Application Data

(62) Division of application No. 13/395,346, filed as application No. PCT/KR2010/006139 on Sep. 9, 2010, now Pat. No. 9,061,078.

(30) Foreign Application Priority Data

Sep. 9, 2009 (KR) .......................... 10-2009-0084943
Jul. 30, 2010 (KR) .......................... 10-2010-0073954

(51) Int. Cl.
| | | |
|---|---|---|
| A61K 49/04 | (2006.01) | |
| A61P 35/00 | (2006.01) | |
| A61P 31/00 | (2006.01) | |
| C07D 487/08 | (2006.01) | |
| A61K 51/04 | (2006.01) | |
| A61K 51/08 | (2006.01) | |
| A61K 51/10 | (2006.01) | |

(52) U.S. Cl.
CPC .......... *C07D 487/08* (2013.01); *A61K 51/0482* (2013.01); *A61K 51/082* (2013.01); *A61K 51/088* (2013.01); *A61K 51/1051* (2013.01)

(58) Field of Classification Search
CPC ............ A61K 51/088; A61K 51/0497; A61K 2300/00; A61K 49/085; A61K 49/223; A61K 51/0482; A61K 49/10; A61K 49/0002; A61K 51/04; A61K 51/0472; A61K 47/48107; A61K 51/0491; A61K 38/00; A61K 41/0028
See application file for complete search history.

(56) References Cited

U.S. PATENT DOCUMENTS

| | | |
|---|---|---|
| 5,103,098 A | 4/1992 | Fenyves |
| 5,109,397 A | 4/1992 | Gordon et al. |
| 5,208,581 A | 5/1993 | Collins |
| 5,210,421 A | 5/1993 | Gullberg et al. |
| 5,272,343 A | 12/1993 | Stearns |
| 5,406,479 A | 4/1995 | Harman |
| 5,446,799 A | 8/1995 | Tuy |
| 5,532,489 A | 7/1996 | Yamashita et al. |
| 5,600,145 A | 2/1997 | Plummer |
| 5,608,221 A | 3/1997 | Bertelsen et al. |
| 5,650,135 A | 7/1997 | Contag et al. |
| 5,900,636 A | 5/1999 | Nellemann et al. |
| 5,946,371 A | 8/1999 | Lai |
| 6,072,177 A | 6/2000 | McCroskey et al. |
| 6,115,446 A | 9/2000 | Pan |
| 6,151,377 A | 11/2000 | Nilsson |
| 6,916,460 B2 | 7/2005 | Liu |
| 2006/0062728 A1 | 3/2006 | Brogan |

FOREIGN PATENT DOCUMENTS

WO    WO 02/26267 A2    4/2002

OTHER PUBLICATIONS

Springborg, Johan et al. "Synthesis and Crystal Structure of a Small Bicyclic Tetraaza Proton Sponge, 1,4,7,10-Tetraazabicyclo[5.5.3]pentadecane Dibromide Perchlorate", Acta Chemica Scandinavica, 1995, 49:547-554.*
Extended European Search Report from European Application No. 10815618.3 dated May 16, 2013.
Written Opinion from International Application No. PCT/KR2010/006139 dated May 26, 2011.
Wong E H et al: "Synthesis and Characterization of Cross-Bridged Cyclams and Pendant-Armed Derivatives and Structural Studies of Their Copper(II) Complexes", Journal of the American Chemical Society, ACS Publications, US, vol. 122, No. 43, Jan. 1, 2000, pp. 10561-10572, XP001039647.
O'Connor P E et al: "Lanthanide complexes of a cross-bridged cyclam ligand: Isolation and structural characterization of unusual trinuclear mu<3>-imido Yb(III) cluster cations and a mixed valence Yb(II/III) salt containing an Yb(II) anion", Inorganica Chimica ACTA, Elsevier BV, NL, vol. 359, No. 9, Jun. 1, 2006, pp. 2870-2878, XP028068701.
Niu W et al: "Two novel zinc(II) complexes of the 1,8-cross-bridged cyclam ligand and their structures", Inorganic Chemistry Communications, Elsevier, Amsterdam, NL, vol. 2, No. 8, Aug. 1, 1999, pp. 358-360, XP027086250.
Johan Springborg et al: "Synthesis of [3(2)]Bis([2(4).3(1)]adamanzane), 1,4,8,11,15,18,22,25-Octaazapentacyclo[20.6.2.2(4,25).2(8,15).2(11,18)]hexatriaconta ne, and Crystal Structure of the Tetrachlorozincate Salt of the Tetraprotonated Octaamine.", ACTA Chemica Scandinavica, vol. 53, Jan. 1, 1999, pp. 985-991, XP055052734.

(Continued)

*Primary Examiner* — Audrea Buckley
(74) *Attorney, Agent, or Firm* — Alston & Bird LLP

(57) ABSTRACT

Provided are a cross-bridged tetraaza macrocyclic compound of a novel structure that can be used, for example, as a contrast agent for diagnostic imaging or a radiopharmaceutical and a method for preparing the same.
The disclosed tetraaza macrocyclic compound is able to form a stable metal complex at a lower temperature and allows easy conjugation with a bioactive substance or a chemically active substance, when compared to the existing cross-bridged tetraaza macrocyclic compounds.

1 Claim, 61 Drawing Sheets

(56) References Cited

OTHER PUBLICATIONS

Ralf Sanzenbacher et al: "Nickel(II) Complexes with [2(4).3(1)]Adamanzane, 1,4,7,10-Tetraazabicyclo[5.5.3]pentadecane.", ACTA Chemica Scandinavica, vol. 53, Jan. 1, 1999, pp. 457-464, XP055052737.

Louise Broge et al: "Cobalt(III) Complexes of [3 5 ]Adamanzane, 1,5,9,13- Tetraazabicyclo[7.7.3]nonadecane. Report of an Inert, Chelate Hydrogen Carbonate Ion", Inorganic Chemistry, vol. 40, No. 13, Jun. 1, 2001, pp. 3124-3129, XP055052750.

Louise Broge et al: "Cobalt(II), Nickel(II), Copper(II), and Zinc(II) Complexes with [3 5 ]Adamanzane, 1,5,9,13-Tetraazabicyclo[7.7.3]nonadecane, and [(2.3) 2 .2 1 ]Adamanzane, 1,5,9,12-Tetraazabicyclo[7.5.2]hexadecane", Inorganic Chemistry, vol. 40, No. 10, May 1, 2001, pp. 2323-2334, XP055052753.

Johan Springborg et al: "Synthesis of [3(5)]Adamanzane, 1,5,9,13-Tetraazabicyclo[7.7.3]nonadecane, by Oxidative C—N. Cleavage of [3(6)]Adamanzane, 1,5,9,13-Tetraazatricyclo[7.7.3.3(5,13)]docosane and Crystal Structure of the Tetraprotonated Bromide Salt of [3(5)]Adamanzane.", ACTA Chemica Scandinavica, vol. 52, Jan. 1, 1998, pp. 212217, XP055052754.

Niu et al. (Inorg. Chem. Comm. 1999, 2, 361-363).

Boswell et al. (J. Med. Chem. 2004, 47, 1465-1474).

Lewis et al. (Chem. Commun. 2004, 2212-2213).

Broge et al. (Dalton Trans. 2007, 3826-3839).

International Search Report from International Patent Application No. PCT/KR2010/006139, mailed May 26, 2011.

Springborg, J., et al.; "Synthesis and crystal structure of a small bicyclic tetraaza proton sponge, 1, 4, 7, 10-tetraazabicyclo[5.5.3]pentadecane dibromide perchlorate"; Acta Chemica Scandinavia (1995), 49(8), 547-554.

Springborg, J., et al.; "Synthetic, thermodynamic and crystallographic studies of pentacoordinated copper (II) complexes with [24.31] adamanzane, 1, 4, 7, 10- tetraazabicyclo[5.5.3] pentadecane, and bromide, iodide, hydroxide, water or ammonia"; Acta Chemica Scandinavica (1997), 51(3, Suppl.), 357-366.

Communication from European Patent Application No. 10815618.3 dated Jan. 17, 2014.

* cited by examiner

| No. | P/V | Wavelength n | Abs. |
|---|---|---|---|
| 1 | ↑ | 655.00 | 0.125 |
| 2 | ↓ | 495.00 | 0.005 |

US 9,353,120 B2

TETRAAZA MACROCYCLIC COMPOUND, PREPARATION METHOD THEREOF AND USE THEREOF

CROSS REFERENCE TO RELATED APPLICATIONS

This application is a divisional of U.S. application Ser. No. 13/395,346, which is a national phase entry of International Application No. PCT/KR2010/006139, filed Sep. 9, 2010, which claims priority to Korean Patent Application No. 10-2009-0084943, filed Sep. 9, 2009, and Korean Patent Application No. 10-2010-0073954, Filed Jul. 30, 2010, the entire contents of which are incorporated herein by reference.

TECHNICAL FIELD

The present disclosure relates to a novel tetraaza macrocyclic compound, a preparation method thereof and a use thereof. More particularly, the disclosure relates to a novel cross-bridged tetraaza macrocyclic compound, a preparation method thereof, and a use thereof as a contrast agent for diagnostic imaging and a radiopharmaceutical.

BACKGROUND ART

Metallopharmaceutical diagnostic and therapeutic agents are finding more and more applications in biological and medical researches, and in diagnostic and therapeutic processes. In general, these agents contain radioisotopes or paramagnetic metals, and, when introduced into a subject, are accumulated at the selected specific organ, tissue or lesion. For diagnostic purposes, the in vivo distribution of the radioisotopes or paramagnetic metals may be imaged in various ways. The distribution of the detected radioisotopes or paramagnetic metals and their relative intensity can elucidate the space occupied by the targeted tissue as well as the presence of receptors and antigens, anomalies, pathological conditions, or the like. In therapeutic applications, the agents tend to contain radioisotopes, and the radiopharmaceuticals deliver a specific dose of radiation to the disease site.

Depending on the targeted organ or tissue of interest and on the desired diagnostic or therapeutic procedures, a range of metallopharmaceuticals can be used. One common type is a conjugate in which a carrier that transports the conjugate to a specific target organ or tissue site is chemically attached to a radioactive or paramagnetic metal. The metal is usually coordinated with the conjugate and, more commonly, is linked in the form of a macrocyclic chelate (For example, refer to Liu's U.S. Pat. No. 6,916,460.).

The Cu-64 radionuclide has attracted special interests in nuclear medicine and imaging, owing to its half-life ($t_{1/2}$=12.7 h), decay properties ($\beta^+$ 19%; $\beta^-$ 39%) and large-scale producibility with high specific activity using a biomedical cyclotron, and hence the potential in positron emission tomography (PET) and targeted radiotherapy. In this regard, one of the most important things is to prepare the radionuclide into stable complexes using various chelating agents, so that they can be delivered to specific/targeted tissues without transmetalation from conjugates to biomolecules. In vivo conditions, there are many circumstances where the kinetic stability of Cu(II) is more important than its thermodynamic stability. The N-acetic acid pendant arm consisting mainly of cyclen and cyclam and its derivatives have been studied as bifunctional chelators (BFCs). DOTA and TETA, which are Cu(II) macrocyclic chelators derived from cyclen and cyclam, have shown comparable or better kinetic and biological stabilities as compared to acyclic chelators such as EDTA or DTPA. However, researches on biodistribution and metabolism of $^{64}$Cu-DOTA and $^{64}$Cu-TETA revealed in vivo instability due to transchelation of $^{64}$Cu as well as accumulation at the liver and high absorption in non-specific tissues resulting therefrom. The applicability of these chelators as radiopharmaceutical is determined by their flexibility, pore size, ability and extent of complexation, separation kinetics of the complex, or the like. In order to improve the in vivo stability of the metal complexes, transchelation and non-specific absorption and accumulation should be reduced. For this, chemical modification of the backbone of this type of polyazamacrocycles has been reported. That is to say, side-bridges and cross-bridges are introduced to improve stability of complexes.

1,4,8,11-Tetraazacyclotetradecane-1,4,8,11-tetraacetic acid (TETA) is widely used as a BFC for various copper and other radionuclides for clinical contrast agents and peptide- and antibody-targeted radiation therapies. However, according to a recent study, TETA is not an ideal BFC because of dissociation of the metal from the chelate and binding with proteins. Anderson et al. have experimentally demonstrated the dissociation of $^{64}$Cu from TETA-D-Phe$^1$-octreotide and its binding with superoxide dismutase (SOD). Weisman and Wong have designed the new-concept ethylene cross-bridged azamacrocyclic chelator CB-TE2A with two acetate pendant arms replaced by ethylene bridge between two non-adjacent nitrogens of TETA. The introduction of 1,8-ethylene cross-bridge in CB-TE2A resulted in improved stability of the metal complex while providing structural rigidity. Anderson et al. also have synthesized and described ethylene cross-bridged CB-DO2A Cu(II) complexes. These cross-bridged ligands, the octahedrally coordinated Cu(II) complexes of CB-TE2A and CB-DO2A, are enclosed by the four nitrogen electron pairs of chelators and the two carboxylate pendant arms to give Cu(II)-CB-TE2A and Cu(II)-CB-DO2A. Research showed that the new cross-bridged ligands were able to form kinetically more stable Cu(II) complexes and biologically more stable radiolabeled complexes when compared to non-cross-bridged DO2A or TETA. The $^{64}$Cu-CB-TE2A-Tyr$_3$-octreotate resulted in faster clearance in blood, liver and kidneys as compared to other similar $^{64}$Cu-TETA derivatives.

In order to prevent the possibility of one carboxylate groups being consumed for conjugation, another pendant arm may be covalently bonded to further improve in vivo stability. Lewis et al. have synthesized a CB-TE2A derivative in which a biotin molecule is covalently attached. However, the kinetic and in vivo stability of the Cu(II)-CB-TE2A-Bz-biotin is not known. Boswell et al. have synthesized cross-bridged TE2A (CB-TE2A), which is similar to CB-TE2A in structure but has a third orthogonally protected arm allowing conjugation with peptides and other targeting agents regardless of the hexacoordination position of Cu(II). Although in vivo experiment was not carried out, in vitro test revealed that the radiolabeled peptide conjugate is a stable radiocopper complex without new transchelation with human serum proteins for 48 hours.

WO 02-26267 and US Patent Publication No. 2006-62728 disclose ethylene cross-bridged tetraaza macrocyclic compounds and uses thereof. More specifically, US Patent Publication No. 2006-62728 discloses a compound represented by the following chemical formula, which is cross-bridged by $C_2$ ethylene between two nitrogens. However, the ethylene cross-bridged tetraaza macrocyclic compound is disadvantageous in that a metal complex is formed by coordination with a metal element only at high temperatures, because the cross-bridging aliphatic hydrocarbon is short. The ethylene cross-bridged tetraaza macrocyclic compound is prepared by reacting cyclam or cyclen with glyoxal (CHO—CHO). However, since a functional group cannot be attached to glyoxal, it is impossible to attach a functional group such as NCS to the cross-bridged ethylene, that can bind with a bioactive substance (*J. Am. Chem. Soc.* 2000, 122, 10561-10572). Accordingly, the only option is to attach the bioactive substance to the functional group bound to the nitrogen atom (e.g., COOH or NCS in the following chemical formula). However, when the bioactive substance is attached to the functional group bound to the nitrogen atom, it is difficult for the functional group to serve as a ligand upon coordination with a metal ion. As a result, the resulting coordination compound has lower in vivo stability and activity.

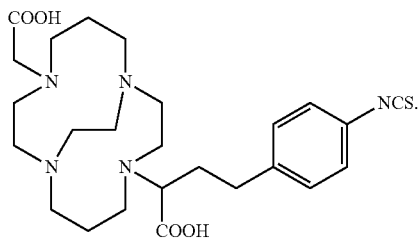

Although the existing ethylene cross-bridged tetraaza macrocyclic compound has good in vivo stability, it requires very high temperature (80-100° C.) to form a coordination complex with a metal element. Accordingly, when it is to be conjugated with a bioactive substance or a chemically active substance (For example, the NCS moiety in the above chemical formula is bound to the bioactive substance or chemically active substance.), the bioactive substance or the chemically active substance can be damaged (e.g., denaturation of protein), making it inapplicable as a therapeutic agent or a diagnostic agent.

For the tetraaza macrocyclic compound to be actually utilized, for example, as a contrast agent for nuclear imaging, it has to form a complex with a radioactive metal element. In this case, because of the short half-life of the radioactive metal element, the actual product is produced as a tetraaza macrocyclic compound with a bioactive substance attached thereto (For products with no bioactive substance attached, the procedure of attaching the bioactive substance has to be carried out in the hospital. But, this is almost impossible except for some special cases. Hence, all the products are sold in the form with the bioactive substance attached to the tetraaza macrocyclic compound.). That is to say, the hospitals purchase the tetraaza macrocyclic compound with the bioactive substance already attached thereto and form a complex with a radioactive metal element for use as a contrast agent or a radioactive therapeutic agent. Accordingly, if the temperature required for the complex formation with the metal ion is high, the bioactive substance (e.g., protein) bound thereto may be denatured. For this reason, the existing ethylene cross-bridged tetraaza macrocyclic compound is not commercially applicable in many cases.

DISCLOSURE

Technical Problem

The present disclosure is directed to providing a cross-bridged tetraaza macrocyclic compound of a novel structure, having superior in vivo stability and capable of coordinating with a metal element at a significantly low temperature.

The present disclosure is also directed to providing a cross-bridged tetraaza macrocyclic compound of a novel structure, allowing attachment of a functional group capable of easily binding with a bioactive substance at the cross-bridged propylene moiety, thereby improving stability during complex formation of the macrocyclic compound with a metal ion.

The present disclosure is also directed to providing a novel preparation method allowing cross-bridging of a propylene moiety having a functional group attached in a tetraaza macrocyclic compound.

The present disclosure is also directed to providing a coordination compound prepared from coordination of a cross-bridged tetraaza macrocyclic compound of a novel structure and a metal element at a significantly low temperature, and a method for preparing the same.

The present disclosure is also directed to providing a conjugate including a bioactive substance or a chemically active substance bound to the coordination compound of the present disclosure, and a method for preparing the conjugate at a significantly low temperature.

The present disclosure is also directed to providing various uses of a composition containing the conjugate of the present disclosure.

Technical Solution

In one general aspect, the present disclosure provides a tetraaza macrocyclic compound represented by Chemical Formula 1 or a pharmaceutically acceptable salt thereof:

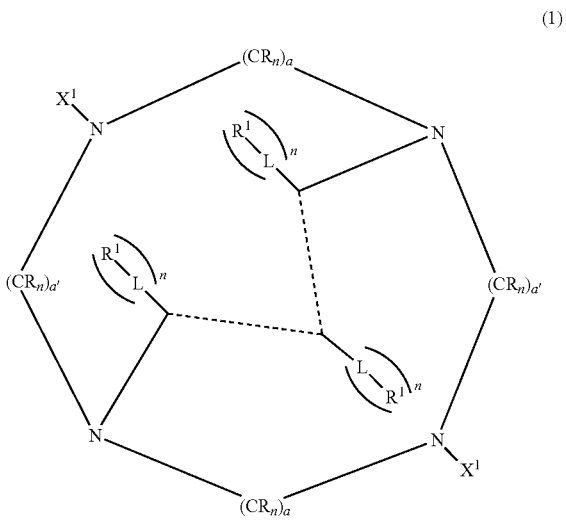

(1)

wherein
each R is independently H, alcohol, amino, amido, nitro, ester, halogen, ketone, cyano, carboxy, hydroxy, thiol, aldehyde, or substituted or unsubstituted $C_{1\sim10}$ alkyl, wherein the substitution is by one or more moiety(ies) selected from a group consisting of amino, amido, nitro, ester, halogen, ketone, cyano, carboxy, hydroxy, thiol and aldehyde;
each $R^1$ is independently H, alcohol, amino, amido, nitro, ether, ester, halogen, ketone, cyano, carboxy, hydroxy, thiol, aldehyde, carbonyl, substituted or unsubstituted $C_{1\sim15}$ alkyl, substituted or unsubstituted $C_{1\sim15}$ alkenyl, substituted or unsubstituted $C_{1\sim15}$ alkynyl, substituted or unsubstituted $C_{1\sim15}$ alkylaryl, substituted or unsubstituted $C_{1\sim15}$ aryl, substituted or unsubstituted $C_{1\sim15}$ heteroalkyl, substituted or unsubstituted $C_{1\sim15}$ heterocycle, or substituted or unsubstituted $C_{1\sim15}$ heteroaryl, wherein the substitution is by one or more moiety(ies) selected from a group consisting of imide, aldehyde, carboxy, ketone, nitro, amino, thiol, succinimide, maleimide, aminooxyl, acetylene, $N_3$, acetamino, azide, ester, halogen, alkyne, and NCS;

each $X^1$ is independently H, —$(CR^2)_1$—COOH, —$CR^2$—$((CR^2)_m$—COOH$)_2$, —$(CR^2)_1$—$CO_2R^3$, —$(CR^2)_i$—$ArOR^3$, —$(CR^2)_1$—$SR^3$, —$(CR^2)_1$—$SO_3H$, —$(CR^2)_1$—$PO_2HR^3$, —$(CR^2)_m N(CR^2)_2$ or —$(CR^2)_m CON(CR^2)_2$, wherein each of $R^2$ and $R^3$ is independently H, substituted or unsubstituted $C_{1\sim10}$ alkyl, substituted or unsubstituted $C_{1\sim10}$ alkenyl, substituted or unsubstituted $C_{1\sim10}$ alkynyl, substituted or unsubstituted $C_{1\sim10}$ alkylaryl, substituted or unsubstituted $C_{1\sim10}$ aryl, substituted or unsubstituted $C_{1\sim10}$ heteroalkyl, or substituted or unsubstituted $C_{1\sim10}$ heteroaryl, Ar is substituted or unsubstituted phenyl, wherein the substitution is by one or more moiety(ies) selected from a group consisting of imide, aldehyde, carboxy, ketone, nitro, amino, thiol, succinimide, maleimide, aminooxyl, $N_3$, acetylene, acetamino, azide, phosphate, alkyne, and NCS, each 1 is independently an integer from 1 to 3, and each m is independently an integer from 1 to 5, with the proviso that at least one of $X^1$ is not H;

each L is independently a linker or nonexistent, and $R^1$ is directly bound to a carbon atom when L is nonexistent;

each a is independently an integer 2 or 3;

each a' is independently an integer 2 or 3; and each n is independently an integer from 0 to 2 satisfying the valence of the carbon atom to which R or L-$R^1$ is covalently bonded.

Each $R^1$ may independently be a functional group capable of binding to an antibody, an amino acid, a nucleoside, a nucleotide, an aptamer, a protein, an antigen, a peptide, a nucleic acid, an enzyme, a lipid, an albumin, a cell, a carbohydrate, a vitamin, a hormone, a nanoparticle, an inorganic support, a polymer, a single molecule or a drug.

In one general aspect, the present disclosure provides a method for preparing a tetraaza macrocyclic compound including reacting a tetraaza macrocyclic compound represented by Chemical Formula 2 with a compound represented by Chemical Formula 3:

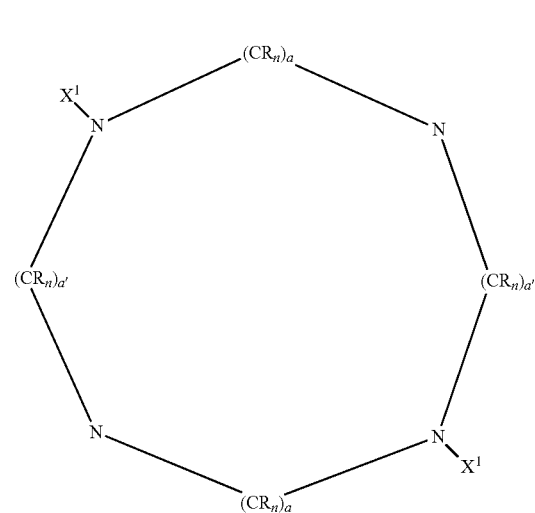

(2)

wherein each R is independently H, alcohol, amino, amido, nitro, ester, halogen, ketone, cyano, carboxy, hydroxy, thiol, aldehyde, or substituted or unsubstituted $C_{1\sim10}$ alkyl, wherein the substitution is by one or more moiety(ies) selected from a group consisting of amino, amido, nitro, ester, halogen, ketone, cyano, carboxy, hydroxy, thiol and aldehyde;

each $X^1$ is independently H, —$(CR^2)_1$—COOH, —$CR^2$—$((CR^2)_m$—COOH$)_2$, —$(CR^2)_1$—$CO_2R^3$, —$(CR^2)_1$—$ArOR^3$, —$(CR^2)_1$—$SR^3$, —$(CR^2)_1$—$SO_3H$, —$(CR^2)_1$—$PO_2HR^3$, —$(CR^2)_m N(CR^2)_2$ or —$(CR^2)_m CON(CR^2)_2$, wherein each of $R^2$ and $R^3$ is independently H, substituted or unsubstituted $C_{1\sim10}$ alkyl, substituted or unsubstituted $C_{1\sim10}$ alkenyl, substituted or unsubstituted $C_{1\sim10}$ alkynyl, substituted or unsubstituted $C_{1\sim10}$ alkylaryl, substituted or unsubstituted $C_{1\sim10}$ aryl, substituted or unsubstituted $C_{1\sim10}$ heteroalkyl, or substituted or unsubstituted $C_{1\sim10}$ heteroaryl, Ar is substituted or unsubstituted phenyl, wherein the substitution is by one or more moiety(ies) selected from a group consisting of imide, aldehyde, carboxy, ketone, nitro, amino, thiol, succinimide, maleimide, aminooxyl, $N_3$, acetylene, acetamino, azide, phosphate, alkyne, and NCS, each 1 is independently an integer from 1 to 3, and each m is independently an integer from 1 to 5, with the proviso that at least one $X^1$ is not H;

each a is independently an integer 2 or 3;

each a' is independently an integer 2 or 3; and each n is an integer from 0 to 2 satisfying the valence of the carbon atom to which R or L-$R^1$ is covalently bonded; and

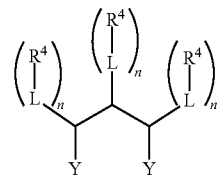

(3)

wherein each $R^4$ is independently H, alcohol, amino, amido, nitro, ether, ester, halogen, ketone, cyano, carboxy, hydroxy, thiol, aldehyde, carbonyl, substituted or unsubstituted $C_{1\sim15}$ alkyl, substituted or unsubstituted $C_{1\sim15}$ alkenyl, substituted or unsubstituted $C_{1\sim15}$ alkynyl, substituted or unsubstituted $C_{1\sim15}$ alkylaryl, substituted or unsubstituted $C_{1\sim15}$ aryl, substituted or unsubstituted $C_{1\sim15}$ heteroalkyl, substituted or unsubstituted $C_{1\sim15}$ heterocycle, or substituted or unsubstituted $C_{1\sim15}$ heteroaryl, wherein the substitution is by one or more moiety(ies) selected from a group consisting of imide, aldehyde, carboxy, ketone, nitro, amino, thiol, succinimide, maleimide, aminooxyl, acetylene, $N_3$, acetamino, azide, and NCS;

each L is independently a linker or nonexistent, and $R^4$ is directly bound to a carbon atom when L is nonexistent;

each Y is independently a leaving group; and each n is independently an integer from 0 to 2 satisfying the valence of the carbon atom to which L-$R^4$ is covalently bonded.

In a specific embodiment of the present disclosure, each R may independently be H or substituted or unsubstituted $C_{1\sim10}$ alkyl; at least one $X^1$ may independently be -A-$CO_2$—$R^5$, A may be nonexistent or $C_{1\sim3}$ alkyl, and $R^5$ may be t-Bu, methyl, ethyl, n-Bu, benzyl or benzylmethoxy. And, $R^4$ may be a functional group capable of binding to an antibody, an amino acid, a nucleoside, a nucleotide, an aptamer, a protein, an antigen, a peptide, a nucleic acid, an enzyme, a lipid, an albumin, a cell, a carbohydrate, a vitamin, a hormone, a nanoparticle, an inorganic support, a polymer, a single molecule or a drug.

In another general aspect, the present disclosure provides a coordination compound including: the tetraaza macrocyclic compound according to the present disclosure; and a metal element coordinated with the tetraaza macrocyclic compound.

In another general aspect, the present disclosure provides a conjugate including: the tetraaza macrocyclic compound or the coordination compound according to the present disclosure; and an antibody, an amino acid, a nucleoside, a nucleotide, an aptamer, a protein, an antigen, a peptide, a nucleic acid, an enzyme, a lipid, an albumin, a cell, a carbohydrate, a vitamin, a hormone, a nanoparticle, an inorganic support, a polymer, a single molecule or a drug bound to the tetraaza macrocyclic compound or the coordination compound.

In another general aspect, the present disclosure provides a method for preparing a conjugate, including: 1) preparing the tetraaza macrocyclic compound according to the present disclosure; 2) binding a bioactive substance or a chemically active substance to the tetraaza macrocyclic compound; and 3) coordinating a metal element with the tetraaza macrocyclic compound to form a complex. The complex may be formed at 30-60° C.

In another general aspect, the present disclosure provides a pharmaceutical composition including: the conjugate according to the present disclosure; and a pharmaceutically acceptable carrier.

The terms used in the specification will be described briefly.

The term "aromatic" refers to an aromatic group which has at least one ring having a conjugated pi electron system and includes both carbocyclic aryl (e.g., phenyl) and heterocyclic aryl groups (e.g., pyridine, furan, indole or purine). The term includes monocyclic or fused-ring polycyclic (i.e., rings which share adjacent pairs of carbon atoms) groups.

The term "heteroatom" refers to an atom other than carbon and hydrogen.

The term "heteroalkyl" refers to an alkyl group with one or more carbon atom(s) substituted by heteroatom(s) (e.g., N, O, S, etc.).

The term "heteroaromatic" refers to an aromatic group which contains at least one heterocyclic ring. More specifically, the heterocyclic ring may be an optionally substituted 5- or 6-membered aromatic group. Specifically, the heteroaromatic group may have 1 or 2 oxygen atom(s), 1 or 2 sulfur atom(s) and/or 1 to 4 nitrogen atom(s) in the ring, and may be bonded to the remainder of the molecule through a carbon atom or a heteroatom. Examples of the heteroaromatic group include furyl, thienyl, pyridyl, oxazolyl, pyrrolyl, indolyl, quinolinyl, isoquinolinyl, etc. The substitution may be, for example, by one or more of hydrocarbyl, substituted hydrocarbyl, ketone, hydroxy, protected hydroxy, acyl, acyloxy, alkoxy, alkeneoxy, alkyneoxy, aryloxy, halogen, amido, amino, nitro, cyano, thiol, ketal, acetal, ester and ether.

The term "heterocyclo" or "heterocyclic" refers to an optionally substituted, fully saturated or unsaturated, monocyclic or bicyclic, aromatic or non-aromatic group having at least one heteroatom in at least one ring, specifically 5 or 6 atoms in each ring. The heterocyclo group may specifically have 1 or 2 oxygen atom(s) and/or 1 to 4 nitrogen atom(s) in the ring, and may be bonded to the remainder of the molecule through a carbon atom or a heteroatom. Exemplary heterocyclo groups include heteroaromatics such as furyl, thienyl, pyridyl, oxazolyl, pyrrolyl, indolyl, quinolinyl or isoquinolinyl. Exemplary substituents include one or more of hydrocarbyl, substituted hydrocarbyl, ketone, hydroxy, protected hydroxy, acyl, acyloxy, alkoxy, alkeneoxy, alkyneoxy, aryloxy, halogen, amido, amino, nitro, cyano, thiol, ketal, acetal, ester and ether.

The term "alkyl" refers to an aliphatic hydrocarbon group. The alkyl moiety may be a "saturated alkyl" group, which means that it does not contain any alkene or alkyne moiety. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The term "acyl" refers to a moiety formed by removal of a hydroxyl group from the —COOH group of an organic carboxylic acid, e.g., RC(O)—, wherein R is R', R'O—, $R^1R^2N$— or $R^1S$—, $R^1$ is hydrocarbyl, heterosubstituted hydrocarbyl or heterocyclo, and $R^2$ is hydrogen, hydrocarbyl or substituted hydrocarbyl.

The term "aryl" or "Ar" refers to an optionally substituted homocyclic aromatic group, specifically a monocyclic or bicyclic group containing 6 to 12 carbons in the ring portion, such as phenyl, biphenyl, naphthyl, substituted phenyl, substituted biphenyl or substituted naphthyl. Specifically, the aryl group may be phenyl or substituted phenyl.

The term "radioisotope" refers to a chemical element with an unstable nucleus which releases excess energy while spontaneously emitting alpha ($\alpha$), beta ($\beta^{+/-}$) or gamma ($\gamma$) rays.

The term "pharmaceutically acceptable salt" refers to a form of a compound that does not cause significant irritation to an organism to which it is administered and does not abrogate the biological activity and properties of the compound.

The term "conjugate" refers to the tetraaza macrocyclic compound of the present disclosure bound to a bioactive substance or a chemically active substance (e.g., antibody), regardless of whether it forms a complex through coordination with a metal element.

Other terms will be interpreted as commonly understood in the art which the present disclosure belongs to.

Other features and aspects will be apparent from the following detailed description, the drawings, and the claims.

Advantageous Effects

The propylene cross-bridged tetraaza macrocyclic compound of the present disclosure is advantageous over the existing ethylene cross-bridged tetraaza macrocyclic compound in that it can form stable metal complexes with various metals at low temperatures and allows easy conjugation with a bioactive substance or a chemically active substance. Accordingly, it is commercially applicable as a therapeutic agent, a diagnostic agent or a contrast agent, since denaturation of the bioactive substance or the chemically active substance bound to the macrocyclic compound can be prevented.

Further, whereas a bioactive substance or a chemically active substance cannot be attached to the ethylene moiety of the existing ethylene cross-bridged tetraaza macrocyclic compound, a functional group that can bind to a bioactive substance may be attached to the cross-bridged propylene moiety of the propylene cross-bridged tetraaza macrocyclic compound according to the present disclosure. As a result, upon binding with a bioactive substance or a chemically active substance, the chelate arm moiety bound to the nitrogen atom may coordinate with a metal ion, since it does not need to be bound to the bioactive substance or the chemically active substance. Hence, a stable complex can be formed.

In addition, since the propylene cross-bridged tetraaza macrocyclic compound is capable of forming stable complexes not only with transition metals but also with main metals and lanthanide metals, it may be easily labeled with various radionuclide metals as well as paramagnetic metals such as Gd for use as radiopharmaceuticals and MRI contrast agents.

DESCRIPTION OF DRAWINGS

The above and other objects, features and advantages of the present disclosure will become apparent from the following description of certain exemplary embodiments given in conjunction with the accompanying drawings, in which.

BEST MODE

Figure 1:
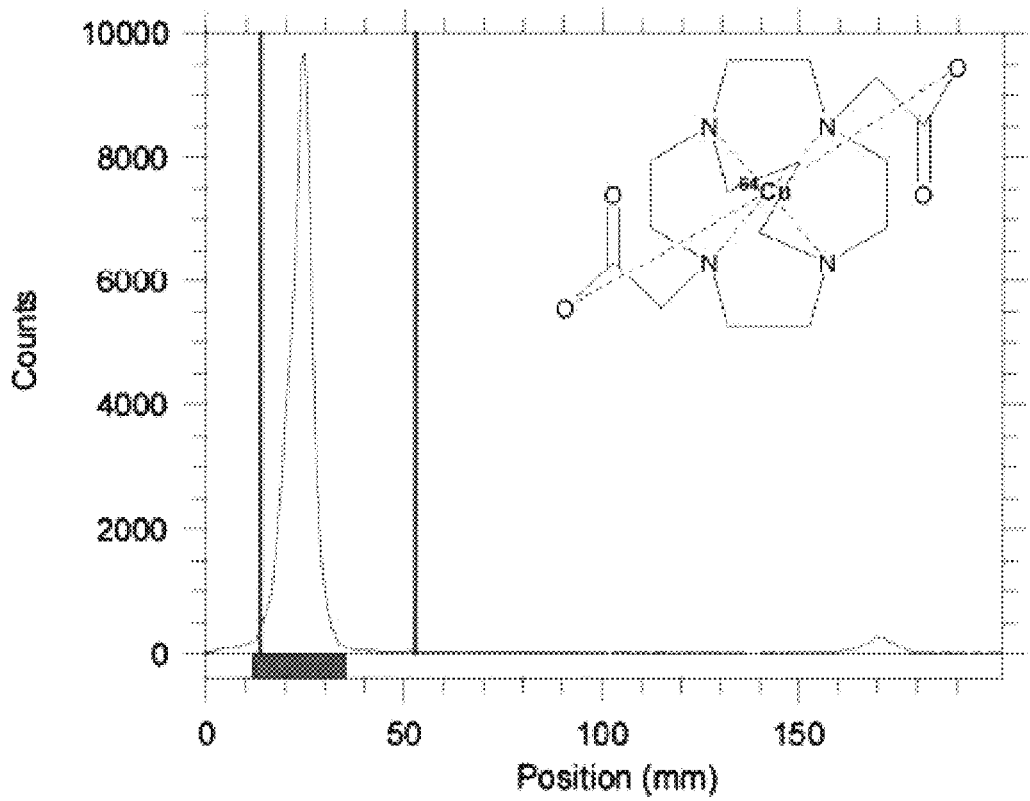
FIGS. 1 to 4 show radio-TLC results of $^{64}$Cu-PCB-TE2A and $^{64}$Cu-PCB-DO2A.

Hereinafter, the embodiments of the present disclosure will be described in detail with reference to accompanying drawings.

As described above, the existing ethylene cross-bridged tetraaza macrocyclic compound is prepared by reacting cyclam or cyclen with glyoxal (CHO—CHO). However, since a functional group cannot be attached to glyoxal, it is impossible to attach a functional group such as NCS to the cross-bridged ethylene, that can bind with a bioactive substance. Accordingly, the only option is to attach the bioactive substance to the functional group bound to the nitrogen atom of tetraaza macrocyclic compound. However, when the bioactive substance is attached to the functional group bound to the nitrogen atom, it is difficult for the functional group to serve as a ligand upon coordination with a metal ion. As a result, the resulting coordination compound has decreased in vivo stability and activity. Although the existing ethylene cross-bridged tetraaza macrocyclic compound has good in vivo stability, it requires very high temperature (80-100° C.) to form a coordination complex with a metal element. Accordingly, when it is to be conjugated with a bioactive substance or a chemically active substance, the bioactive substance or the chemically active substance may be damaged (e.g., denaturation of protein). Thus, it is difficult to use it as a therapeutic agent or a diagnostic agent. For the tetraaza macrocyclic compound to be actually utilized, for example, as a contrast agent, it has to form a complex with a radioactive metal element. In this case, because of the short half-life of the radioactive metal element, the actual product is produced as a tetraaza macrocyclic compound with a bioactive substance attached thereto (For products with no bioactive substance attached, the procedure of attaching the bioactive substance has to be carried out in the hospital. But, this is almost impossible except for some special cases. Hence, all the products are sold in the form with the bioactive substance attached to the tetraaza macrocyclic compound.). That is to say, the hospitals purchase the tetraaza macrocyclic compound with the bioactive substance already attached thereto and form a complex with a radioactive metal element for use as a contrast agent or a radioactive therapeutic agent. Accordingly, if the temperature required for the complex formation with the metal ion is high, the bioactive substance (e.g., protein) bound thereto may be denatured. For this reason, the existing ethylene cross-bridged tetraaza macrocyclic compound is not commercially applicable in many cases.

Thus, in this disclosure, a propylene cross-bridged tetraaza macrocyclic compound and tetraaza macrocyclic compounds with various functional groups capable of binding to a bioactive substance or a chemically active substance are provided.

Specifically, the present disclosure provides a tetraaza macrocyclic compound represented by Chemical Formula 1 or a pharmaceutically acceptable salt thereof:

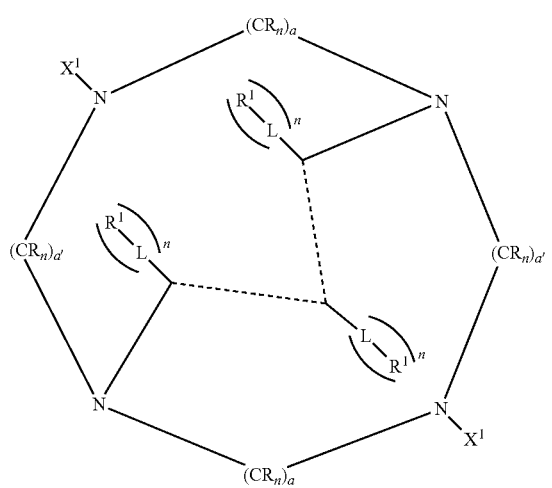

(1)

wherein each R is independently H, alcohol, amino, amido, nitro, ester, halogen, ketone, cyano, carboxy, hydroxy, thiol, aldehyde, or substituted or unsubstituted $C_{1\sim10}$ alkyl, wherein the substitution is by one or more moiety(ies) selected from a group consisting of amino, amido, nitro, ester, halogen, ketone, cyano, carboxy, hydroxy, thiol and aldehyde; each $R^1$ is independently H, alcohol, amino, amido, nitro, ether, ester, halogen, ketone, cyano, carboxy, hydroxy, thiol, aldehyde, carbonyl, substituted or unsubstituted $C_{1\sim15}$ alkyl, substituted or unsubstituted $C_{1\sim15}$ alkenyl, substituted or unsubstituted $C_{1\sim15}$ alkynyl, substituted or unsubstituted $C_{1\sim15}$ alkylaryl, substituted or unsubstituted $C_{1\sim15}$ aryl, substituted or unsubstituted $C_{1\sim15}$ heteroalkyl, substituted or unsubstituted $C_{1\sim15}$ heterocycle, or substituted or unsubstituted $C_{1\sim15}$ heteroaryl, wherein the substitution is by one or more moiety(ies) selected from a group consisting of imide, aldehyde, carboxy, ketone, nitro, amino, thiol, succinimide, maleimide, aminooxyl, $N_3$, acetylene, acetamino, azide, ester, halogen, alkyne, and NCS; each $X^1$ is independently H, —$(CR^2)_1$—COOH, —$CR^2$—$((CR^2)_m$—$COOH)_2$, —$(CR^2)_1$—$CO_2R^3$, —$(CR^2)_1$—$ArOR^3$, —$(CR^2)_1$—$SR^3$, —$(CR^2)_1$—$SO_3H$, —$(CR^2)_1$—$PO_2HR^3$, —$(CR^2)_m N(CR^2)_2$ or —$(CR^2)_m CON(CR^2)_2$, wherein each of $R^2$ and $R^3$ is independently H, substituted or unsubstituted $C_{1\sim10}$ alkyl, substituted or unsubstituted $C_{1\sim10}$ alkenyl, substituted or unsubstituted alkynyl, substituted or unsubstituted $C_{1\sim10}$ alkylaryl, substituted or unsubstituted $C_{1\sim10}$ aryl, substituted or unsubstituted $C_{1\sim10}$ heteroalkyl, or substituted or unsubstituted $C_{1\sim10}$ heteroaryl, Ar is substituted or unsubstituted phenyl, wherein the substitution is by one or more moiety(ies) selected from a group consisting of imide, aldehyde, carboxy, ketone, nitro, amino, thiol, succinimide, maleimide, aminooxyl, $N_3$, acetylene, acetamino, azide, phosphate, alkyne, and NCS, each 1 is independently an integer from 1 to 3, and each m is independently an integer from 1 to 5, with the proviso that at least one $X^1$ is not H; each L is independently a linker or nonexistent, and $R^1$ is directly bound to a carbon atom when L is nonexistent; each a is independently an integer 2 or 3; each a' is independently an integer 2 or 3; and each n is independently an integer from 0 to 2 satisfying the valence of the carbon atom to which R or L-$R^1$ is covalently bonded. For example, if n=2, the same or different two R's are bonded to the corresponding carbon atom, and, if n=0, two H's are bonded to the corresponding carbon atom.

Specifically, the tetraaza macrocyclic compound of Chemical Formula 1 may be a cyclam compound with a' being 2 and a being 3 or a cyclen compound with a' being 2 and a being 2. More specifically, the tetraaza macrocyclic compound of Chemical Formula 1 may be a cyclam compound with a' being 2 and a being 3.

Figure 5:
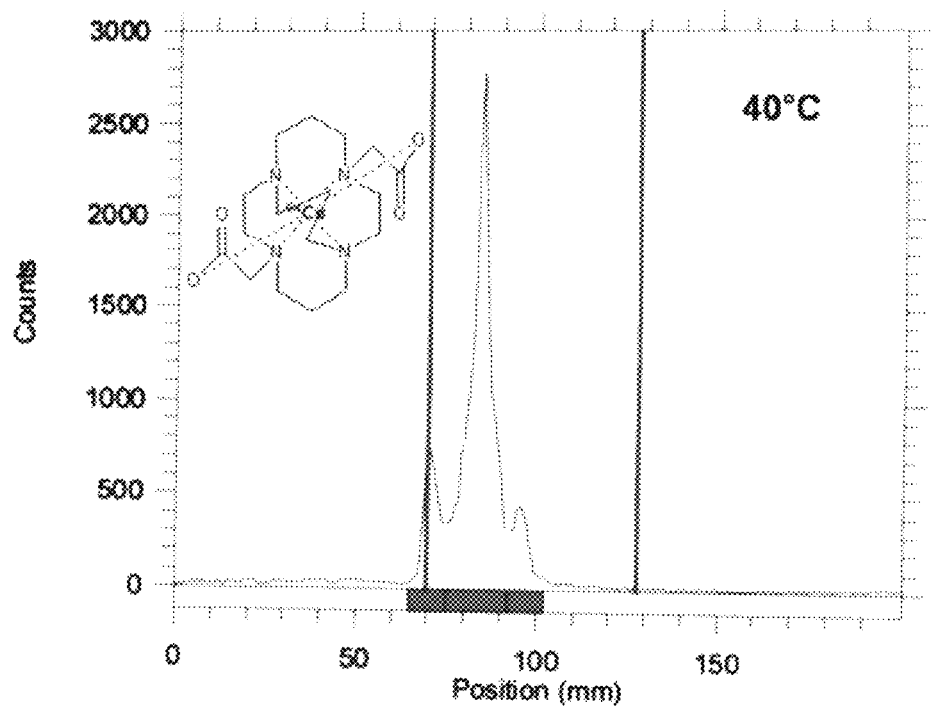
FIGS. 5 to 9 show radio-TLC results of $^{64}$Cu-PCB-TE2A at different temperatures.
Figure 6:
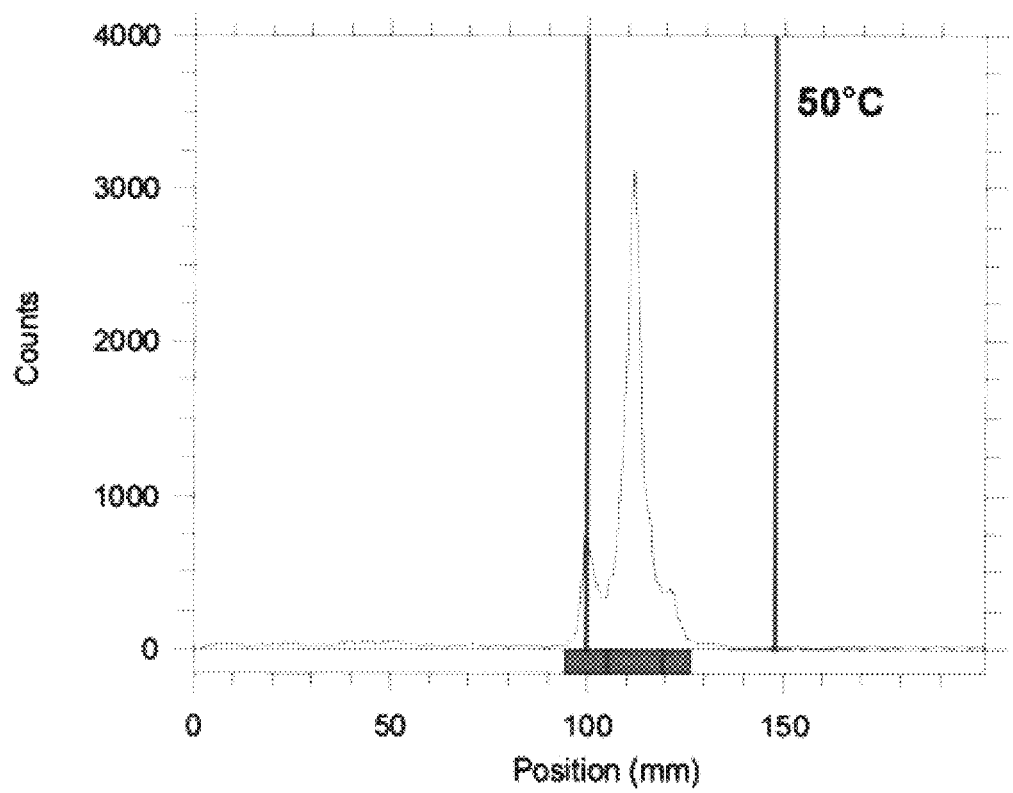
Figure 7:
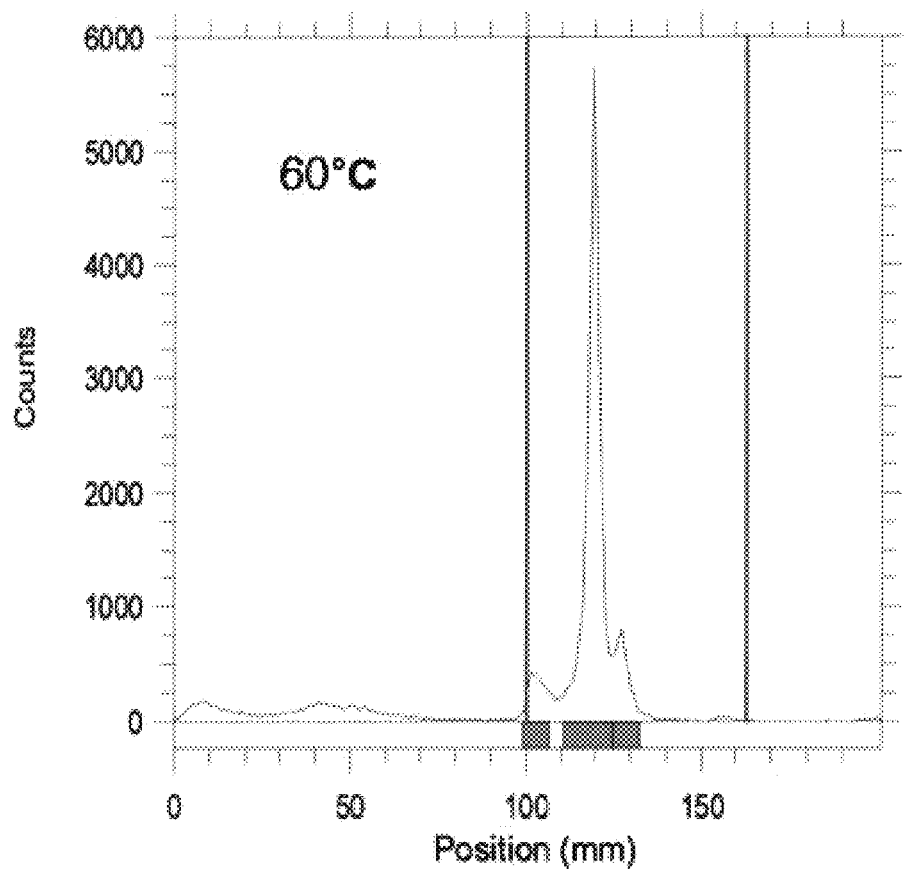
Figure 8:
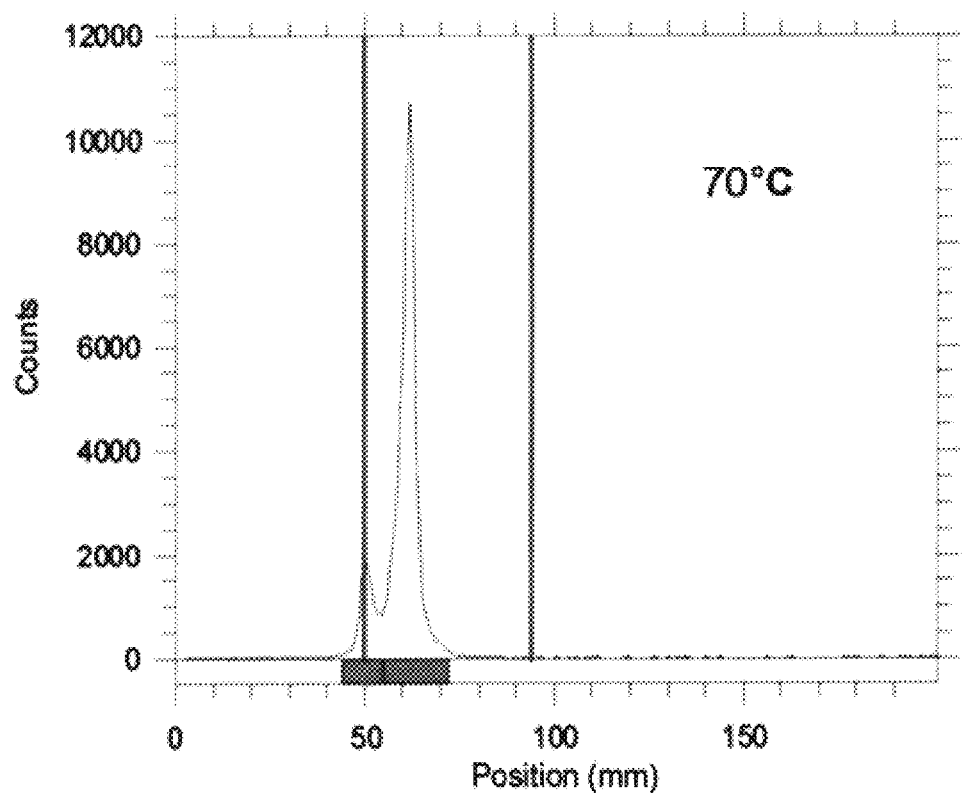
Figure 9:
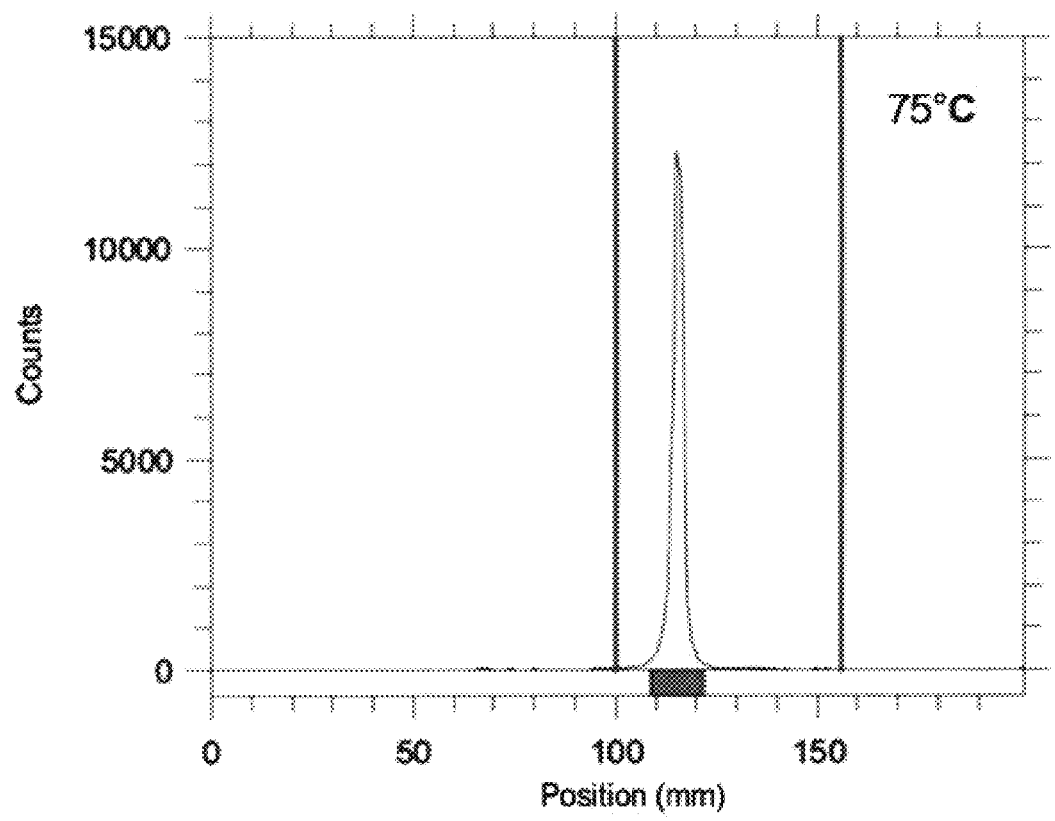
Figure 10:
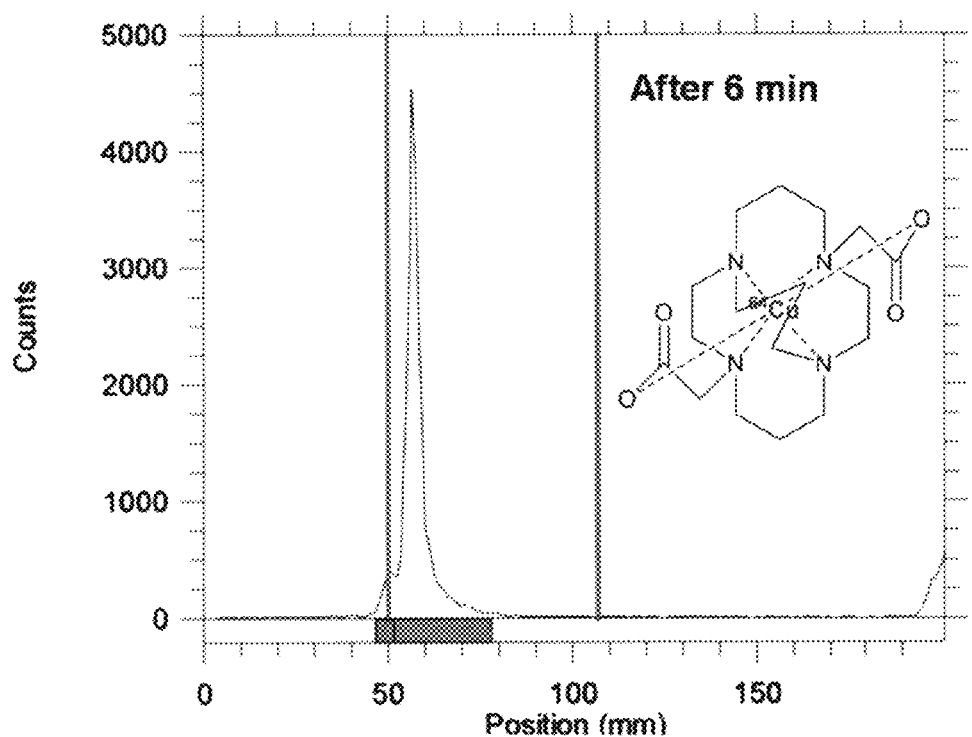
FIGS. 10 to 15 show radio-TLC results of $^{64}$Cu-PCB-TE2A after addition to an acid.
Figure 11:
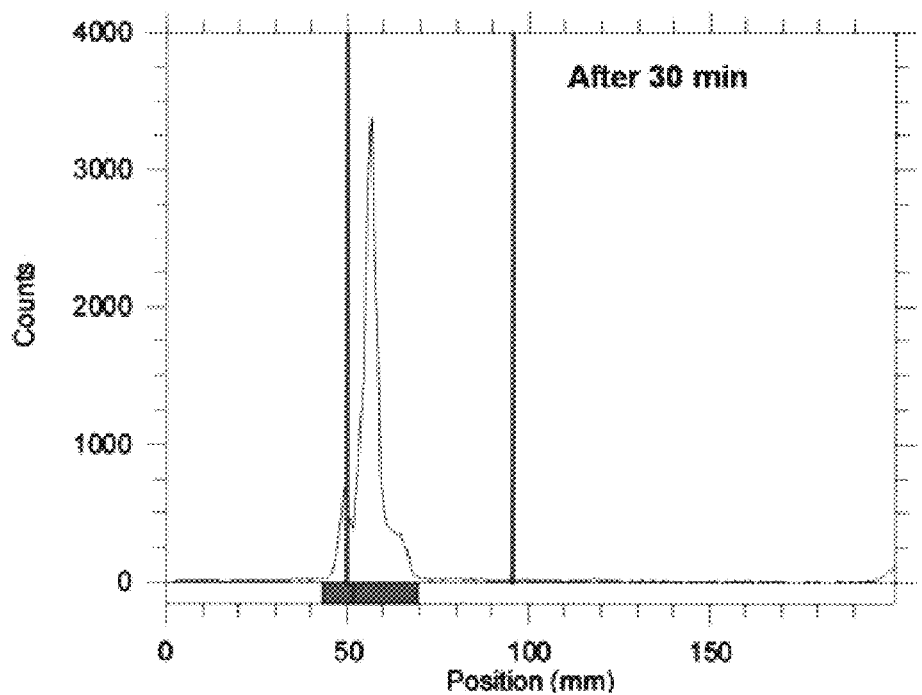
Figure 12:
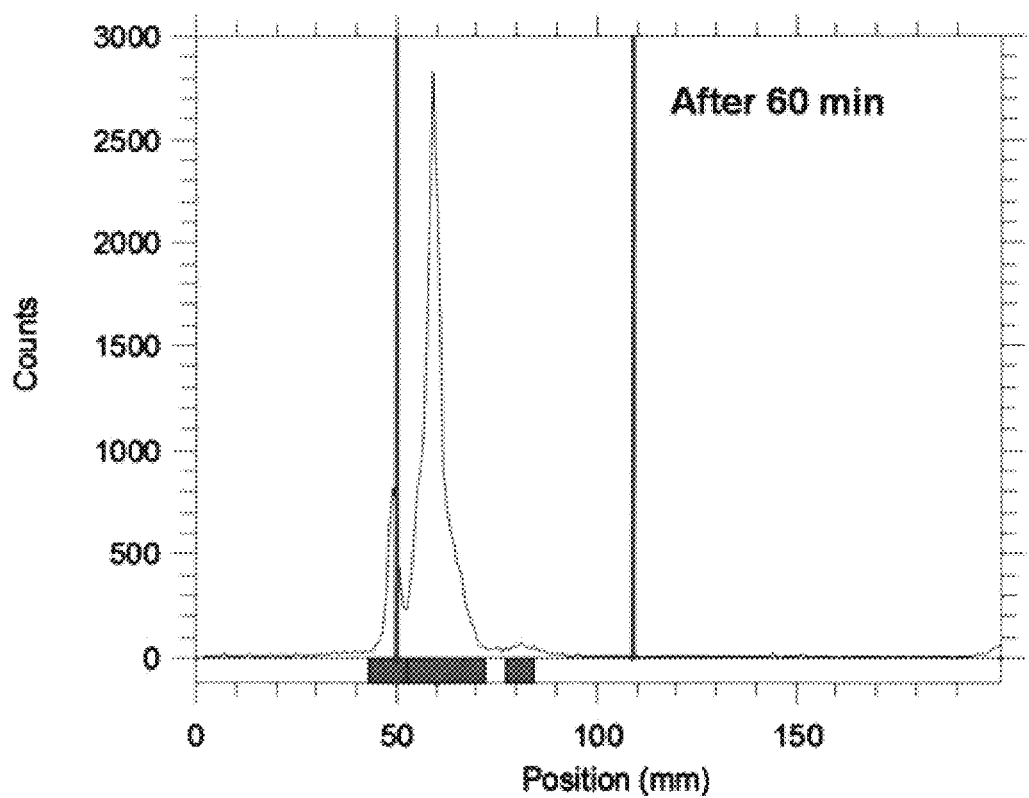
Figure 13:
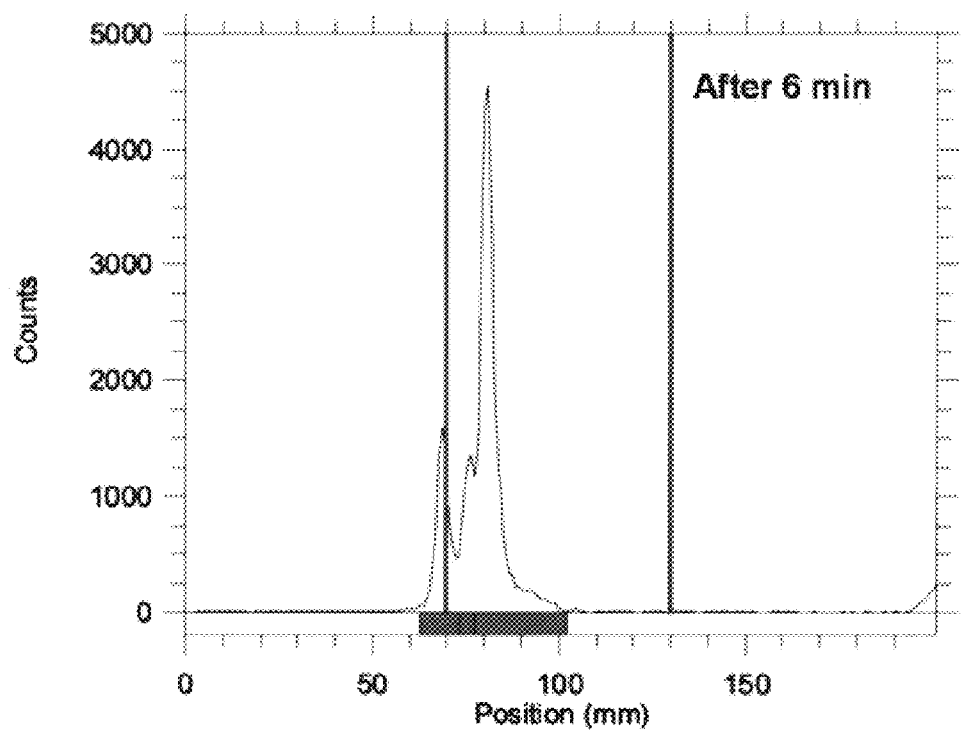
Figure 14:
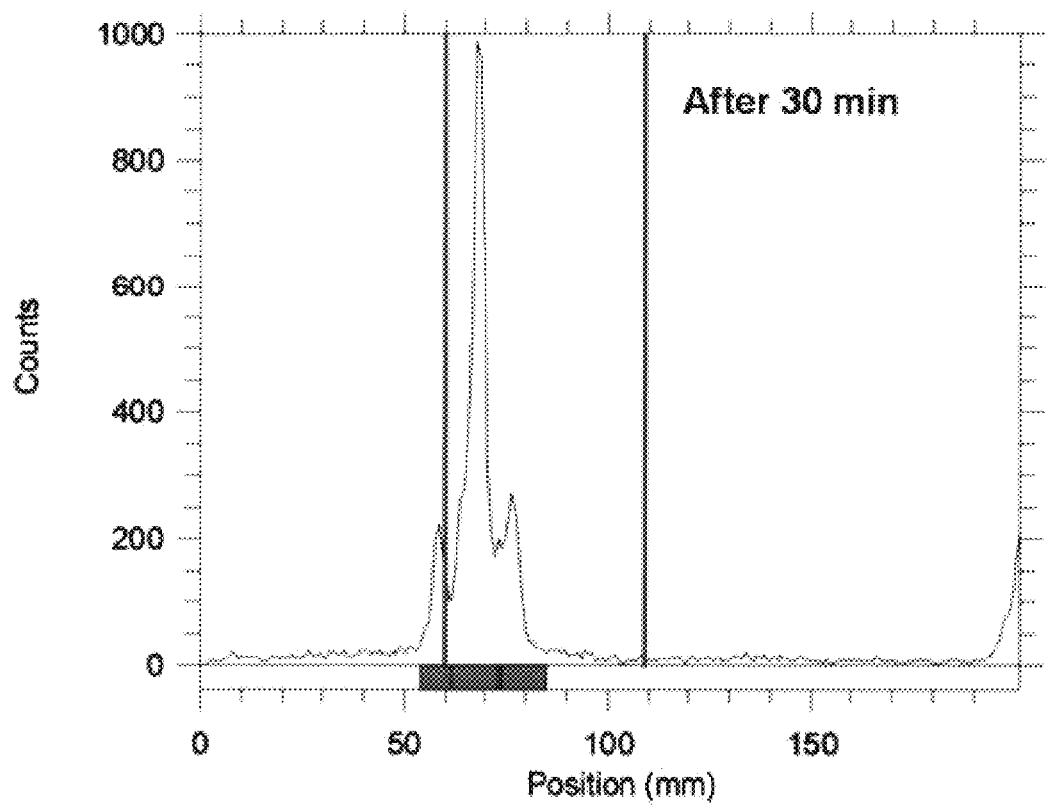
Figure 15:
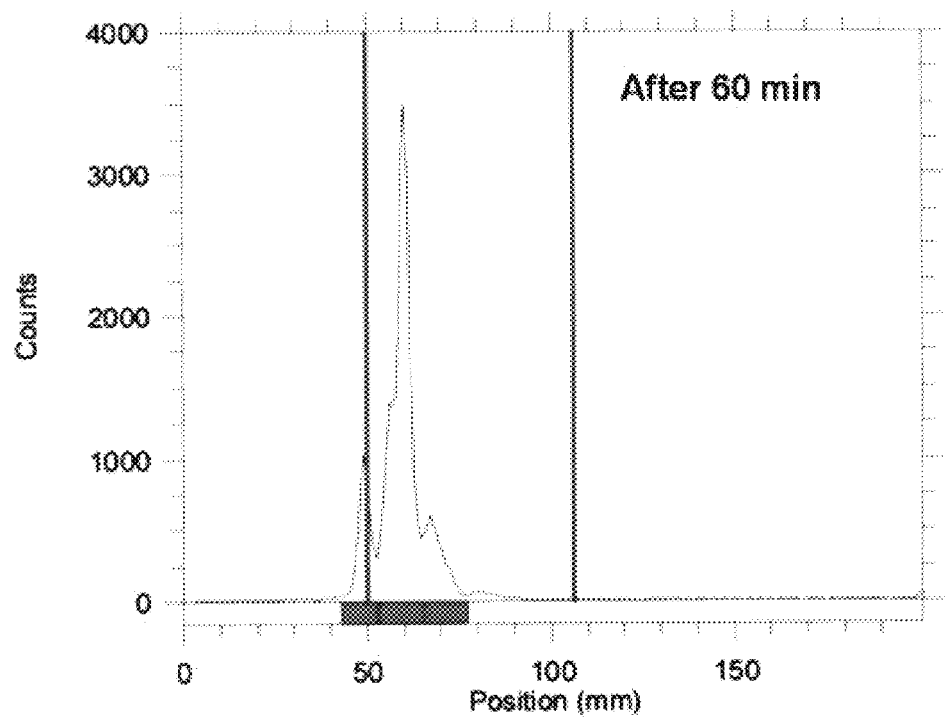
Figure 16:
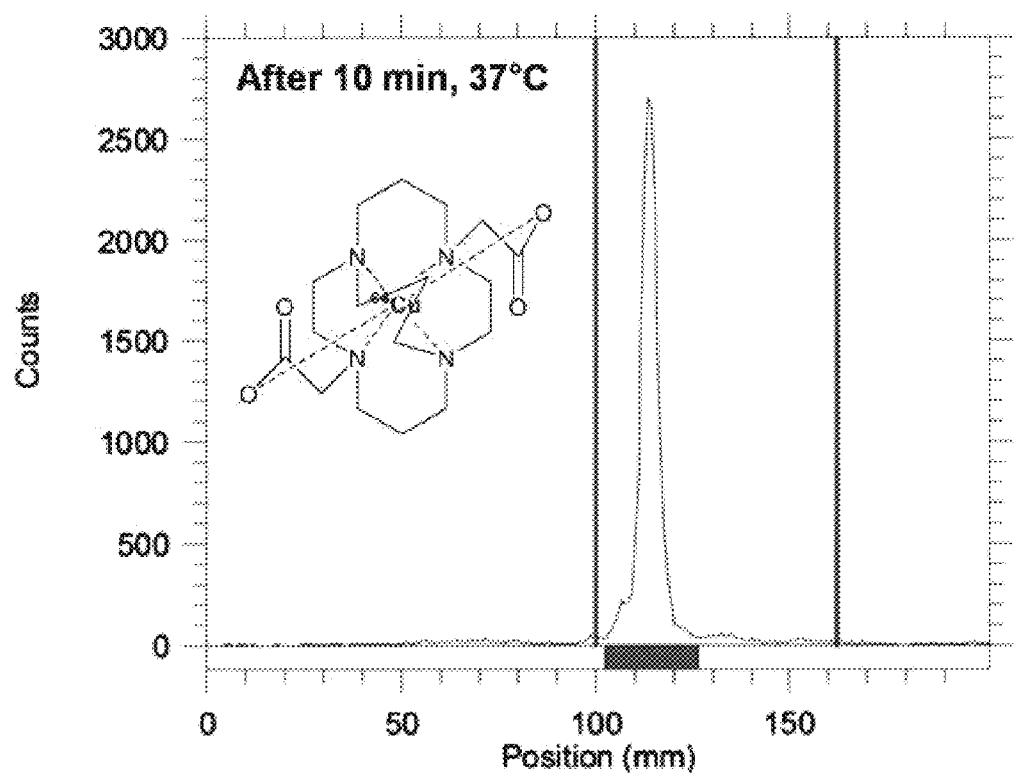
FIGS. 16 to 23 show radio-TLC results of $^{64}$Cu-PCB-TE2A after addition to FBS.
Figure 17:
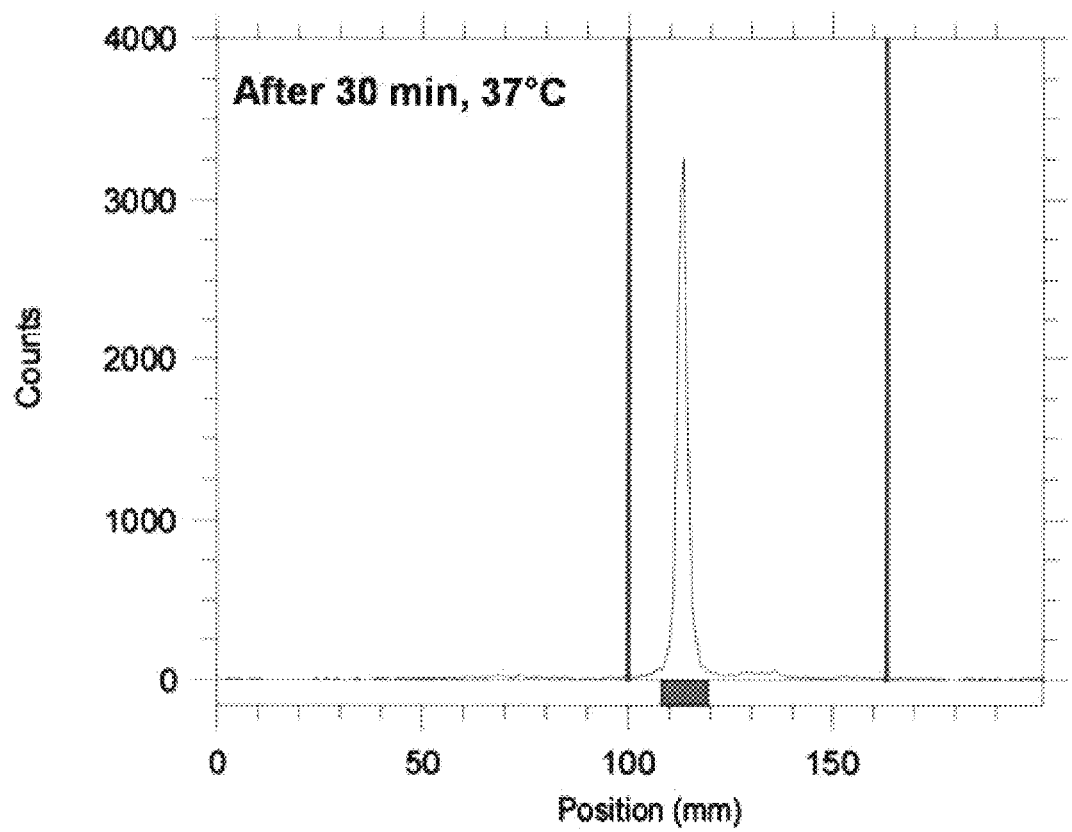
Figure 18:
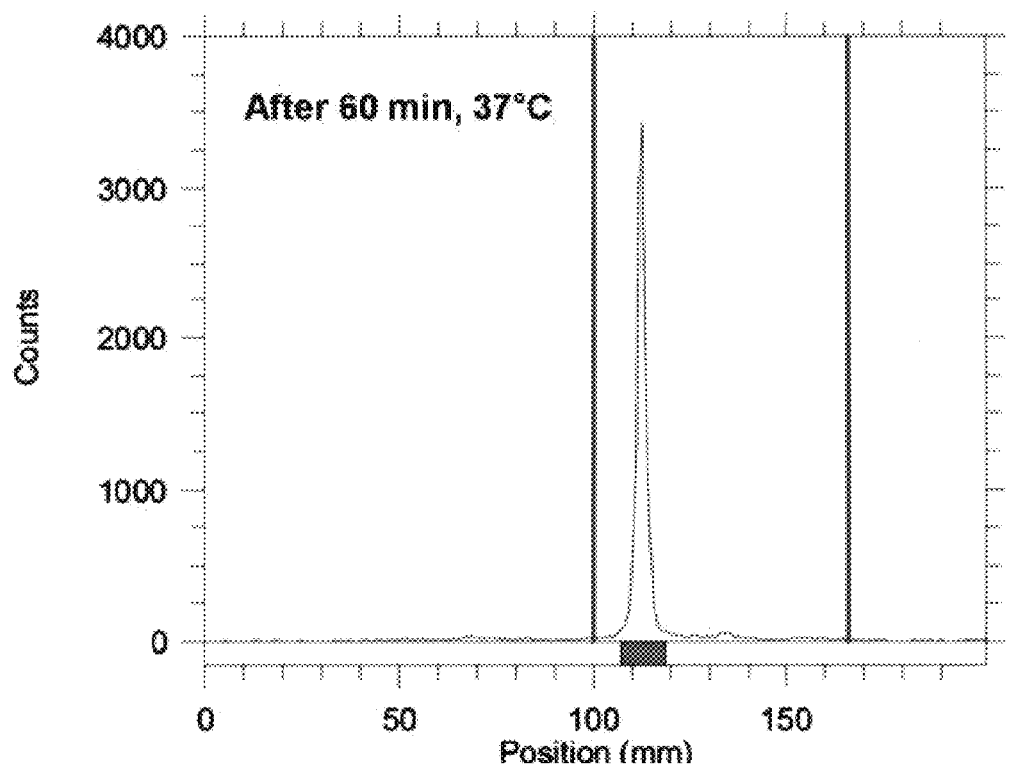
Figure 19:
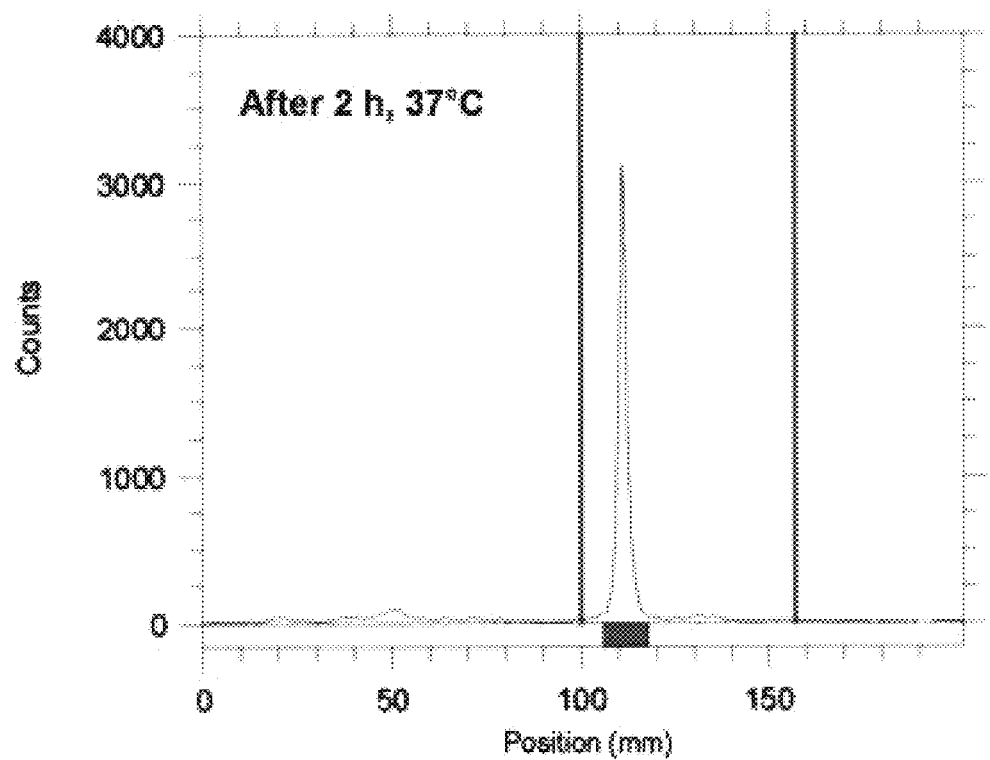
Figure 20:
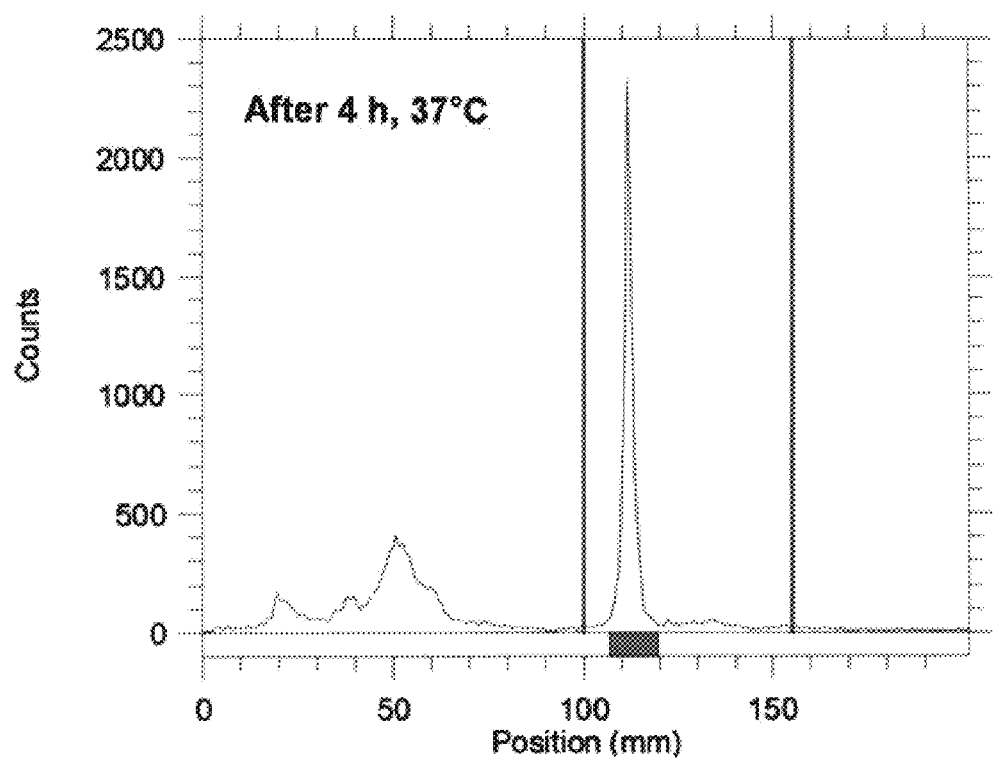
Figure 21:
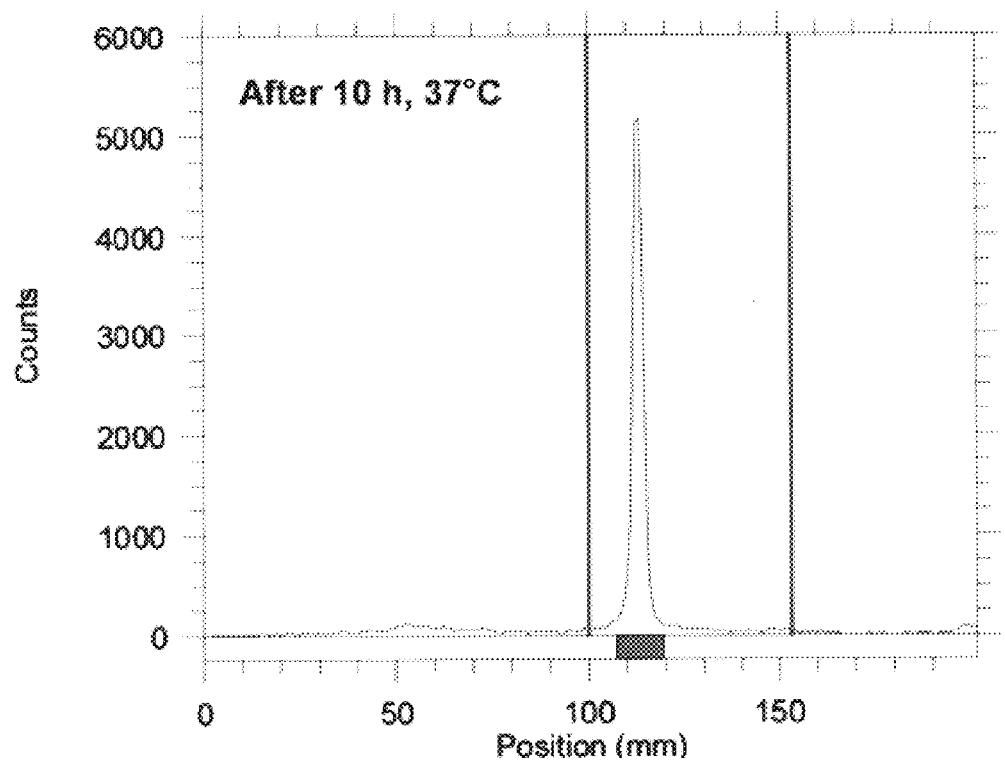
Figure 22:
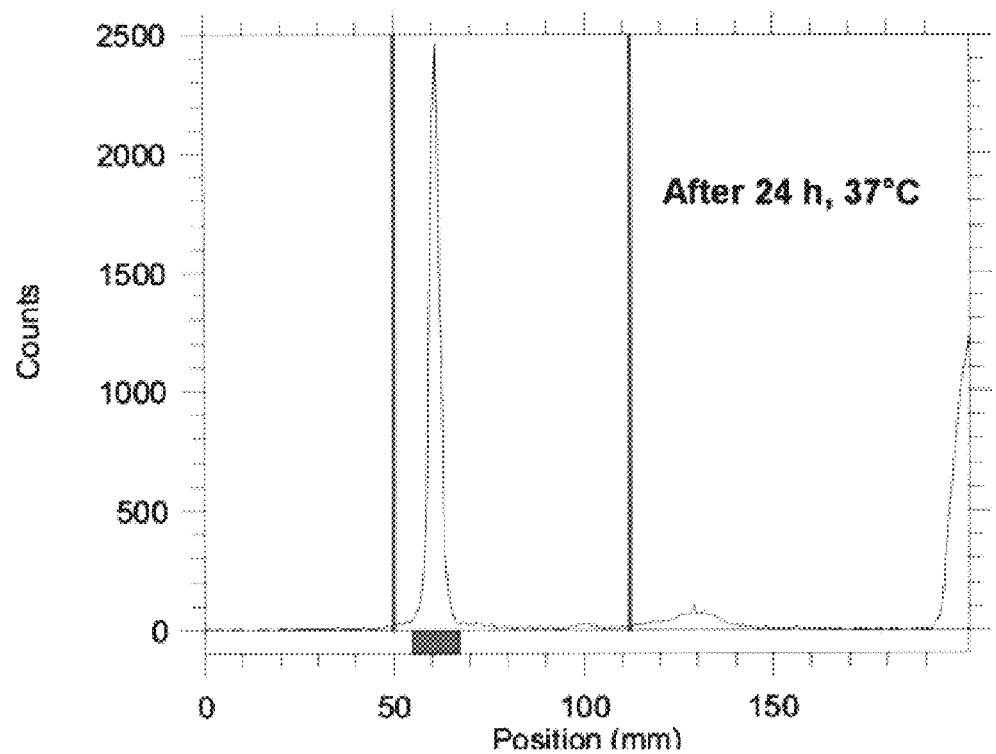

The compound of Chemical Formula 1 is a tetraaza macrocyclic compound with propylene cross-bridged between two nitrogen atoms with no $X^1$ attached, and is capable of forming a complex with a metal atom at 30-60° C. (see FIGS. 5-7). Considering that the existing ethylene cross-bridged tetraaza macrocyclic compound requires a high temperature of 80° C. or above for complex formation with a metal atom, this is a remarkable improvement. Particularly, when the tetraaza macrocyclic compound to which a bioactive substance (e.g., protein) is attached is to form a complex with a metal atom, denaturation of the protein during the complex formation may be prevented since it can be achieved at a temperature below the denaturation temperature. Hence, the tetraaza macrocyclic compound represented by Chemical Formula 1 may be purchased in the state with the bioactive substance attached thereto and may be formed into a complex with a radioactive metal element for use as a contrast agent, a radioactive therapeutic agent, or the like. Thus, the propylene cross-bridged tetraaza macrocyclic compound will be commercially useful.

R in Chemical Formula 1 may be any functional group that can be substituted at a tetraaza macrocyclic compound commonly used for, e.g., a contrast agent, without limitation, and may include the functional groups that can be used for $R^1$ or $X^1$, which will be described below. Specifically, if $R^1$ is a functional group that cannot bind to a bioactive substance (e.g., antibody), R may be a functional group that can bind to the bioactive substance. More specifically, R may be a functional group to which the bioactive substance cannot bind easily. Specifically, each R may independently be H, alcohol, amino, amido, nitro, ester, halogen, ketone, cyano, carboxy, hydroxy, thiol, aldehyde, or substituted or unsubstituted $C_{1\sim10}$ alkyl, and the substitution may be by one or more moiety(ies) selected from a group consisting of amino, amido, nitro, ester, halogen, ketone, cyano, carboxy, hydroxy, thiol and aldehyde. Most specifically, each R may independently be H, halogen, ketone or $C_{1\sim10}$ alkyl. That is to say, although R may be any functional group, it may be a functional group to which a bioactive substance cannot bind easily if $R^1$ is a functional group to which the bioactive substance can bind.

In a specific embodiment of the present disclosure, each $R^1$ may independently be H, alcohol, amino, amido, nitro, ether, ester, halogen, ketone, cyano, carboxy, hydroxy, thiol, aldehyde, carbonyl, substituted or unsubstituted $C_{1\sim15}$ alkyl, substituted or unsubstituted $C_{1\sim15}$ alkenyl, substituted or unsubstituted $C_{1\sim15}$ alkynyl, substituted or unsubstituted $C_{1\sim15}$ alkylaryl, substituted or unsubstituted $C_{1\sim15}$ aryl, substituted or unsubstituted $C_{1\sim15}$ heteroalkyl, substituted or unsubstituted $C_{1\sim15}$ heterocycle, or substituted or unsubstituted $C_{1\sim15}$ heteroaryl, and the substitution may be by one or more moiety(ies) selected from a group consisting of imide, aldehyde, carboxy, ketone, nitro, amino, thiol, succinimide, maleimide, aminooxyl, acetylene, $N_3$, acetamino, azide, ester, halogen, alkyne, and NCS. Specifically, R' may be a functional group to which an antibody, an amino acid, a nucleoside, a nucleotide, an aptamer, a protein, an antigen, a peptide, a nucleic acid, an enzyme, a lipid, an albumin, a cell, a carbohydrate, a vitamin, a hormone, a nanoparticle, an inorganic support, a polymer, a single molecule, a drug, or the like can bind. In this case, since $X^1$ does not need to bind to the bioactive substance (e.g., antibody), it may serve its intended role as a ligand when the compound of Chemical Formula 1 forms a complex with a metal ion, thereby stabilizing the complex. That is to say, if $R^1$ binds to a bioactive substance or a chemically active substance, $X^1$ may contribute to the stabilization of the complex with a metal ion, as intended. Therefore, R' may be any functional group that has been used for binding with a bioactive substance or a chemically active substance. For example, all the $X^1$s described in US Patent Publication No. 2006-62728 may be used as $R^1$ in the present disclosure.

In a specific embodiment of the present disclosure, each R', as the functional group capable of binding to a bioactive substance or a chemically active substance, may be independently H, substituted or unsubstituted $C_{1\sim15}$ alkyl, substituted or unsubstituted $C_{1\sim15}$ alkenyl, substituted or unsubstituted $C_{1\sim15}$ alkynyl, substituted or unsubstituted $C_{1\sim15}$ alkylaryl, substituted or unsubstituted $C_{1\sim15}$ aryl, substituted or unsubstituted $C_{1\sim15}$ heteroalkyl, substituted or unsubstituted $C_{1\sim15}$ heterocycle, or substituted or unsubstituted $C_{1\sim15}$ heteroaryl, and the substitution may be by one or more moiety(ies) selected from a group consisting of imide, aldehyde, carboxy, ketone, nitro, amino, thiol, succinimide, maleimide, aminooxyl, acetylene, $N_3$, acetamino, azide, ester, halogen, alkyne, and NCS, with the proviso that at least one $R^1$ is not H. Specifically, among the $R^1$s, which are the functional groups bonded to the three carbon atoms of the cross-bridged propylene, the $R^1$ bonded to the central carbon may be a functional group to which a bioactive substance or a chemically active substance can bind, such as imide, and the other $R^1$s bonded to the remaining two carbon atoms may be hydrogen or a functional group to which a bioactive substance or a chemically active substance cannot bind.

In a more specific embodiment of the present disclosure, each $R^1$ may independently be H, substituted or unsubstituted $C_{1\sim10}$ alkyl, substituted or unsubstituted $C_{1\sim10}$ alkenyl, substituted or unsubstituted $C_{1\sim10}$ alkynyl, substituted or unsubstituted $C_{1\sim10}$ alkylaryl, substituted or unsubstituted $C_{1\sim10}$ aryl, or substituted or unsubstituted $C_{1\sim10}$ heteroalkyl, and the substitution may be by one or more moiety(ies) selected from a group consisting of imide, aldehyde, carboxy, ketone, nitro, amino, thiol, succinimide, maleimide, aminooxyl, acetylene, $N_3$, acetamino, azide, ester, halogen, alkyne, and NCS, with the proviso that at least one $R^1$ is not H.

In a more specific embodiment of the present disclosure, each $R^1$ may independently be H or $(CR^5{}_2)_a$—P—$(CR^5{}_2)_b$-Q-$(CR^5{}_2)_c$—R—$(CR^5{}_2)_d$-A, wherein each $R^5$ may independently be H, alcohol, amino, amido, nitro, ester, halogen, ketone, cyano, carboxy, hydroxy, thiol, aldehyde or $C_{1\sim3}$ alkyl; each of P, Q and R may independently be nonexistent or Ar, $CO_2$, NH, CO or O; A may be imide, aldehyde, carboxy, ketone, nitro, amino, thiol, succinimide, maleimide, aminooxyl, acetylene, N3, acetamino, azide, NCS, ester, halogen, $C_{2\sim6}$ alkene, $C_{2\sim6}$ alkyne or $CO_2R^5$; each Ar may independently be substituted or unsubstituted phenyl, and the substitution may be by halogen; each a may independently be an integer from 1 to 5; each b may independently be an integer from 0 to 5; each c may independently be an integer from 0 to 5; and each d may independently be an integer from 0 to 5, with the proviso that at least one $R^1$ is not H. For example, if P is nonexistent, $(CR^5{}_2)_a$ is bonded directly to $(CR^5{}_2)_b$, and, if b is 0, $(CR^5{}_2)_a$ is bonded directly to Q.

In a more specific embodiment of the present disclosure, each $R^1$ may independently be H, $(CR^5{}_2)_n\text{Ar}(CR^5{}_2)_m$-A, $(CR^5{}_2)_n\text{Ar}(CR^5=CR^5)_n$-A, $(CR^5{}_2)_n\text{Ar}_p(CR^5{}_2)_n\text{CO}_2(CR^5{}_2)_m$-A, $(CR^5{}_2)_n\text{Ar}_p(CR^5{}_2)_m\text{CO}(CR^5{}_2)_m$-A, $(CR^5{}_2)_n\text{CO}_2(CR^5{}_2)_m\text{Ar}_p$-A, $(CR^5{}_2)_n\text{Ar}_p(CR^5{}_2)_m\text{NHCO}(CR^5{}_2)_m$-A, $(CR^5{}_2)_n\text{CONH}(CR^5{}_2)_m$-A or $(CR^5{}_2)_n$-A, wherein each $R^5$ may independently be H, alcohol, amino, amido, nitro, ester, halogen, ketone, cyano, carboxy, hydroxy, thiol, aldehyde or $C_{1\sim3}$ alkyl; A may be imide, aldehyde, carboxy, ketone, nitro, amino, thiol, succinimide, maleimide, aminooxyl, acetylene, N3, acetamino, azide, NCS, ester, halogen, $C_{2\sim6}$ alkene, $C_{2\sim6}$ alkyne or $CO_2R^5$; each Ar may independently be substituted or unsubstituted phenyl, and the substitution may be by halogen; each n may independently be an integer from 1 to 5; each m may independently be an integer from 0 to 5; each p may independently be an integer 0 or 1; and, if m is 0, A may be bonded directly to NH, CO, Ar, $SO_2$ or $CO_2$, with the proviso that at least one $R^1$ is not H. As described earlier, if p in $(CR^5{}_2)_n\text{Ar}_p(CR^5{}_2)_m\text{CO}(CR^5{}_2)_m$-A is 0, $(CR^5{}_2)_n$ is bonded directly to $(CR^5{}_2)_m$, and if m is 0, $(CR^5{}_2)_n$ is bonded directly to CO.

Most specifically, as a functional group that can bind with a bioactive substance or a chemically active substance, each $R^1$ may independently be one of the functional groups represented by Chemical Formula a:

[Chemical Formula a]

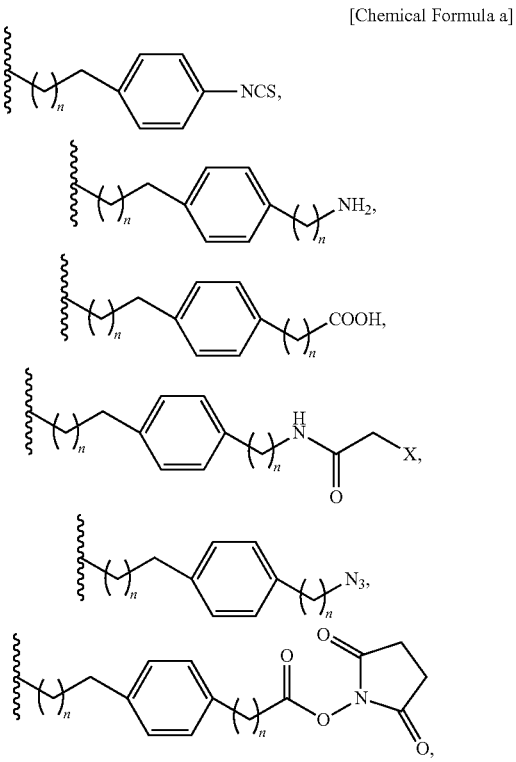

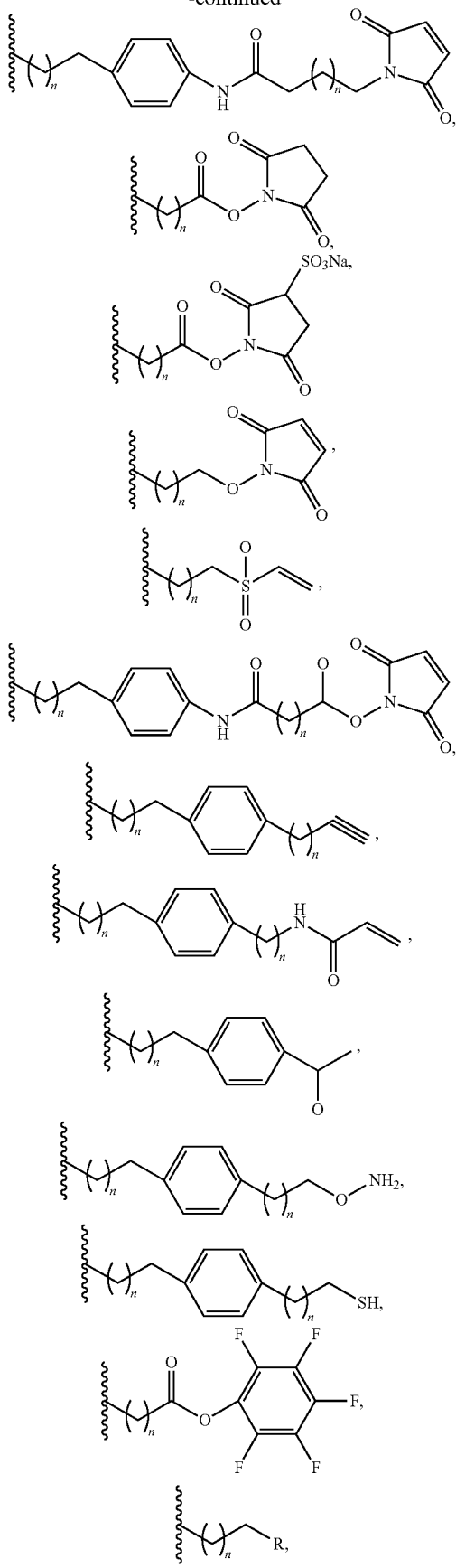
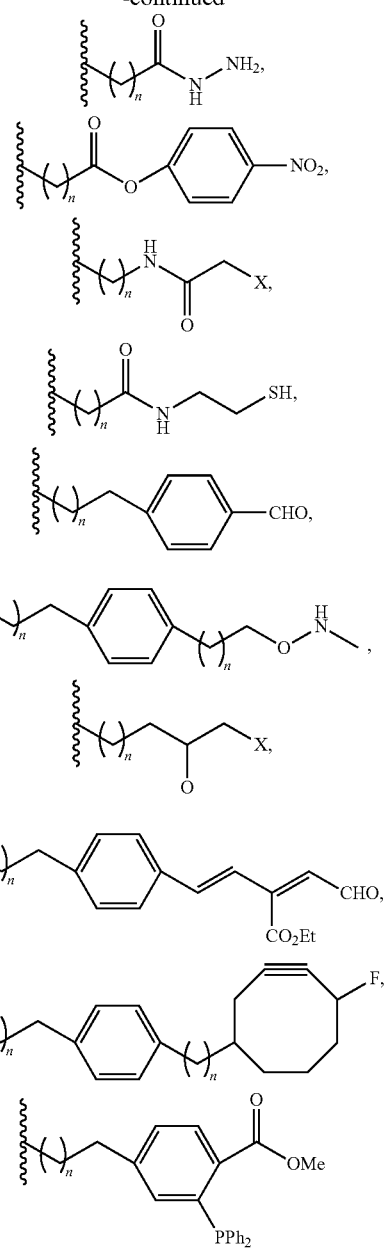

wherein each R is independently $NH_2$, COOH, $N_3$, CHO, NCO, SH or $C_{2-6}$ alkyne; each X is independently Cl or Br; and each n is independently an integer from 0 to 5.

Although a total of six $R^1$s may be attached to the carbon atoms of the cross-bridged propylene, specifically, only one functional group that can bind to a bioactive substance or a chemically active substance may be attached to the 2-position carbon atom of the propylene and hydrogens may be attached to all the other carbon atoms.

In this case, $R^1$ may be attached directly to the carbon atom of the cross-bridged propylene or may be bonded to the carbon atom via a linker. The linker may be any one that is commonly used to link a functional group to a carbon atom in a tetraaza macrocyclic compound, without limitation. Specifically, the linker (L) may be one of those represented by the following formula:

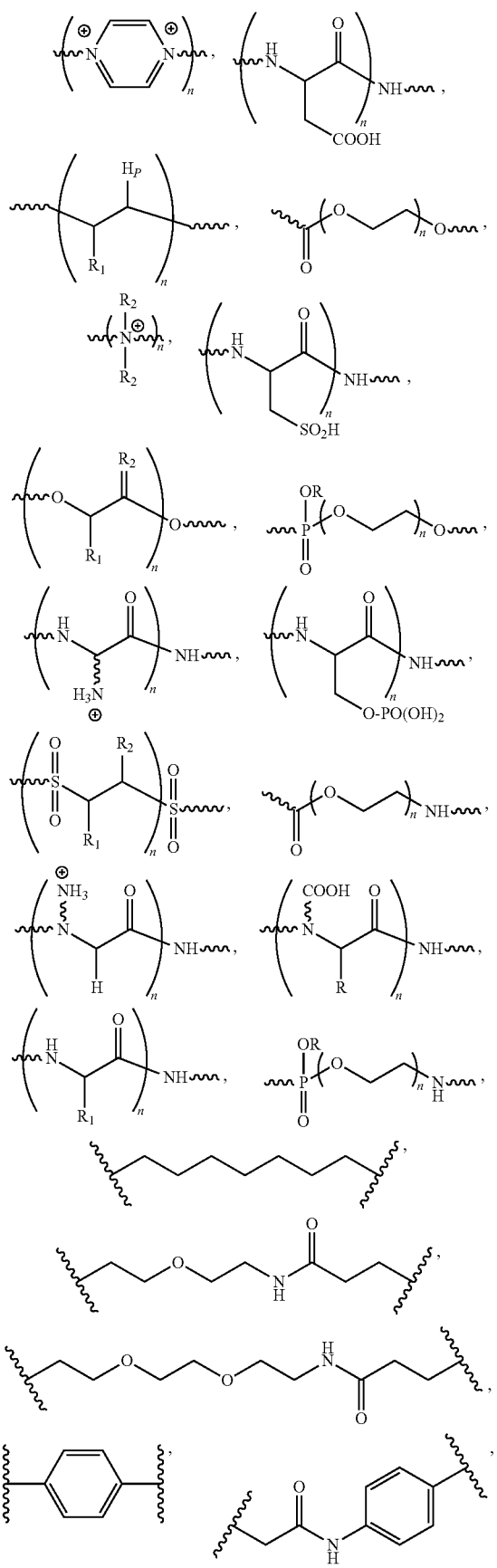

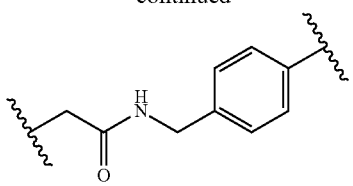

wherein each of R, $R_1$ and $R_2$ is independently $C_{1\sim10}$ alkyl, $C_{1\sim10}$ alkenyl, $C_{1\sim10}$ alkynyl, $C_{1\sim10}$ aryl, $C_{1\sim10}$ arylalkyl or $C_{1\sim10}$ heteroaryl; and each n is independently an integer from 1 to 20.

Specifically, in another embodiment of the present disclosure, each $X^1$ may independently be H, $-(CR^2)_l-COOH$, $-CR^2-((CR^2)_m-COOH)_2$, $-(CR^2)_l-CO_2R^3$, $-(CR^2)_l-ArOR^3$, $-(CR^2)_l-SR^3$, $-(CR^2)_l-SO_3H$, $-(CR^2)_l-PO_2HR^3$, $-(CR^2)_mN(CR^2)_2$ or $-(CR^2)_mCON(CR^2)_2$; each of $R^2$ and $R^3$ may independently be H, substituted or unsubstituted $C_{1\sim10}$ alkyl, substituted or unsubstituted $C_{1\sim10}$ alkenyl, substituted or unsubstituted $C_{1\sim10}$ alkynyl, substituted or unsubstituted $C_{1\sim10}$ alkylaryl, substituted or unsubstituted $C_{1\sim10}$ aryl, substituted or unsubstituted $C_{1\sim10}$ heteroalkyl, or substituted or unsubstituted $C_{1\sim10}$ heteroaryl; Ar may be substituted or unsubstituted phenyl, and the substitution may be by one or more moiety(ies) selected from a group consisting of imide, aldehyde, carboxy, ketone, nitro, amino, thiol, succinimide, maleimide, aminooxyl, $N_3$, acetylene, acetamino, azide, phosphate, alkyne, and NCS; each l may independently be an integer from 1 to 3; and each m may independently be an integer from 1 to 5, with the proviso that at least one $X^1$ is not H. Specifically, in this case, $X^1$ may be a functional group capable of coordinating with a metal ion, and it may serve the intended purpose as a ligand during complex formation of the compound of Chemical Formula 1 with a metal ion, thereby stabilizing the complex. For example, if the metal ion is $^{64}Cu$ having a coordination number of 6, four nitrogen atoms and two $X^1$s of the tetraaza macrocyclic compound of Chemical Formula 1 may coordinate with the metal ion to form a complex. Thus, $X^1$ may be any functional group that can participate in coordination during complex formation with a metal ion, without limitation. For example, all the $X^1$s described in US Patent Publication No. 2006-62728 may be used.

In a specific embodiment of the present disclosure, as a functional group that can participate in coordination during complex formation with a metal ion, each $X^1$ may independently be H, $-(CR^2)_mN(CR^2)_2$, $-(CR^2)_mCON(CR^2)_2$ or $-(CR^2)_m-E-(CR^2)_l-F$; E may be nonexistent or CONH or NHCO; F may be COOH, $PO_3H_2$, $SO_3H$, OH, $NH_2$, $CONH_2$, NCS or $C_2$ alkyne; each $R^2$ may independently be H, carboxy, halogen or $C_{1\sim3}$ alkyl; each l may independently be an integer from 0 to 3; and each m may independently be an integer from 1 to 3, with the proviso that at least one $X^1$ is not H. More specifically, each of $R_2$ and $R_3$ may independently be H, t-Bu, Et, Me, benzyl, methoxybenzyl or $-CH_2CO_2$-t-Bu.

Most specifically, at least one $X^1$ may independently be one of the functional groups represented by Chemical Formula b:

[Chemical Formula b:]

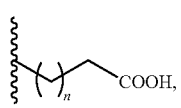

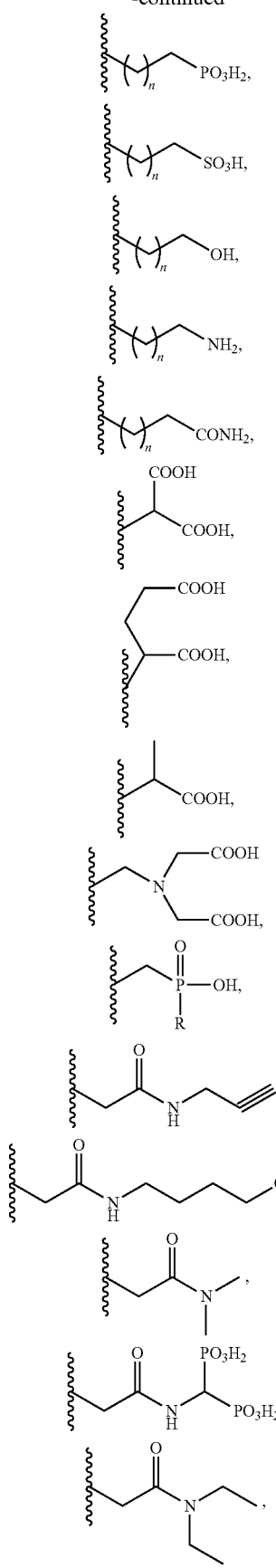

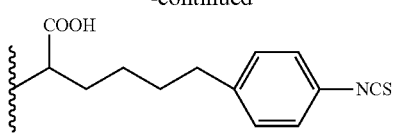

wherein R is Ph, Bn, Me, Et or n-Bu; and each n is independently an integer 0 or 1.

More specifically, $R^1$ may be a functional group that can bind to a bioactive substance or a chemically active substance and/or $X^1$ may be a functional group that can coordinate with a metal ion. Especially, if $R^1$ is a functional group that can bind to a bioactive substance or a chemically active substance and, at the same time, if $X^1$ is a functional group that can coordinate with a metal ion, $R^1$ may bind to a bioactive substance or a chemically active substance (e.g., protein) and $X^1$ may coordinate with a metal ion, thereby stabilizing the coordinated complex and enabling complex formation at a significantly low temperature. Consequently, the propylene cross-bridged tetraaza macrocyclic compound may be purchased in the state with the bioactive substance or the chemically active substance attached thereto and may be formed into a complex with a radioactive metal at a significantly low temperature capable of preventing denaturation of the bioactive substance or the chemically active substance for use as a contrast agent, a radioactive therapeutic agent, or the like.

Specifically, the functional groups $R^1$ and $X^1$ may be an independent combination of those described above. More specifically, at least one $X^1$ may independently be one of the functional groups represented by Chemical Formula b, and at least one $R^1$ may independently be one of the functional groups represented by Chemical Formula a.

Specifically, in a specific embodiment of the present disclosure, the tetraaza macrocyclic compound may be one of the compounds represented by the following chemical formula:

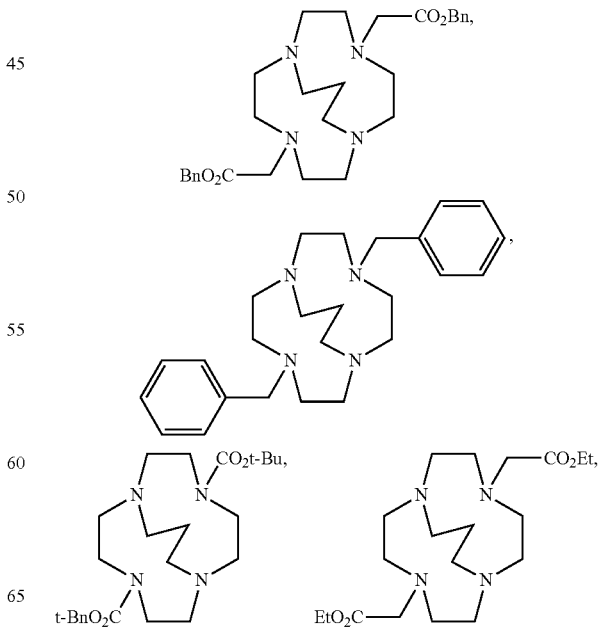

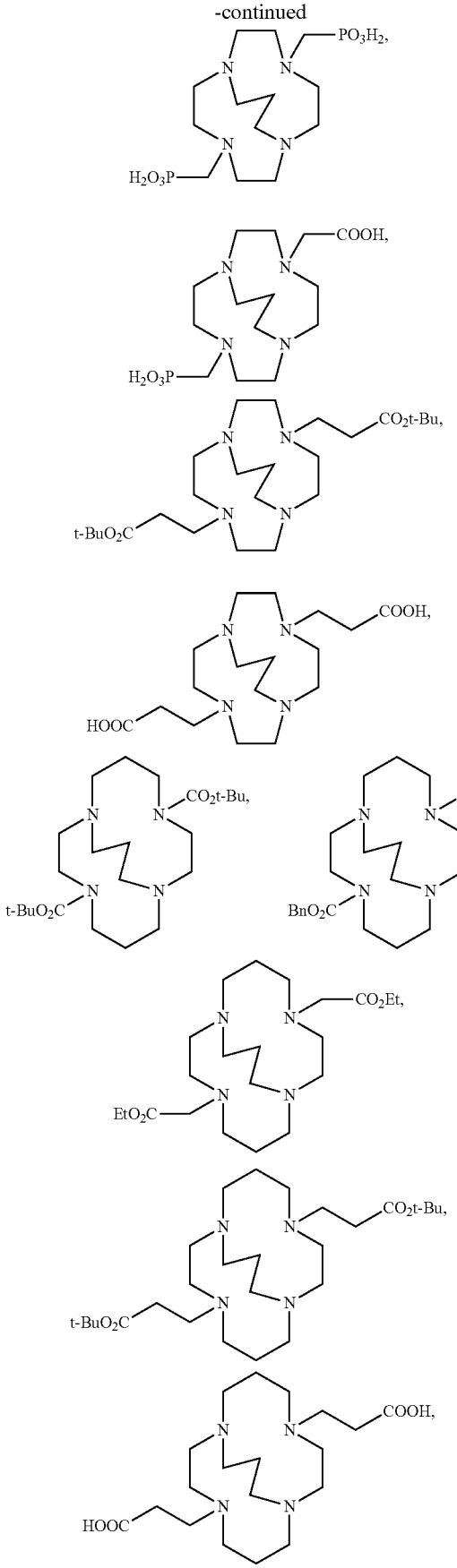
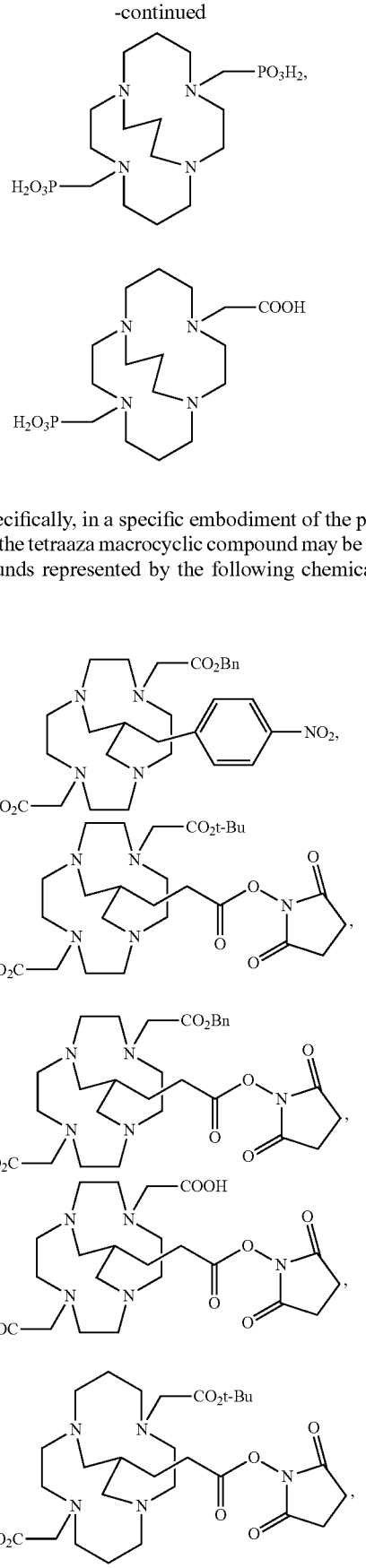
More specifically, in a specific embodiment of the present disclosure, the tetraaza macrocyclic compound may be one of the compounds represented by the following chemical formula:

-continued

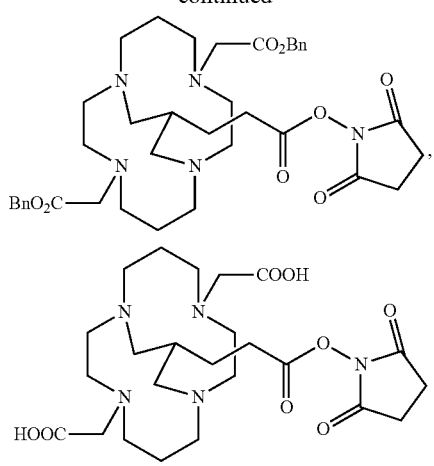

Specifically, in a specific embodiment of the present disclosure, the tetraaza macrocyclic compound may be one of the compounds represented by the following chemical formula:

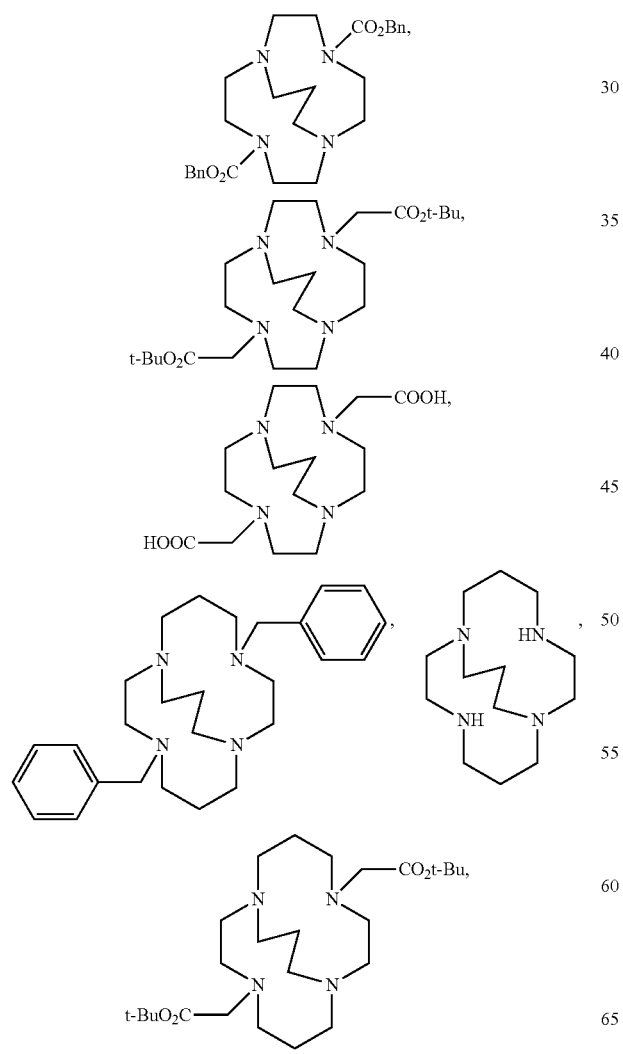

-continued

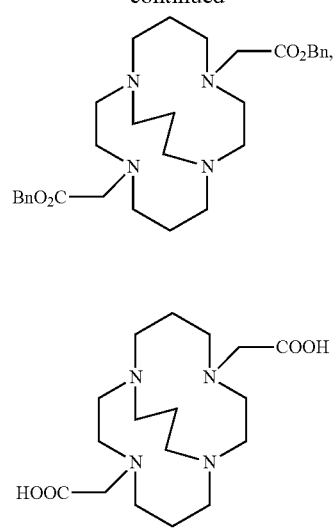

More specifically, in a specific embodiment of the present disclosure, the tetraaza macrocyclic compound may be one of the compounds represented by the following chemical formula:

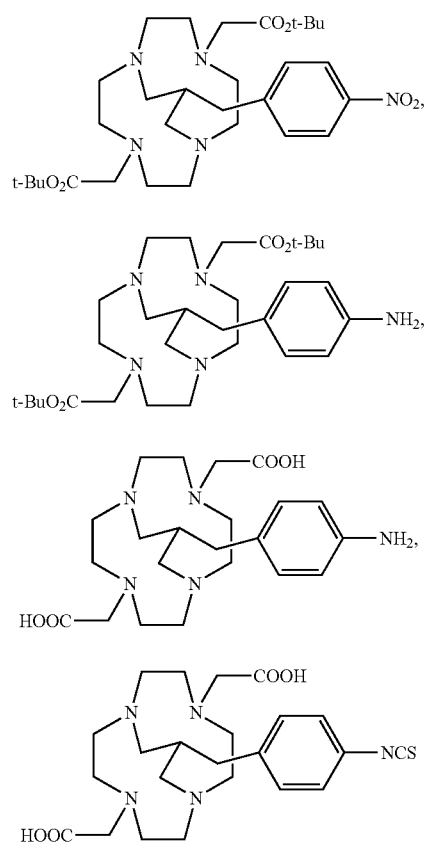

More specifically, in a specific embodiment of the present disclosure, the tetraaza macrocyclic compound may be one of the compounds represented by the following chemical formula:

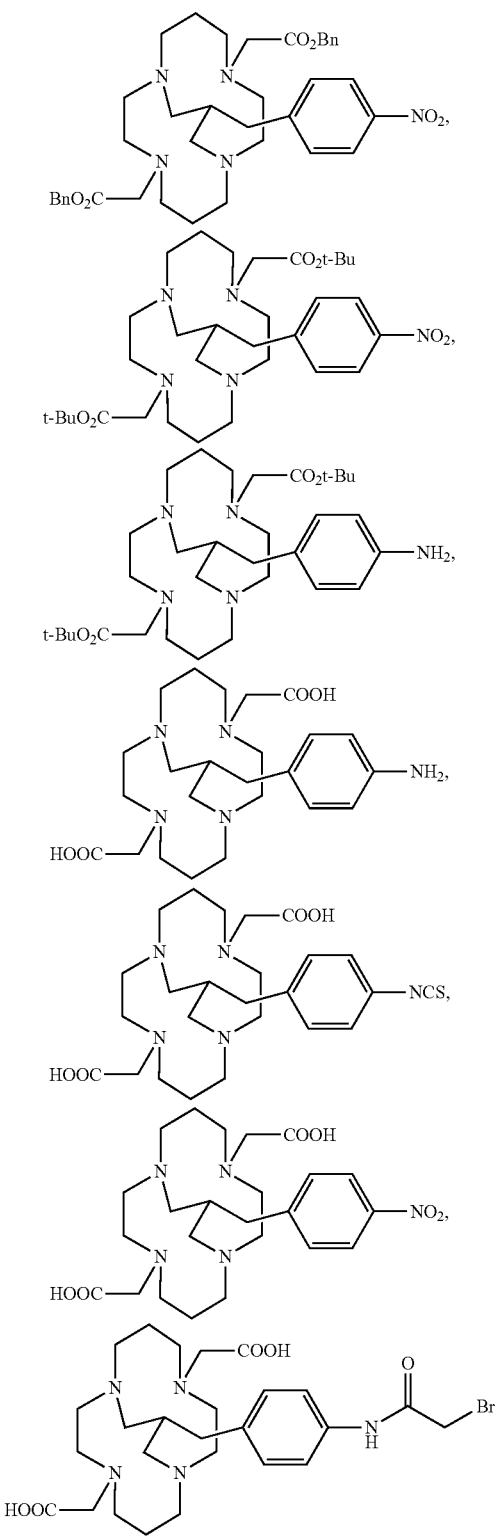

Since the propylene cross-bridged tetraaza macrocyclic compound of the present disclosure is capable of complex formation at a lower temperature than the existing ethylene cross-bridged tetraaza macrocyclic compound, it can be purchased in the state with a bioactive substance or a chemically active substance attached thereto and may be formed into a complex with a radioactive metal at a low temperature capable of preventing denaturation of the bioactive substance or the chemically active substance for use as a contrast agent, a radioactive therapeutic agent, or the like.

In addition, since the chelate arms ($X^1$) of the tetraaza macrocyclic compound with the functional group(s) that can bind to a bioactive substance or a chemically active substance attached to the cross-bridged propylene does not need to bind to the bioactive substance or the chemically active substance, all the chelate arms may participate in coordination, thereby stabilizing the complex.

The present disclosure further provides a method for preparing a tetraaza macrocyclic compound allowing easy attachment of a functional group to cross-bridged propylene. As described earlier, the existing ethylene cross-bridged tetraaza macrocyclic compound is prepared by reacting cyclam or cyclen with glyoxal. However, since a functional group cannot be attached to glyoxal, it is impossible to attach a functional group such as NCS to the cross-bridged ethylene, that can bind with a bioactive substance. Accordingly, the only option is to attach the bioactive substance to the functional group bound to the nitrogen atom.

To solve this problem, the present disclosure provides a method for preparing a tetraaza macrocyclic compound by reacting a tetraaza macrocyclic compound represented by Chemical Formula 2 with a compound represented by Chemical Formula 3:

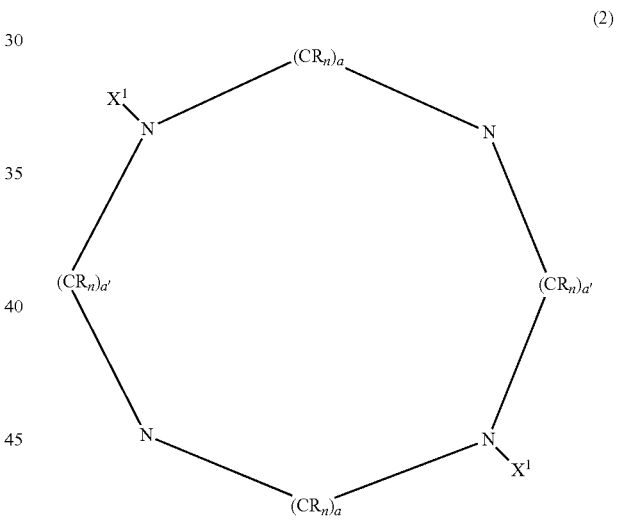

(2)

wherein each R is independently H, alcohol, amino, amido, nitro, ester, halogen, ketone, cyano, carboxy, hydroxy, thiol, aldehyde, or substituted or unsubstituted $C_{1\sim10}$ alkyl, wherein the substitution is by one or more moiety(ies) selected from a group consisting of amino, amido, nitro, ester, halogen, ketone, cyano, carboxy, hydroxy, thiol and aldehyde;

each $X^1$ is independently H, $-(CR^2)_1-COOH$, $-CR^2-((CR^2)_m-COOH)_2$, $-(CR^2)_1-CO_2R^3$, $-(CR^2)_1-ArOR^3$, $-(CR^2)_1-SR^3$, $-(CR^2)_1-SO_3H$, $-(CR^2)_1-PO_2HR^3$, $-(CR^2)_mN(CR^2)_2$ or $-(CR^2)_mCON(CR^2)_2$, wherein each of $R^2$ and $R^3$ is independently H, substituted or unsubstituted $C_{1\sim10}$ alkyl, substituted or unsubstituted $C_{1\sim10}$ alkenyl, substituted or unsubstituted $C_{1\sim10}$ alkynyl, substituted or unsubstituted $C_{1\sim10}$ alkylaryl, substituted or unsubstituted $C_{1\sim10}$ aryl, substituted or unsubstituted $C_{1\sim10}$ heteroalkyl, or substituted or unsubstituted $C_{1\sim10}$ heteroaryl, Ar is substituted or unsubstituted phenyl, wherein the substitution is by one or more moiety(ies) selected from a group consisting of imide, aldehyde, carboxy, ketone, nitro, amino, thiol, succinimide, maleimide, aminooxyl, $N_3$, acetylene, acetamino, azide, phosphate, alkyne, and NCS, each l is independently an integer from 1 to 3, and each m is independently an integer from 1 to 5, with the proviso that at least one $X^1$ is not H;

each a is independently an integer 2 or 3;
each a' is independently an integer 2 or 3; and
each n is an integer from 0 to 2 satisfying the valence of the carbon atom to which R or L-R' is covalently bonded; and

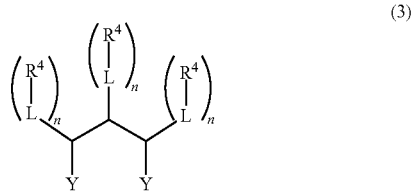

(3)

wherein each $R^4$ is independently H, alcohol, amino, amido, nitro, ether, ester, halogen, ketone, cyano, carboxy, hydroxy, thiol, aldehyde, carbonyl, substituted or unsubstituted $C_{1\sim15}$ alkyl, substituted or unsubstituted $C_{1\sim15}$ alkenyl, substituted or unsubstituted $C_{1\sim15}$ alkynyl, substituted or unsubstituted $C_{1\sim15}$ alkylaryl, substituted or unsubstituted $C_{1\sim15}$ aryl, substituted or unsubstituted $C_{1\sim15}$ heteroalkyl, substituted or unsubstituted $C_{1\sim15}$ heterocycle, or substituted or unsubstituted $C_{1\sim15}$ heteroaryl, wherein the substitution is by one or more moiety(ies) selected from a group consisting of imide, aldehyde, carboxy, ketone, nitro, amino, thiol, succinimide, maleimide, aminooxyl, acetylene, $N_3$, acetamino, azide, and NCS;

each L is independently a linker or nonexistent, and $R^4$ is directly bound to a carbon atom when L is nonexistent;

each Y is independently a leaving group; and each n is independently an integer from 0 to 2 satisfying the valence of the carbon atom to which L-$R^4$ is covalently bonded.

Since the compound of Chemical Formula 3 may have a functional group ($R^4$) that can bind to a bioactive substance or a chemically active substance (e.g., antibody) attached on the propylene backbone, when it is reacted with the bifunctional chelator compound of Chemical Formula 2 to prepare the propylene cross-bridged tetraaza macrocyclic compound of Chemical Formula 1, the functional group remains bonded to the cross-bridged propylene. Thus, as described above, when compared with the existing ethylene cross-bridged tetraaza macrocyclic compound with a functional group attached to the cyclic moiety of the tetraaza macrocyclic compound rather than to the cross-bridged moiety, in the present disclosure where the functional group is bonded to the cross-bridged propylene, complex formation by coordination with a metal element may be performed at 30-60° C., not at at least 80° C. Consequently, since the complex formation may be performed at a lower temperature, denaturation of the bioactive substance or the chemically active substance (e.g., protein) bound to the functional group may be prevented and the tetraaza macrocyclic compound is commercially useful. In addition, since various functional groups may be attached through the same synthesis process, synthesis time, cost and yield may be remarkably improved and the associated process is simplified.

R and $X^1$ in Chemical Formula 2 and $R^4$ in Chemical Formula 3 may be the same as the R, $X^1$ and le in Chemical Formula 1. Also, the linker may be the same. Adequate $X^1$ may be selected depending on the particular $X^1$ and starting materials and the selected synthesis strategy. During the synthesis process, $X^1$ may be variously substituted or modified.

Y may be any leaving group that can be used for substitution, without limitation. Specifically, each Y may independently be tosylate, mesylate, brosylate, tresylate, triflate, nosylate, Br, Cl or I.

In an embodiment of the present disclosure, the tetraaza macrocyclic compound represented by Chemical Formula 2 and the compound represented by Chemical Formula 3 may be reacted at a molar ratio of 1:10 to 10:1. If the molar ratio is outside the above range, reaction yield may decrease or loss of starting materials may be excessive.

Specifically, a reaction solvent that can be used in the reaction may be MeCN, MeOH, EtOH, THF, toluene or a mixture thereof. More specifically, MeCN, EtOH, toluene or a mixture thereof may be used. Most specifically, when toluene is used, side reactions may be reduced, separation of product from the reactants may be easy, and high yield may be attained.

Specifically, the compound of Chemical Formula 2 may be cyclam, cyclen or a derivative thereof (for example, with R being methyl).

The present disclosure further provides a coordination compound comprising: the tetraaza macrocyclic compound represented by Chemical Formula 1 according to the present disclosure; and a metal element coordinated with the tetraaza macrocyclic compound.

Specifically, in an embodiment of the present disclosure, the metal element may be a non-radioactive metal element or a radioactive metal element. Specifically, the metal element may be selected from a group consisting of an alkali metal, an alkaline earth metal and a transition metal having a charge from +1 to +7.

Specifically, in another embodiment of the present disclosure, the metal element may be selected from a group consisting of Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III) and Ru(IV).

More specifically, in another embodiment of the present disclosure, the metal element may be one or more element selected from a group consisting of a Group 1 metal element (Li or Na), a Group 2 metal element (Be, Ca, Mg, Sr, Ba or Ra), a Group 13 element (Ga or In), a Group 14 element (Si or Ge), a Group 15 element (As, Sb or Bi), a Group 16 element (S, Se or Te), a transition metal (Sr, Ti, V, Cu, Y, Zr, Nb, Mo, Tc, Ru, Rh, Pd, Ag, Cd, Hf, Ta, W, Re, Os, Ir, Pt, Au or Hg), and a lanthanide or actinide element (La, Ce, Pr, Nd, Pm, Sm, Eu, Gd, Tb, Dy, Ho, Er, Tm or Yb), or one or more radioisotope selected from a group consisting of $^{43}$Sc, $^{44}$Sc, $^{45}$Ti, $^{51}$Mn, $^{51}$Cr, $^{52}$Mn, $^{52}$Fe, $^{53}$Fe, $^{55}$Co, $^{56}$Co, $^{57}$Co, $^{58}$Co, $^{59}$Fe, $^{60}$Cu, $^{61}$Cu, $^{62}$Cu, $^{62}$Zn, $^{63}$Zn, $^{64}$Cu, $^{65}$Zn, $^{66}$Ga, $^{66}$Ge, $^{67}$Ge, $^{67}$Cu, $^{67}$Ga, $^{68}$Ga, $^{69}$Ge, $^{69}$As, $^{70}$As, $^{70}$Se, $^{71}$Se, $^{71}$As, $^{72}$As, $^{73}$Se, $^{74}$Kr, $^{74}$Br, $^{75}$Se, $^{75}$Br, $^{76}$Br, $^{77}$Br, $^{77}$Kr, $^{78}$Br, $^{78}$Rb, $^{79}$Rb, $^{79}$Kr, $^{81}$Rb, $^{82}$Rb, $^{83}$Sr, $^{84}$Rb, $^{84}$Zr, $^{85}$Y, $^{86}$Y, $^{87}$Y, $^{87}$Zr, $^{88}$Y, $^{90}$Y, $^{89}$Zr, $^{92}$Tc, $^{93}$Tc, $^{94}$Tc, $^{95}$Tc, $^{95}$Ru, $^{95}$Rh, $^{96}$Rh, $^{97}$Rh, $^{97}$RU, $^{98}$Rh, $^{99}$Rh, $^{94m}$Tc, $^{99m}$Tc, $^{100}$Rh, $^{101}$Ag, $^{102}$Ag, $^{102}$Rh, $^{103}$Ag, $^{103}$Ru, $^{104}$Ag, $^{105}$Ag, $^{105}$Ru, $^{106}$Ag, $^{108}$In, $^{109}$In, $^{110}$In, $^{111}$In, $^{115}$Sb, $^{116}$Sb, $^{117}$Sb, $^{115}$Te, $^{116}$Te, $^{117}$Te, $^{117}$I, $^{118}$I, $^{118}$Xe, $^{119}$Xe, $^{119}$I, $^{119}$Te, $^{120}$I, $^{120}$Xe, $^{121}$Xe, $^{121}$I, $^{122}$I, $^{123}$Xe, $^{124}$I, $^{126}$I, $^{128}$I, $^{129}$La, $^{130}$La, $^{131}$La, $^{132}$La, $^{133}$La, $^{135}$La, $^{136}$La, $^{140}$Sm, $^{141}$Sm, $^{142}$Sm, $^{144}$Gd, $^{145}$Gd, $^{145}$Eu, $^{146}$Gd, $^{146}$Eu, $^{147}$Eu, $^{147}$Gd, $^{148}$Eu, $^{149}$Pr, $^{150}$Eu, $^{153}$Sm, $^{159}$Gd, $^{166}$Ho, $^{169}$Yb, $^{177}$Lu, $^{186}$Re, $^{188}$Re, $^{190}$AU, $^{191}$AU, $^{192}$AU, $^{193}$AU, $^{193}$Tl, $^{194}$Tl, $^{194}$Au, $^{195}$Tl, $^{196}$Tl, $^{197}$Tl, $^{198}$Tl, $^{200}$Tl, $^{200}$Bi, $^{201}$Tl, $^{202}$Bi, $^{203}$Bi, $^{205}$Bi, $^{206}$Bi, $^{211}$As, $^{212}$Bi and $^{225}$Ac.

More specifically, the metal element may be a transition metal selected from a group consisting of Ba, Cr, Mn, Fe, Co, Ni, Cu, Zn, Cd, Hg, Nb, Mo, Zr, Te, W, Pd, Ag, Pt and Au, a Group 13-15 element selected from a group consisting of Ga, In, Sn, Pb and Bi, a lanthanide or actinide metal element selected from a group consisting of Gd, Tb, Dy, Ho, Er, Sm and Nd, or a radioisotope thereof. Most specifically, the metal element may be selected from Cu, Mn, Fe, Co, Ni or a radioisotope (specifically, $^{111}$In, $^{67}$Ga, $^{68}$Ga, $^{86}$Y, $^{90}$Y, $^{99m}$Tc, $^{57}$Co, $^{58}$Co, $^{51}$Cr, $^{59}$Fe, $^{75}$Se, $^{169}$Yb, $^{60}$Cu, $^{61}$Cu, $^{62}$Cu, $^{64}$Cu or $^{67}$Cu).

And, specifically, the tetraaza macrocyclic compound represented by Chemical Formula 1 may have a bioactive substance or a chemically active substance attached to R'.

The present disclosure further provides a conjugate comprising: the tetraaza macrocyclic compound represented by Chemical Formula 1 or a coordination compound thereof; and a bioactive substance or a chemically active substance bound to the tetraaza macrocyclic compound or the coordination compound. Specifically, the conjugate of the present disclosure comprises one or more bioactive substance(s) (also known as a biomolecule) or chemically active substance(s) directing the conjugate to a targeted tissue, organ, receptor or other biologically expressed composition. Desirably, the bioactive substance or the chemically active substance is selective or specific for the targeted organ or tissue.

The bioactive substance or the chemically active substance may be an antibody, an amino acid, a nucleoside, a nucleotide, an aptamer, a protein, an antigen, a peptide, a nucleic acid, an enzyme, a lipid, an albumin, a cell, a carbohydrate, a vitamin, a hormone, a nanoparticle, an inorganic support, a polymer, a single molecule or a drug. Specific examples of the bioactive substance or the chemically active substance include: steroid hormones for the treatment of breast and prostate lesions; somatostatin, bombesin, CCK, and neurotensin receptor binding molecules for the treatment of neuroendocrine tumors; CCK receptor binding molecules for the treatment of lung cancer; ST receptor and carcinoembryonic antigen (CEA) binding molecules for the treatment of colorectal cancer; dihyroxyindolecarboxylic acid and other melanin producing biosynthetic intermediates for the treatment of melanoma; integrin receptor and atherosclerotic plaque binding molecules for the treatment of vascular diseases; and amyloid plaque binding molecules for the treatment of brain lesions. Examples of the bioactive substance or the chemically active substance also include synthetic polymers such as polyaminoacids, polyols, polyamines, polyacids, oligonucleotides, aborols, dendrimers, and aptamers.

In an embodiment of the present disclosure, the bioactive substance or the chemically active substance may be selected from among nanoparticles, antibodies (e.g., NeutroSpect®, Zevalin® and Herceptin®), proteins (e.g., TCII, HSA, annexin and Hb), peptides (e.g., octreotide, bombesin, neurotensin and angiotensin), nitrogen-containing simple or complex carbohydrates (e.g., glucosamine and glucose), nitrogen-containing vitamins (e.g., vitamin A, $B_1$, $B_2$, $B_{12}$, C, $D_2$, $D_3$, E, H and K), nitrogen-containing hormones (e.g., estradiol, progesterone and testosterone), nitrogen-containing active pharmaceuticals (e.g., celecoxib or other nitrogen-containing NSAIDs, AMD3100, CXCR4 and CCR5 antagonists) and nitrogen-containing steroids.

As mentioned above, some embodiments of the present disclosure may include conjugates having multiple bioactive substances or chemically active substances. For instance, to increase specificity for a particular target tissue, organ receptor or other biologically expressed composition, multiple bioactive substances or chemically active substances may be utilized. In such instances, the bioactive substances or chemically active substances may be the same or different. For example, a single conjugate may possess multiple antibodies or antibody fragments, which are directed against a desired antigen or hapten. Typically, the antibodies used in the conjugate are monoclonal antibodies or antibody fragments that are directed against a desired antigen or hapten. Thus, for example, the conjugate may include two or more monoclonal antibodies having specificity for a desired epitope and thereby increasing concentration of the conjugate at the desired site. Similarly, and independently, a conjugate may include two or more different bioactive substances or chemically active substances each of which is targeted to a different site on the same target tissue or organ. By utilizing multiple bioactive substances or chemically active substances in this manner, the conjugate is advantageously concentrated at several areas of the target tissue or organ, potentially increasing the effectiveness of therapeutic treatment. Further, the conjugate may have a ratio of bioactive substances or chemically active substances, designed to concentrate the conjugate at a target tissue or organ and optimally achieve the desired therapeutic and/or diagnostic results while minimizing non-target deposition.

The present disclosure further provides a method for preparing a conjugate, including: 1) preparing the tetraaza macrocyclic compound according to the present disclosure; 2) binding a bioactive substance or a chemically active substance to the tetraaza macrocyclic compound; and 3) coordinating a metal element with the tetraaza macrocyclic compound to form a complex. The order of the steps 2) and 3) is interchangeable, but, most specifically, the steps 1), 2) and 3) are performed sequentially. As described above, since the complex formation may be performed at a low temperature of 30-60° C., denaturation of the bioactive substance or the chemically active substance may be prevented and the resulting complex may be utilized variously as a therapeutic agent, a diagnostic agent or a contrast agent.

The present disclosure further provides a pharmaceutical composition comprising the conjugate of the present disclosure and a pharmaceutically acceptable carrier. Specifically, the pharmaceutical composition of the present disclosure comprises a conjugate, which forms a complex with a metal, dispersed in a pharmaceutically acceptable carrier. The pharmaceutically acceptable carrier (also known in the art as an excipient, vehicle, auxiliary, adjuvant, or diluent) is typically a substance which is pharmaceutically inert, confers a suitable consistency or form to the composition, and does not diminish the therapeutic or diagnostic efficacy of the conjugate. The carrier is generally considered to be "pharmaceutically or pharmacologically acceptable" if it does not produce an unacceptably adverse, allergic or other untoward reaction when administered to a mammal, especially human.

The selection of the pharmaceutically acceptable carrier tends, at least in part, to be a function of the desired route of administration. In general, metallopharmaceutical compositions of the present disclosure can be formulated for any route of administration so long as the target tissue is available via that route. For example, suitable routes of administration include, but are not limited to, oral, parenteral (e.g., intravenous, intraarterial, subcutaneous, rectal, intramuscular, intraorbital, intracapsular, intraspinal, intraperitoneal or intrasternal), topical (nasal, transdermal or intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal routes.

Examples of the pharmaceutically acceptable carrier for use in pharmaceutical compositions of the present disclosure are well known to those of ordinary skill in the art and may be selected by considering a number of factors. The pharmaceutical composition of the present disclosure is effective for treating tumors, cardiac diseases, brain diseases or fractures, but without being limited thereto. Adequate bioactive substances or chemically active substances and radioactive metals may be used depending on the desired purposes.

Pharmaceutically acceptable solvents for use in the present disclosure are well known to those of ordinary skill in the art, and are described, for example, in The Chemotherapy Source Book (Williams & Wilkens Publishing).

Dosage and regimens for the administration of the pharmaceutical compositions of the present disclosure can be readily determined by those with ordinary skill in diagnosing or treating diseases. It is understood that the dosage of the conjugates will be dependent upon the age, sex, health and body weight of the recipient, kind of concurrent treatment, if any, frequency of treatment, and the nature of the effect desired. For any mode of administration, the actual amount of the conjugate delivered, as well as the dosing schedule necessary to achieve the advantageous effects described herein, will also depend, in part, on such factors as the bioavailability of the conjugate, the disorder being treated or diagnosed, the desired therapeutic or diagnostic dose, and other factors that will be apparent to those of ordinary skill in the art. The dose administered to an animal, particularly human, in the context of the present disclosure should be sufficient to affect the desired therapeutic or diagnostic response in the animal over a reasonable period of time. Specifically, the dosage of the pharmaceutical composition may vary depending on the body weight, age, sex and health condition of the patient, diet, administration time, administration route, excretion ratio and severity of disease. In case of an adult patient, a dosage of 20-200 mg/day may be administered once or several times a day.

Radiolabeled scintigraphic imaging agents having a suitable amount of radioactivity are also provided by the present disclosure. In forming diagnostic radioactive complexes, it is generally preferred to form radioactive complexes in solutions containing radioactivity at concentrations of from about 0.01 millicurie (mCi) to 100 mCi per mL. Generally, the unit dose to be administered has a radioactivity of about 0.01 mCi to about 100 mCi, specifically about 1 mCi to about 30 mCi. The volume of the solution to be injected at unit dosage is from about 0.01 mL to about 10 mL. The amount of the radiolabeled conjugate appropriate for administration is dependent upon the distribution profile of the chosen conjugate in the sense that a rapidly cleared conjugate may need to be administered in higher doses than one that is cleared less rapidly. In vivo distribution and localization can be tracked by standard scintigraphic techniques at an appropriate time subsequent to administration, typically between 30 minutes and 180 minutes depending upon the rate of accumulation at the target site with respect to the rate of clearance at the non-target tissue.

Typically, a diagnostic dose of In-111 is 3-6 mCi while a typical does of Tc-99m is 10-30 mCi. Generally, radiotherapeutic doses of radiopharmaceuticals vary, to a greater extent, depending on the tumor and number of injections of cycles. For example, cumulative doses of Y-90 range from about 100 to 600 mCi (20-150 mCi/dose), while cumulative doses of Lu-177 range from about 200 to 800 mCi (50-200 mCi/dose).

The present disclosure further provides a contrast agent and a radioactive therapeutic agent comprising the conjugate of the present disclosure. In a specific embodiment of the present disclosure, the contrast agent may be a contrast agent for ultrasonography, computed tomography (CT), magnetic resonance imaging (MRI), single photon emission computed tomography (SPECT) or positron emission tomography (PET).

The contrast agent of the present disclosure may be used to obtain both PET and MR images. This allows to take advantages of both the PET and MR imaging and, thus, provides images with superior sensitivity and high temperoal resolution of PET and high spatial resolution of MR. Methods and apparatuses for PET imaging are described in U.S. Pat. Nos. 6,151,377, 6,072,177, 5,900,636, 5,608,221, 5,532,489, 5,272,343 and 5,103,098, which are incorporated herein by reference. And, methods and apparatuses for SPECT are described in U.S. Pat. Nos. 6,115,446, 6,072,177, 5,608,221, 5,600,145, 5,210,421 and 5,103,098, which are also incorporated herein by reference.

If a fluorophore or a luminophore is attached, the conjugate or the coordination compound of the present disclosure may be used for optical imaging and spectroscopy. Specifically, when an optical image is to be obtained using the compound of the present disclosure, a luminescent, fluorescent, Cerenkov radiating or chemiluminescent material may be attached thereto. Non-limiting examples of the fluorophore include fluorescein, rhodamine, Lucifer yellow, B-phycoerythrin, 9-acridine isothiocyanate, Lucifer yellow VS, 4-acetamido-4'-isothiocyanatostilbene 2,2'-disulfonic acid, 7-diethylamino-3-(4'-isothiocyanatophenyl)-4-methylcoumarin, succinimidylpyrene butyrate, 4-acetamido-4'-isothiocyanatostilbene 2,2'-disulfonic acid derivatives, LC™-Red 640, LC™-Red 705, Cy5, Cy5.5, lissamine, isothiocyanate, erythrosin isothiocyanate, diethylenetriamine pentaacetate, 1-dimethylaminonaphthyl 5-sulfonate, 1-anilino-8-naphthalene sulfonate, 2-p-touidinyl-6-naphthalene sulfonate, 3-phenyl-7-isocyanatocoumarin, 9-isothiocyanatoacridine, acridine orange, 9-(isothio-(2-benzoxazolyl)phenyl)maleimide, benzoxadiazole, stilbene, pyrene, fluorophore-containing silica, a nanoparticle, a Group II/IV semiconductor quantum dot, a Group III/V semiconductor quantum dot, a Group IV semiconductor quantum dot, or a bi- or multi-hybrid structure. Generals about optical imaging are disclosed in U.S. Pat. No. 5,650,135.

Also, the conjugate or the coordination compound of the present disclosure may be combined with various materials providing contrast effect for X-ray imaging (e.g., barium sulfate, iodine, iodine-containing derivatives, or multi-hybrid structures thereof) to obtain CT images. The CT imaging may be carried out according to the disclosure of U.S. Pat. Nos. 6,151,377, 5,946,371, 5,446,799, 5,406,479, 5,208,581 or 5,109,397.

Further, the conjugate or the coordination compound of the present disclosure may be combined with a diagnostic agent for ultrasound imaging (e.g., microbubbles) for use in ultrasound imaging.

As described above, the contrast agent comprising the conjugate or the coordination compound of the present disclosure basically allows imaging and may further serve other chemical/biological functions (e.g., cell tracking or tumor treatment) thanks to the bioactive substance or the chemically active substance. For example, attachment of an antibody specifically binding to a tumor cell to the conjugate according to the present disclosure allows a tumor-specific imaging.

For another example, attachment of a drug inducing apoptosis of a tumor cell to the conjugate of the present disclosure allows imaging and treatment at the same time.

When the contrast agent of the present disclosure is to be labeled, it may be labeled with fluorescent markers (e.g., fluorescein, phycoerythrin, rhodamine, lissamine, and Cy3 and Cy5 (Pharmacia)), chromophores, chemiluminescent compounds, magnetic particles, radioisotopes, mass spectroscopy tags, electron-dense particles, enzymes (e.g., alkaline phosphatase or horseradish peroxidase), cofactors, substrates of enzymes, heavy metals (e.g., gold), antibodies, streptavidin, biotin, digoxigenin, and haptens having specific binding partners such as a chelating group, without being limited thereto. The labeling provides signals that can be detected based on fluorescence, radiation, luminescence, weight change, X-ray diffraction or absorption, magnetization, enzymatic activation, mass analysis, binding affinity, hybridization frequency, nanocrystal, or the like.

MODE FOR INVENTION

The examples and experiments will now be described. The following examples and experiments are for illustrative purposes only and not intended to limit the scope of the present disclosure.

Unless specified otherwise, the starting materials were used as received from the manufacturers. Flash chromatography was performed using silica gel (70-230 mesh) and aluminum oxide 90 active (neutral, 70-230 mesh). All $^1$H NMR (500 MHz) and $^{13}$C (125 MHz) NMR spectra were recorded using TMS as internal standard and using CDCl$_3$. MeCN was used as second internal standard in NMR spectroscopy using D$_2$O solution. Mass spectra (MS) were recorded by fast atom bombardment (FABMS) and electron spray ionization (ESIMS). All ESIMS spectra were recorded using MeOH as solvent. LRMS-FAB and HRMS-FAB were recorded at the Korea Basic Science Institute (Daegu, Korea). Large-scale solvent removal was carried out by low-pressure rotary evaporation, and the remaining solvent was removed using a vacuum pump. All the reactants and solvents were purchased from Sigma-Aldrich and Fluka. Cyclam and cyclen were purchased from CheMatech and Marocyclics.

Example 1

Synthesis of 4,10-bis(carboxymethyl)-1,4,7,10-tetraazabicyclo[5.5.3]pentadecane.2TFA] (6.2TFA, "PCB-DO2A")

[Scheme 1]

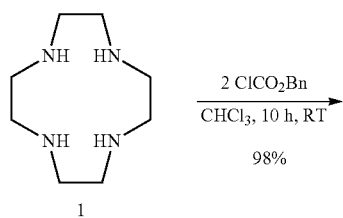

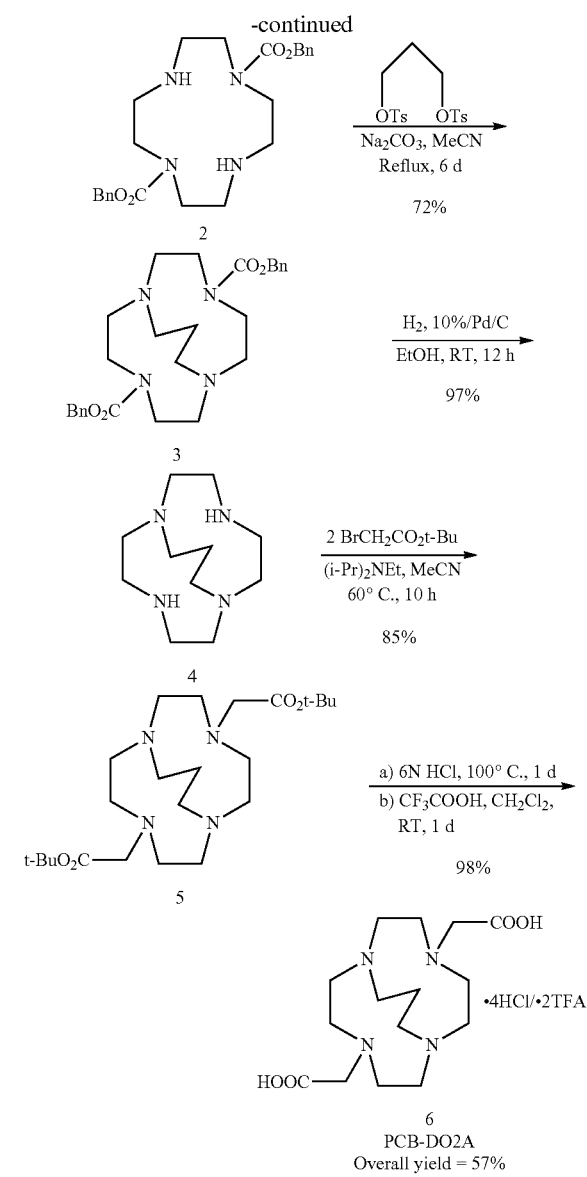

6
PCB-DO2A
Overall yield = 57%

1-a) Synthesis of 1,7-bis-(benzyloxycarbonyl)-1,4,7,10-tetraazacyclododecane (2)

To a solution of cyclen 1 (20 g, 116.1 mmol) in chloroform (200 mL) in an ice bath was added benzyl chloroformate (34.32 mL, 41.59 g, 243.8 mmol) dropwise, with temperature being kept below 0° C. After complete addition, the reaction mixture was stirred at room temperature for 10 hours, giving abundant solid formation. The solvent was evaporated under reduced pressure to afford white solid and ether (200 mL) was added. The solid was filtered, washed with ether (2×50 mL) and dried under vacuum at 45° C., yielding 59.01 g (99%) of the dihydrochloride salt as a white solid. The free base was obtained by adding 3 M NaOH (250 mL) to the solid. The aqueous phase was extracted with chloroform (3×200 mL). The combined extracts were washed by brine and dried over MgSO$_4$. The solvent was removed by rotary evaporation and the residue was dried under vacuum for several hours, giving of a transparent oil 2 (50.12 g, 98% yield) which solidified on standing.

¹H NMR (400 MHz, CDCl₃): δ 7.52-7.32 (m, 10H), 5.18 (s, 4H), 3.83-3.65 (m, 8H), 3.10-2.83 (m, 8H); ¹³C NMR (100.6 MHz, CDCl₃): δ 156.5, 136.3, 136.2, 129.0, 128.8, 128.7, 128.4 128.3, 128.2 68.1, 68.0, 50.9, 50.8, 50.6, 50.5, 50.3, 50.0, 49.6, 49.3.

1-b) Synthesis of 4,10-bis-(benzyloxycarbonyl)-1,4,7,10-tetraazabicyclo[5.5.3]pentadecane (3)

A solution of 2 (5.18 g, 11.76 mmol), 1,3-propanediol di-p-tosylate (4.52 g, 11.76 mmol) and anhydrous Na₂CO₃ (2.87 g, 27.05 mmol) in anhydrous toluene (220 mL) was refluxed for 6 days. The solvent was evaporated from the reaction mixture under reduced pressure and CH₂Cl₂ (200 mL) was added. The resulting brown slurry was filtered off through a celite pad and washed with CH₂Cl₂ (2×20 mL). The solvent was evaporated from the combined filtrate and washings under reduced pressure. The resulting residue was purified via column chromatography on alumina (basic) and eluted with CH₂Cl₂/methanol (20:1) to afford a pale oil as the tosylate salt. The oil was dissolved in 20% aq NaOH (100 mL). After stirring for 4 hours, the resultant solution was extracted with CHCl₃ (3×100 mL). The combined organic phases were washed by brine, dried over MgSO₄, and solvent was evaporated under reduced pressure to give off-white powder 3 (4.07 g, 72% yield).

¹H NMR (500 MHz, CDCl₃): δ 7.38-7.30 (m, 10H), 5.30 (brs, 2H), 5.09 (brs, 2H), 4.10 (brs, 2H), 3.9 (brs, 2H), 3.81-2.62 (m, 16H), 1.55 (s, 2H); ¹³C NMR (125 MHz, CDCl₃): 155.3, 135.6, 128.69, 128.64, 67.6, 57.1, 56.1, 54.7, 54.6, 54.4, 48.3, 47.8, 46.9, 18.9, 18.8; HRMS (FAB): calculated for C₂₇H₃₇N₄O₄, 481.2815 [(M+H)⁺]. found: 481.2816 [M+H)⁺].

1-c) Synthesis of 1,4,7,10-tetraazabicyclo[5.5.3]pentadecane (4)

To a solution of 3 (3.67 g, 7.64 mmol) in ethanol (60 mL) was added 10% Pd/C (1.10 g). The resulting mixture was stirred under H₂ (g) atmosphere at room temperature for 12 hours. The reaction mixture was filtered through a celite pad and washed with ethanol (2×10 mL). The combined filtrate was evaporated in vacuo to give an oily residue which was triturated with Et₂O to provide an off-white solid 4 (1.57 g, 97% yield).

¹H NMR (400 MHz, CD₃OD): δ 3.20-3.16 (m, 8H), 2.96-2.86 (m, 12H), 2.00-1.96 (m, 2H); ¹³C NMR (100.6 MHz, CD₃OD): δ 57.9, 55.1, 47.5, 20.7; HRMS (FAB): calculated for C₁₁H₂₅N₄, 213.2079 [(M+H)⁺]. found: 213.2083 [(M+H)⁺].

1-d) Synthesis of 4,10-bis(carbo-tert-butoxymethyl)-1,4,7,10-tetraazabicyclo[5.5.3]pentadecane (5)

To a solution of 4 (1.2 g, 5.65 mmol) in anhydrous acetonitrile (50 mL) were added N,N'-diisopropylethylamine (4.92 mL, 3.65 g, 28.25 mmol) and t-butyl bromoacetate (1.83 mL, 2.42 g, 12.43 mmol). The reaction mixture was slowly heated to 60° C. and allowed to stir for 10 hours. After evaporation of the solvent under reduced pressure, the residual material was dissolved in water (50 mL). The aqueous solution was extracted with methylene chloride (3×50 mL). The combined extracts were washed by brine, dried over MgSO₄, and concentrated to give pale oil. Crude product was purified via column chromatography on alumina (basic) and eluted with methylene chloride:methanol (20:1) to afford a clear oil 5 (2.12 g, 85% yield) which solidified on standing.

¹H NMR (500 MHz, CDCl₃): δ 3.28 (s, 4H), 3.26-3.25 (m, 4H), 3.08-2.88 (m, 16H), 1.92-1.86 (m, 2H), 1.35 (s, 18H); ¹³C NMR (100.6 MHz, CDCl₃): δ 170.7, 82.0, 57.4, 55.8, 55.3, 51.8, 28.5, 21.4; HRMS (FAB): calculated for C₂₃H₄₅N₄O₄, 441.3441 [(M+H)⁺]. found: 441.3438 [(M+H)⁺].

1-e) Synthesis of 4,10-bis(carboxymethyl)-1,4,7,10-tetraazabicyclo[5.5.3]pentadecane.4HCl (6a.4HCl) (6)

Compound 5 (1.12 g, 2.54 mmol) was dissolved in 6 N HCl (60 mL), and slowly heated to 100° C. with stirring for 24 hours. After evaporation of all the solvents, the crude product was recrystallized from ethanol/diethyl ether to give white solid 6 (1.18 g, 98% yield) (4 equiv HCl calculated on the basis of mass).

¹H NMR (400 MHz, D₂O): δ 4.10 (s, 4H), 3.59 (s, 8H), 3.5-3.2 (m, 12H), 2.14-2.08 (m, 2H); ¹³C NMR (100.6 MHz, D₂O): δ 172.5, 59.5, 54.4, 53.9, 5.8, 18.3; HRMS (FAB): calculated for C₁₅H₂₉N₄O₄, 329.2189 [(M+H)⁺]. found: 329.2189 [(M+H)⁺)].

To conclude, in accordance with the embodiment of the present disclosure of Example 1, the existing synthesis procedure of preparing 2 from cyclen via regioselective transalkylation and reaction with 2 equiv benzyl chloroformate in chloroform solvent for the synthesis of propylene cross-bridged DO2A (PCB-DO2A) was simplified. The reaction proceeded quickly due to the solidification. Thus, upon completion of the reaction, di-Cbz-cyclen was produced in large yield in the form of dihydrochloride salt. A free base could be obtained by adding 3 M NaOH. After the trans-disubstituted cyclen [1,7-bis-(benzyloxycarbonyl)-1,4,7,10-tetraazacyclododecane, 2] was prepared, propylene was cross-bridged between two non-adjacent nitrogen atoms by refluxing with ditosyl ester of 1,3-propanediol and sodium carbonate in MeCN solvent. As a result, a tosylate salt of the cross-bridged compound 3 was produced. For removal of the tosylate counteranion and improvement of yield, 20% NaOH was added.

The synthetic intermediate 3 was deprotected by catalytic hydrogenation in EtOH solvent to give propylene cross-bridged cyclen 4. The precursor, propylene cross-bridged cyclen (1,4,7,10-tetraazabicyclo[5.5.3]pentadecane) with bis(t-butyl ester) pendant arms, being dialkylated with t-butyl bromoacetate and convenient to handle, was produced with high yield (85%) enough to be quantitated. The synthetic intermediate 5 was deprotected with trifluoroacetic acid in dichloromethane to give PCB-DO2A 6 as a bis(trifluoroacetic acid) salt. This synthesis procedure of PCB-DO2A according to an embodiment of the present disclosure is remarkably improved over the existing cross-bridged cyclen synthesis method in terms of overall yield (57%), simple procedure, selectivity, or the like.

Example 2

Synthesis of 4,10-bis(carboxymethyl)-1,4,7,10-tetraazabicyclo[5.5.3]pentadecane.2TFA (6.2TFA, "PCB-DO2A")

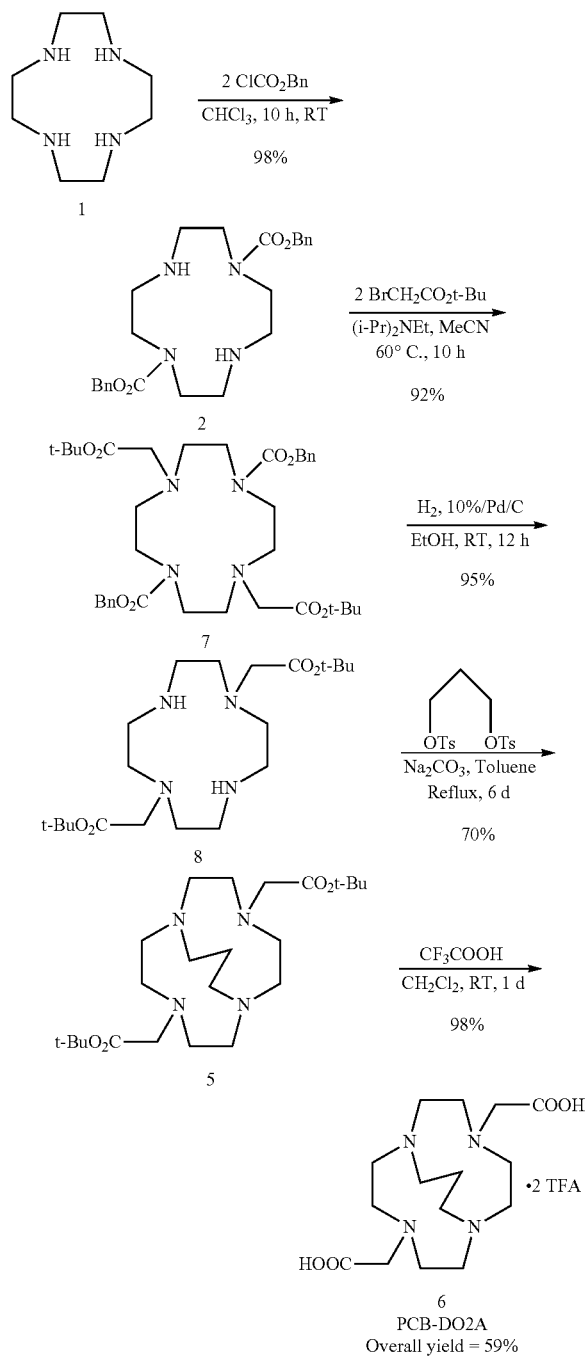

[Scheme 2]

2-a) Synthesis of 1,7-bis-(benzyloxycarbonyl)-4,10-bis(carbo-tert-butoxymethyl)-1,4,7,10-tetraazacyclododecane (7)

To a solution of 2 (6.84 g, 15.53 mmol) in anhydrous acetonitrile (150 mL) were added N,N'-diisopropylethylamine (13.52 mL, 10.03 g, 77.63 mmol) and t-butyl bromoacetate (4.82 mL, 6.36 g, 32.61 mmol). The reaction mixture was slowly heated to 60° C. and allowed to stir for 10 hours. After evaporation of solvents under reduced pressure, the residual material was dissolved in $Na_2CO_3$ solution (100 mL). The aqueous solution was extracted with methylene chloride (3×100 mL). The combined extracts were washed by brine, dried over $MgSO_4$, and concentrated to give pale oil, which was recrystallized in diethyl ether to give white solid 7 (9.55 g, 92% yield).

$^1$H NMR (500 MHz, $CDCl_3$): δ 7.26-7.19 (m, 10H), 5.04 (s, 4H), 3.34-3.05 (m, 12H), 2.9-2.6 (m, 8H), 1.35 (s, 18H); $^{13}$C NMR (125 MHz, $CDCl_3$): δ 170.4, 156.3, 136.7, 128.3, 127.8, 127.7, 80.8, 66.8, 55.8, 54.2, 46.9, 46.5, 28.1; HRMS (FAB): calculated for $C_{36}H_{51}N_4O_8$, 669.3863 [(M+H)$^+$]. found: 669.3860 [(M+H)$^+$].

2-b) Synthesis of 1,7-bis(carbo-tert-butoxymethyl)-1,4,7,10-tetraazacyclododecane (8)

To a solution of 7 (8.52 g, 12.74 mmol) in ethanol (130 mL) was added 10% Pd/C (2.6 g). The resulting mixture was stirred under $H_2$ (g) atmosphere at room temperature for 12 hours. The reaction mixture was filtered through a celite pad and washed with ethanol (2×20 mL). The combined filtrate was evaporated in vacuo to give an oily residue which was triturated with $Et_2O$ to provide an off-white solid 8 (4.85 g, 97% yield).

$^1$H NMR (500 MHz, $CD_3OD$): δ 3.44 (s, 4H), 2.91 (s, 16H), 1.47 (s, 18H); $^{13}$C NMR (125 MHz, $CD_3OD$): δ 173.0, 82.8, 57.4, 52.2, 46.5, 28.5; HRMS (FAB): calculated for $C_{20}H_{41}N_4O_4$, 401.3128 [(M+H)$^+$]. found: 401.3132 [(M+H)$^+$].

2-c) Synthesis of 4,10-bis(carbo-tert-butoxymethyl)-1,4,7,10-tetraazabicyclo[5.5.3]pentadecane (5)

A solution of 8 (4.2 g, 10.48 mmol), 1,3-propanediol di-p-tosylate (4.03 g, 10.48 mmol) and anhydrous $Na_2CO_3$ (2.56 g, 24.10 mmol) in anhydrous toluene (200 mL) was refluxed for 6 days. The solvent was evaporated from the reaction mixture under reduced pressure and $CH_2Cl_2$ (200 mL) was added. The resulting brown slurry was filtered off through a celite pad and washed with $CH_2Cl_2$ (2×20 mL). The solvent was evaporated from the combined filtrate and washings under reduced pressure. The resulting residue was purified via column chromatography on alumina (basic) and eluted with $CH_2Cl_2$/methanol (20:1) to afford a pale oil as the tosylate salt. The oil was dissolved in 20% aq NaOH (100 mL). After stirring for 4 hours, the resultant solution was extracted with $CHCl_3$ (3×100 mL). The combined organic phases were washed by brine, dried over $MgSO_4$, and solvent was evaporated under reduced pressure to give off-white powder 5 (3.23 g, 70% yield).

$^1$H NMR (500 MHz, $CDCl_3$): δ 3.28 (s, 4H), 3.26-3.25 (m, 4H), 3.08-2.88 (m, 16H), 1.92-1.86 (m, 2H), 1.35 (s, 18H); $^{13}$C NMR (100.6 MHz, $CDCl_3$): δ 170.7, 82.0, 57.4, 55.8, 55.3, 51.8, 28.5, 21.4; HRMS (FAB): calculated for $C_{23}H_{45}N_4O_4$, 441.3441 [(M+H)$^+$]. found: 441.3438 [(M+H)$^+$].

2-d) Synthesis of 4,10-bis(carboxymethyl)-1,4,7,10-tetraazabicyclo[5.5.3]pentadecane.2TFA (6.2TFA)

Compound 5 (1.25 g, 2.84 mmol) was dissolved in a 1:1 (vol:vol) mixture of $CF_3CO_2H$ (TFA) and $CH_2Cl_2$ (45 mL). The mixture was stirred at room temperature for 24 hours.

The solvent was removed under reduced pressure to give an oily residue which was triturated with Et$_2$O to provide white solid 6 (1.55 g, 98% yield).

$^1$H NMR (400 MHz, D$_2$O): δ 4.10 (s, 4H), 3.59 (s, 8H), 3.5-3.2 (m, 12H), 2.14-2.08 (m, 2H); $^{13}$C NMR (100.6 MHz, D$_2$O): δ 172.5, 59.5, 54.4, 53.9, 5.8, 18.3; HRMS (FAB): calculated for C$_{15}$H$_{29}$N$_4$O$_4$, 329.2189 [(M+H)$^+$]. found: 329.2189 [(M+H)$^+$].

Example 3

Synthesis of 4,11-bis(carboxymethyl)-1,4,8,11-tetraazabicyclo[6.6.3]heptadecane.2TFA (12.2TFA, "PCB-TE2A")

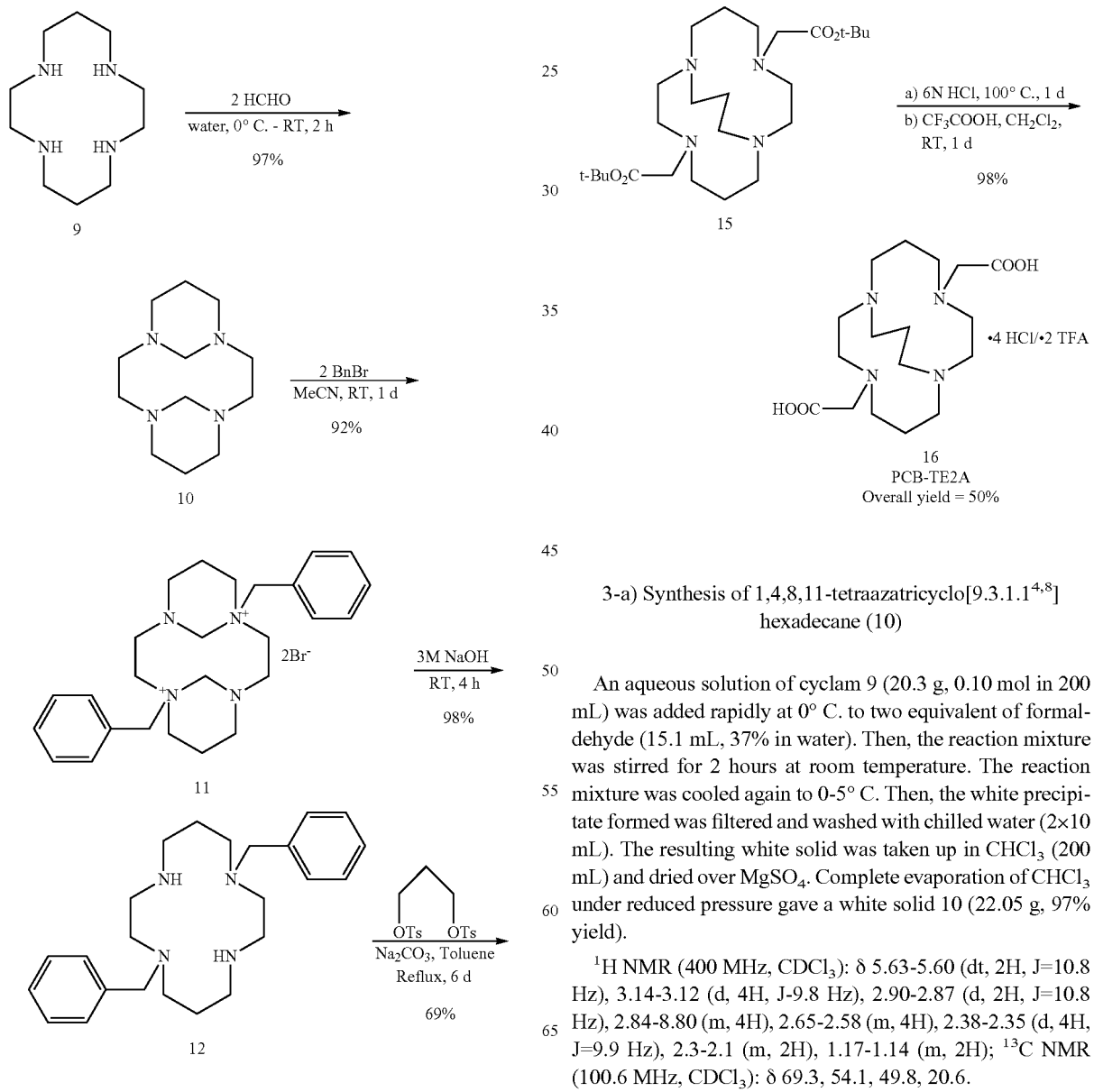

3-a) Synthesis of 1,4,8,11-tetraazatricyclo[9.3.1.1$^{4,8}$]hexadecane (10)

An aqueous solution of cyclam 9 (20.3 g, 0.10 mol in 200 mL) was added rapidly at 0° C. to two equivalent of formaldehyde (15.1 mL, 37% in water). Then, the reaction mixture was stirred for 2 hours at room temperature. The reaction mixture was cooled again to 0-5° C. Then, the white precipitate formed was filtered and washed with chilled water (2×10 mL). The resulting white solid was taken up in CHCl$_3$ (200 mL) and dried over MgSO$_4$. Complete evaporation of CHCl$_3$ under reduced pressure gave a white solid 10 (22.05 g, 97% yield).

$^1$H NMR (400 MHz, CDCl$_3$): δ 5.63-5.60 (dt, 2H, J=10.8 Hz), 3.14-3.12 (d, 4H, J-9.8 Hz), 2.90-2.87 (d, 2H, J=10.8 Hz), 2.84-8.80 (m, 4H), 2.65-2.58 (m, 4H), 2.38-2.35 (d, 4H, J=9.9 Hz), 2.3-2.1 (m, 2H), 1.17-1.14 (m, 2H); $^{13}$C NMR (100.6 MHz, CDCl$_3$): δ 69.3, 54.1, 49.8, 20.6.

3-b) Synthesis of 1,8-bis-(benzyl)-4,11-diazoniatricyclo[9.3.1.1^{4,8}]hexadecane dibromide (11)

A solution of 10 (3.17 g, 14.13 mmol) in MeCN (50 mL) was added to two equivalent of benzyl bromide (3.36 mL, 4.83 g, 28.26 mmol). The reaction mixture was stirred at room temperature for 24 hours. The white precipitate formed was then filtered, washed with MeCN (2×10 mL) and dried under vacuum. The crude product was recrystallized in THF/water to give white solid 11 (7.36 g, 92% yield).
$^1$H NMR (500 MHz, D$_2$O): δ 7.51 (m, 10H), 5.50 (d, 2H), 4.65 (d, 4H), 4.40 (t, 2H), 3.5-3.2 (m, 10H), 2.90 (d, 4H), 2.70-2.20 (m, 4H), 1.85 (m, 2H); $^{13}$C NMR (125 MHz, D$_2$O): δ 135.5, 133.5, 131.9, 128.5, 82.2, 77.0, 63.5, 60.1, 51.5, 48.0, 19.8.

3-c) Synthesis of 1,8-bis-(benzyl)-1,4,8,11-tetraazacyclotetradecane (12)

A 3 M NaOH solution (200 mL) was added to 11 (6.92 g, 12.22 mmol). After stirring for 4 hours at room temperature, the resultant solution was extracted with CHCl$_3$ (3×100 mL). The combined organic phases were washed by brine and dried over MgSO$_4$, and solvent was evaporated under reduced pressure to give an oil 12 (4.56 g, 98% yield) which solidified on standing.
$^1$H NMR (400 MHz, CDCl$_3$): δ 7.25-7.12 (m, 10H), 3.64 (s, 4H), 2.67-2.43 (m, 18H), 1.80-1.74 (m, 4H); $^{13}$C NMR (100.6 MHz, CDCl$_3$): δ 137.7, 129.9, 128.5, 127.4, 58.3, 54.1, 51.9, 50.4, 48.1, 26.1; HRMS (FAB): calculated for C$_{24}$H$_{37}$N$_4$, 381.3013 [(M+H)$^+$]. found: 381.3014 [(M+H)$^+$].

3-d) Synthesis of 4,11-bis-(dibenzyl)-1,4,8,11-tetraazabicyclo[6.6.3]heptadecane (13)

A solution of 12 (3.56 g, 9.73 mmol), 1,3-propanediol di-p-tosylate (3.74 g, 9.73 mmol) and anhydrous Na$_2$CO$_3$ (2.37 g, 22.38 mmol) in anhydrous toluene (200 mL) was refluxed for 6 days. The solvent was evaporated from the reaction mixture under reduced pressure and CH$_2$Cl$_2$ (200 mL) was added. The resulting brown slurry was filtered off through a celite pad and washed with CH$_2$Cl$_2$ (2×20 mL). The solvent was evaporated from the combined filtrate and washings under reduced pressure. The resulting residue was purified via column chromatography on alumina (basic) and eluted with CH$_2$Cl$_2$/methanol (20:1) to afford pale oil as the tosylate salt. The oil was dissolved in 20% aq NaOH (100 mL) After stirring for 4 hours, the resultant solution was extracted with CHCl$_3$ (3×100 mL). The combined organic phases were washed by brine, dried over MgSO$_4$, and solvent was evaporated under reduced pressure to give off-white powder 13 (4.56 g, 69% yield).
$^1$H NMR (500 MHz, CDCl$_3$): δ 7.26-7.14 (m, 10H), 3.68-3.65 (d, 2H, J=14 Hz), 3.52-3.49 (d, 2H, J=14 Hz), 3.08-2.51 (m, 20H), 1.80 (brs, 4H), 1.60-1.26 (m, 2H); $^{13}$C NMR (125 MHz, CDCl$_3$): δ 135.8, 129.8, 128.3, 127.4, 56.8, 56.6, 54.2, 52.8, 47.4, 22.6, 19.9; HRMS (FAB): calculated for C$_{27}$H$_{41}$N$_4$, 421.3331 [(M+H)$^+$]. found: 421.3333 [(M+H)$^+$].

3-e) Synthesis of 1,4,8,11-tetraazabicyclo[6.6.3]heptadecane (14)

To a solution of 13 (3.23 g, 7.68 mmol) in EtOH (80 mL) was added 20% Pd(OH)$_2$ (0.97 g). The resulting mixture was stirred under H$_2$ (g) atmosphere at room temperature for 24 hours. The reaction mixture was filtered through a celite pad and washed with EtOH (2×10 mL). The combined filtrate was evaporated in vacuo to give a yellow oily residue which was triturated with Et$_2$O to provide an off-white solid 14 (1.75 g, 95% yield).
HRMS (FAB): calculated for C$_{13}$H$_{29}$N$_4$, 241.2392 [(M+H)$^+$]. found: 241.2397 [(M+H)$^+$].

3-f) Synthesis of 4,11-bis-(carbo-tert-butoxymethyl)-1,4,8,11-tetraazabicyclo[6.6.3]heptadecane (15)

To a solution of 14 (1.56 g, 6.49 mmol) in anhydrous acetonitrile (50 mL) were added N,N'-diisopropylethylamine (5.65 mL, 4.19 g, 32.45 mmol) and t-butyl bromoacetate (2.01 mL, 2.66 g, 13.63 mmol). The reaction mixture was slowly heated to 60° C. and allowed to stir for 10 hours. After evaporation of solvents under reduced pressure, the residual material was dissolved in water (50 mL). The aqueous solution was extracted with methylene chloride (3×50 mL). The combined extracts were washed by brine, dried over MgSO$_4$, and concentrated to give pale oil. Crude product was purified via column chromatography on alumina (basic) and eluted with methylene chloride:methanol (20:1) to afford a clear oil 15 (2.74 g, 90% yield).
$^1$H NMR (500 MHz, CDCl$_3$): δ 3.26-3.22 (d, 4H, J=17.5 Hz), 3.12-3.09 (d, 4H, J=17.5 Hz), 3.01 (brs, 4H) 2.86-2.69 (m, 16H), 1.96 (brs, 4H), 1.67-1.62 (m, 2H), 1.43 (s, 18H); $^{13}$C NMR (125 MHz, CDCl$_3$): δ 169.8, 81.3, 56.2, 55.6, 52.3, 49.1, 27.9, 22.5, 19.6; HRMS (FAB): calculated for C$_{25}$H$_{49}$N$_4$O$_4$, 469.3754 [(M+H)$^+$]. found: 469.3759 [(M+H)$^+$].

3-g) Synthesis of 4,11-bis-(carboxymethyl)-1,4,8,11-tetraazabicyclo[6.6.3]heptadecane.4HCl (16.4HCl)

Compound 15 (1.05 g, 2.24 mmol) was dissolved in 6 N HCl (60 mL), and slowly heated to 100° C. with stirring for 24 hours. After evaporation of all the solvents, the crude product was recrystallized from ethanol/diethyl ether to give white solid 16 (1.10 g, 98% yield) (4 equiv HCl calculated on the basis of mass).
$^1$H NMR (500 MHz, DMSO-d$_6$): δ 3.63-3.16 (m, 8H) 3.12-2.5 (m, 16H), 1.85 (brs, 4H), 1.68 (brs, 2H); $^{13}$C NMR (125 MHz, DMSO-d$_6$): δ 172.1, 55.3, 54.0, 51.7, 48.6, 48.04, 21.6, 19.2; HRMS (FAB): calculated for C$_{17}$H$_{33}$N$_4$O$_4$, 357.2502 [(M+H)$^+$]. found: 357.2504 [(M+H)$^+$].

Example 4

Synthesis of 4,11-bis(carboxymethyl)-1,4,8,11-tetraazabicyclo[6.6.3]heptadecane.2TFA (12.2TFA, "PCB-TE2A")

[Scheme 4]

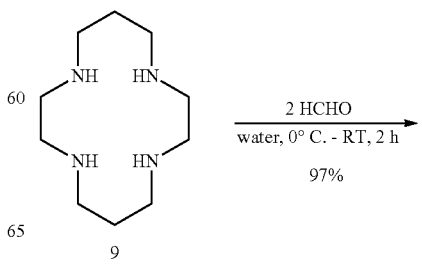

9

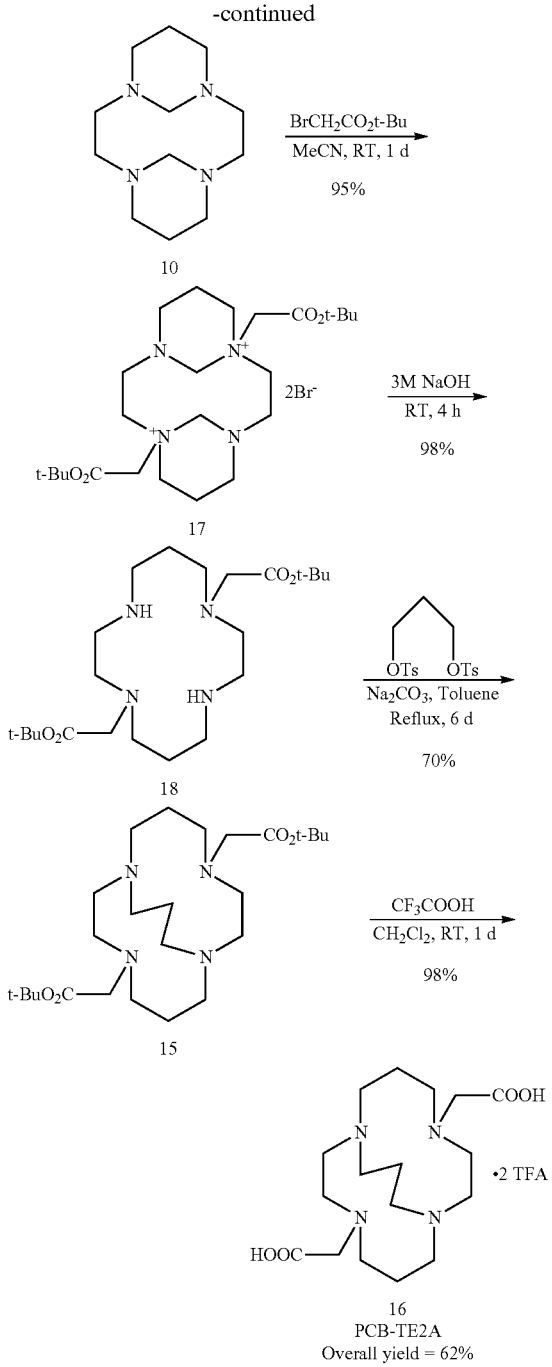

4-a) Synthesis of 1,4,8,11-tetraazatricyclo[9.3.1.1^{4,8}] hexadecane (10)

Two equivalent of formaldehyde (15.1 mL, 37% in water) was added rapidly to an aqueous solution of cyclam 9 (20.3 g, 0.10 mol in 200 mL) at 0° C. Then, the reaction mixture was stirred for 2 hours at room temperature. The reaction mixture was cooled again to 0-5° C. Then, the white precipitate formed was filtered and washed with chilled water (2×10 mL). The resulting white solid was taken up in $CHCl_3$ (200 mL) and dried over $MgSO_4$. Complete evaporation of $CHCl_3$ under reduced pressure gave a white solid 10 (22.05 g, 97% yield).

$^1$H NMR (400 MHz, $CDCl_3$): δ 5.63-5.60 (dt, 2H, J=10.8 Hz), 3.14-3.12 (d, 4H, J=9.8 Hz), 2.90-2.87 (d, 2H, J=10.8 Hz), 2.84-8.80 (m, 4H), 2.65-2.58 (m, 4H), 2.38-2.35 (d, 4H, J=9.9 Hz), 2.3-2.1 (m, 2H), 1.17-1.14 (m, 2H); $^{13}$C NMR (100.6 MHz, $CDCl_3$): δ 69.3, 54.1, 49.8, 20.6.

4-b) Synthesis of 1,8-bis-(carbo-tert-butoxymethyl)-4,11-diazoniatricyclo[9.3.1.1^{4,8}]hexadecane dibromide (17)

A solution of 10 (3.56 g, 15.87 mmol) in MeCN (100 mL) was added to four equivalent of t-butylbromoacetate (9.38 mL, 12.38 g, 63.48 mmol). The reaction mixture was stirred at room temperature for 24 hours. The yellowish white precipitate formed was then filtered, washed with MeCN (2×20 mL) and dried under vacuum. The crude product was recrystallized in ethanol to give white solid 17 (9.26 g, 95% yield).

$^1$H NMR (500 MHz, DMSO-$d_6$): δ 1.48 (s, 18H), 1.76-1.78 (d, 2H, J=8.5 Hz), 2.35-2.45 (m, 4H), 2.70-2.73 (d, 2H, J=15 Hz), 3.08-3.09 (d, 2H, J=5 Hz), 3.24-3.38 (m, 4H), 3.53-3.58 (m, 2H), 3.64-3.66 (d, 2H, J=10 Hz), 3.79-3.81 (d, 2H, J=11.5 Hz), 4.33-4.38 (t, 2H, J=14 Hz), 4.43-4.46 (d, 2H, J=16.5 Hz), 4.59-4.62 (d, 2H, J=16.5 Hz), 5.23-5.25 (d, 2H, J-9.5 Hz); $^{13}$C NMR (125 MHz, DMSO-$d_6$): δ 163.5, 84.2, 76.5, 59.8, 57.2, 50.6, 47.7, 46.3, 27.5, 19.2; HRMS (ESI) calculated for $C_{24}H_{47}N_4O_4$, 455.3591 [(M+H)$^+$]. found: 455.3594 [(M+H)$^+$]; anal. calcd. for $C_{24}H_{46}Br_2N_4O_4$.: C, 46.91; H, 7.55; N, 9.12. found C, 46.63; H, 7.74; N, 9.21.

4-c) Synthesis of 1,8-bis-(carbo-tert-butoxymethyl)-1,4,8,11-tetraazacyclotetradecane (18)

A 3 M NaOH solution (200 mL) was added to 17 (9.15 g, 14.89 mmol). After stirring for 3 hours, the resultant solution was extracted with $CHCl_3$ (3×100 mL). The combined organic phases were washed by brine, dried over $MgSO_4$, and solvent was evaporated under reduced pressure to give an oil 18 (6.25 g, 98% yield) which solidified on standing.

$^1$H NMR (500 MHz, $CDCl_3$): δ 3.25 (s, 4H), 2.72-2.59 (m, 16H), 1.71-1.69 (m, 4H), 1.37 (s, 18H); $^{13}$C NMR (125 MHz, $CDCl_3$): δ 170.43, 80.57, 54.74, 54.13, 52.47, 50.02, 47.59, 28.09, 25.78; HRMS (FAB): calculated for $C_{22}H_{45}N_4O_4$, 429.3441 [(M+H)$^+$]. found: 429.3439[(M+H)$^+$].

4-d) Synthesis of 4,11-bis-(carbo-tert-butoxymethyl)-1,4,8,11-tetraazabicyclo[6.6.3]heptadecane (15)

A solution of 1,8-bis-(carbo-tert-butoxymethyl)-1,4,8,11-tetraazacyclotetradecane 18 (4.68 g, 10.92 mmol), 1,3-propanediol di-p-tosylate (4.68 g, 10.92 mmol) and anhydrous $Na_2CO_3$ (2.66 g, 25.12 mmol) in anhydrous toluene (220 mL) was refluxed for 6 days. The solvent was evaporated from the reaction mixture under reduced pressure and $CH_2Cl_2$ (250 mL) was added. The resulting brown slurry was filtered off through a celite pad and washed with $CH_2Cl_2$ (2×30 mL). The solvent was evaporated from the combined filtrate and washings under reduced pressure. The resulting residue was purified via column chromatography on alumina (basic) and eluted with $CH_2Cl_2$/methanol (20:1) to afford pale oil as the tosylate salt. The oil was dissolved in 20% aq NaOH (100 mL). After stirring for 4 hours, the resultant solution was extracted with $CHCl_3$ (3×100 mL). The combined organic phases were washed by brine, dried over $MgSO_4$, and solvent was evaporated under reduced pressure to give off-white powder 15 (3.58 g, 70% yield).

$^1$H NMR (500 MHz, CDCl$_3$): δ 3.26-3.22 (d, 4H, J=17.5 Hz), 3.12-3.09 (d, 4H, J=17.5 Hz), 3.01 (brs, 4H) 2.86-2.69 (m, 16H), 1.96 (brs, 4H), 1.67-1.62 (m, 2H), 1.43 (s, 18H); $^{13}$C NMR (125 MHz, CDCl$_3$): δ 169.8, 81.3, 56.2, 55.6, 52.3, 49.1, 27.9, 22.5, 19.6; HRMS (FAB): calculated for C$_{25}$H$_{49}$N$_4$O$_4$, 469.3754 [(M+H)$^+$]. found: 469.3759 [(M+H)$^+$].

4-e) Synthesis of 4,11-bis-(carboxymethyl)-1,4,8,11-tetraazabicyclo[6.6.3]heptadecane.2TFA (12.2TFA) (16)

Compound 15 (1.23 g, 2.62 mmol) was dissolved in a 1:1 (vol:vol) mixture of CF$_3$CO$_2$H (TFA) and CH$_2$Cl$_2$ (45 mL). The mixture was stirred at room temperature for 24 hours. The solvent was removed under reduced pressure to give an oily residue which was triturated with Et$_2$O to provide white solid 16 (31.505 g, 98% yield) (2 equiv TFA calculated on the basis of mass).
$^1$H NMR (500 MHz, DMSO-d$_6$): δ 3.63-3.16 (m, 8H) 3.12-2.5 (m, 16H), 1.85 (brs, 4H), 1.68 (brs, 2H); $^{13}$C NMR (125 MHz, DMSO-d$_6$): δ 172.1, 55.3, 54.0, 51.7, 48.6, 48.04, 21.6, 19.2; HRMS (FAB): calculated for C$_{17}$H$_{33}$N$_4$O$_4$, 357.2502 [(M+H)$^+$]. found: 357.2504 [(M+H)$^+$].

Synthesis of selectively trans-disubstituted cyclam derivatives has attracted attentions in the past years. Especially, it has drawn special interests since the selectively trans-disubstituted cyclam derivatives can lead to hexacoordinated complexes having equivalent chelators. Although direct trans-dialkylation is carried out easily at the cyclen backbone, it is very difficult for cyclam. Especially, preparation of regio selectively trans-disubstituted products by direct alkylation of unprotected cyclam is almost impractical. Usually, a mixture of mono-, di- and tri-N-substituted products is obtained. A scheme of transalkylating cyclam via a mixture of bisaminal macrotricyclic mixture followed by deprotection provides a very effective and facile method. Use of adequate alkylating agents and conversion of two non-adjacent nitrogen atoms of two aminal bridges to quarternay amines (quarternization) give the desired trans-disubstituted cyclam. The bisaminal macrotricyclic compound is obtained by adding formaldehyde to cyclam. As can be seen from Scheme 4, the macrotricycle 10 could be obtained quantitatively through reaction of cyclam 9 with formaldehyde at room temperature. For selective trans-dialkylation, the 1,4,8,11-tetraazatricyclo[9.3.1.1$^{4,8}$]hexadecane ligand 10 was dissolved in CH$_3$CN and 4 equiv. of t-butylbromoacetate was rapidly added to afford the di-substituted macrotricycle 17 having two non-adjacent quaternary nitrogen atoms. Use of 2 equivalent of alkylating agent afforded a very low yield whereas an excess use afforded the trans-dialkyalated products in very good yields. Due to their ionic character, compound 17 was insoluble in CH$_3$CN and so was quantitatively isolated by simple filtration. There was no indication of formation of cis-disubstituted products during the course of the reaction.

The cleavage of the bisaminal bonds of compound 17 was carried out easily by basic hydrolysis using a 3 M NaOH aqueous solution at room temperature to give the trans-disubstituted cyclam 18. This synthesis scheme to produce trans-disubstituted cyclam derivatives is advantageous in that no further column purification or crystallization is required and the synthetic procedure becomes more economical. After making the trans-disubstituted cyclam (1,8-bis-(carbo-tert-butoxymethyl)-1,4,8,11-tetraazacyclotetradecane, 18), the propylene cross-bridging of the non-adjacent nitrogens was achieved by refluxing 18 with the ditosyl ester of 1,3-propanediol in the presence of sodium carbonate in toluene, which gave the tosylate salt of the cross-bridged product 15. The tosylate counteranion was removed by treatment with 20% NaOH, yielding 70% of free base of the compound 15.

The deprotection of the t-butyl ester from the synthetic intermediate 15 was carried out with trifluoroacetic acid in dichloromethane to afford PCB-TE2A as a bis(trifluoroacetic acid) salt. All the steps involved in the synthesis of PCB-TE2A 16 are very high yielding in terms of overall yield (62%).

Example 5

Synthesis of 4,11-bis(carboxymethyl)-1,4,8,11-tetraazabicyclo[6.6.3]heptadecane.2TFA ("PCB-TE2A") (16)

[Scheme 5]

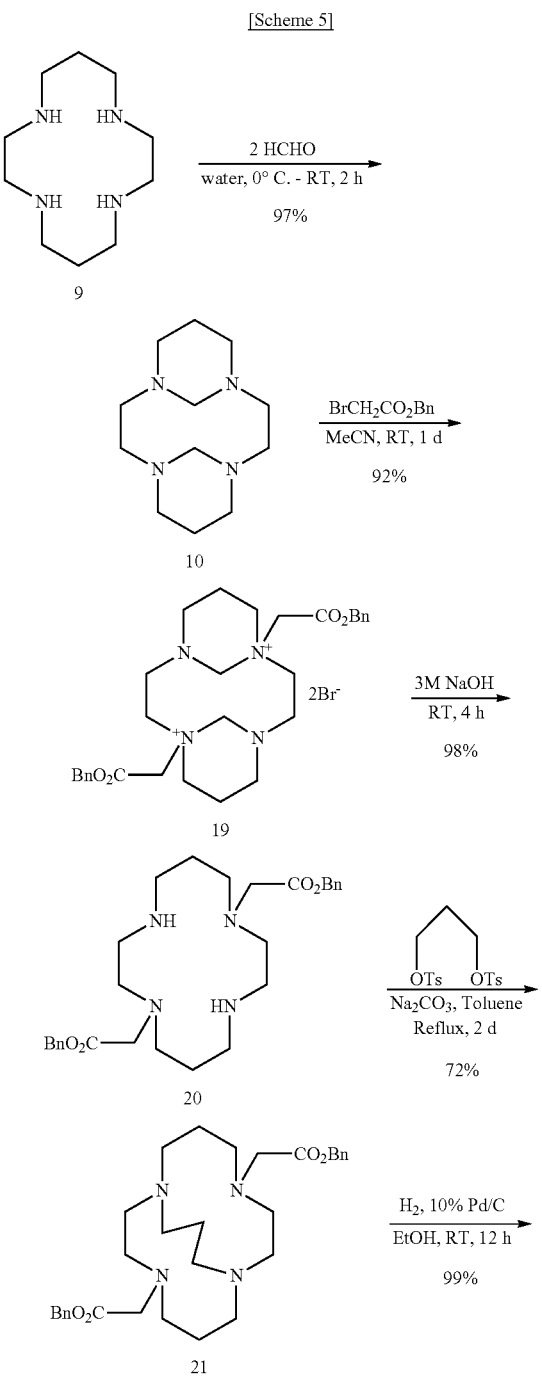

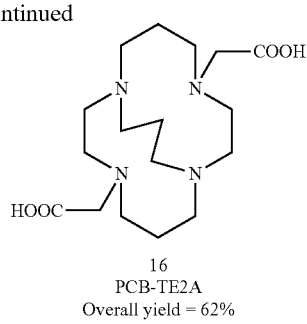

16
PCB-TE2A
Overall yield = 62%

5-a) Synthesis of 1,8-bis-(benzyloxycarbonylmethyl)-4,11-diazoniatricyclo[9.3.1.1[4,8]]hexadecane dibromide (19)

A solution of 10 (3.56 g, 15.87 mmol) in MeCN (100 mL) was added to four equivalent of benzyl 2-bromoacetate (10.29 mL, 15.03 g, 65.6 mmol). The reaction mixture was stirred at room temperature for 24 hours. The yellowish white precipitate formed was then filtered, washed with MeCN (2×20 mL) and dried under vacuum. The crude product was recrystallized in ethanol to give white solid 19 (10.3 g, 92% yield).

$^1$H NMR (500 MHz, DMSO-$d_6$): δ 7.32-7.41 (m, 10H, ArH), 5.16 (s, 4H), 3.52 (s, 4H), 3.33 (s, 4H), 3.09 (brs, 8H), 2.85 (brs, 4H), 2.76-2.74 (t, 4H, J=5 Hz), 1.86 (brs, 4H); $^{13}$C NMR (125 MHz, DMSO-$d_6$): δ 172.20, 135.54, 128.46, 128.21, 128.03, 66.43, 55.97, 54.06, 52.80, 51.27, 47.39, 44.15, 22.15, 18.52; HRMS (ESI) calculated for $C_{30}H_{42}N_4O_4$, 523.3284 [(M+H)$^+$]. found: 523.3281 [(M+H)$^+$].

5-b) Synthesis of 1,8-bis-(benzyloxycarbonylmethyl)-1,4,8,11-tetraazacyclotetradecane (20)

A 3 M NaOH solution (200 mL) was added to 19 (9.23 g, 13.52 mmol). After stirring for 3 hours, the resultant solution was extracted with CHCl$_3$ (3×100 mL). The combined organic phases were washed by brine, dried over MgSO$_4$, and solvent was evaporated under reduced pressure to give oil 20 (6.58 g, 98% yield) which solidified on standing.

$^1$H NMR (500 MHz, CDCl$_3$): δ 7.20-7.14 (m, 10H, ArH), 4.92 (s, 4H), 3.25 (s, 4H), 2.71-2.66 (m, 12H), 2.49-2.47 (t, 4H, J=4.2 Hz), 1.70 (brs, 4H); $^{13}$C NMR (125 MHz, CDCl$_3$): δ 171.36, 135.09, 128.34, 128.12, 127.84, 66.21, 54.70, 54.01, 51.96, 49.12, 46.36, 24.39; HRMS (FAB): calculated for $C_{28}H_{41}N_4O_4$, 497.3128 [(M+H)$^+$]. found: 497.3129 [(M+H)$^+$].

5-c) Synthesis of 4,11-bis-(benzyloxycarbonylmethyl)-1,4,8,11-tetraazabicyclo[6.6.3]heptadecane (21)

A solution of 1,8-bis-(benzyloxycarbonylmethyl)-1,4,8,11-tetraazacyclotetradecane 20 (4.27 g, 8.59 mmol), 1,3-propanediol di-p-tosylate (3.3 g, 8.59 mmol) and anhydrous Na$_2$CO$_3$ (2.09 g, 19.76 mmol) in anhydrous toluene (220 mL) was refluxed for 6 days. The solvent was evaporated from the reaction mixture under reduced pressure and CH$_2$Cl$_2$ (250 mL) was added. The resulting brown slurry was filtered off through a celite pad and washed with CH$_2$Cl$_2$ (2×30 mL). The solvent was evaporated from the combined filtrate and washed under reduced pressure. The resulting residue was purified via column chromatography on alumina (basic) and eluted with CH$_2$Cl$_2$/methanol (20:1) to afford pale oil as the tosylate salt. The oil was dissolved in 20% aq NaOH (100 mL). After stirring for 4 hours, the resultant solution was extracted with CHCl$_3$ (3×100 mL). The combined organic phases were washed by brine, dried over MgSO$_4$, and solvent was evaporated under reduced pressure to give off-white powder 21 (3.32 g, 72% yield).

HRMS (FAB): calculated for $C_{31}H_{45}N_4O_4$ 537.3435 [(M+H)$^+$]. found: 537.3437 [(M+H)$^+$].

5-d) Synthesis of 4,11-bis-(carboxymethyl)-1,4,8,11-tetraazabicyclo[6.6.3]heptadecane (16)

To a solution of 21 (3.19 g, 5.94 mmol) in ethanol (120 mL) was added 10% Pd/C (0.96 g). The resulting mixture was stirred under H$_2$ (g) atmosphere at room temperature for 12 hours. The reaction mixture was filtered through a celite pad and washed with ethanol (2×20 mL). The combined filtrate was evaporated under vacuum to give an oily residue which was triturated with Et$_2$O to provide white solid 16 (2.1 g, 99% yield).

$^1$H NMR (500 MHz, DMSO-$d_6$): δ 3.63-3.16 (m, 8H) 3.12-2.5 (m, 16H), 1.85 (brs, 4H), 1.68 (brs, 2H); $^{13}$C NMR (125 MHz, DMSO-$d_6$): δ 172.1, 55.3, 54.0, 51.7, 48.6, 48.04, 21.6, 19.2; HRMS (FAB): calculated for $C_{17}H_{33}N_4O_4$, 357.2502 [(M+H)$^+$]. found: 357.2504 [(M+H)$^+$].

Example 6

Synthesis of 2-[(4-nitrophenyl)methyl]propan-1,3-diol bis(4-methylbenzenesulfonate)] (25)

6-a) Synthesis of diethyl 2-[(4-nitrophenyl)methyl]propanedioate (23)

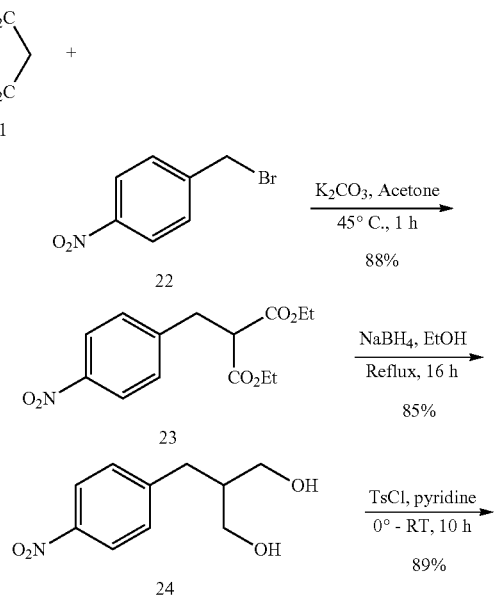

-continued

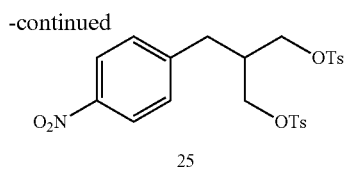

25

4-Nitrobenyl bromide 22 (10.57 g, 48.93 mmol) was added to a solution of diethyl malonate 21 (52 mL, 54.86 g, 342.51 mmol) and K$_2$CO$_3$ (14.21 g, 102.8 mmol) in acetone (40 mL). The reaction mixture was heated at 45° C. for 1 hour. The mixture was allowed to cool to room temperature and the resulting yellow slurry was filtered off to remove K$_2$CO$_3$ and washed with acetone (2×20 mL). The solvent was evaporated from the combined filtrate and washings under reduced pressure. The excess of diethylmalonate was removed by horizontal distillation (2 hr, 80-130° C., and 0.005 mbar). The yellow oily residue was dissolved in ethanol (200 mL). The precipitated white solid (dialkylated product) was filtered and washed with ethanol (2×20 mL). The solvent was evaporated from the combined filtrate and washings under reduced pressure to give a solid, which was recrystallized from hexane/Et$_2$O (1:1) to afford white crystalline needles 23 (12.72 g, 88% yield).

$^1$H NMR (500 MHz, CDCl$_3$): δ 1.20-1.23 (t, 6H, J=7 Hz), 3.31-3.32 (d, 2H, J=7.5 Hz), 3.65 (t, 1H, J=7.7 Hz), 4.13-4.21 (m, 4H), 7.38-7.40 (d, 2H, J=8.5 Hz), 8.13-8.15 (dd, 2H, J=2 Hz, 7 Hz); $^{13}$C NMR (125 MHz, CDCl$_3$): δ 15.5, 35.8, 54.6, 63.3, 125.2, 131.3, 147.1, 148.5, 169.7; HRMS (FAB) C$_{14}$H$_{17}$NO$_6$, 296.1129 [(M+H)$^+$]: 296.1134 [(M+H)$^+$].

6-b) Synthesis of 2-[(4-nitrophenyl)methyl]propan-1,3-diol (24)

To a suspension of NaBH$_4$ (14.35 g, 379.3 mmol) in EtOH (200 mL) was added dropwise a solution of 23 (11.2 g, 37.93 mmol) in EtOH (100 mL) and the mixture was refluxed for 16 hours. After addition of an aqueous NH$_4$Cl solution (5%, 150 mL) in small portions, the solution was distilled under vacuum to remove EtOH. CH$_2$Cl$_2$ (200 mL) was added and the mixture was filtered. The two layers were separated, and the aqueous phase was extracted with CH$_2$Cl$_2$ (3×50 mL). The combined organic phases were washed with aqueous NaHCO$_3$ (5%, 100 mL), dried over MgSO$_4$ and concentrated under vacuum. The resulting yellow oil was recrystallized from EtOAC/hexane to give off-white powder 24 (6.81 g, 85% yield).

$^1$H NMR (500 MHz, CD3OD): δ 1.93-1.96 (h, 1H, J=6 Hz, 7 Hz, 13 Hz), 277-2.79 (d, 2H, J=8 Hz), 3.53-3.54 (d, 4H, J=5 Hz), 7.43-7.45 (d, 2H, J=8.5 Hz), 8.11-8.12 (d, 2H, J=2 Hz, 6.5 Hz); $^{13}$C NMR (125 MHz, CD$_3$OD): δ 35.0, 46.5, 62.8, 124.4, 131.3, 147.8, 150.4; HRMS (FAB) C$_{10}$H$_{13}$NO$_4$, 212.0917 [(M+H)$^+$]. found: 212.0923 [(M+H)$^+$].

6-c) Synthesis of 2-[(4-nitrophenyl)methyl]propan-1,3-diol bis(4-methylbenzenesulfonate) (25)

A solution of 24 (6.43 g, 30.44 mmol) in pyridine (20 mL) was added dropwise to a solution of p-toluenesulfonyl chloride (14.51 g, 76.11 mmol) in pyridine (30 mL), with temperature being kept below 0° C. After complete addition, the reaction mixture was stirred at room temperature for 10 hours, and then it was poured into ice-cold aqueous 5 M HCl (100 mL). The aqueous phase was extracted with CH$_2$Cl$_2$ (3×100 mL). The combined organic phase was washed with brine (2×100 mL), dried over MgSO4, and evaporated under reduced pressure to afford pale yellow oil, which was crystallized from ethanol (100 mL) to give white solid 25 (14.08 g, 89% yield).

$^1$H NMR (500 MHz, CDCl$_3$): δ 2.32-2.34 (m, 1H), 2.46 (s, 6H, 2×ArCH$_3$), 2.72-2.74 (d, 2H, J=7.5 Hz), 3.85-3.89 (dd, 2H, J=5.5 Hz, 10.5 Hz), 3.96-3.99 (dd, 2H, J=5.5 Hz, 10.5 Hz), 7.13-7.15 (d, eH, J=8 Hz), 7.33-7.35 (d, 4H, J=8.5 Hz), 7.70-7.72 (d, 4H, J=8 Hz), 8.00-8.02 (d, 2H, J=9 Hz); $^{13}$C NMR (125 MHz, CDCl$_3$): δ 21.5, 32.9, 39.6, 67.6, 123.7, 127.8, 129.7, 129.9, 132.0, 145.0, 145.3, 146.7; HRMS (FAB) C$_{24}$H$_{25}$NO$_8$S$_2$, 520.1094 [(M+H)+] found: 520.1097 [(M+H)$^+$].

Although PCB-TE2A is a good chelator having an octahedral coordination site with metals like Cu, one of its two pendant arms has to be sacrificed whenever it is conjugated with biomolecules. To keep intact the octahedral coordination structure while allowing further conjugation with biomolecules, introduction of an extra functional group in the backbone is necessary. For this purpose, the inventors have synthesized a suitably tailored nitro-derivative of ditosyl ester of 1,3-propanediol, 25. The precursor was used for the construction of propylene bridge having one extra functionality. The inventors have designed the compound 25 and performed synthesis by condensation of 1 equiv. of 4-nitrobenzyl bromide with 7 equivalent of diethyl malonate in the presence of K$_2$CO$_3$ in acetone to give 23 in 88% yield (Scheme 6). In this reaction a mild base rather than metal alkoxide and excess of diethyl malonate were used in order to prevent the formation of dialkylate product. The diethyl-2-[(4-nitrophenyl)methyl]propanedioate 23 was reduced with sodium borohydride to afford the diol compound 24 in 85% yield. The diol 24 was tosylated by tosyl chloride in pyridine to afford the precursor 25 in 89% yield. According to Scheme 6,2-[(4-nitrophenyl)methyl]propan-1,3-diol bis(4-methylbenzene-sulfonate) (25) was prepared in high overall yield (66%).

Example 7

Synthesis of 4,11-bis-(carboxymethyl)-16-(4-isothiocyanatobenzyl)-1,4,8,11-tetraazabicyclo[6.6.3]-heptadecane-2TFA (29.2TFA)

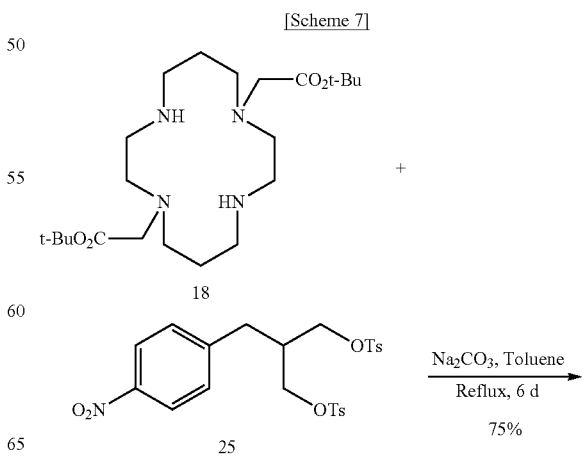

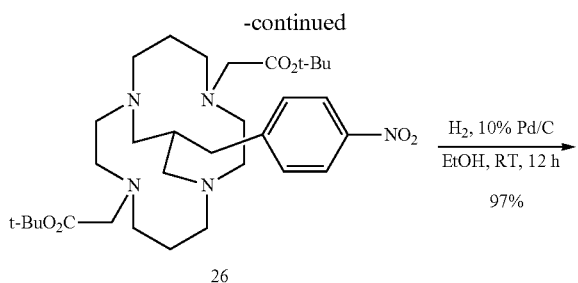

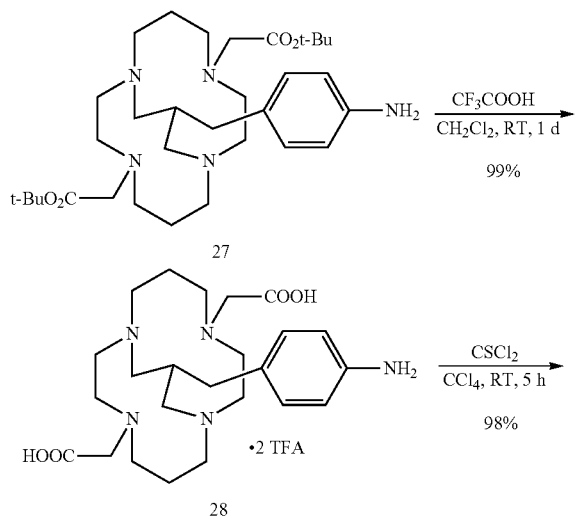

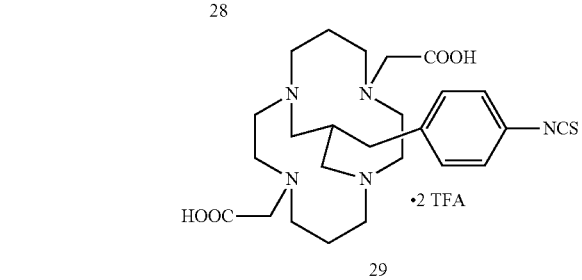

7-a) Synthesis of 4,11-bis-(carbo-tert-butoxymethyl)-16-(4-nitrobenzyl)-1,4,8,11-tetraazabicyclo[6.6.3]heptadecane (26)

A solution of 1,8-bis-(carbo-tert-butoxymethyl)-1,4,8,11-tetraazacyclotetradecane 18 (5.23 g, 12.20 mmol), 2-[(4-nitrophenyl)methyl]propan-1,3-diol bis(4-methylbenzenesulfonate) 25 (6.34 g, 12.20 mmol) and anhydrous $Na_2CO_3$ (2.97 g, 28.06 mmol) in anhydrous toluene (200 mL) was refluxed for 6 days. The solvent was evaporated from the reaction mixture under reduced pressure and $CH_2Cl_2$ (200 mL) was added. The resulting brown slurry was filtered off to remove $Na_2CO_3$ through a celite pad and washed with $CH_2Cl_2$ (2×20 mL). The solvent was evaporated from the combined filtrate and washings under reduced pressure. The resulting residue was purified via column chromatography on alumina (basic) and eluted with $CH_2Cl_2$/methanol (20:1) to afford a pale oil as the tosylate salt. The oil was dissolved in 20% aq NaOH (120 mL). After stirring for 4 hours, the resultant solution was extracted with $CHCl_3$ (3×100 mL). The combined organic phases were washed by brine, dried over $MgSO_4$, and solvent was evaporated under reduced pressure to give off-white powder 26 (5.53 g, 75% yield).

$^1$H NMR (500 MHz, $C_6D_6$): δ 8.19-8.17 (d, 2H, J=8 Hz), 7.83-7.82 (d, 2H, J=8 Hz), 4.06 (t, 1H, J=12 Hz), 3.48-2.79 (m, 16H), 2.79-2.27 (m, 8H), 1.55-1.17 (m, 24H); $^{13}$C NMR (125 MHz, $C_6D_6$): δ 171.5, 170.5, 149.3, 147.4, 131.7, 124.2, 81.1, 81.0, 61.3, 60.9, 56.9, 56.1, 56.0, 50.9, 50.7, 47.6, 37.0, 32.5, 28.6, 24.1, 23.1; HRMS (FAB): calculated for $C_{32}H_{54}N_5O_6$, 604.4074 [(M+H)$^+$]. found: 604.4077 [(M+H)$^+$].

7-b) Synthesis of 4,11-bis-(carbo-tert-butoxymethyl)-16-(4-aminobenzyl)-1,4,8,11-tetraazabicyclo[6.6.3]heptadecane (27)

To a solution of compound 26 (4.26 g, 7.06 mmol) in ethanol (100 mL) was added 10% Pd/C (1.28 g). The resulting mixture was stirred under $H_2$ (g) atmosphere at room temperature for 12 hours. The reaction mixture was filtered through a celite pad and washed with ethanol (2×20 mL). The combined filtrate was evaporated in vacuo to give an oily residue which was triturated with $Et_2O$ to provide an off-white solid 27 (3.93 g, 97% yield).

$^1$H NMR (500 MHz, $C_6D_6$): δ 7.25-7.23 (d, 2H, J=8 Hz), 6.90-6.88 (d, 2H, J=8 Hz), 3.41 (t, 1H, J=12 Hz), 3.29-2.88 (m, 8H), 2.73-1.98 (m, 16H), 1.51-1.10 (m, 24H); $^{13}$C NMR (125 MHz, $C_6D_6$): δ 175.6, 171.3, 170.5, 147.8, 130.6, 127.5, 115.8, 81.0, 61.8, 61.0, 56.7, 55.9, 55.7, 50.5, 47.1, 36.5, 32.4, 28.6, 24.6, 23.7, 22.7; HRMS (FAB): calculated for $C_{32}H_{56}N_5O_4$, 574.4332 [(M+H)$^+$]. found: 574.4330 [(M+H)$^+$].

7-c) Synthesis of 4,11-bis-(carboxymethyl)-16-(4-aminobenzyl)-1,4,8,11-tetraazabicyclo[6.6.3]heptadecane.2TFA (28.2TFA, "PCB-TE2A-NH$_2$")

Compound 27 (2.56 g, 4.46 mmol) was dissolved in a 1:1 (vol:vol) mixture of $CF_3CO_2H$ (TFA) and $CH_2Cl_2$ (70 mL). The mixture was stirred at room temperature for 24 hours. The solvent was removed under reduced pressure to give an oily residue which was triturated with $Et_2O$ to provide white solid 28 (3.05 g, 99% yield) (2 equiv TFA calculated on the basis of mass).

$^1$H NMR (500 MHz, DMSO-$d_6$): δ 6.92-6.90 (d, 2H, J=8.5 Hz), 6.50-6.48 (d, 2H, J=8.5 Hz), 3.42-3.16 (m, 8H), 2.92-2.50 (m, 12H), 2.38-1.79 (m, 5H), 1.63-1.16 (m, 4H); $^{13}$C NMR (125 MHz, DMSO-$d_6$): δ 174.2, 173.2, 146.8, 145.7, 137.5, 129.1, 128.0, 125.5, 114.1, 60.4, 59.8, 54.5, 50.3, 46.8, 35.4, 30.2, 23.1, 21.2, 20.7; HRMS (FAB): calculated for $C_{24}H_{40}N_5O_4$, 462.3080 [(M+H)$^+$]. found: 462.3085 [(M+H)$^+$].

7-d) Synthesis of 4,11-bis-(carboxymethyl)-16-(4-isothiocyanatobenzyl)-1,4,8,11-tetraazabicyclo[6.6.3]heptadecane.2TFA (29.2TFA, "PCB-TE2A-NCS")

A solution of compound 28 (1.21 g, 1.75 mmol) in 0.5 M HCl (50 mL) was carefully added to thiophosgene ($CSCl_2$) (4.03 mL, 6.04 g, 52.5 mmol). The reaction mixture was stirred for 5 hours at room temperature and the layers were allowed to separate. The aqueous layer was removed and the organic $CHCl_3$ layer was then washed with water (2×50 mL). The combined aqueous layers were washed with $CHCl_3$ (3×50 mL) to remove unreacted thiophosgene. Finally, the aqueous layer was lyophilized to afford white crystalline solid 29 (1.26 g, 98% yield).

$^1$H NMR (500 MHz, DMSO-$d_6$): δ 7.26 (s, 4H, ArH), 4.01 (d, 4H), 3.62-3.15 (m, 8H), 2.97-2.49 (m, 12H), 2.28-1.86 (m, 5H), 1.61-1.22 (m, 4H); $^{13}$C NMR (125 MHz, DMSO-$d_6$): δ 187.9, 174.4, 173.2, 145.7, 137.5, 136.8, 135.1, 129.1, 128.6, 125.5, 122.6, 121.6, 60.4, 59.7, 57.8, 57.2, 56.9, 56.1, 54.5, 48.5, 35.5, 29.7, 23.3, 20.7; HRMS (FAB): calculated for $C_{25}H_{38}N_5O_4S$, 504.2645 [(M+H)$^+$]. found: 504.2647 [(M+H)$^+$].

According to Scheme 7, the propylene cross-bridged compound with the linker NO$_2$ could be achieved by refluxing the compound 18 with the ditosyl ester of 2-[(4-nitrophenyl)methyl]1,3-propanediol 25 in the presence of sodium carbonate in toluene, which gave the tosylate salt of the cross-bridged product 26. The tosylate counteranion was removed by treatment with 20% NaOH, yielding 75% of free base 26. The reduction of the nitro group of the compound 26 was carried out by catalytic hydrogenation to provide 27 quantitatively. Deprotection of the tert-butyl groups of the compound 27 was carried out in trifluoroacetic acid, and further reacted with thiophosgene to afford the PCB-TE2A-NCS compound as bis(trifluoroacetic acid) salt, so as to allow binding of the PCB-TE2A-NCS compound to an antibody. This procedure of PCB-TE2A-NCS synthesis is very effective when compared with the existing process of attaching the NH$_2$ and NCS groups to a bifunctional chelator in that the functional groups can be selectively attached to the propylene moiety via a simplified process.

Example 8

Synthesis of 4,11-bis-(carboxymethyl)-16-(4-isothiocyanatobenzyl)-1,4,8,11-tetraazabicyclo[6.6.3]heptadecane (29)

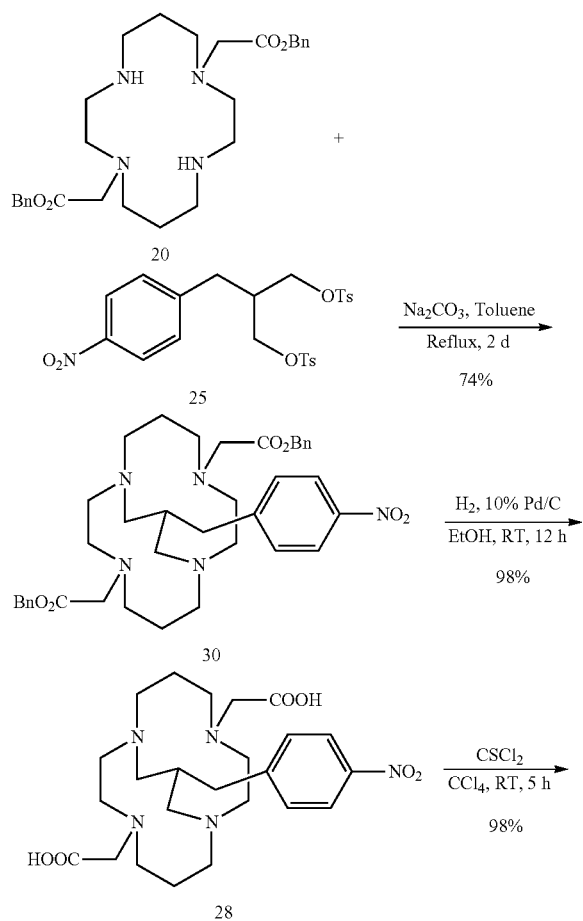

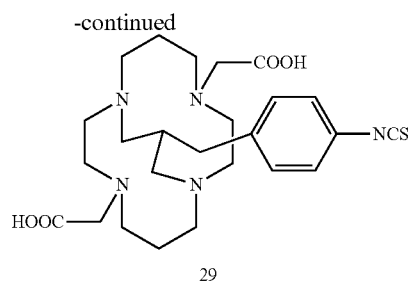

8-a) Synthesis of 4,11-bis-(benzyloxycarbonylmethyl)-16-(4-nitrobenzyl)-1,4,8,11-tetraazabicyclo[6.6.3]heptadecane (30)

A solution of 4,11-bis-(benzyloxycarbonylmethyl)-1,4,8,11-tetraazabicyclo[6.6.3]heptadecane 20 (4.12 g, 8.29 mmol), 2-[(4-nitrophenyl)methyl]propan-1,3-diol bis(4-methylbenzenesulfonate) 25 (4.31 g, 8.29 mmol) and anhydrous Na$_2$CO$_3$ (2.02 g, 19.07 mmol) in anhydrous toluene (200 mL) was refluxed for 6 days. The solvent was evaporated from the reaction mixture under reduced pressure and CH$_2$Cl$_2$ (200 mL) was added. The resulting brown slurry was filtered off to remove Na$_2$CO$_3$ through a celite pad and washed with CH$_2$Cl$_2$ (2×20 mL). The solvent was evaporated from the combined filtrate and washings under reduced pressure. The resulting residue was purified via column chromatography on alumina (basic) and eluted with CH$_2$Cl$_2$/methanol (20:1) to afford a pale oil as the tosylate salt. The oil was dissolved in 20% aq NaOH (120 mL). After stirring for 4 hours, the resultant solution was extracted with CHCl$_3$ (3×100 mL). The combined organic phases were washed by brine, dried over MgSO$_4$, and solvent was evaporated under reduced pressure to give off-white powder 30 (4.12 g, 74% yield).

HRMS (FAB): calculated for $C_{38}H_{50}N_5O_6$, 672.3761 [(M+H)$^+$]. found: 672.3757 [(M+H)$^+$].

8-b) Synthesis of 4,11-bis-(carboxymethyl)-16-(4-aminobenzyl)-1,4,8,11-tetraazabicyclo[6.6.3]heptadecane (28)

10% Pd/C (1.19 g) was added to a solution of compound 30 (3.97 g, 5.91 mmol) in ethanol (100 mL). The resulting mixture was stirred under H$_2$ (g) atmosphere at room temperature for 12 hours. The reaction mixture was filtered through a celite pad and washed with ethanol (2×20 mL). The combined filtrate was evaporated in vacuo to give an oily residue which was triturated with Et$_2$O to provide an off-white solid 28 (2.67 g, 98% yield).

$^1$H NMR (500 MHz, DMSO-d$_6$): δ 6.92-6.90 (d, 2H, J=8.5 Hz), 6.50-6.48 (d, 2H, J=8.5 Hz), 3.42-3.16 (m, 8H), 2.92-2.50 (m, 12H), 2.38-1.79 (m, 5H), 1.63-1.16 (m, 4H); $^{13}$C NMR (125 MHz, DMSO-d$_6$): δ 174.2, 173.2, 146.8, 145.7, 137.5, 129.1, 128.0, 125.5, 114.1, 60.4, 59.8, 54.5, 50.3, 46.8, 35.4, 30.2, 23.1, 21.2, 20.7; HRMS (FAB): calculated for $C_{24}H_{40}N_5O_4$, 462.3080 [(M+H)$^+$]. found: 462.3085 [(M+H)$^+$].

8-c) Synthesis of 4,11-bis-(carboxymethyl)-16-(4-isothiocyanatobenzyl)-1,4,8,11-tetraazabicyclo[6.6.3]heptadecane] (29)

A solution of compound 28 (1.21 g, 1.75 mmol) in 0.5 M HCl (50 mL) was carefully added to thiophosgene (CSCl$_2$) (4.03 mL, 6.04 g, 52.5 mmol) in CHCl$_3$ (50 mL). The reaction mixture was stirred for 5 hours at room temperature and the layers were allowed to separate. The aqueous layer was removed and the organic CHCl$_3$ layer was then washed with water (2×50 mL). The combined aqueous layers were washed with CHCl$_3$ (3×50 mL) to remove unreacted thiophosgene. Finally, the aqueous layer was lyophilized to afford white crystalline solid 29 (1.26 g, 98% yield).

$^1$H NMR (500 MHz, DMSO-d$_6$): δ 6.92-6.90 (d, 2H, J=8.5 Hz), 6.50-6.48 (d, 2H, J=8.5 Hz), 3.42-3.16 (m, 8H), 2.92-2.50 (m, 12H), 2.38-1.79 (m, 5H), 1.63-1.16 (m, 4H); $^{13}$C NMR (125 MHz, DMSO-d$_6$): δ 174.2, 173.2, 146.8, 145.7, 137.5, 129.1, 128.0, 125.5, 114.1, 60.4, 59.8, 54.5, 50.3, 46.8, 35.4, 30.2, 23.1, 21.2, 20.7; HRMS (FAB): calculated for C$_{24}$H$_{40}$N$_5$O$_4$, 462.3080 [(M+H)$^+$]. found: 462.3085 [(M+H)$^+$].

Example 9

Synthesis of 4,10-bis-(carboxymethyl)-14-(4-isothiocyanatobenzyl)-1,4,7,10-tetraazabicyclo[5.5.3]pantadecane.2TFA (34.2TFA) (34)

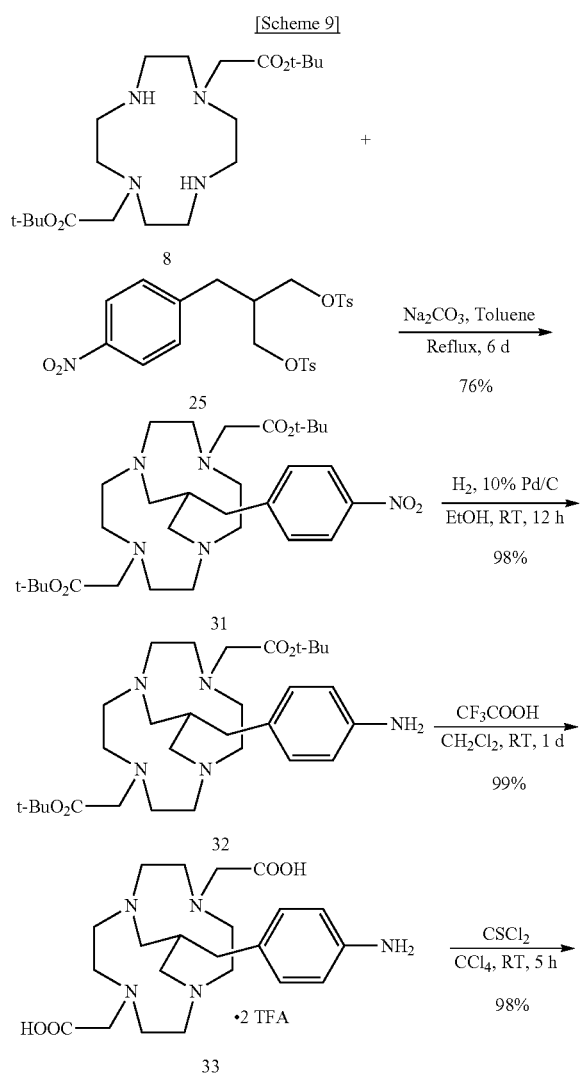

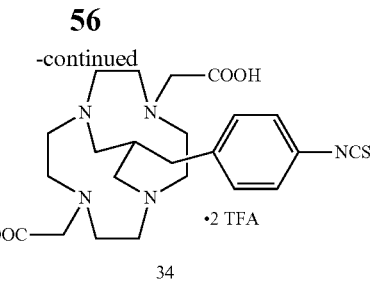

9-a) Synthesis of 4,10-bis-(carbo-tert-butoxymethyl)-14-(4-nitrobenzyl)-1,4,7,10-tetraazabicyclo[5.5.3]pentadecane (31)

A solution of 1,7-bis(carbo-tert-butoxymethyl)-1,4,7,10-tetraazacyclododecane 8 (4.19 g, 10.46 mmol), 2-[(4-nitrophenyl)methyl]propan-1,3-diol bis(4-methylbenzenesulfonate) 25 (5.44 g, 10.46 mmol) and anhydrous Na$_2$CO$_3$ (2.55 g, 24.06 mmol) in anhydrous toluene (200 mL) was refluxed for 6 days. The solvent was evaporated from the reaction mixture under reduced pressure and CH$_2$Cl$_2$ (200 mL) was added. The resulting brown slurry was filtered off to remove Na$_2$CO$_3$ through a celite pad and washed with CH$_2$Cl$_2$ (2×20 mL). The solvent was evaporated from the combined filtrate and washings under reduced pressure. The resulting residue was purified via column chromatography on alumina (basic) and eluted with CH$_2$Cl$_2$/methanol (20:1) to afford a pale oil as the tosylate salt. The oil was dissolved in 20% aq NaOH (120 mL). After stirring for 4 hours, the resultant solution was extracted with CHCl$_3$ (3×100 mL). The combined organic phases were washed by brine, dried over MgSO$_4$, and solvent was evaporated under reduced pressure to give off-white powder 31 (4.58 g, 76% yield).

MS (ESI): calculated for C$_{30}$H$_{50}$N$_5$O$_6$, 576.38 [(M+H)$^+$]. found: 576.45 [(M+H)$^+$].

9-b) Synthesis of 4,10-bis-(carbo-tert-butoxymethyl)-14-(4-aminobenzyl)-1,4,7,10-tetraazabicyclo[5.5.3]pentadecane (32)

To a solution of compound 31 (4.18 g, 7.26 mmol) in ethanol (100 mL) was added 10% Pd/C (1.25 g). The resulting mixture was stirred under H$_2$ (g) atmosphere at room temperature for 12 hours. The reaction mixture was filtered through a celite pad and washed with ethanol (2×20 mL) The combined filtrate was evaporated in vacuo to give an oily residue which was triturated with Et$_2$O to provide an off-white solid 32 (3.88 g, 98% yield).

9-c) Synthesis of 4,10-bis-(carboxymethyl)-14-(4-aminobenzyl)-1,4,7,10-tetraazabicyclo[5.5.3]pentadecane.2TFA (33.2TFA)

Compound 32 (2.69 g, 4.93 mmol) was dissolved in a 1:1 (vol:vol) mixture of CF$_3$CO$_2$H (TFA) and CH$_2$Cl$_2$ (70 mL). The mixture was stirred at room temperature for 24 hours. The solvent was removed under reduced pressure to give an oily residue which was triturated with Et$_2$O to provide white solid 33 (3.23 g, 99% yield) (2 equiv TFA calculated on the basis of mass).

9-d) Synthesis of 4,10-bis-(carboxymethyl)-14-(4-isothiocyanatobenzyl)-1,4,7,10-tetraazabicyclo[5.5.3]pantadecane.2TFA (34.2TFA)

A solution of compound 33 (1.39 g, 2.1 mmol) in 0.5 M HCl (50 mL) was carefully added to thiophosgene (CSCl$_2$)

(4.83 mL, 7.24 g, 63 mmol) in CHCl₃ (50 mL). The reaction mixture was stirred for 5 hours at room temperature and the layers were allowed to separate. The aqueous layer was removed and the organic CHCl₃ layer was then washed with water (2×50 mL). The combined aqueous layers were washed with CHCl₃ (3×50 mL) to remove unreacted thiophosgene. Finally, the aqueous layer was lyophilized to afford white crystalline solid 34 (1.45 g, 98% yield).

Example 10

Synthesis of Cu-PCB-DO2A (35)

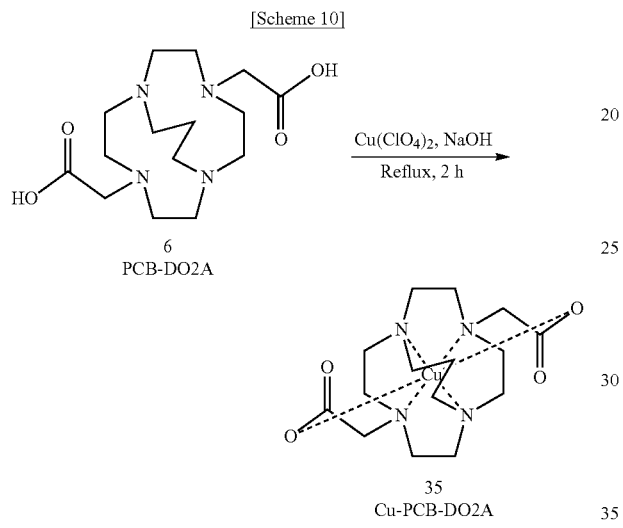

A solution of PCB-DO2A.2CF₃COOH 6 (187 mg, 0.34 mmol) and Cu(ClO₄)₂.6H₂O (126 mg, 0.34 mmol) in methanol (20 mL) was prepared. An aqueous solution (2 mL, 1.02 N) of NaOH (2.04 mmol) was added. The resulting clear blue solution was refluxed for 2 hours, cooled, and filtered through a celite pad. The filtrate was subjected to diethyl ether diffusion. The deposited blue crystals were collected and dried (0.115 g, 88% yield).

HRMS (FAB): calculated for $C_{15}H_{27}N_4O_4Cu$, 390.1323 [(M+H)⁺]. found: 390.1325 [(M+H)⁺].

Example 11

Synthesis of Cu-PCB-DO2A (36)

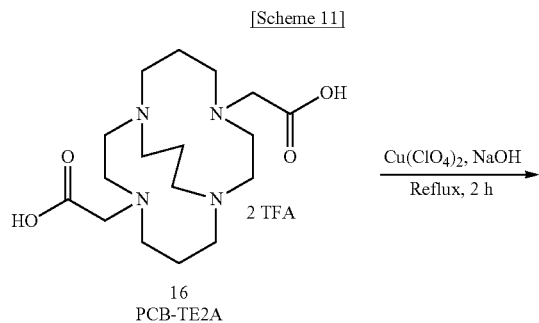

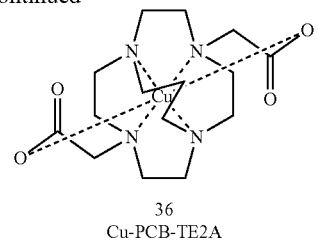

Cu-PCB-DO2A 36 (0.115 g, 88% yield) was synthesized in the same manner as in Example 10, except for using compound 16 synthesized in Example 4 as the starting material.

HRMS (FAB): calculated for $C_{17}H_{31}N_4O_4Cu$, 418.1641 [(M+H)⁺]. found: 418.1643 [(M+H)⁺].

Example 12

Synthesis of ⁶⁴Cu-PCB-DO2A (37)

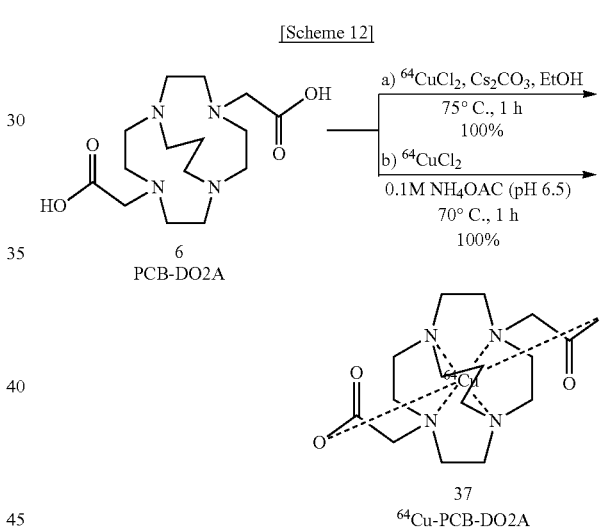

Figure 2:
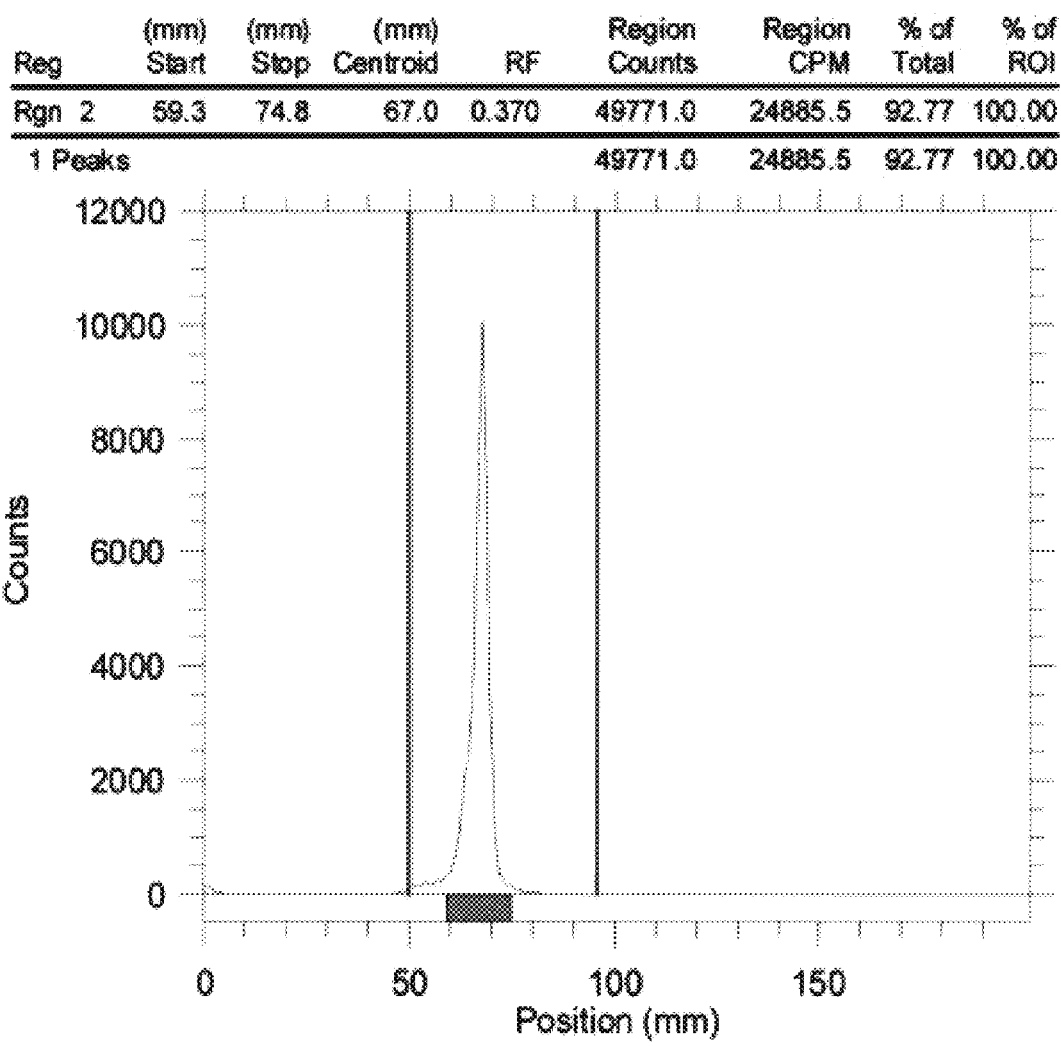

Complexation of ⁶⁴Cu with PCB-DO2A was achieved by 30-minute preincubation of PCB-DO2A 6 (5 mM) in EtOH with an excess of Cs₂CO₃ at 75° C. with constant mixing. Following centrifugation, addition of no-carrier-added ⁶⁴CuCl₂ to the isolated supernatant was accompanied by precipitation of CsCl. The mixture was vortexed and incubated at 75° C. for another 30 minutes. The supernatants was then transferred to 0.1 M NH₄OAC buffer (pH 6.5), and the ethanol was evaporated. Formation of ⁶⁴Cu-PCB-DO2A complex was verified by radio-TLC (FIG. 1) using a mobile phase consisting of 1:1 MeOH:10% ammonium acetate on a silica plate.

b) Complexation of ⁶⁴Cu with PCB-DO2A was achieved by addition of no-carrier added ⁶⁴CuCl₂ in 0.01 N HCl to a 5 mM solution of PCB-DO2A 6 in 0.1 M ammonium acetate (pH=6.5) followed by 1-hour incubation at 70° C. Formation of the ⁶⁴Cu-PCB-DO2A complex was verified by radio-TLC (FIG. 2) using a mobile phase 1:1 methanol: 10% ammonium acetate on a silica plate.

Example 13

Synthesis of $^{64}$Cu-PCB-TE2A (38)

[Scheme 13]

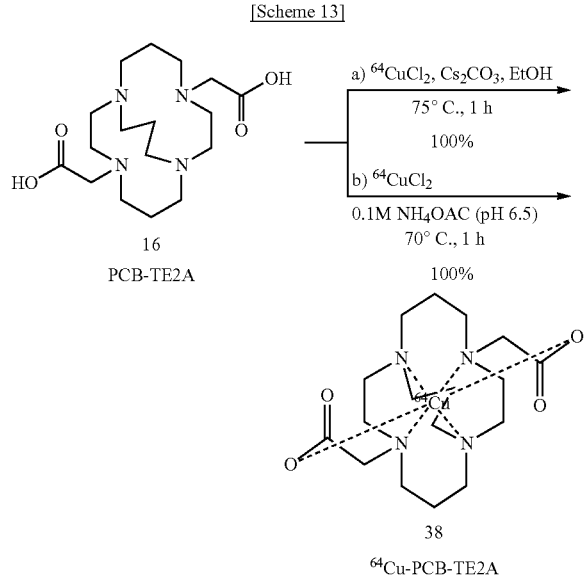

Figure 3:
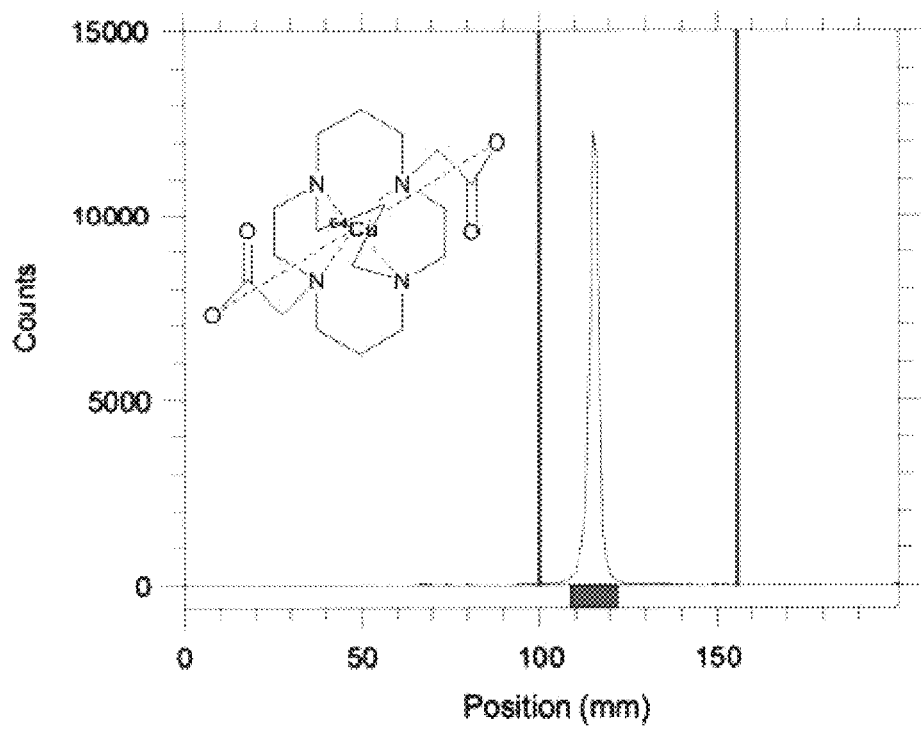
Figure 4:
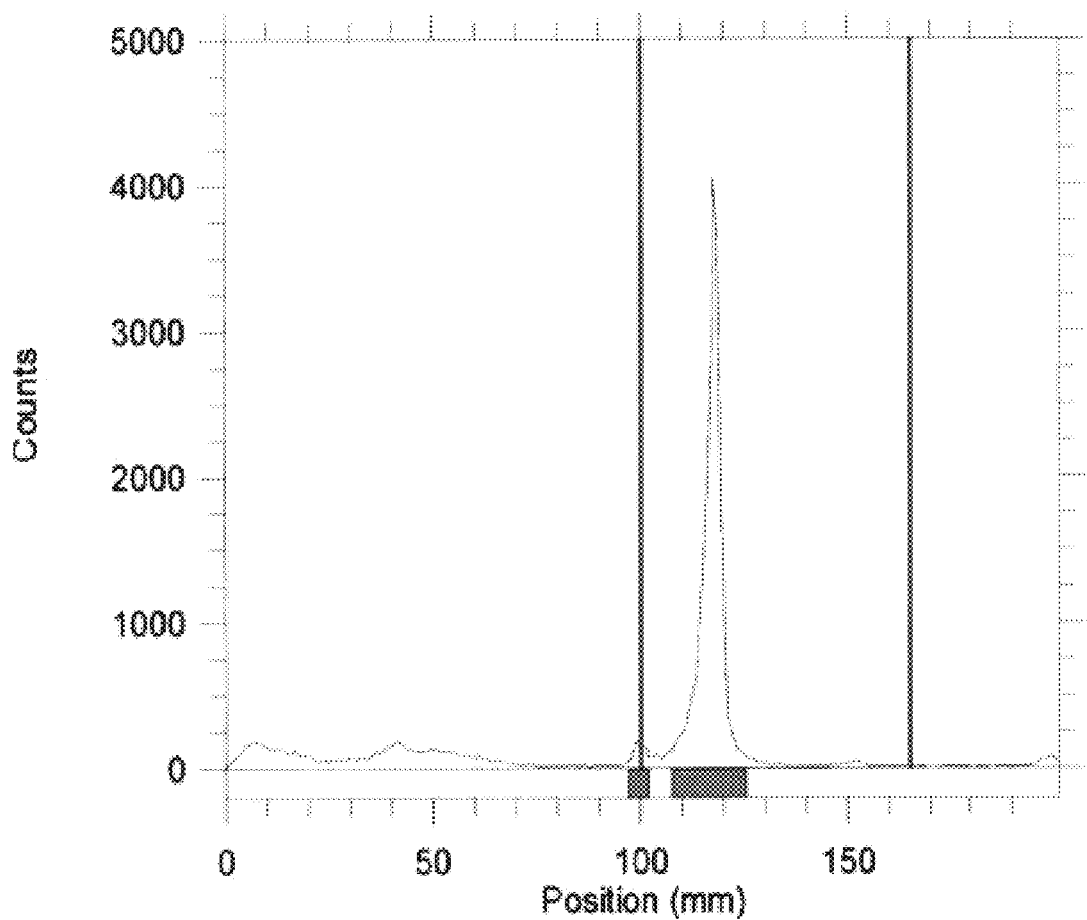

Complexation of $^{64}$Cu with PCB-TE2A was achieved by 30-minute preincubation of PCB-TE2A 16 (5 mM) in EtOH with an excess of $Cs_2CO_3$ at 75° C. with constant mixing. Following centrifugation, addition of no-carrier-added $^{64}CuCl_2$ to the isolated supernatant was accompanied by precipitation of CsCl. The mixture was vortexed and incubated at 75° C. for another 30 minutes. The supernatants was then transferred to 0.1 M $NH_4OAC$ buffer (pH 6.5), and the ethanol was evaporated. Formation of $^{64}$Cu-PCB-TE2A complex was verified by radio-TLC (FIG. 3) using a mobile phase consisting of 1:1 MeOH:10% ammonium acetate on a silica plate.

b) Complexation of $^{64}$Cu with PCB-TE2A was achieved by addition of no-carrier added $^{64}CuCl_2$ in 0.01 N HCl to a 5 mM solution of PCB-TE2A 16 in 0.1 M ammonium acetate (pH=6.5) followed by 1-hour incubation at 75° C. Formation of $^{64}$Cu-PCB-TE2A complex was verified by radio-TLC (FIG. 4) using a mobile phase 1:1 methanol: 10% ammonium acetate on a silica plate.

FIGS. 5-9 show the radio-TLC results of $^{64}$Cu-PCB-TE2A complexes formed at 40° C., 50° C., 60° C., 70° C. and 75° C., respectively. It was verified that the $^{64}$Cu-PCB-TE2A of the present disclosure can form complexes with a metal ion at a significantly lower temperature as compared to $^{64}$Cu-ECB-TE2A (90° C.).

Comparative Example 1

1,4,8,11-Tetraazacyclotetradecane-1,4,8,11-tetraacetic acid (TETA) was reacted with $Cu(ClO_4)_2 \cdot 6H_2O$ to prepare $^{64}$Cu-TETA.

Comparative Example 2

1,4,8,11-Tetraazacyclotetradecane-1,8-diacetic acid (TE2A) was reacted with $Cu(ClO_4)_2 \cdot 6H_2O$ to prepare $^{64}$Cu-TE2A.

Comparative Example 3

1,4,7,10-Tetraazacyclododecane-1,4,7,10-tetraacetic acid (DOTA) was reacted with $Cu(ClO_4)_2 \cdot 6H_2O$ to prepare $^{64}$Cu-DOTA.

Comparative Example 4

1,4,7,10-Tetraazacyclododecane-1,7-diacetic acid (DO2A) was reacted with $Cu(ClO_4)_2 \cdot 6H_2O$ to prepare $^{64}$Cu-DO2A.

Comparative Example 5

4,10-Bis(carboxymethyl)-1,4,7,10-tetraazabicyclo[5.5.2] tetradecane (ECB-DO2A) was reacted with $Cu(ClO_4)_2 \cdot 6H_2O$ to prepare $^{64}$Cu-ECB-DO2A.

Comparative Example 6

4,11-bis(carboxymethyl)-1,4,8,11-tetraazabicyclo[6.6.2] hexadecane (ECB-TE2A) was reacted with $Cu(ClO_4)_2 \cdot 6H_2O$ to prepare $^{64}$Cu-ECB-TE2A.

Test Example 1

1. Kinetic Inertness Via Acid Decomplexation

Acid decomplexation of $^{64}$Cu-PCB-TE2A was tested by adding 20 μL of $^{64}$Cu-PCB-TE2A (1-2 mM, 52 μCi) to 100 μL of 5 M and 10 M HCl. The solution was heated at 90° C., and samples were analyzed by radio-TLC at 6, 30 and 60 minutes post-addition to 5 M and 10 M HCl (FIGS. 10-15).

The data show that $^{64}$Cu-PCB-TE2A exhibit unusually high kinetic inertness towards acid decomplexation. It was confirmed that both the propylene cross-bridged cyclam backbone and the presence of two enveloping carboxymethyl arms provided this unusual kinetic inertness of 64Cu-PCB-TE2A.

2. In Vitro Serum Stability

Figure 23:
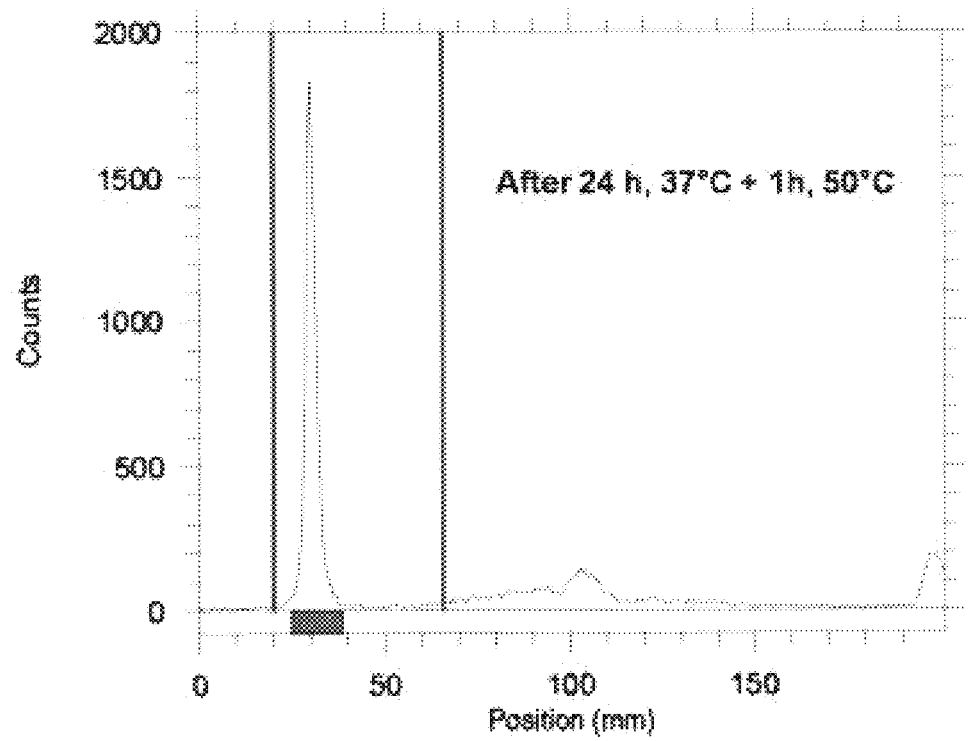

In vitro serum stability of $^{64}$Cu-PCB-TE2A was tested by adding 20 μL of $^{64}$Cu-PCB-TE2A (1-2 mM, 50 μCi) to 0.5 mL of fetal bovine serum (FBS). The solution was incubated at 37° C., and samples were analyzed by radio-TLC at 10, 30 and 60 minutes and at 2, 4, 10 and 24 hours post-addition to FBS (FIGS. 16-22). After 24 hours, the solution was incubated at 50° C. for 1 hour and once again samples were analyzed by radio-TLC (FIG. 23).

As seen from FIGS. 16-23, $^{64}$Cu-PCB-TE2A was intact in the FBS for 24 hours without degradation. This suggests that $^{64}$Cu-PCB-TE2A will also have good in vivo stability.

3. Biodistribution of $^{64}$Cu-PCB-DO2A and $^{64}$Cu-PCB-TE2A $^{64}$Cu-PCB-DO2A synthesized in Example 12 or $^{64}$Cu-PCB-TE2A synthesized in Example 13 (20 μCi in 200 μL saline per rat), diluted with saline, was injected to mature Sprague-Dawley rats (180-200 g, n=5) via tail vein. The animals were sacrificed at 4 hours and 24 hours post-injection. Organs and tissues of interest were removed and weighed.

TABLE 1

Rat biodistribution data for $^{64}$Cu-PCB-TE2A at 4 hours post-injection (% ID/organ ± sd)

| Tissue/Organ | % ID/g | % ID/organ |
|---|---|---|
| Blood | 0.013 ± 0.003 | 0.192 ± 0.048 |
| Heart | 0.015 ± 0.001 | 0.011 ± 0.000 |
| Lungs | 0.022 ± 0.003 | 0.022 ± 0.003 |
| Muscle | 0.033 ± 0.006 | 2.743 ± 0.525 |
| Fat | 0.060 ± 0.013 | 1.686 ± 0.322 |
| Bone | 0.030 ± 0.004 | 0.656 ± 0.110 |
| Spleen | 0.025 ± 0.006 | 0.013 ± 0.004 |
| Kidney | 0.421 ± 0.019 | 0.794 ± 0.056 |
| Liver | 0.213 ± 0.032 | 1.679 ± 0.241 |
| Tail | 0.046 ± 0.039 | 0.252 ± 0.213 |

TABLE 2

Rat biodistribution data for $^{64}$Cu-PCB-TE2A at 24 hours post-injection (% ID/organ ± sd)

| Tissue/Organ | % ID/g | % ID/organ |
|---|---|---|
| Blood | 0.006 ± 0.001 | 0.108 ± 0.029 |
| Heart | 0.007 ± 0.002 | 0.006 ± 0.001 |
| Lungs | 0.013 ± 0.002 | 0.015 ± 0.003 |
| Muscle | 0.018 ± 0.006 | 1.987 ± 0.703 |
| Fat | 0.036 ± 0.005 | 1.328 ± 0.311 |
| Bone | 0.020 ± 0.005 | 0.569 ± 0.181 |
| Spleen | 0.015 ± 0.009 | 0.009 ± 0.004 |
| Kidney | 0.049 ± 0.007 | 0.112 ± 0.011 |
| Liver | 0.015 ± 0.001 | 0.122 ± 0.013 |
| Tail | 0.039 ± 0.014 | 0.276 ± 0.115 |

TABLE 3

Rat biodistribution data for $^{64}$Cu-PCB-DO2A at 24 hours post-injection (% ID/organ ± sd)

| Tissue/Organ | % ID/g | % ID/organ |
|---|---|---|
| Blood | 0.045 ± 0.005 | 0.579 ± 0.066 |
| Heart | 0.027 ± 0.005 | 0.017 ± 0.003 |
| Lungs | 0.043 ± 0.009 | 0.046 ± 0.011 |
| Muscle | 0.008 ± 0.001 | 0.631 ± 0.080 |
| Fat | 0.026 ± 0.011 | 0.661 ± 0.301 |
| Bone | 0.037 ± 0.005 | 0.740 ± 0.107 |
| Spleen | 0.040 ± 0.005 | 0.015 ± 0.001 |
| Kidney | 0.249 ± 0.027 | 0.383 ± 0.052 |
| Liver | 0.205 ± 0.012 | 0.569 ± 0.079 |
| Tail | 0.136 ± 0.045 | 0.728 ± 0.238 |

As seen from Tables 1-3, $^{64}$Cu-PCB-DO2A and $^{64}$Cu-PCB-DO2A were quickly cleared from the blood, liver, kidneys, or the like.

TABLE 4

Rat biodistribution data for cross-bridged and non-cross-bridged chelators derived from cyclen and cyclam at 24 hours post-injection (% ID/organ ± sd)

| Ligands | Blood | Liver | Kidney |
|---|---|---|---|
| Comp. Ex. 1 | 0.21 ± 0.05 | 0.49 ± 0.11 | 0.21 ± 0.03 |
| Comp. Ex. 2 | 0.02 ± 0.003 | 0.143 ± 0.035 | 0.119 ± 0.008 |
| Comp. Ex. 3 | 0.58 ± 0.19 | 1.05 ± 0.16 | 0.54 ± 0.08 |
| Comp. Ex. 4 | 0.46 ± 0.08 | 0.86 ± 0.14 | 0.35 ± 0.10 |
| Comp. Ex. 5 | 0.14 ± 0.049 | 0.39 ± 0.030 | 0.064 ± 0.007 |
| Comp. Ex. 6 | 0.032 ± 0.014 | 0.14 ± 0.03 | 0.064 ± 0.012 |
| Ex. 11 | 0.045 ± 0.005 | 0.249 ± 0.027 | 0.205 ± 0.012 |
| Ex. 12 | 0.012 ± 0.004 | 0.142 ± 0.009 | 0.064 ± 0.008 |

Table 4 compares clearance of the labeled compounds of Examples 11-12 and Comparative Examples 1-6 from the blood, liver and kidneys at 24 hours post-injection (blood: 0.012±0.004 vs 0.21±0.05, liver: 0.142±0.004 vs 0.49±0.11, kidneys: 0.064±0.009 vs 0.21±0.03). The two complexes show difference in overall charge. Whereas Cu(II)-TETA has an overall charge of −2 due to the two free carboxylate groups, PCB-TE2A forms a neutral complex with the Cu(II) cation completely enclosed.

From Table 3, it can be seen that the $^{64}$Cu complex of PCB-TE2A is more resistant to transchelation than $^{64}$Cu-TETA. A similar pattern was observed for PCB-DO2A and CB-DO2A. The ethylene cross-bridged compounds and the propylene cross-bridged compounds showed similar clearance.

They differ by only one carbon length. As for cyclam, complexation of the cyclam structure with Cu(II) resulted in a biologically stable complex. Also, PCB-TE2A showed faster clearance than PCB-DO2A.

The $^{64}$Cu-labeled propylene cross-bridged chelates showed much better clearance from the blood, liver and kidneys than their non-cross-bridged counterparts ($^{64}$Cu-TETA). That is to say, $^{64}$Cu-PCB-TE2A had the lowest amount of $^{64}$Cu remaining in the blood and these tissues. The higher in vivo stability of the Cu(II) cross-bridged macrocyclic compounds than the non-cross-bridged macrocyclic compounds may be due to the difference in coordination chemistry. The size of the parent molecule also greatly influences the in vivo stability.

4. Acid Decomplexation Studies by Spectrophotometry

Figure 24:
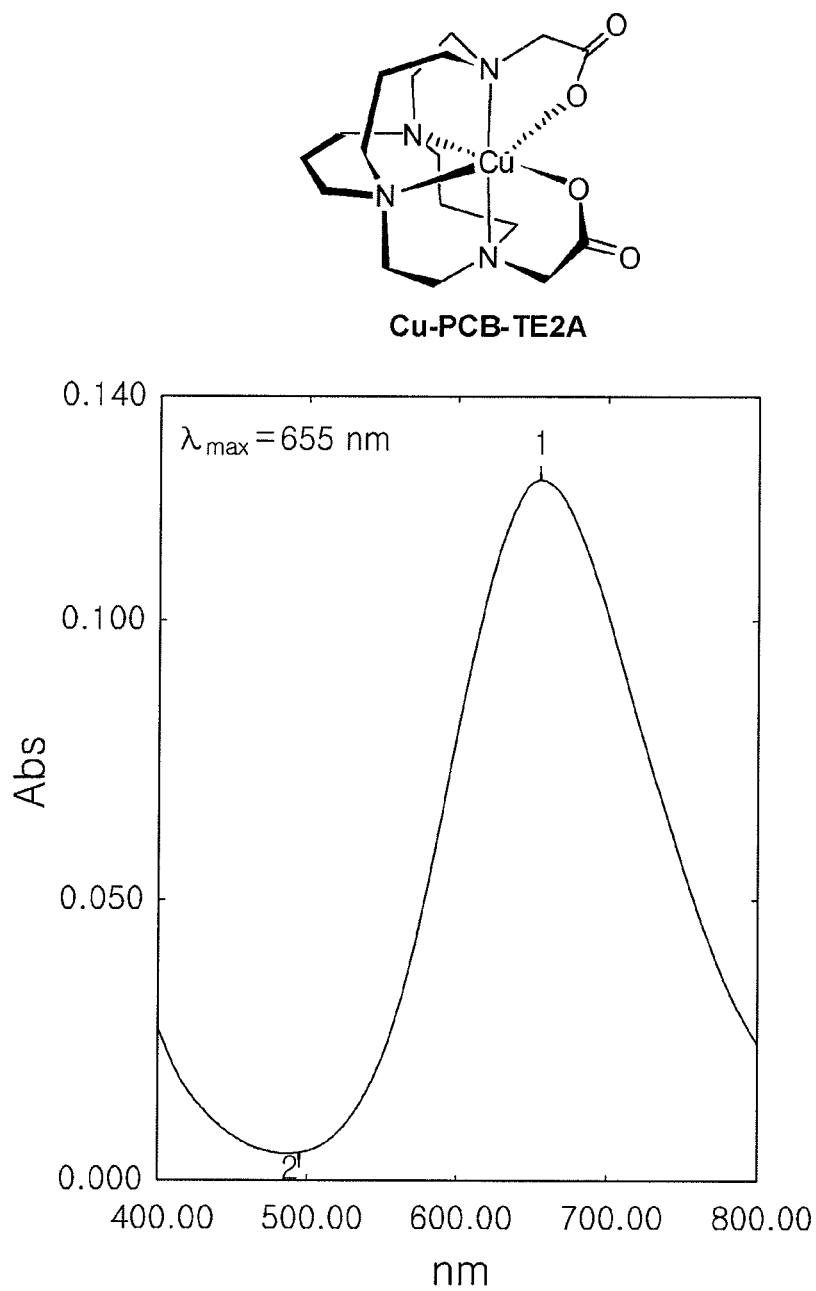
FIGS. 24 and 25 respectively show $\lambda_{max}$ measurement results of Cu-PCB-TE2A and Cu-PCB-DO2A in 5 M HCl.
Figure 25:
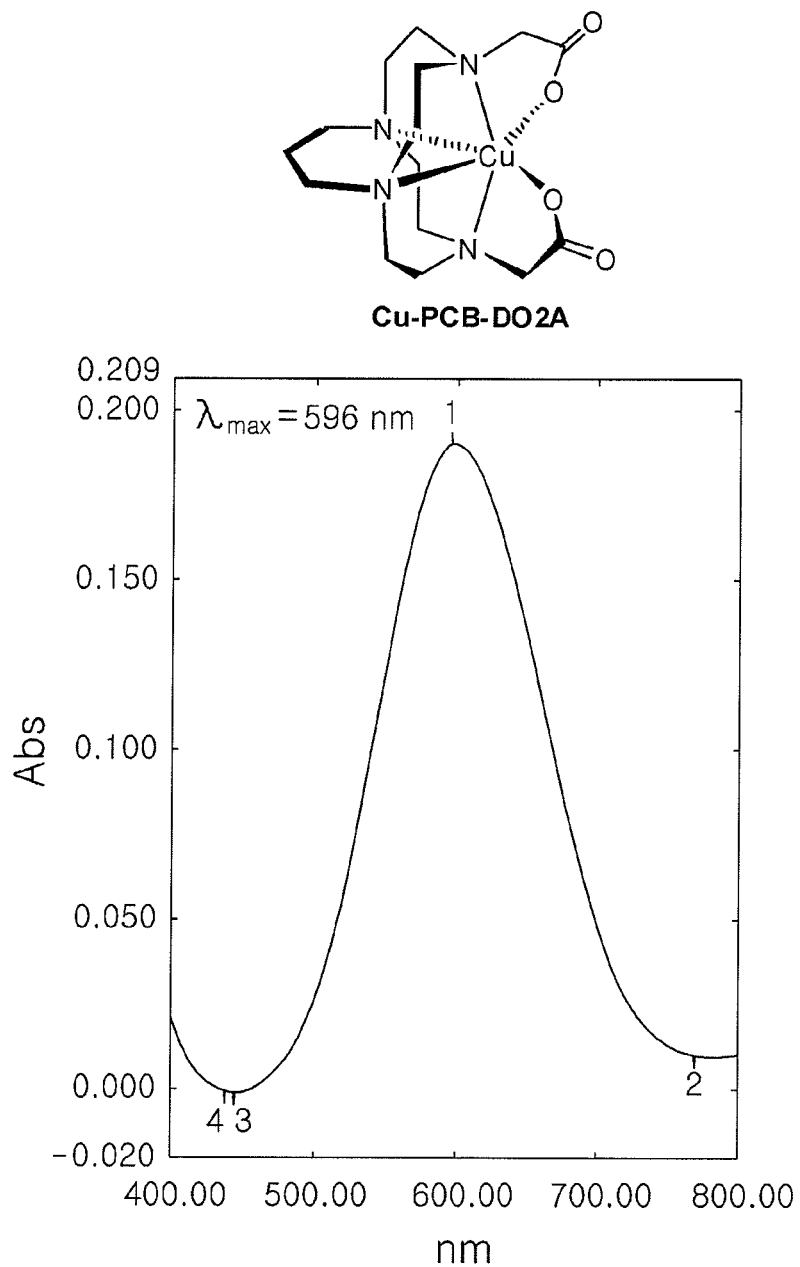

Acid decomplexation studies were performed under pseudo first-order conditions with the same concentration of 3 mmol in 5 M HCl at 90° C. Changes in the absorption maxima with time were monitored using a Shimadzu UV-Vis spectrophotometer (UV-1650PC) in thermostated cells. The decreasing absorbance at the $\lambda_{max}$ of each spectrum (Cu-PCB-TE2A: 655 nm, Cu-PCB-DO2A: 596 nm) was used to monitor the progress of the decomplexation reaction (FIGS. 24-25). Half-lives were calculated from the slopes of linear ln(absorbance) vs. time plots. Each experiment was repeated two to three times and mean values of half-lives are reported. The result is shown in FIGS. 24-27.

Figure 26:
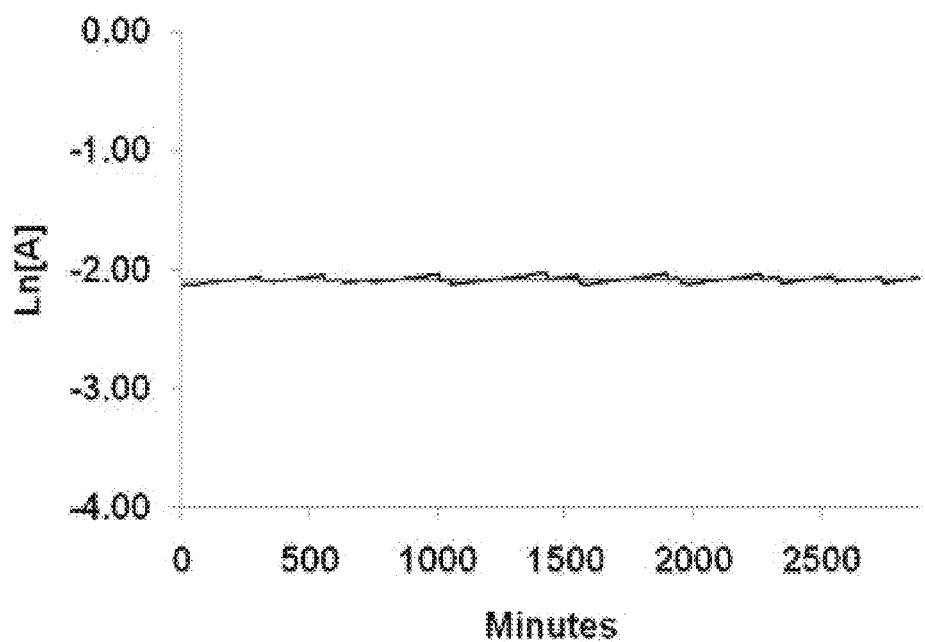
FIGS. 26 and 27 show ln(absorbance) vs. time curves of Cu-PCB-TE2A and Cu-PCB-DO2A in 5 M HCl at 90° C.
Figure 27:
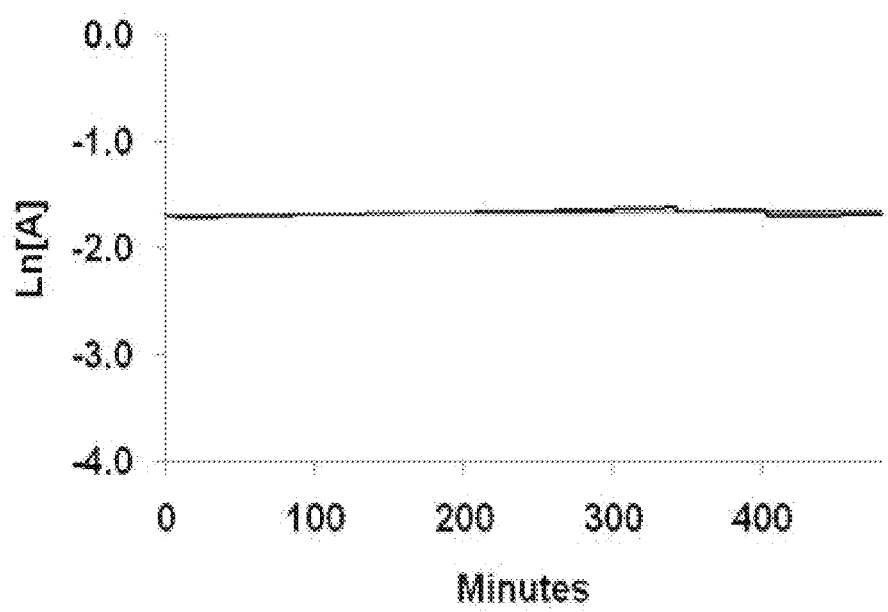

Specifically, FIGS. 24 and 25 show $\lambda_{max}$ measurement results of Cu-PCB-TE2A and Cu-PCB-DO2A, respectively, and FIGS. 26 and 27 show ln(absorbance) vs. time curves of $^{64}$Cu-PCB-TE2A and $^{64}$Cu-PCB-DO2A in 5 M HCl at 90° C., respectively.

As seen from the figures, PCB-TE2A forms a more stable copper complex than PCB-DO2A, with half-lives of Cu-PCB-TE2A and Cu-PCB-DO2A DO2A in 5 M HCl at 90° C. being 231 and 144 minutes, respectively.

5. Electrochemical Studies

Cyclic voltammetry was conducted using Biologic model SP-150 with three-electrode configuration. The system consisted of a glassy carbon (diameter=3 mm) as a working electrode, an Ag/AgCl (sat. KCl) reference electrode, and a Pt wire counter electrode. Samples were run in 0.1 M aqueous acetic acid adjusted to pH 7.0 with glacial acetic acid at scan rate 100 mV/s. The solutions were deoxygenated for 30 minutes with argon (Ar) prior to use and kept under Ar atmosphere during measurement.

Figure 28:
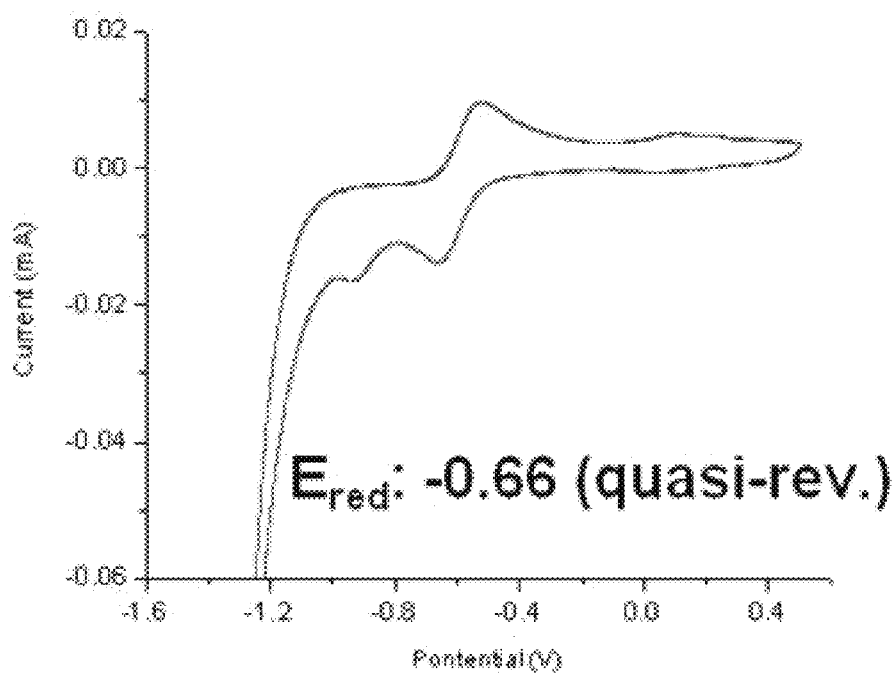
FIGS. 28 and 29 respectively show cyclic voltammograms of Cu-PCB-TE2A and Cu-PCB-DO2A.
Figure 29:
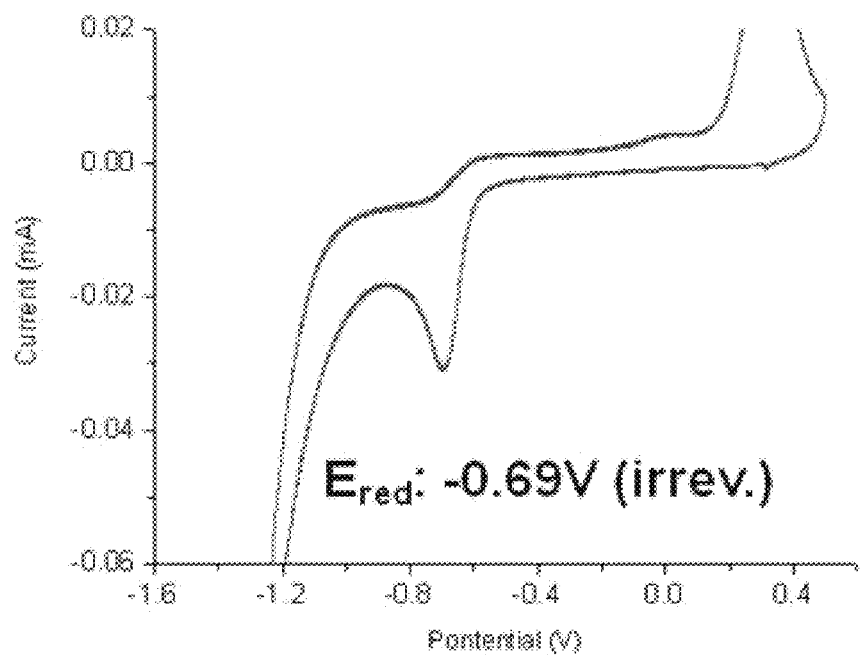

FIGS. 28 and 29 respectively show the cyclic voltammograms of Cu-PCB-TE2A and Cu-PCB-DO2A. Table 5 shows half-lives and reduction potentials of Cu(II) complexes for acid decomplexation. Although the reduction potentials of Cu-PCB-TE2A and Cu-PCB-DO2A are similar at −0.66 and −0.69 V, Cu-PCB-TE2A exhibits quasi-reversible redox reaction whereas Cu-PCB-DO2A exhibits irreversible redox reaction. Thus, the Cu-PCB-TE2A complex is expected to be more stable than Cu-PCB-DO2A complex in in-vivo environments.

TABLE 5

Half-lives and reduction potentials of copper(II) complexes for acid decomplexation

| Complex | 5M HCl, 90° C. | $E_{red}$(V) vs Ag/AgCl |
| --- | --- | --- |
| Cu-PCB-TE2A | 231(2)h | −0.66(qitasi-rev) |
| CU-PCB-DO2A | 144(3)h | −0.69(irrev) |

Example 14

Synthesis of PCB-TE2A-c(RGDyK) and Labeling with Copper-64

[Scheme 14]

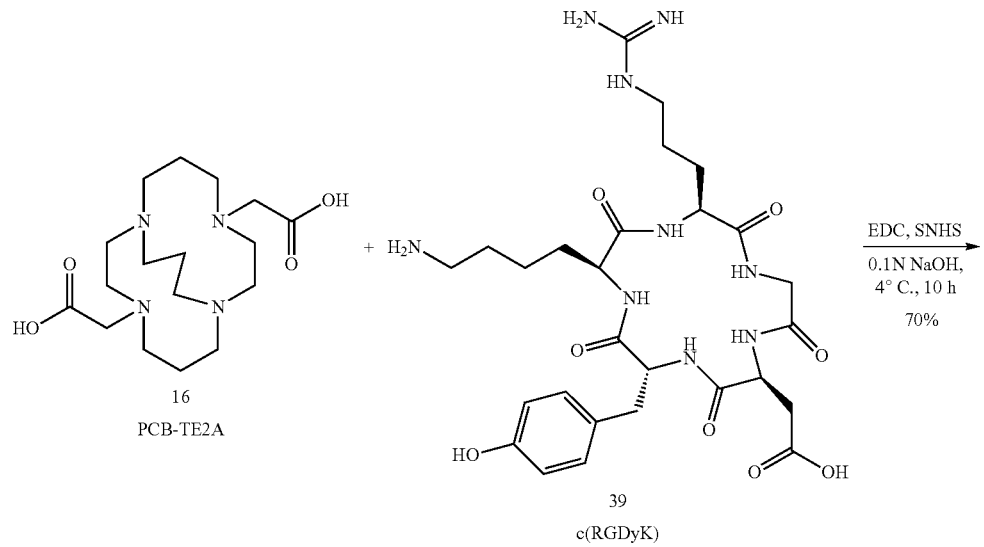

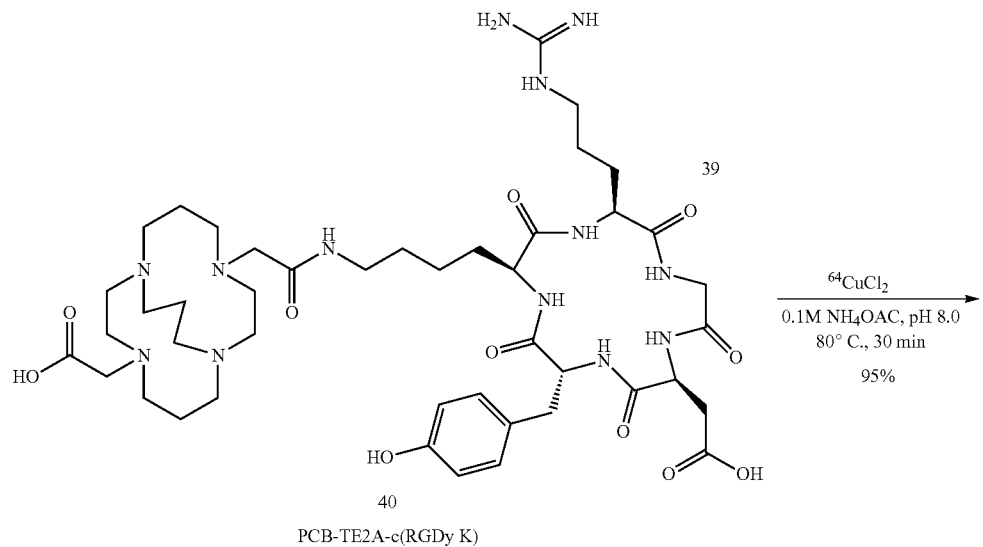

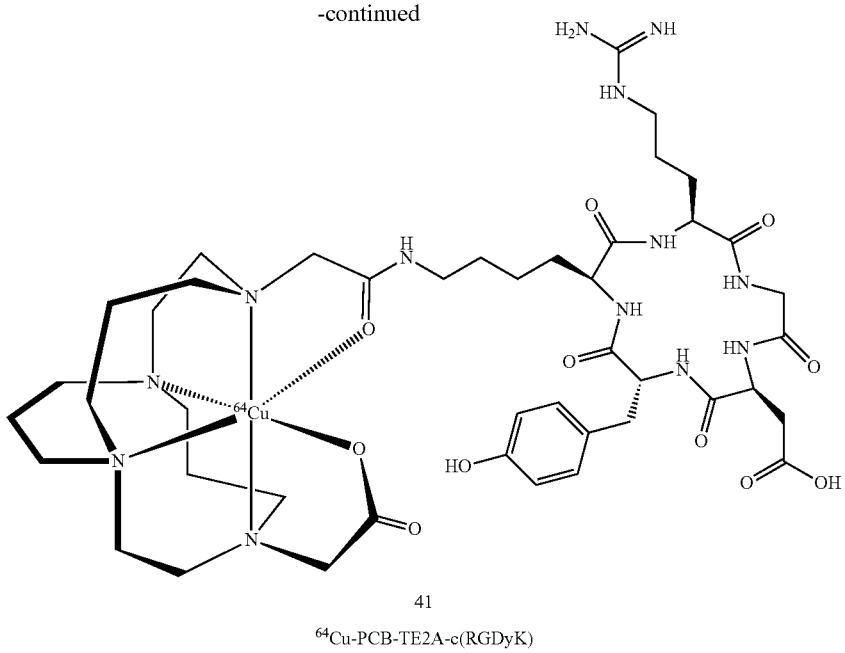

41

$^{64}$Cu-PCB-TE2A-c(RGDyK)

14-a) Synthesis of PCB-TE2A-c(RGDyK) (40)

PCB-TE2A 16 (13.5 mg, 37.9 μmol) prepared in Example 5, EDC (3.6 mg, 18.9 μmol) and SNHS (4.9 mg, 22.7 μmol) were dissolved in water (500 μL) and 0.1 N NaOH (200 μL) was added at 4° C. to adjust pH to 5.5. The reaction mixture was stirred for 30 minutes at 4° C. Cyclic RGDyK peptide 39 (1.42 mg, 2.3 μmol) was dissolved in water (100 μL) and added to the reaction mixture, and the pH was adjusted to 8.5 with 0.1 N NaOH (200 μL). The reaction mixture was incubated overnight at 4° C.

The resulting PCB-TE2A-c(RGDyK) 40 was purified by semipreparative HPLC (Zorbax Agilent Prep-C18; 21.2×100 mm; mobile phase: starting from 95% solvent A (0.1% TFA in water) and 5% solvent B (0.1% TFA in acetonitrile) at 0-2 min to 35% solvent A and 65% solvent B at 32 min; flow rate: 3 mL/min). The fraction containing the PCB-TE2A-c(RGDyK) conjugate was collected and lyophilized to afford the final product as white powder. The PCB-TE2A-c(RGDyK) 40 was obtained in 70% yield with 12.2-minute retention time on analytical HPLC (Vydac TP C18, 3 μm, 4.6×100 mm; flow rate 1 mL/min, with the mobile phase consisting of 0.1% TFA/H$_2$O (solvent A) and 0.1% TFA/acetonitrile (solvent B), and a gradient of 1% B to 70% B in 20 min). The purified PCB-TE2A-c(RGDyK) compound was identified by electrospray mass spectrometry (m/z calculated for $C_{44}H_{72}N_{13}O_{11}$ 958.54, found m/z for [MH]$^+$ and [MH$_2$]$^{+2}$ was 958.5 and 480.0, respectively).

Figure 30:
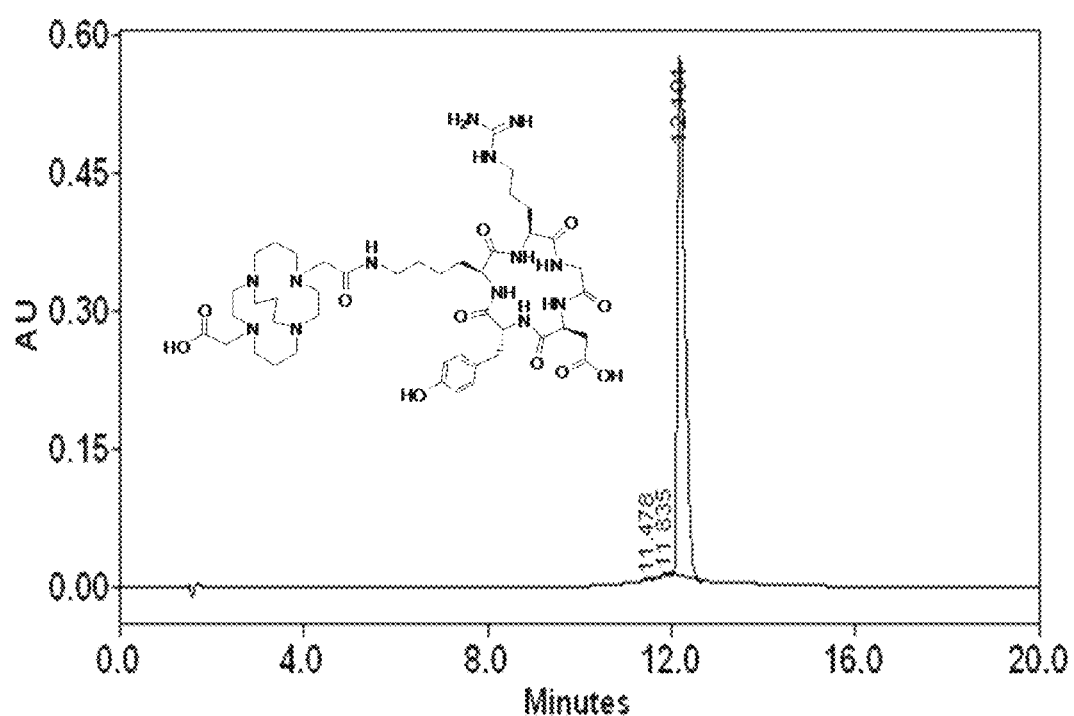
FIG. 30 shows an HPLC chromatogram of PCB-TE2A-c (RGDyK) obtained using an analytical HPLC system, and FIGS. 31 and 32 respectively show mass spectra of PCB-TE2A-c(RGDyK) in positive and negative modes.
Figure 31:
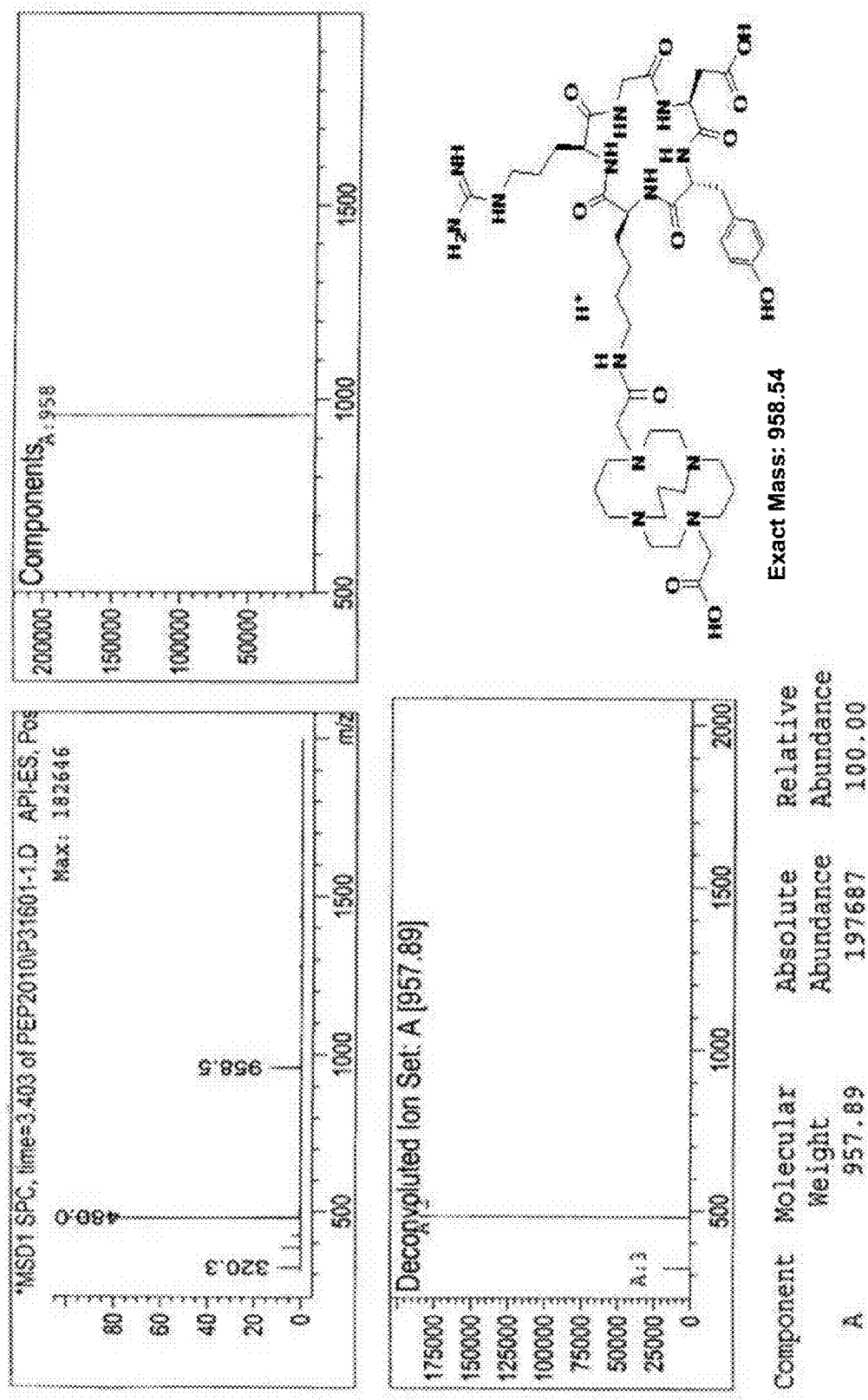
Figure 32:
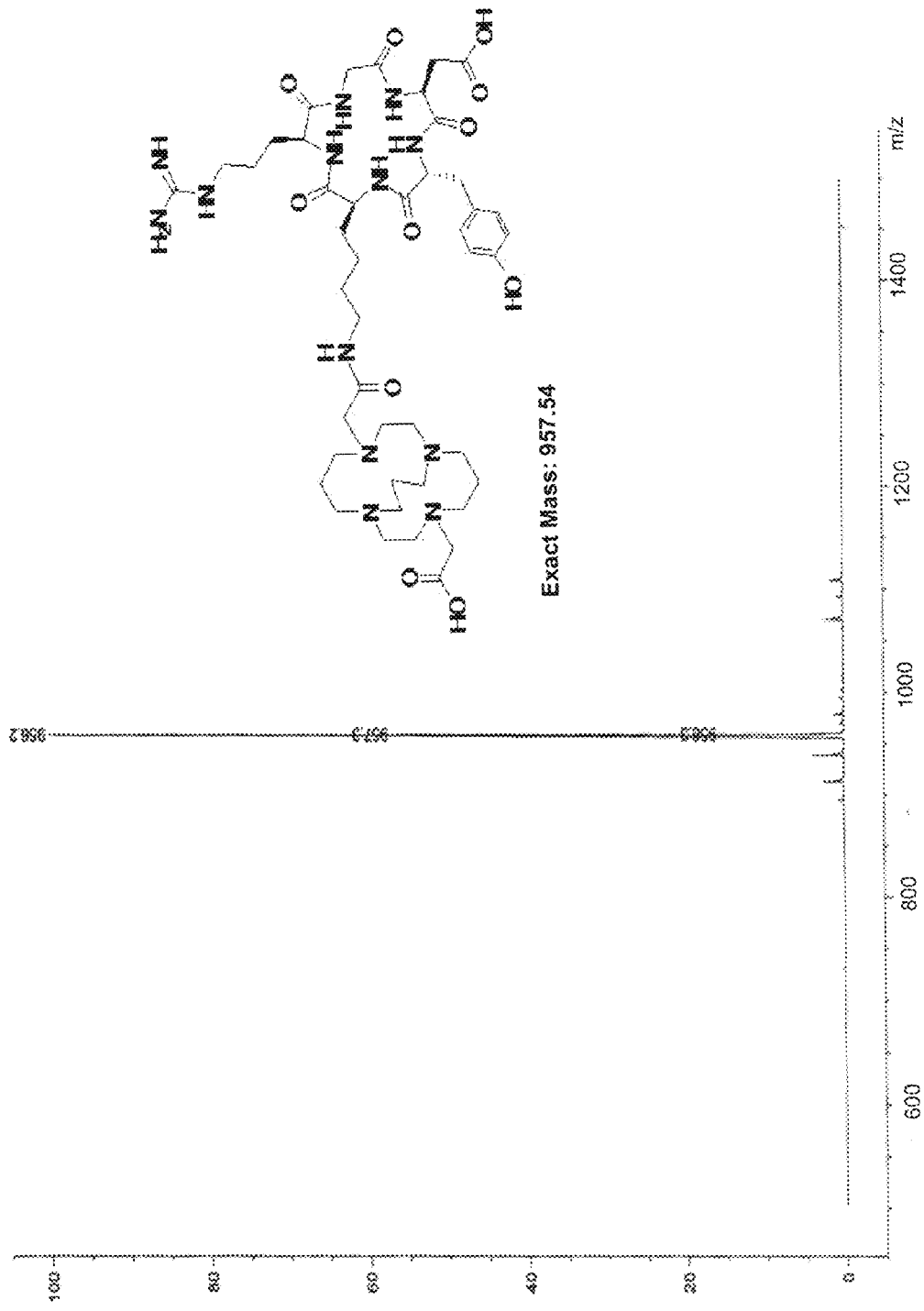

FIG. 30 shows an HPLC chromatogram of PCB-TE2A-c(RGDyK), and FIGS. 31 and 32 respectively show mass spectra of PCB-TE2A-c(RGDyK) in positive and negative modes. It was confirmed that the compound prepared in Example 14-a is pure, purified PCB-TE2A-c(RGDyK) 40.

14-b) Synthesis of $^{64}$Cu-PCB-TE2A-c(RGDyK) (41)

$^{64}$Cu (0.5-2 mCi) in 100 μL 0.1 M NH$_4$OAc buffer (pH 8.0) was added to 5 μg of PCB-TE2A-c(RGDyK) 40 in 100 μL 0.1 M NH$_4$OAc buffer (pH 8.0). The reaction mixture was incubated at 80° C. for 30 minutes. The reaction was monitored by radio-TLC using Whatman MKC18F TLC plates developed with 30:70 10% NH$_4$OAc/methanol ($^{64}$Cu-PCB-TE2A-c(RGDyK) $R_f$=0.9). The $^{64}$Cu-labeled peptide was further purified (if required) by reverse-phase HPLC (RP-HPLC) using Vydac TP C18, 3 μm, 4.6×100 mm column eluted with the mobile phase consisting of 0.1% TFA/H$_2$O (solvent A) and 0.1% TFA/acetonitrile (solvent B), and a gradient of 1% B to 70% B in 20 min at a flow rate of 1 mL/min. $^{64}$Cu-PCB-TE2A-c(RGDyK) 41 (retention time [$t_R$] 13.5 min) was collected in 1-2 mL of HPLC solvent. After evaporating the solvent, the labeled $^{64}$Cu-PCB-TE2A-c(RGDyK) 41 was collected in PBS and passed through a 0.22-μm Millipore filter into a sterilized vial for use in animal experiments.

Figure 33:
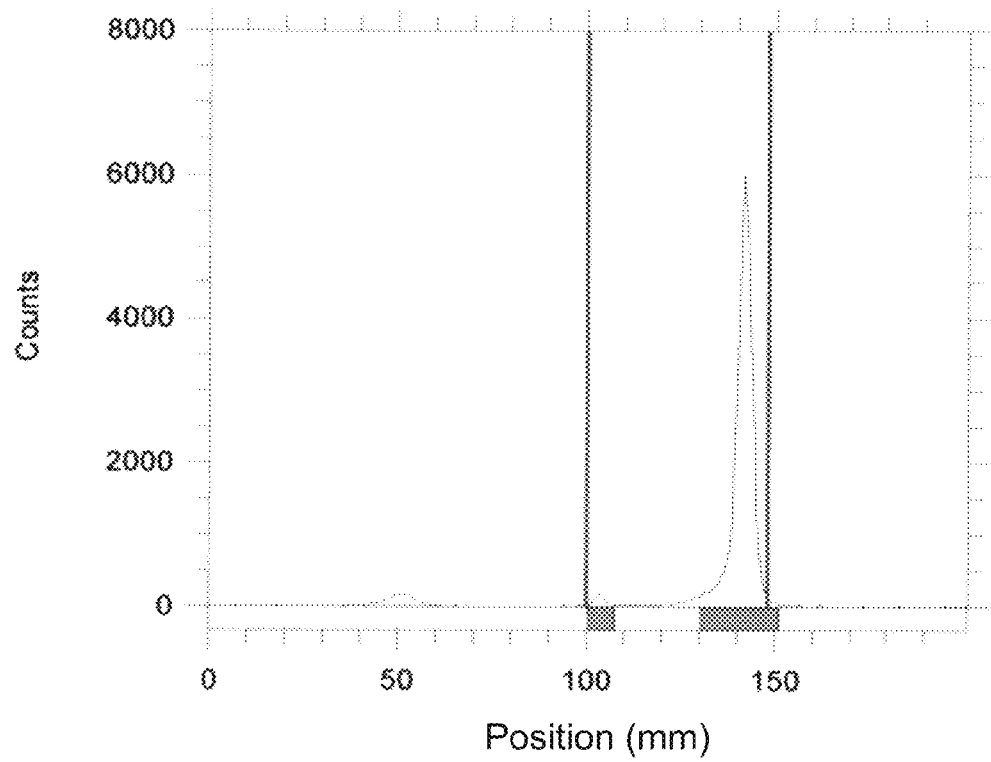
FIG. 33 shows a radio-TLC result of $^{64}$Cu-PCB-TE2A-c (RGDyK)
Figure 34:
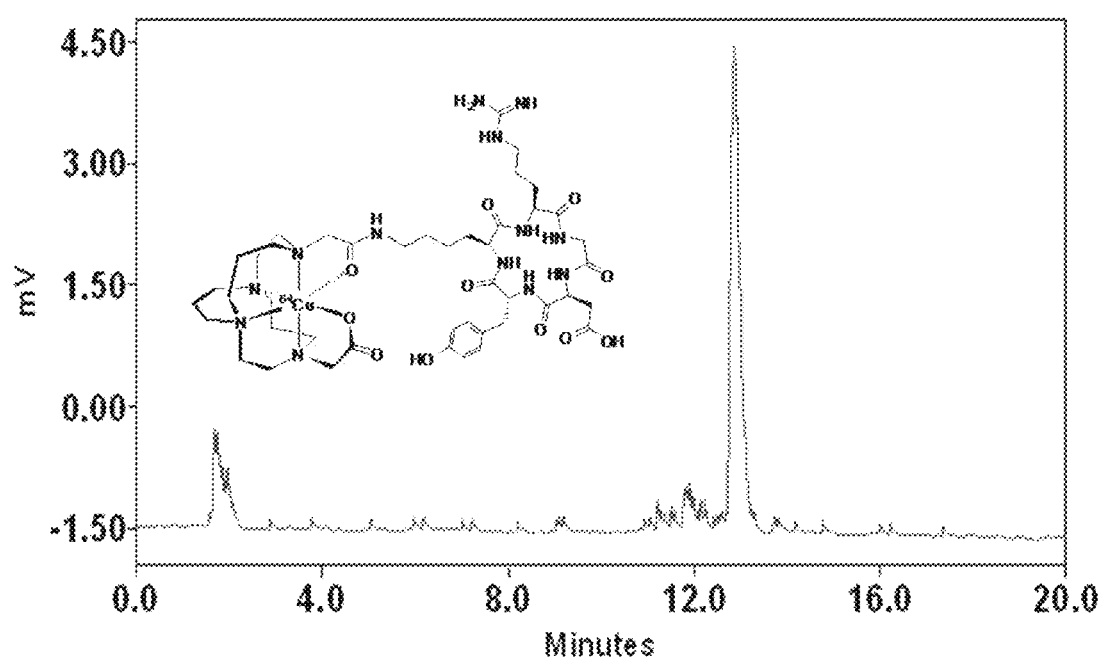
FIG. 34 shows a radio-HPLC chromatogram of $^{64}$Cu-PCB-TE2A-c(RGDyK) obtained using an analytical HPLC system.
Figure 35:
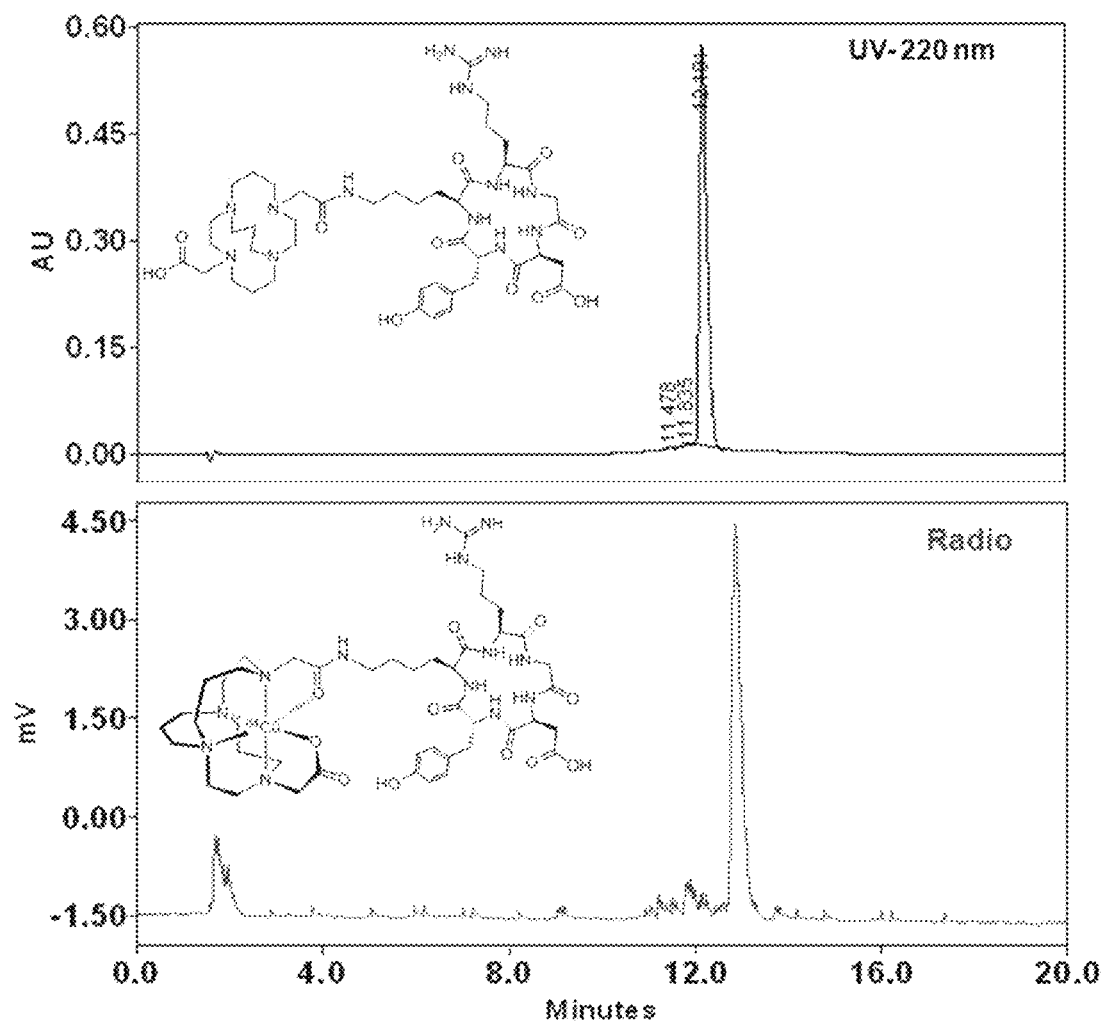
FIG. 35 shows UV- and radio-HPLC chromatograms of PCB-TE2A-c(RGDyK) probed with UV at 220 nm obtained using an analytical HPLC system (black) and $^{64}$Cu-PCB-TE2A-c(RGDyK) (red) obtained using an analytical HPLC system.

FIG. 33 shows a radio-TLC result of $^{64}$Cu-PCB-TE2A-c(RGDyK), and FIG. 34 shows a radio-HPLC chromatogram of $^{64}$Cu-PCB-TE2A-c(RGDyK) obtained using an analytical HPLC system. FIG. 35 shows a chromatogram of PCB-TE2A-c(RGDyK) probed with UV at 220 nm obtained using an analytical HPLC system (top) and a radio-HPLC chromatogram of $^{64}$Cu-PCB-TE2A-c(RGDyK) (bottom).

As seen from FIGS. 33-35, PCB-TE2A-c(RGDyK) was labeled with $^{64}$Cu at a yield of 97% or more, and the similarity of the UV peak of PCB-TE2A-c(RGDyK) and the radioactive peak of $^{64}$Cu-PCB-TE2A-c(RGDyK) confirmed that the labeled radioactive substance was $^{64}$Cu-PCB-TE2A-c(RGDyK).

Test Example 2

MicroPET Imaging

PET scans and image analysis were performed using a microPET R4 rodent model scanner. Imaging studies were carried out on female nude mice bearing 21-day U87MG tumors. $^{64}$Cu-PCB-TE2A-c(RGDyK) (231 µCi) was injected to the mice via tail vein. At 1 hour after the injection, the mice were anesthetized with 1-2% isoflurane, positioned porne, and imaged. The images were reconstructed by the 2-dimensional ordered-subsets expectation maximum (OSEM) algorithm. No correction was necessary for attenuation or scatter correction.

Figure 36:
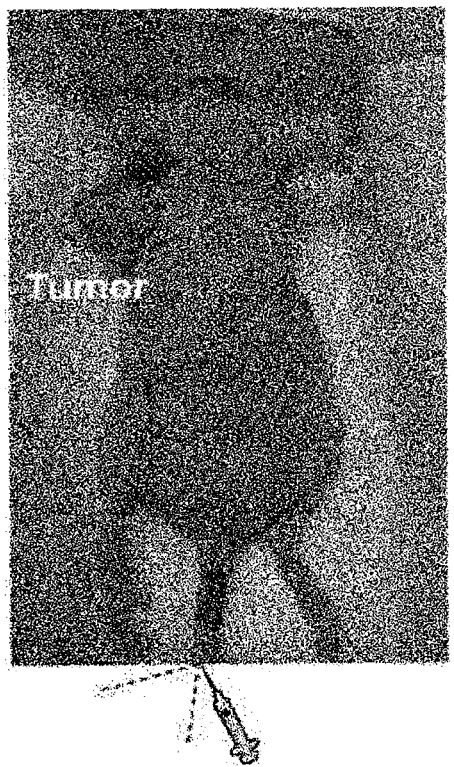
FIG. 36 shows a U87MG tumor model.
Figure 37:
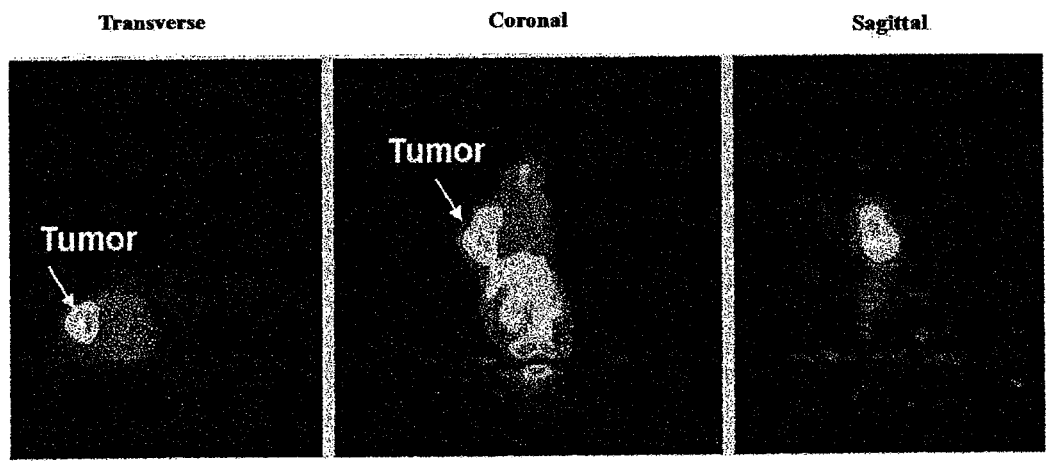
FIG. 37 shows microPET images of a female nude mouse bearing U87MG tumor cells at 1 hour post-injection of $^{64}$Cu-PCB-TE2A-c (RGDyK) (231 μCi)

FIG. 36 shows a U87MG tumor model, and FIG. 37 shows microPET images of a nude mouse bearing U87MG tumor cells at 1 hour post-injection of $^{64}$Cu-PCB-TE2A-c(RGDyK) 41 (231 µCi). It can be seen that radiation uptake is very high in the tumors as compared to other organs. Thus, it was confirmed that $^{64}$Cu-PCB-TE2A-c(RGDyK) can be stably accumulated in vivo in the U87MG model without release of the copper ion, suggesting that PCB-TE2A can be widely used for diagnosis of diseases using disease-specific peptides.

Example 15

Synthesis of PCB-TE2A-NCS-c(RGDyK) and Labeling with Copper-64

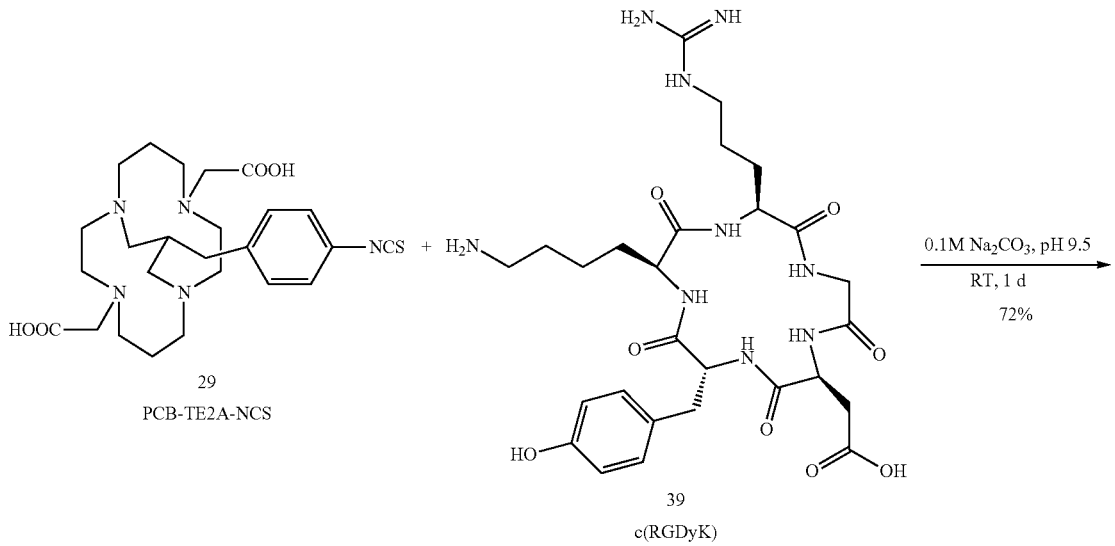

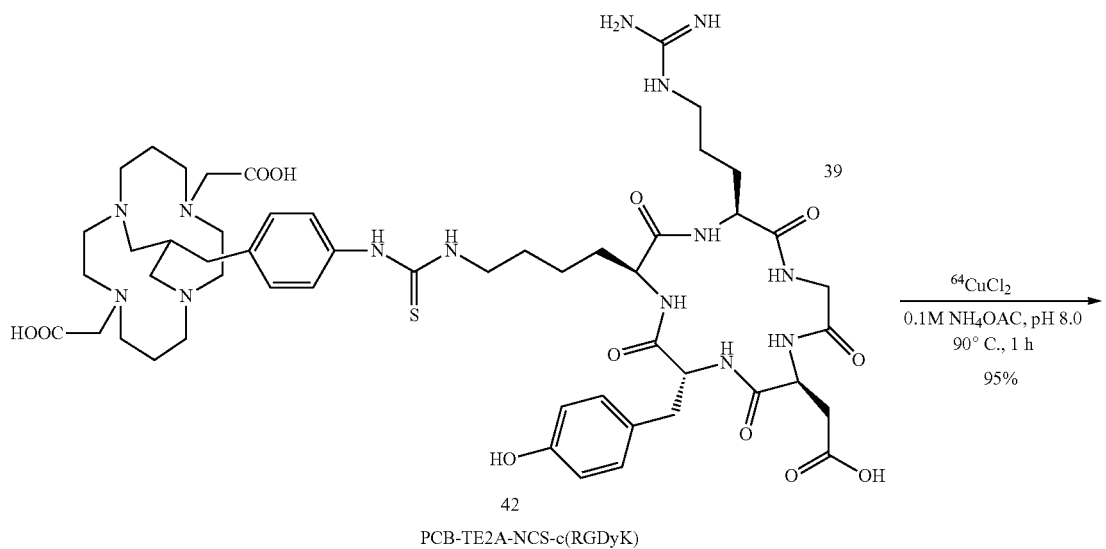

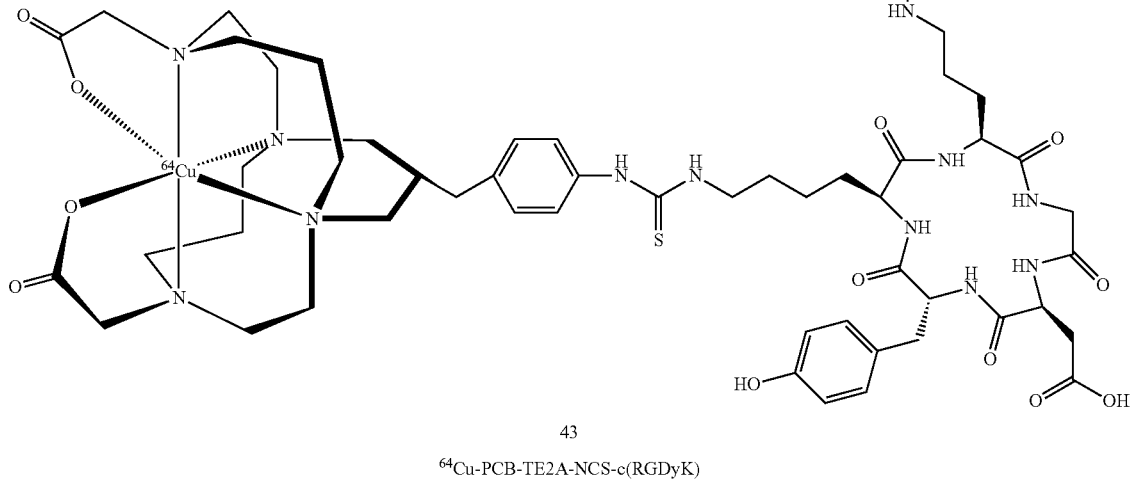

43

$^{64}$Cu-PCB-TE2A-NCS-c(RGDyK)

15-a) Synthesis of PCB-TE2A-NCS-c(RGDyK) (43)

A solution of PCB-TE2A-NCS 29 (8.61 μmol, 4.33 mg) was mixed with c(RGDyK) (2.87 μmol, 1.78 mg) in 0.1 M Na$_2$CO$_3$ buffer (pH 9.5). After stirring at room temperature for 1 day in the dark, the PCB-TE2A-NCS-conjugated c(RGDyK) peptide 39 was isolated by semi-preparative HPLC (Waters μbondapak C18; 10 μm, 7.8×300 mm; flow rate 3 mL/min, with the mobile phase starting from 95% solvent A [0.1% TFA in water] and 5% solvent B [0.1% TFA in acetonitrile at 0-2 min to 35% solvent A and 65% solvent B at 32 min). The fraction containing the PCB-TE2A-NCS-c(RGDyK) 42 conjugate was collected at a retention time of 17.2 minutes. The collected fraction was combined and lyophilized to afford the final product as white powder. The PCB-TE2A-NCS-c(RGDyK) 42 was obtained in 72% yield with 15.7-minute retention time on analytical HPLC (Vydac TP C$_{18}$; 3 μm, 4.6×250 mm; flow rate 1 mL/min, with the mobile phase consisting of 0.1% TFA/H$_2$O (solvent A) and 0.1% TFA/acetonitrile (solvent B), and a gradient of 1% B to 70% B in 20 min). The purified PCB-TE2A-NCS-c(RGDyK) compound was identified by electrospray mass spectrometry (m/z calculated for C$_{52}$H$_{79}$N$_{14}$O$_{12}$S 1123.57, found m/z for [MH]$^+$ and [MH$_2$]$^{+2}$ was 1123.55 and 562.66, respectively).

Figure 38:
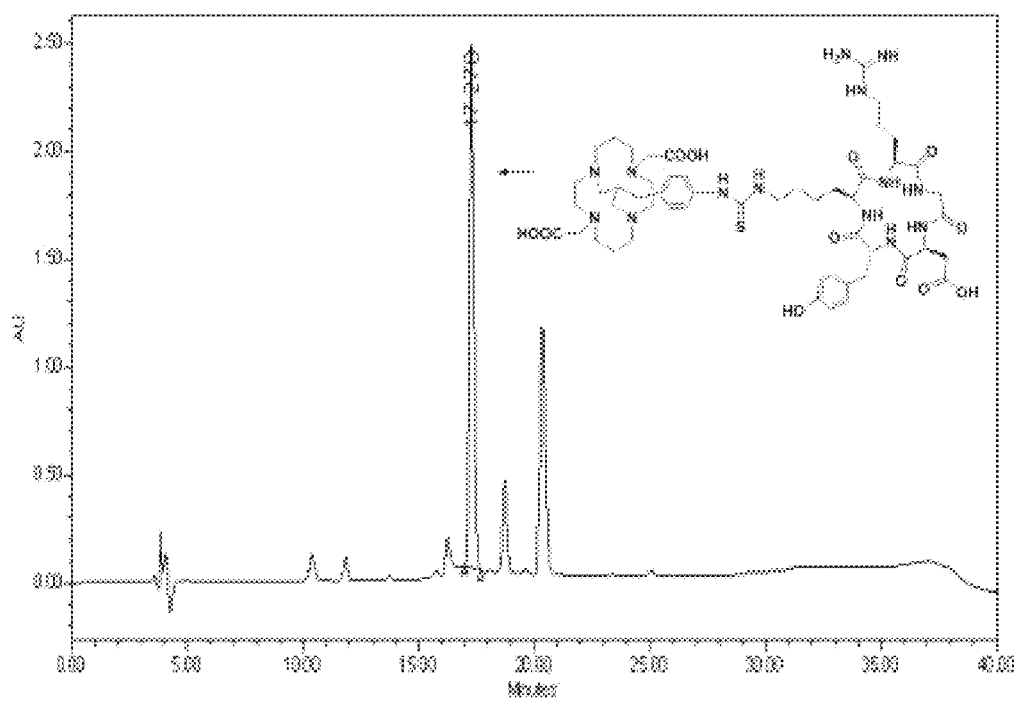
FIG. 38 shows an HPLC chromatogram of PCB-TE2A-NCS-c(RGDyK) obtained using a semipreparative HPLC system.
Figure 39:
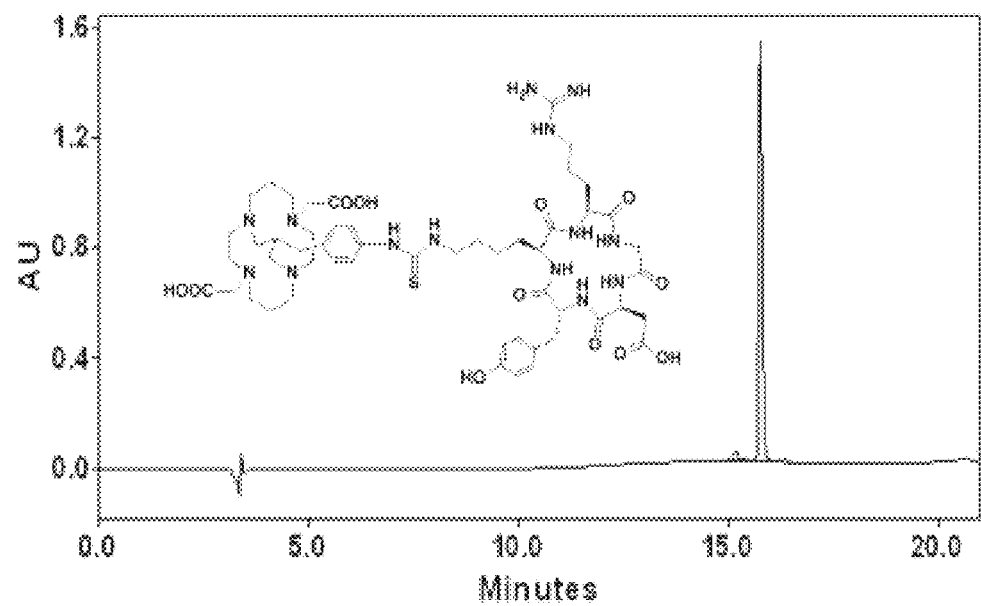
FIG. 39 shows an HPLC chromatogram of purified PCB-TE2A-NCS-c(RGDyK) obtained using an analytical HPLC system, and FIGS. 40 and 41 respectively show mass spectra of PCB-TE2A-NCS-c(RGDyK) in positive and negative modes.
Figure 40:
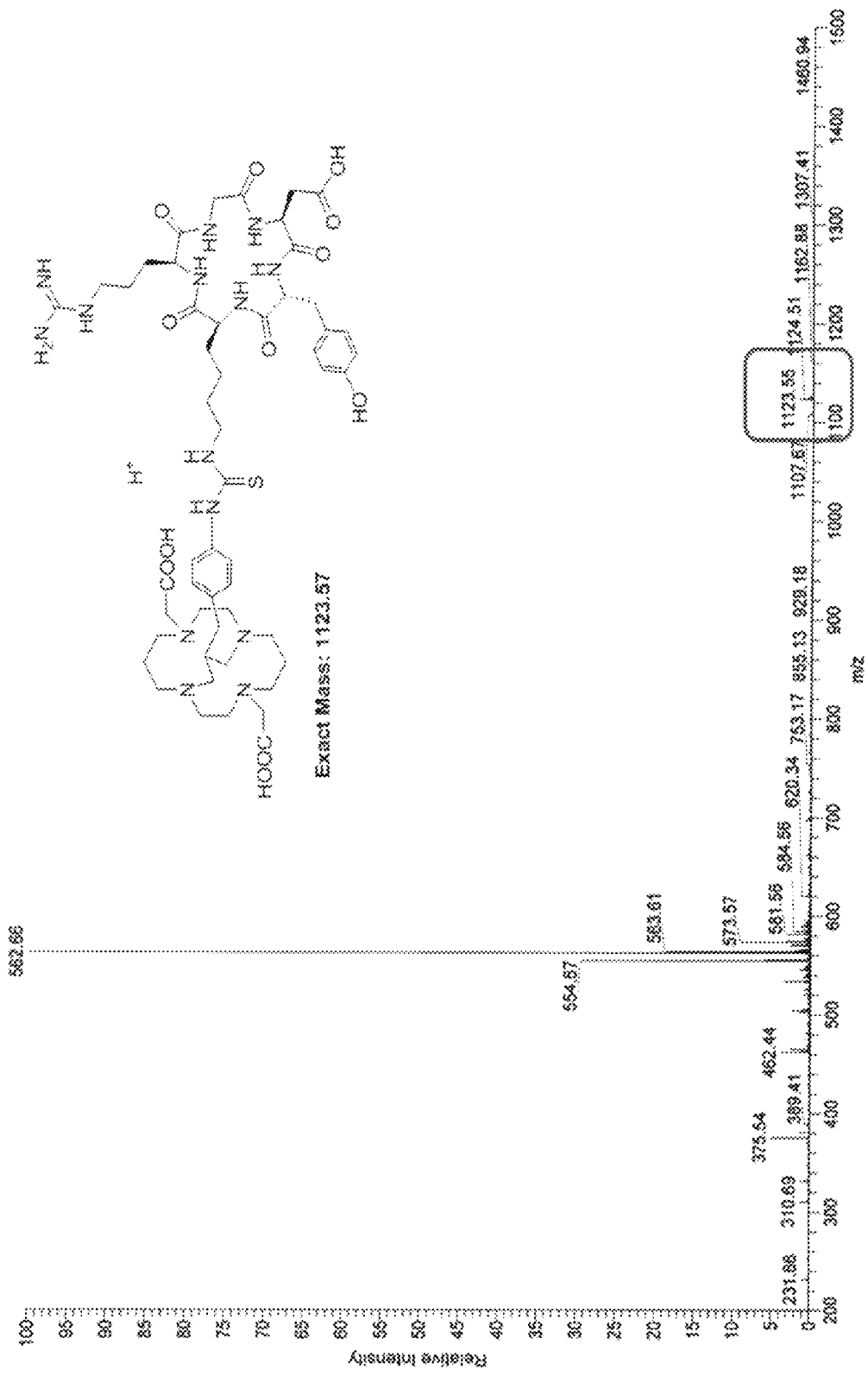
Figure 41:
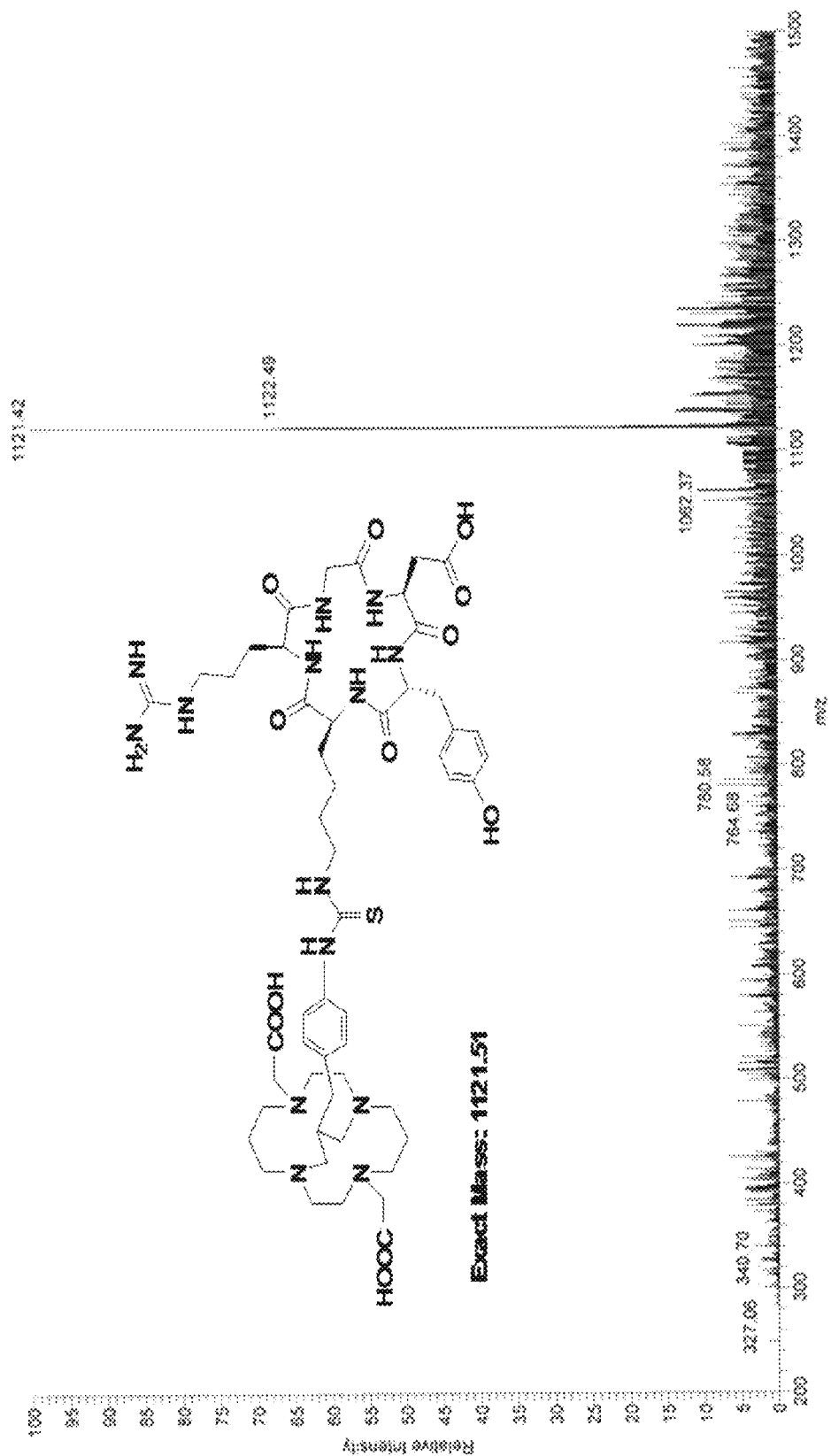

FIG. 38 shows an HPLC chromatogram of PCB-TE2A-NCS-c(RGDyK) obtained using a semipreparative HPLC system, FIG. 39 shows an HPLC chromatogram of purified PCB-TE2A-NCS-c(RGDyK) obtained using an analytical HPLC system, and FIGS. 40 and 41 respectively show mass spectra of PCB-TE2A-NCS-c(RGDyK) in positive and negative modes. It was confirmed that the compound prepared in Example 15-a was cleanly purified PCB-TE2A-NCS-c(RGDyK) 42.

15-b) $^{64}$Cu Radiolabeling of PCB-TE2A-NCS-c(RGDyK) (43)

$^{64}$Cu (0.5-2 mCi) in 100 μL of 0.1 M NH$_4$OAc buffer (pH 8.0) was added to 5 pg of PCB-TE2A-NCS-c(RGDyK) 42 in 100 μL of 0.1 M NH$_4$OAc buffer (pH 8.0). The reaction mixture was incubated at 90° C. for 1 hour. The reaction was monitored by radio-TLC using Whatman MKC18F TLC plates developed with 30:70 10% NH$_4$OAc/methanol ($^{64}$Cu-PCB-TE2A-NCS-c(RGDyK) R$_f$=0.9). The $^{64}$Cu-labeled peptide was further purified (if required) by reverse-phase HPLC (RP-HPLC) using Grace smart RP C18 (5 μm, 4.6×250 mm) column eluted with the mobile phase consisting of 0.1% TFA/H$_2$O (solvent A) and 0.1% TFA/acetonitrile (solvent B), and a gradient of 1% B to 70% B in 20 min at a flow rate of 1 mL/min. $^{64}$Cu-PCB-TE2A-NCS-c(RGDyK) 43 (retention time [t$_R$] 17.1 min) was collected in 1-2 mL of HPLC solvent. After evaporating the solvent, the labeled $^{64}$Cu-PCB-TE2A-NCS-c(RGDyK) 43 was collected in PBS and passed through a 0.22-μm Millipore filter into a sterilized vial for use in animal experiments.

Figure 42:
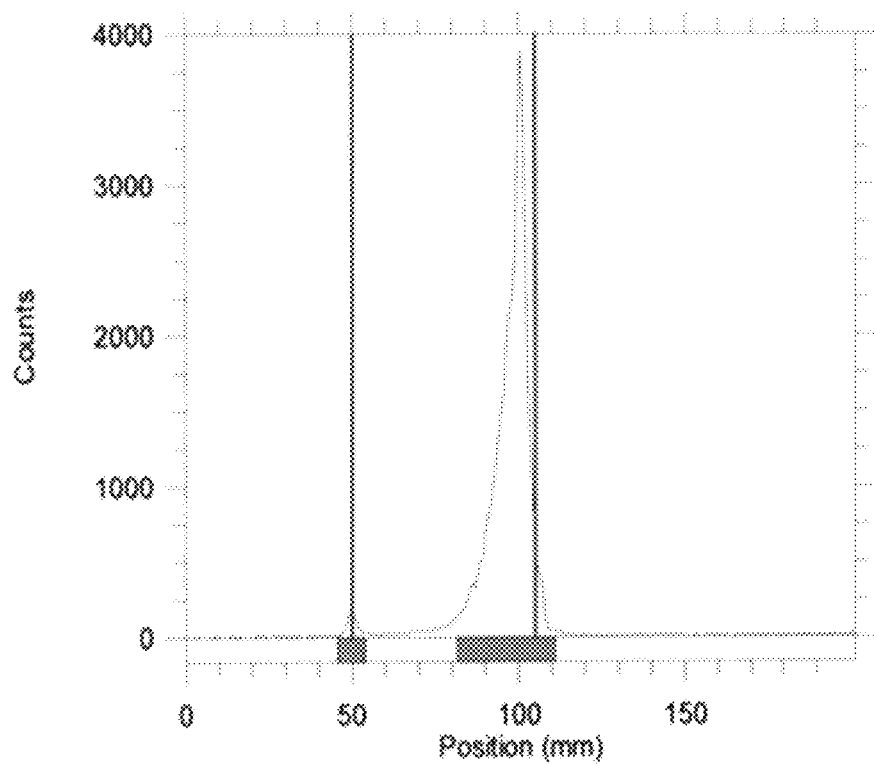
FIG. 42 shows a radio-TLC result of $^{64}$Cu-PCB-TE2A-NCS-c(RGDyK)
Figure 43:
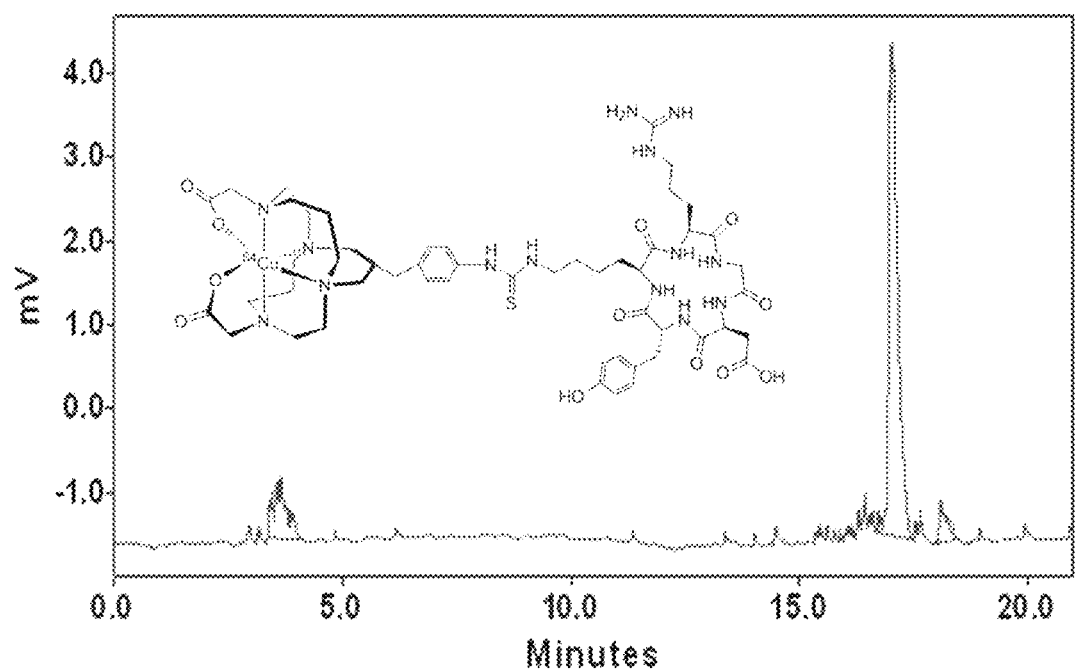
FIG. 43 shows a radio-HPLC chromatogram of $^{64}$Cu-PCB-TE2A-NCS-c(RGDyK) obtained using an analytical HPLC system.
Figure 44:
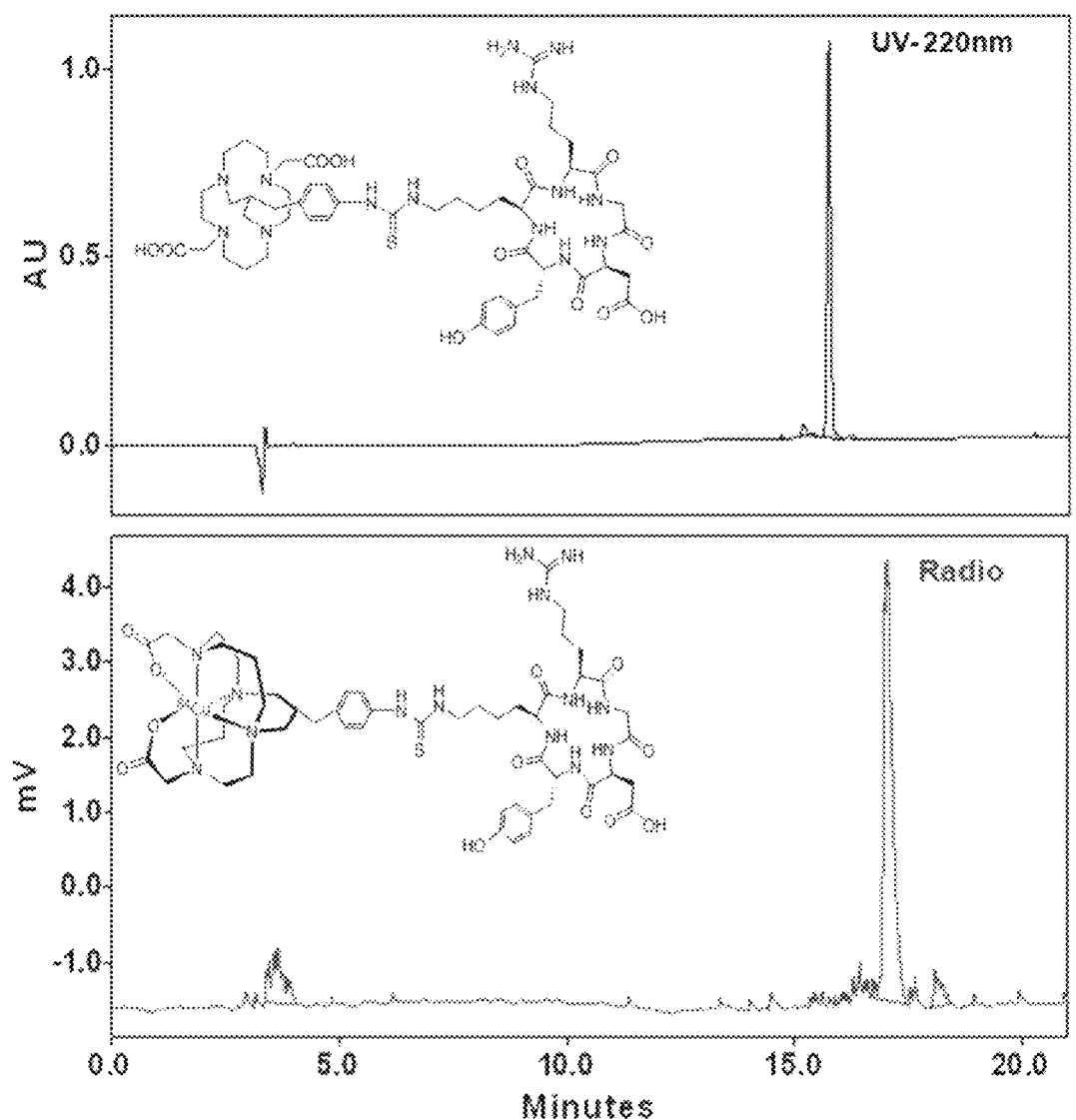
FIG. 44 shows UV- and radio-HPLC chromatograms of PCB-TE2A-NCS-c (RGDyK) probed with UV at 220 nm obtained using an analytical HPLC system (black) and $^{64}$Cu-PCB-TE2A-NCS-c(RGDyK) (red)

FIG. 42 shows a radio-TLC result of $^{64}$Cu-PCB-TE2A-NCS-c(RGDyK), FIG. 43 shows a radio-HPLC chromatogram of $^{64}$Cu-PCB-TE2A-NCS-c(RGDyK) obtained using an analytical HPLC system, and FIG. 44 compares radio-HPLC chromatograms of PCB-TE2A-NCS-c(RGDyK) probed with UV at 220 nm obtained using an analytical HPLC system (top) and $^{64}$Cu-PCB-TE2A-NCS-c(RGDyK) (bottom).

As seen from FIGS. 42-44, it was confirmed that PCB-TE2A-NCS-c(RGDyK) was labeled with $^{64}$Cu at a high yield of 97% or more. The HPLC analysis revealed pure $^{64}$Cu-PCB-TE2A-NCS-c(RGDyK) without degradation of the peptide. Further, the comparison of HPLC retention time confirmed that the $^{64}$Cu-labeled compound is $^{64}$Cu-PCB-TE2A-NCS-c(RGDyK).

Test Example 3

Biodistribution Studies

16 μCi of $^{64}$Cu-PCB-TE2A-NCS-c(RGDyk) in 120 μL of PBS was injected to female nude mice bearing U87MG xenografts via tail vein. One group (n=4) was examined at 1 hour post-injection (pi). Following euthanasia, tissues and organs of interest were removed and weighed, and the radioactivity was measured using a γ-counter. The percent doses per gram (% ID/g) were then calculated by comparison with known standards.

TABLE 6

Biodistribution of $^{64}$Cu-PCB-TE2A-NCS-c(RGDyK) (% ID/g ± SD, n = 4) at 1 hr pi in U87MG tumor bearing nude mice

| Tissue | % ID/g (1 h) |
|---|---|
| Blood | 0.74 ± 0.19 |
| Lung | 2.99 ± 0.37 |
| Muscle | 0.97 ± 0.45 |
| Fat | 3.31 ± 1.65 |
| Bone | 1.30 ± 0.15 |
| Spleen | 2.21 ± 0.02 |
| Kidneys | 8.58 ± 1.32 |
| stomach | 1.21 ± 0.26 |
| intestine | 6.28 ± 0.74 |

TABLE 6-continued

Biodistribution of $^{64}$Cu-PCB-TE2A-NCS-c(RGDyK) (% ID/g ± SD, n = 4) at 1 hr pi in U87MG tumor bearing nude mice

| Tissue | % ID/g (1 h) |
|---|---|
| liver | 5.64 ± 0.75 |
| tumor1 | 4.37 ± 1.93 |
| tumor2 | 5.15 ± 2.10 |

Figure 45:
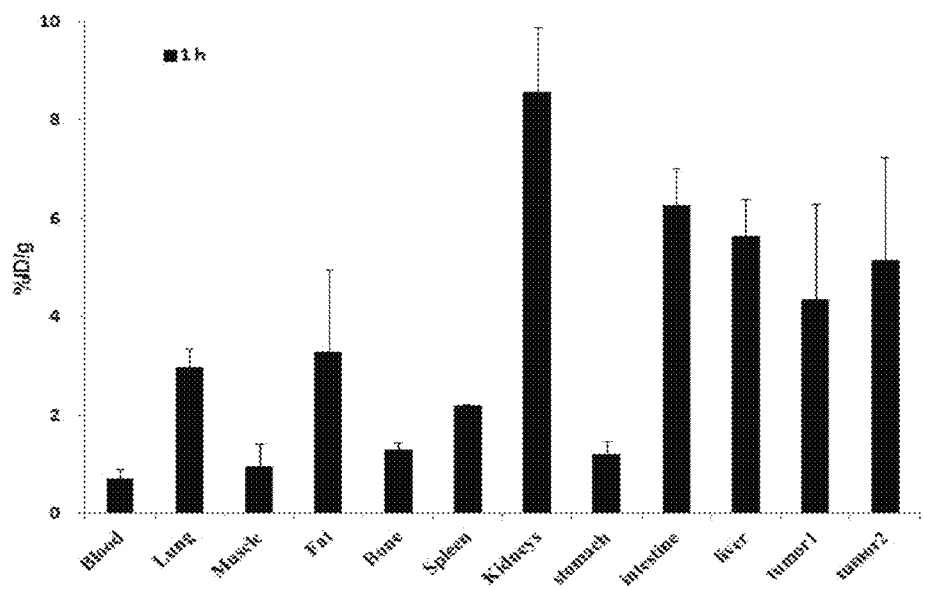
FIG. 45 shows in vivo distribution of $^{64}$Cu-TE2A-NCS-c (RGDyK) in U87MG-transplanted nude mice at 1 hour post-injection (% ID/g±SD, n=4)

Table 6 and FIG. 45 show in vivo distribution of $^{64}$Cu-TE2A-NCS-c(RGDyK) in U87MG-transplanted nude mice at 1 hour post-injection (% ID/g±SD, n=4). It can be seen that uptake of $^{64}$Cu-TE2A-NCS-c(RGDyK) in the tumor was high with a mean of 4.76% ID/g, 6.4 times and 4.9 times that of the blood and muscle, respectively.

Example 16

Conjugation of PCB-TE2A-NCS with Trastuzumab and Labeling with Copper-64

[Scheme 16]

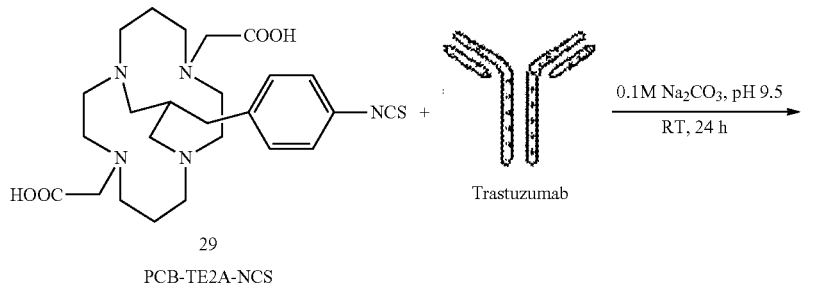

29
PCB-TE2A-NCS

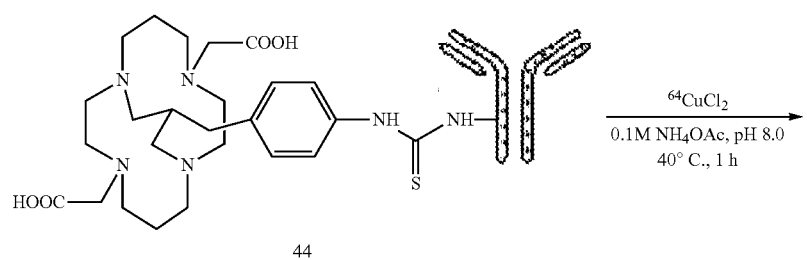

44
PCB-TE2A-NCS-Trastuzumab

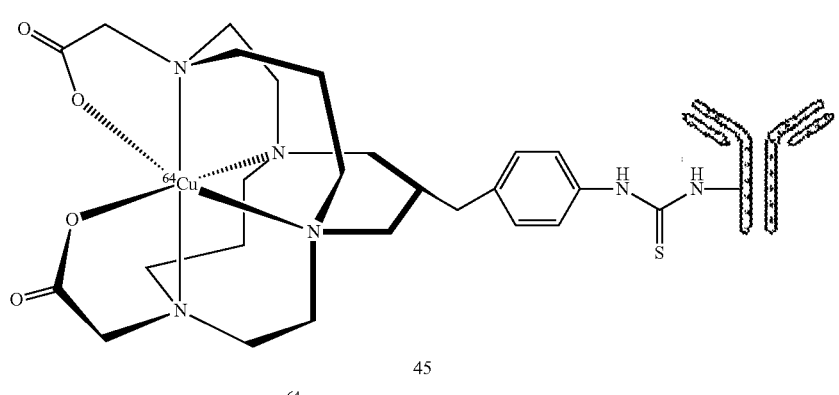

45
$^{64}$Cu-PCB-TE2A-NCS-Tratuzumab

16-a) Conjugation of PCB-TE2A-NCS with trastuzumab (44)

PCB-TE2A-NCS 29 (0.55 mg) in 0.1 M $Na_2CO_3$ (pH 9.5, 1 mL) was added to trastuzumab (4 mg). The resulting solution was gently agitated at room temperature for 24 hours. The following day, this solution was placed on Centricon YM-50 and rotated to reduce the volume. PBS (pH 7.2, 3×2 mL) was added to the remaining solution of the PCB-TE2A-NCS-trastuzumab conjugate 44, followed by centrifugation in order to remove unreacted ligand. After adding PBS (2 mL), the purified antibody conjugate was stored at −20° C. The purity of the PCB-TE2A-NCS-trastuzumab conjugate 44 was determined by size-exclusion HPLC (Bio Silect SEC 250-5 300×7.8 mm; flow rate 1 mL/min, with PBS (pH=7.4) as isocratic mobile phase).

Figure 46:
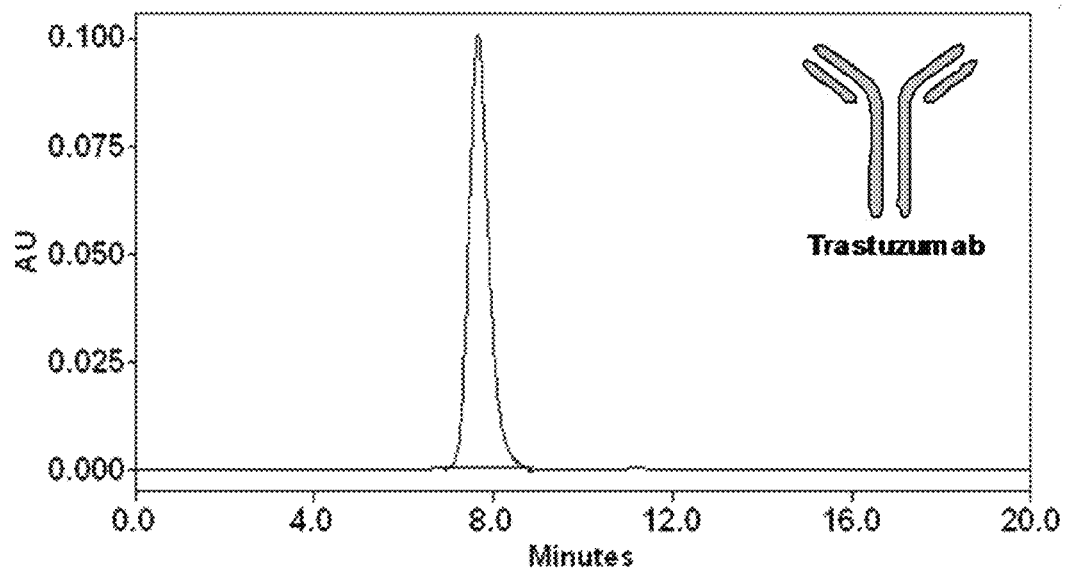
FIG. 46 shows an SE-HPLC chromatogram of trastuzumab probed with UV at 280 nm obtained using an SE-HPLC system.
Figure 47:
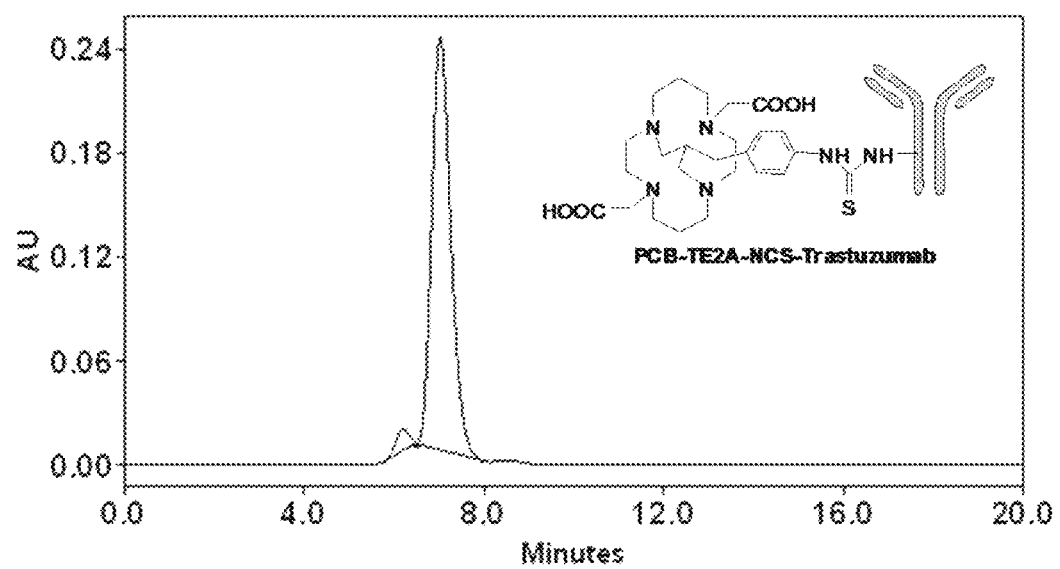
FIG. 47 shows an SE-HPLC chromatogram of PCB-TE2A-NCS-trastuzumab probed with UV at 280 nm obtained using an SE-HPLC system, and FIG. 48 compares SE-HPLC chromatograms of trastuzumab probed with UV at 280 nm obtained using an SE-HPLC system(black) and PCB-TE2A-NCS-trastuzumab (red)
Figure 48:
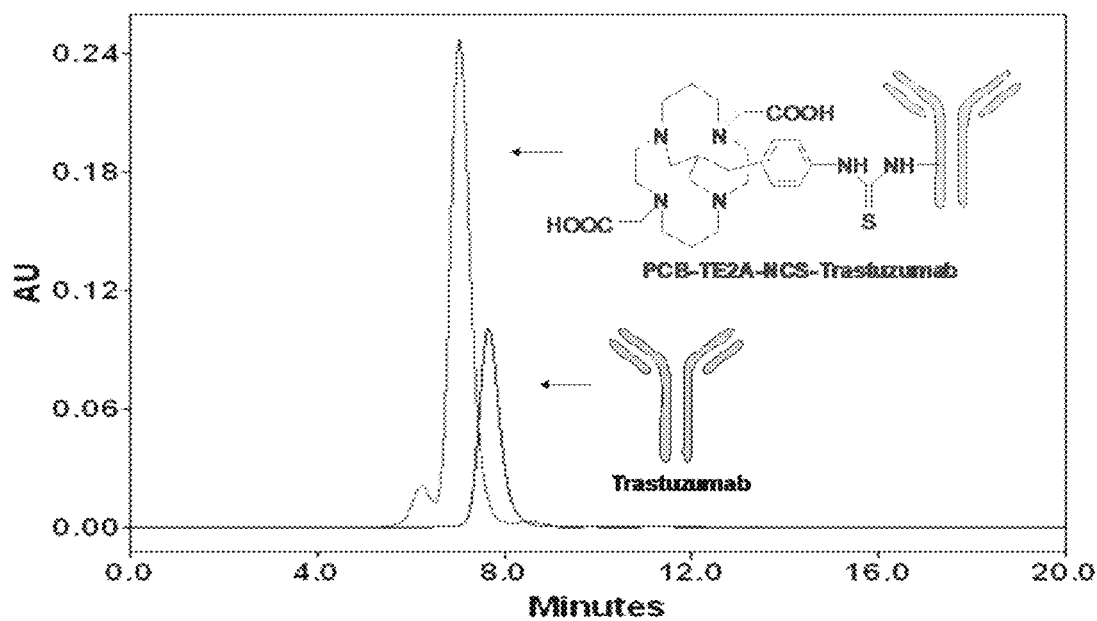

FIG. 46 shows an SE-HPLC chromatogram of trastuzumab probed with UV at 280 nm obtained using an SE-HPLC system, FIG. 47 shows an SE-HPLC chromatogram of PCB-TE2A-NCS-trastuzumab probed with UV at 280 nm obtained using an SE-HPLC system, and FIG. 48 compares SE-HPLC chromatograms of trastuzumab probed with UV at 280 nm obtained using an SE-HPLC system (black) and PCB-TE2A-NCS-trastuzumab (red). It was confirmed that the compound prepared in Example 16-a was PCB-TE2A-NCS-trastuzumab 44.

16-b) $^{64}$Cu radiolabeling of PCB-TE2A-NCS-trastuzumab (45)

$^{64}$Cu (0.5-2 mCi) in 100 μL of 0.1 M $NH_4OAC$ buffer (pH 8.0) was added to 50 μg of PCB-TE2A-NCS-trastuzumab 44 in 100 μL of 0.1 M $NH_4OAC$ buffer (pH 8.0). The reaction mixture was incubated at 40° C. for 1 hour. The $^{64}$Cu-labeled PCB-TE2A-NCS-trastuzumab 45 was further purified by centrifugation using Centricon YM-50. Radiochemical purity was determined by instant thin layer chromatography (ITLC-SG, developed with saline).

Figure 49:
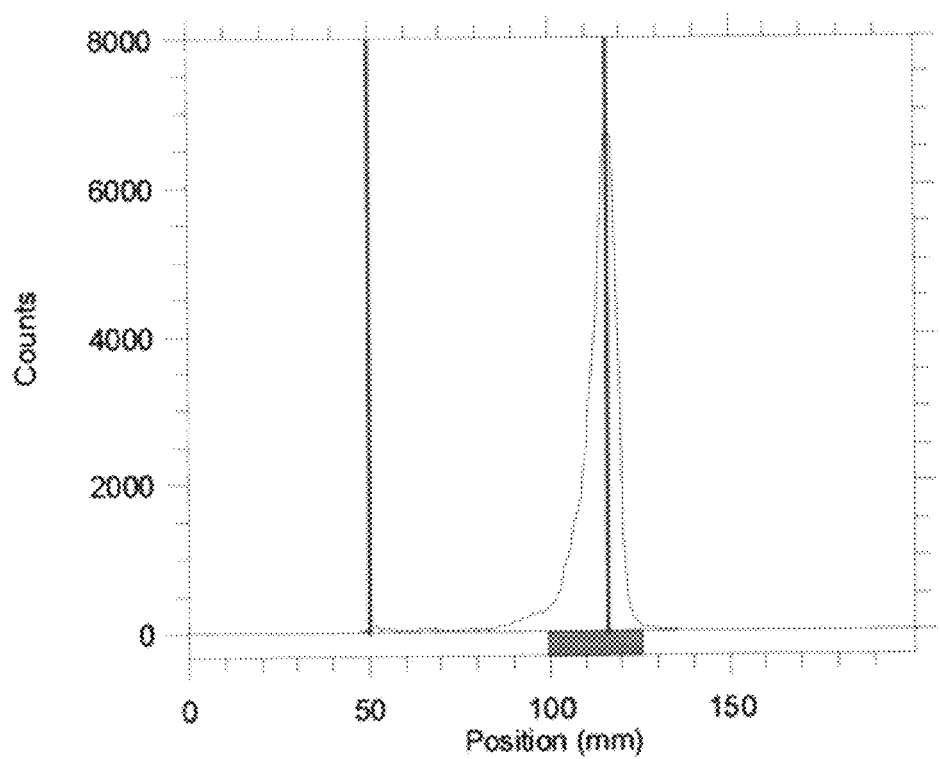
FIG. 49 shows a radio-ITLC result of $^{64}$CuCl$_2$.
Figure 50:
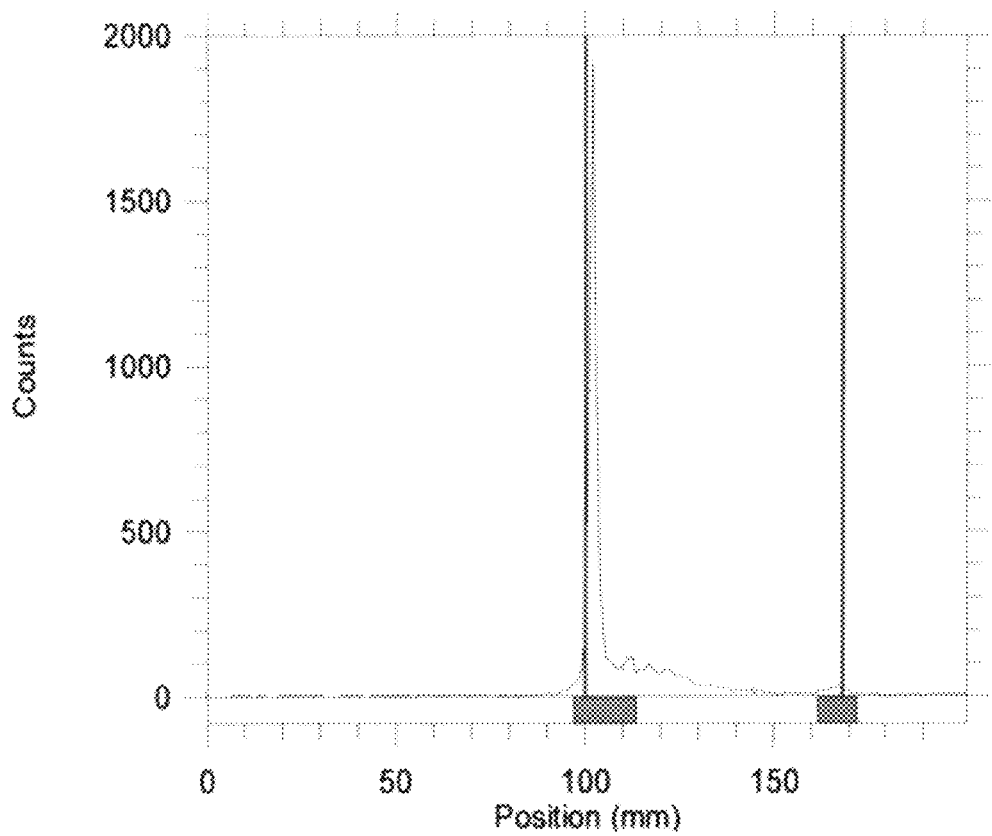
FIG. 50 shows a radio-ITLC result of $^{64}$Cu-PCB-TE2A-NCS-trastuzumab.

FIG. 49 shows a radio-ITLC result of $^{64}CuCl_2$, and FIG. 50 shows a radio-ITLC result of $^{64}$Cu-PCB-TE2A-NCS-trastuzumab. It was confirmed that PCB-TE2A-NCS-trastuzumab was labeled with $^{64}$Cu at a yield of 96% or higher.

Example 17

Conjugation of PCB-TE2A with Trastuzumab and Labeling with Copper-64

[Scheme 17]

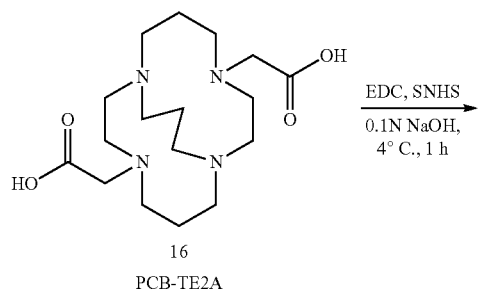

16
PCB-TE2A

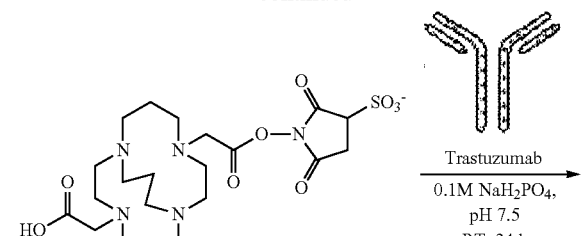

46
PCB-TE2A-OSSu

47
PCB-TE2A-Trastuzumab

48
$^{64}$Cu-PCB-TE2A-Trastuzumab

17-a) Conjugation of PCB-TE2A with trastuzumab (47)

PCB-TE2A 16 was conjugated with trastuzumab using N-hydroxysulfosuccinimidyl PCB-TE2A 46 (TETA-OSSu). A solution of 13.5 mg (37.8 μmol) of PCB-TE2A in 400 μL of $H_2O$ was adjusted to pH 5.5 with 0.1 N NaOH at 4° C. To this solution were added sulfo-NHS (8.2 mg, 37.8 μmol) and EDC (0.72 mg, 3.8 μmol). The reaction mixture was stirred at 4° C. for 1 hour, after which it was used immediately, without purification, to prepare the PCB-TE2A-conjugated antibody. The pH of the PCB-TE2A-OSSu solution 46 was adjusted to 7.5 by addition of 0.1 M $Na_2HPO_4$, pH 7.5. Trastuzumab (4 mg) was added to the stirred solution of the PCB-TE2A-OSSu in 0.1 M $Na_2HPO_4$, pH 7.5. The resulting solution was gently agitated at room temperature for 24 hours. The following day, this solution was placed on Centricon YM-50 and rotated to reduce the volume. PBS (pH 7.2, 3×2 mL) was added to the remaining solution of the PCB-TE2A-trastuzumab conjugate 47, followed by centrifugation in order to remove unreacted ligand. After adding PBS (2.00 mL), the purified conjugate antibody was stored at −20° C. The purity of the resulting PCB-TE2A-NCS-trastuzumab conjugate was determined by size-exclusion HPLC (Bio Silect SEC 250-5 300×7.8 mm; flow rate 1 mL/min, with PBS (pH=7.4) as isocratic mobile phase).

Figure 51:
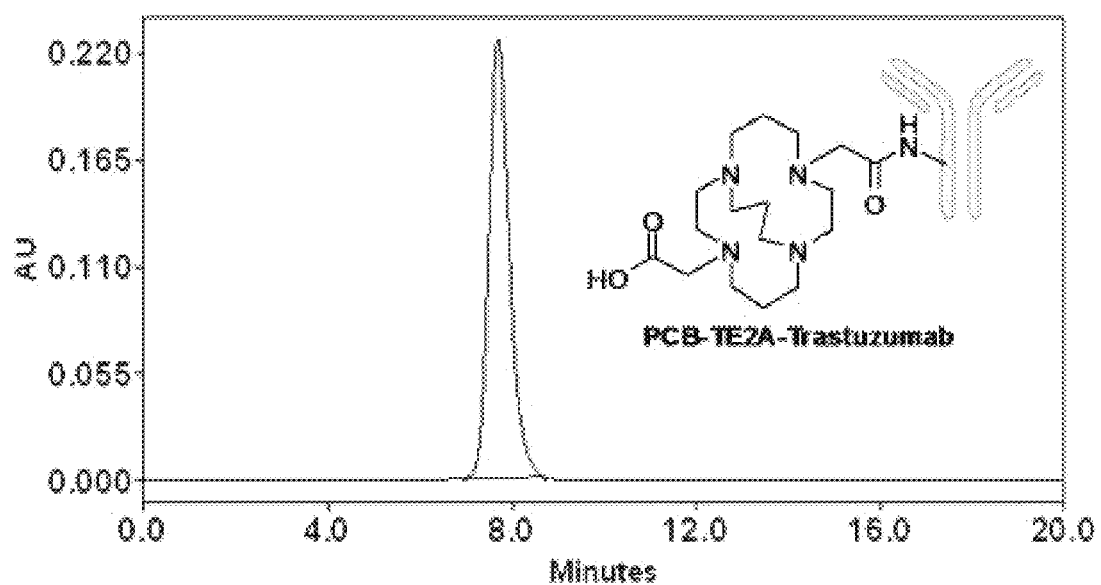
FIG. 51 shows an SE-HPLC chromatogram of PCB-TE2A-trastuzumab probed with UV at 280 nm obtained using an SE-HPLC system.

FIG. 51 shows an SE-HPLC chromatogram of PCB-TE2A-trastuzumab probed with UV at 280 nm obtained using an SE-HPLC system. It was confirmed that the compound prepared in Example 17-a was PCB-TE2A-trastuzumab 47.

17-b) $^{64}$Cu Radiolabeling of PCB-TE2A-trastuzumab (48)

$^{64}$Cu (0.5-2 mCi) in 100 μL of 0.1 M NH$_4$OAc buffer (pH 8.0) was added to 50 μg of PCB-TE2A-trastuzumab 47 in 100 μL of 0.1 M NH$_4$OAC buffer (pH 8.0). The reaction mixture was incubated at 40° C. for 1 hour. The $^{64}$Cu-labeled PCB-TE2A-trastuzumab 48 was further purified by centrifugation using Centricon YM-50. Radiochemical purity was determined by instant thin layer chromatography (ITLC-SG, developed with saline).

Figure 52:
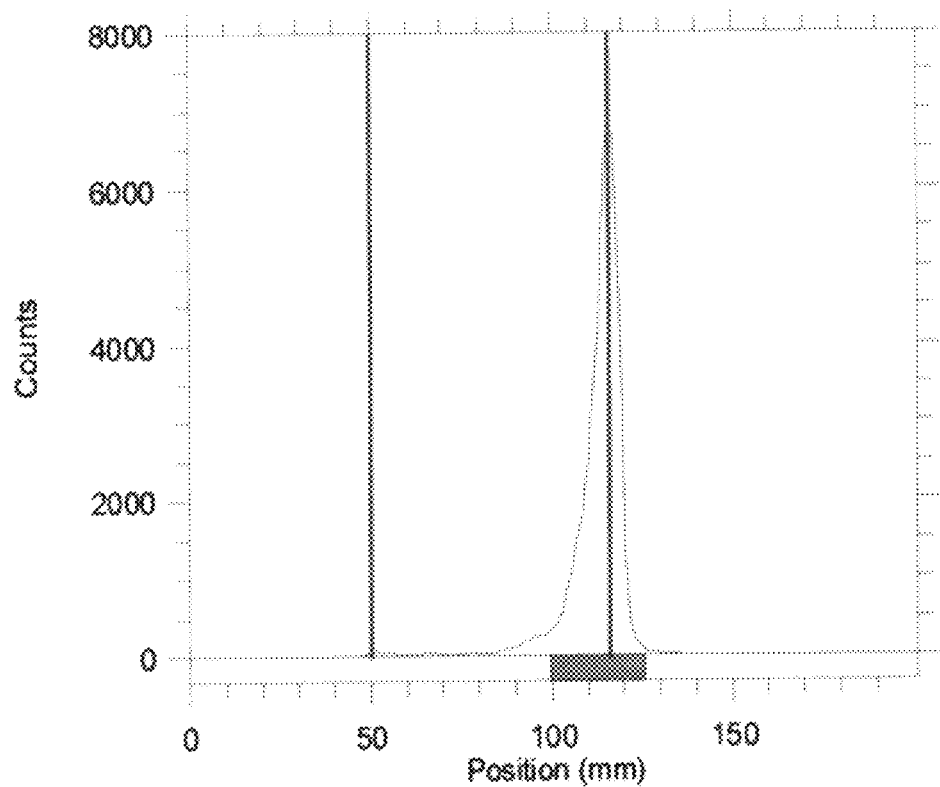
FIG. 52 shows a radio-ITLC result of $^{64}$CuCl$_2$.
Figure 53:
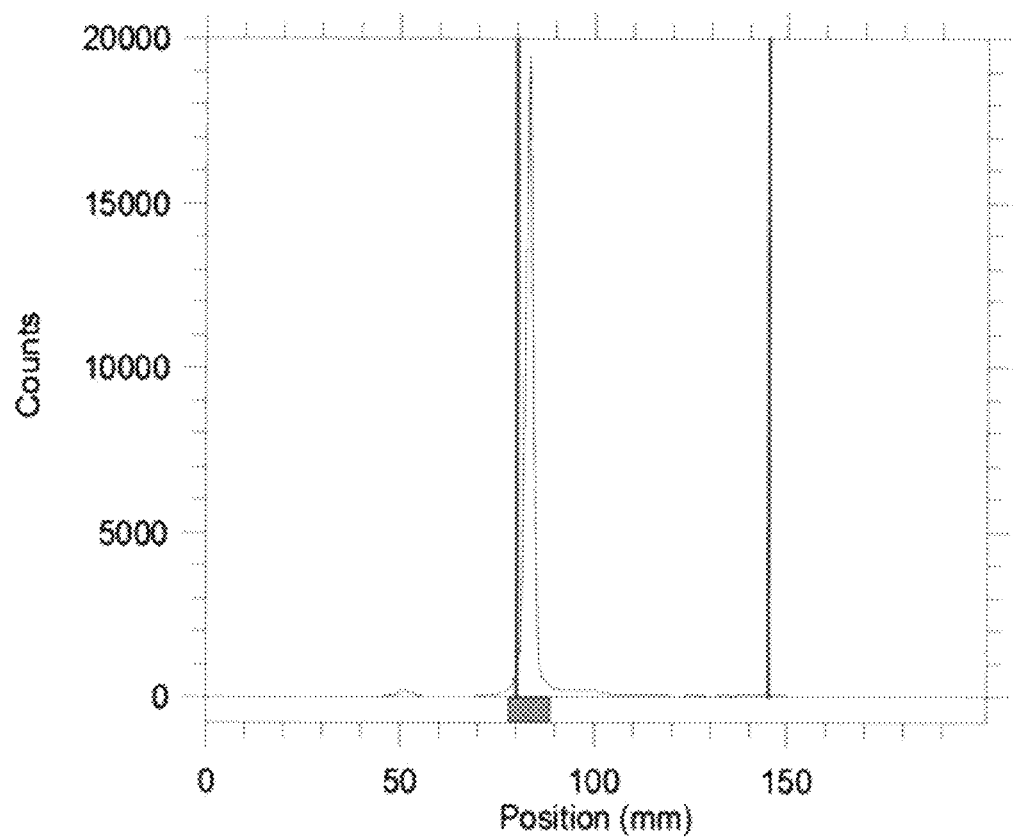
FIG. 53 shows a radio-ITLC result of $^{64}$Cu-PCB-TE2A-trastuzumab.

FIG. 52 shows a radio-ITLC result of $^{64}$CuCl$_2$, and FIG. 53 shows a radio-ITLC result of $^{64}$Cu-PCB-TE2A-trastuzumab. It was confirmed that PCB-TE2A-trastuzumab was labeled with $^{64}$Cu with 100% purity.

Test Example 4

Biodistribution Studies

17 μCi of $^{64}$Cu-PCB-TE2A-trastuzumab 48 in 120 μL of PBS were injected to a female nude mouse bearing U87MG tumors via tail vein. Following euthanasia, tissues and organs of interest were removed and weighed, and the radioactivity was measured using a γ-counter.

TABLE 7

Biodistribution of $^{64}$Cu-PCB-TE2A-trastuzumab (% ID/g ± SD, n = 1) at 48 hr pi in tumor bearing nude mouse

| Tissue | dose/weight (48 h) |
|---|---|
| Blood | 2051.37 |
| Lung | 7002.61 |
| Muscle | 1768.97 |
| Fat | 10053.33 |
| Bone | 2616.67 |
| Spleen | 4378.74 |
| Kidneys | 7526.09 |
| stomach | 3053.99 |
| intestine | 2795.52 |
| liver | 12202.76 |
| tumor1 | 6802.08 |
| tumor2 | 4594.51 |

Figure 54:
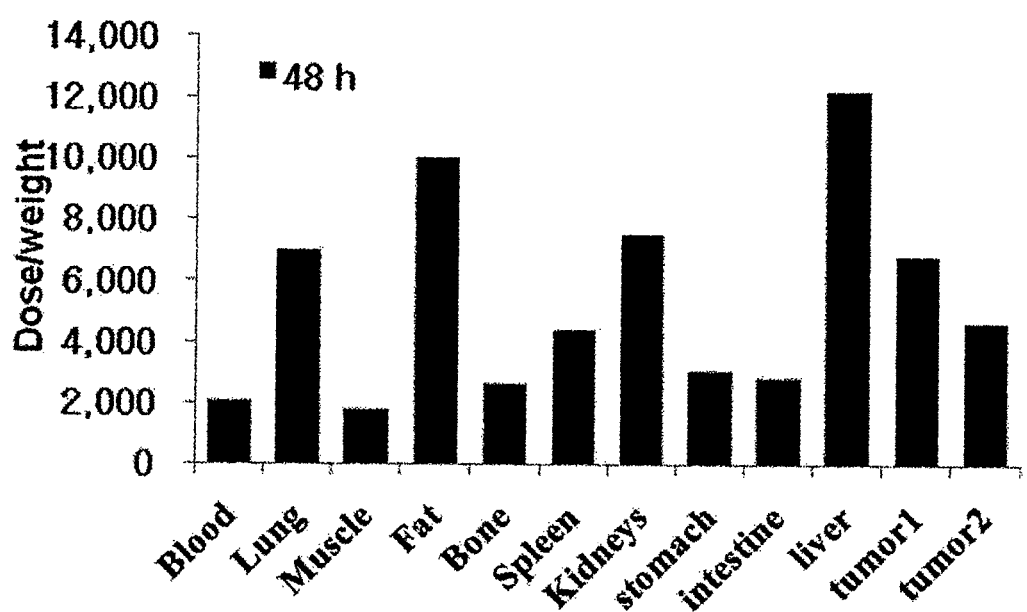
FIG. 54 shows in vivo distribution of $^{64}$Cu-PCB-TE2A-trastuzumab in an NIH3T6.7-transplanted nude mouse at 48 hours post-injection (administration dose/weight, n=1)

Table 7 and FIG. 54 show in vivo distribution of $^{64}$Cu-PCB-TE2A-trastuzumab in an the tumor-transplanted nude mouse at 48 hours post-injection (activity/weight, n=1). It can be seen that $^{64}$Cu-PCB-TE2A-trastuzumab was selectively accumulated in the tumors without release of $^{64}$Cu, with the uptake of $^{64}$Cu-PCB-TE2A-trastuzumab in the tumors reaching 2.2 and 2.6 times and 3.3 and 3.9 times that of blood and muscle, respectively.

Example 18

Synthesis of Zn-PCB-TE2A

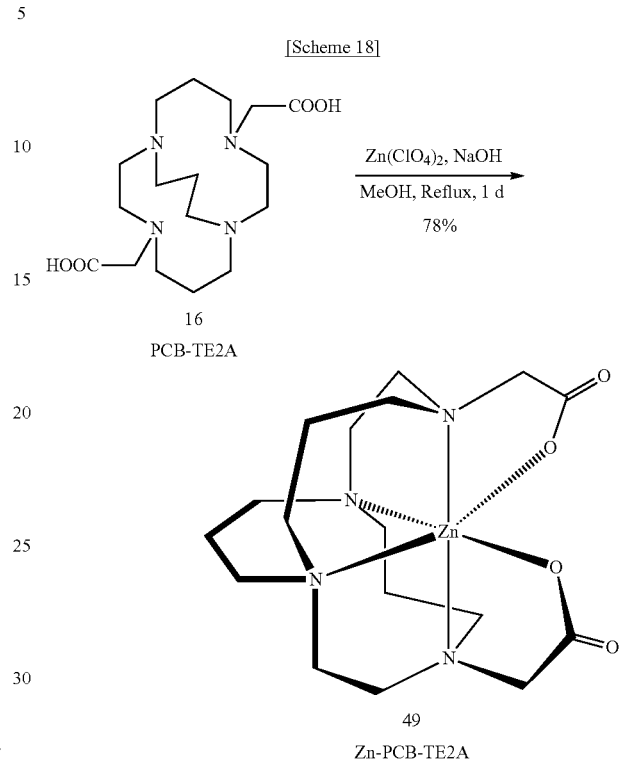

[Scheme 18]

16
PCB-TE2A

49
Zn-PCB-TE2A

An aqueous solution of NaOH (1M, 1.55 mL, 1.55 mmol) was added to a MeOH solution (10 mL) of PCB-TE2A.2CF$_3$COOH 16 (151 mg, 0.258 mmol). A MeOH solution (6 mL) of Zn(ClO$_4$)$_2$.6H$_2$O (99 mg, 0.265 mmol) was then added to this solution. After refluxing for 1 day and cooling to room temperature, this MeOH solution was centrifuged and only the MeOH solution was collected with the small amount of precipitate removed. Et$_2$O vapor diffusion into the supernatant yielded 85 mg (78%) of a white crystalline solid 49.

MS (ESI): calculated for C$_{17}$H$_{30}$N$_4$NaO$_4$Zn, 441.15 [(M+Na)$^+$]. found: 441.37 [(M+Na)$^+$].

Figure 55:
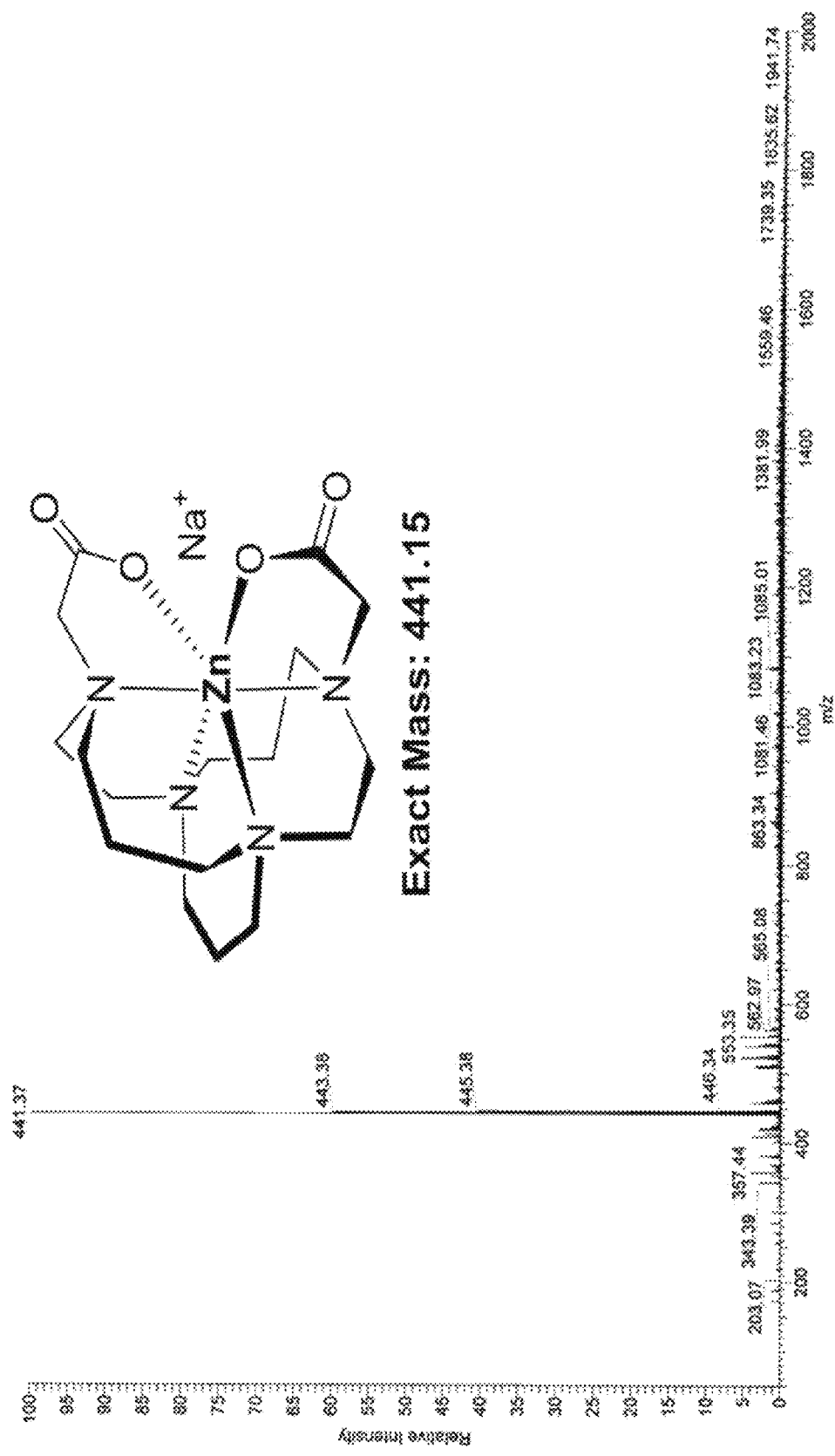
FIGS. 55 to 59 and FIGS. 63 to 68 show mass spectra of the compounds synthesized according to the present disclosure.

FIG. 55 shows a mass spectrum of the prepared white solid 49. It was confirmed that the white solid was Zn-PCB-TE2A.

Example 19

Synthesis of Zn-PCB-DO2A

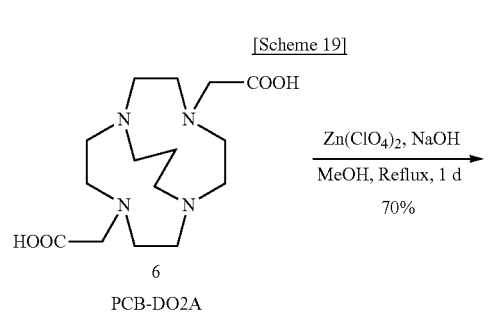

[Scheme 19]

6
PCB-DO2A

-continued

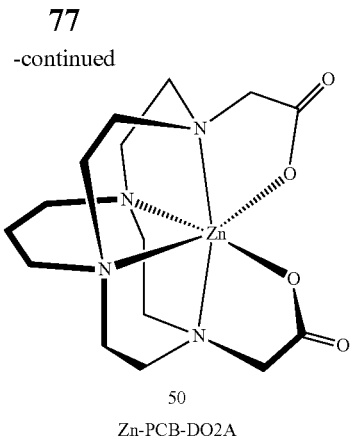

50
Zn-PCB-DO2A

An aqueous solution of NaOH (1M, 3.05 mL, 3.05 mmol) was added to a MeOH solution (15 mL) of PCB-DO2A 6 (167 mg, 0.508 mmol). A MeOH solution (10 mL) of Zn(ClO$_4$)$_2$·6H$_2$O (192 mg, 0.515 mmol) was then added to this solution. After refluxing for 1 day and cooling to room temperature, this MeOH solution was centrifuged and only the MeOH solution was collected with the small amount of precipitate removed. Et$_2$O vapor diffusion into the supernatant yielded 139 mg (70%) of a white solid 50.

MS (FAB): calculated for C$_{15}$H$_{26}$N$_4$NaO$_4$Zn, 413.11 [(M+Na)$^+$]. found: 412.87 [(M+Na)$^+$].

Figure 56:
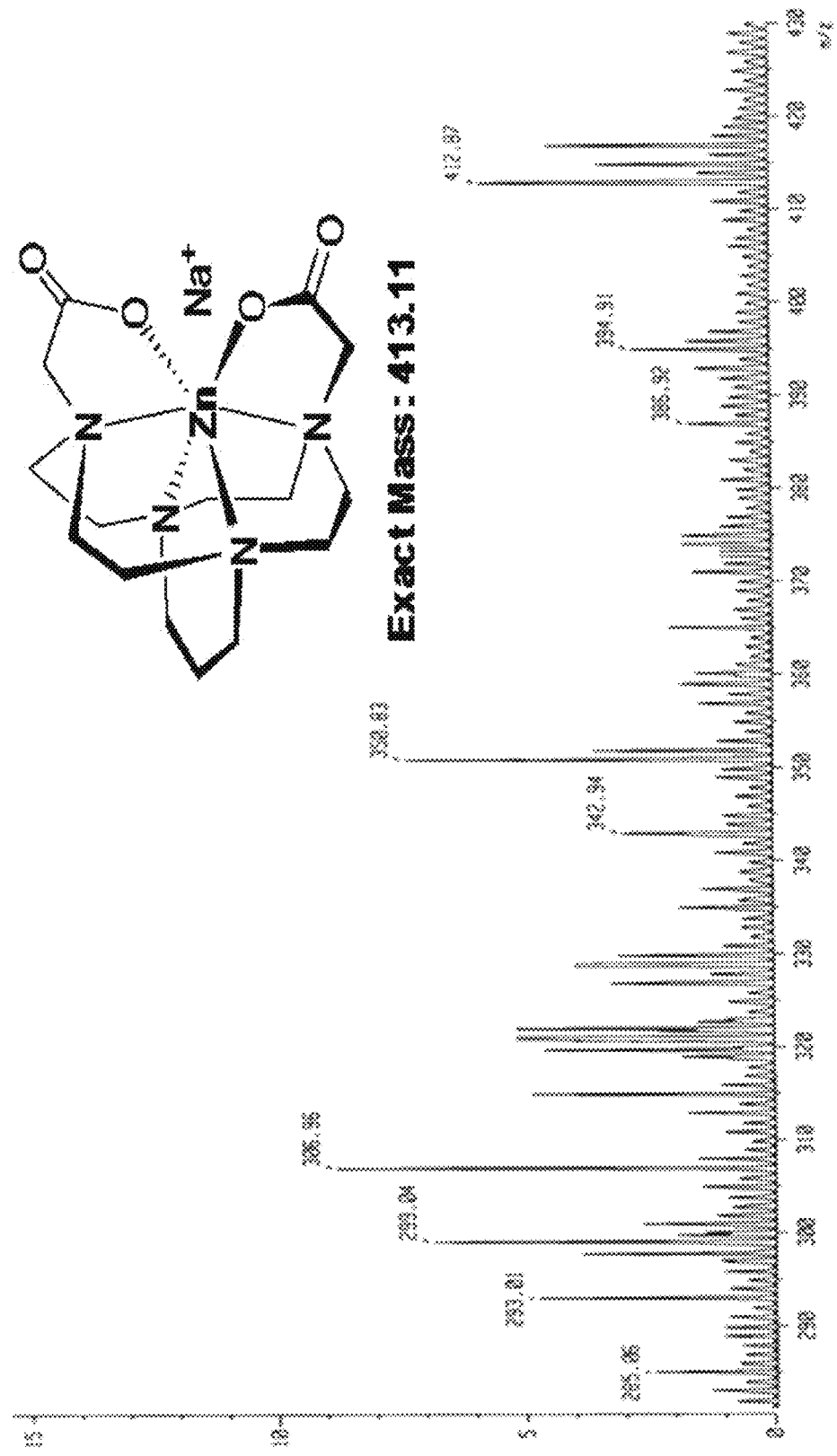

FIG. 56 shows a mass spectrum of the prepared white solid 50. It was confirmed that the white solid was Zn-PCB-DO2A.

Example 20

Synthesis of Cu-PCB-TE2A-NH$_2$

[Scheme 20]

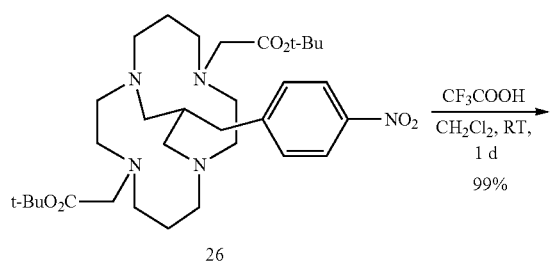

26

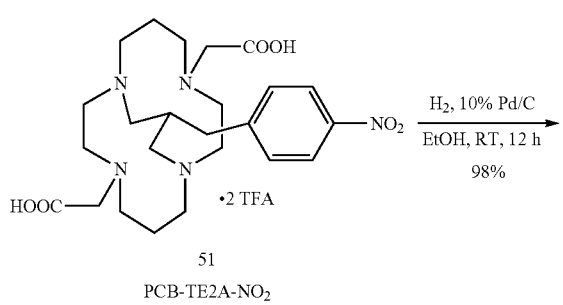

51
PCB-TE2A-NO$_2$

-continued

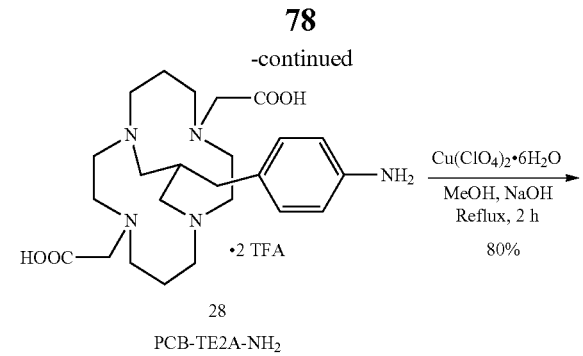

28
PCB-TE2A-NH$_2$

52
Cu-PCB-TE2AQ-NH$_2$ 20-a) Synthesis of 4,11-bis-(carbo-tert-butoxymethyl)-16-(4-nitrobenzyl)-1,4,8,11-tetraazabicyclo[6.6.3]heptadecane (2.2TFA) (51)

Compound 26 (0.45 g, 0.745 mmol) was dissolved in a 1:1 (vol:vol) mixture of CF$_3$CO$_2$H (TFA) and CH$_2$Cl$_2$ (12 mL). The mixture was stirred at room temperature for 24 hours. The solvent was removed under reduced pressure to give an oily residue which was triturated with Et$_2$O to provide yellow solid 51 (0.53 g, 99% yield) (2 equiv TFA calculated on the basis of mass).

MS (ESI) calculated for C$_{24}$H$_{38}$N$_5$O$_6$, 492.28 [(M+H)$^+$]. found: 492.04 [(M+H)$^+$].

Figure 57:
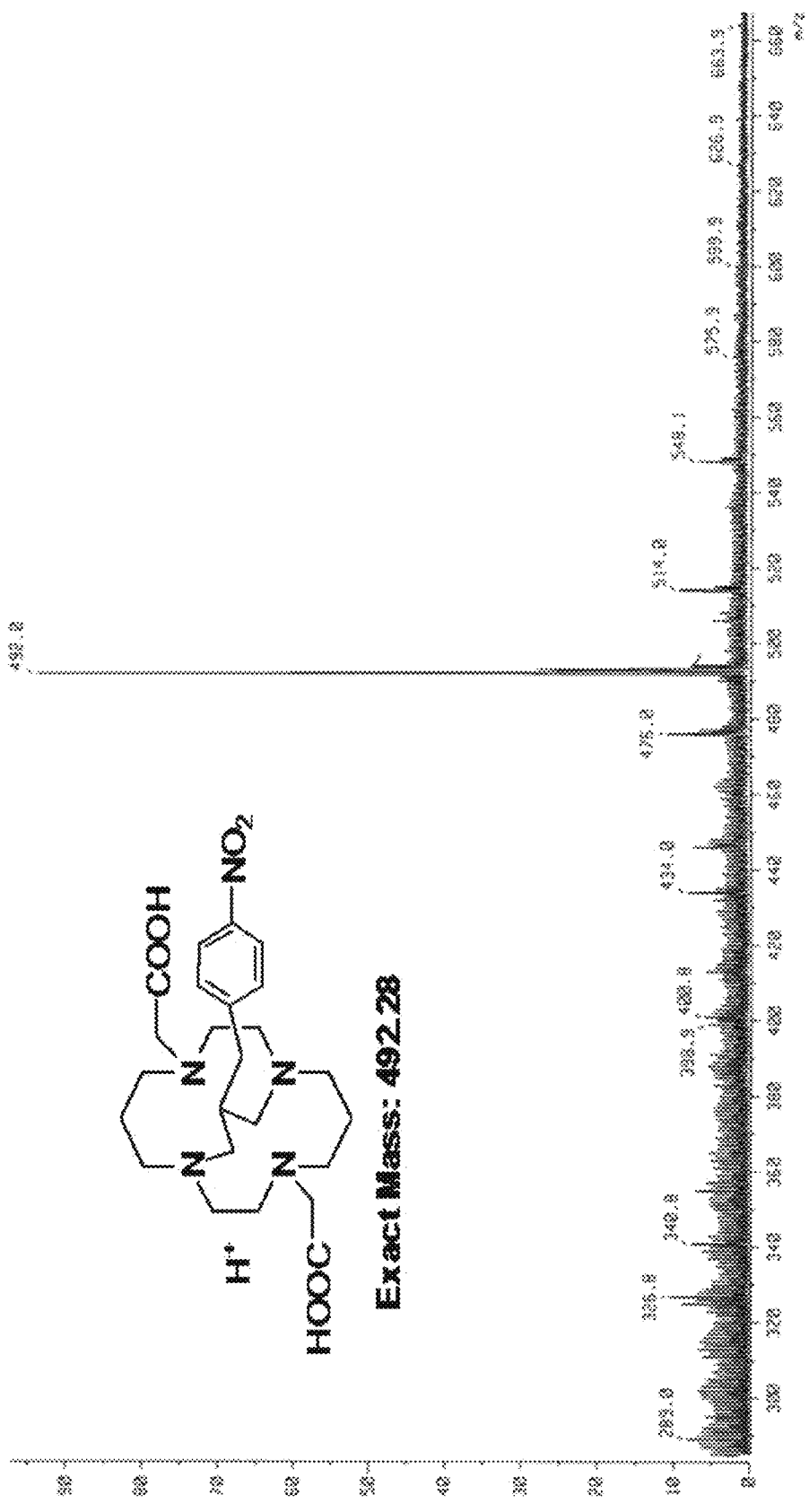

FIG. 57 shows a mass spectrum of the prepared yellow solid 51. It was confirmed that the solid was PCB-TE2A-NO$_2$.

20-b) Synthesis of 4,11-bis-(carboxymethyl)-16-(4-aminobenzyl)-1,4,8,11-tetraazabicyclo[6.6.3]heptadecane.2TFA (3.2TFA) (28)

To a solution of 51 (0.42 g, 0.58 mmol) in ethanol (50 mL) was added 10% Pd/C (0.13 g). The resulting mixture was stirred under H$_2$ (g) atmosphere at room temperature for 12 hours. The reaction mixture was filtered through a celite pad and washed with ethanol (2×20 mL). The combined filtrate was evaporated under vacuum to give an oily residue which was triturated with Et$_2$O to provide yellow solid 28 (0.39 g, 98% yield) (2 equiv TFA calculated on the basis of mass).

$^1$H NMR (500 MHz, DMSO-d$_6$): δ 6.92-6.90 (d, 2H, J=8.5 Hz), 6.50-6.48 (d, 2H, J=8.5 Hz), 3.42-3.16 (m, 8H), 2.92-2.50 (m, 12H), 2.38-1.79 (m, 5H), 1.63-1.16 (m, 4H); $^{13}$C NMR (125 MHz, DMSO-d$_6$): δ 174.2, 173.2, 146.8, 145.7, 137.5, 129.1, 128.0, 125.5, 114.1, 60.4, 59.8, 54.5, 50.3, 46.8, 35.4, 30.2, 23.1, 21.2, 20.7; HRMS (FAB): calculated for $C_{24}H_{40}N_5O_4$, 462.31 [(M+H)$^+$]. found: 462.60 [(M+H)$^+$].

Figure 58:
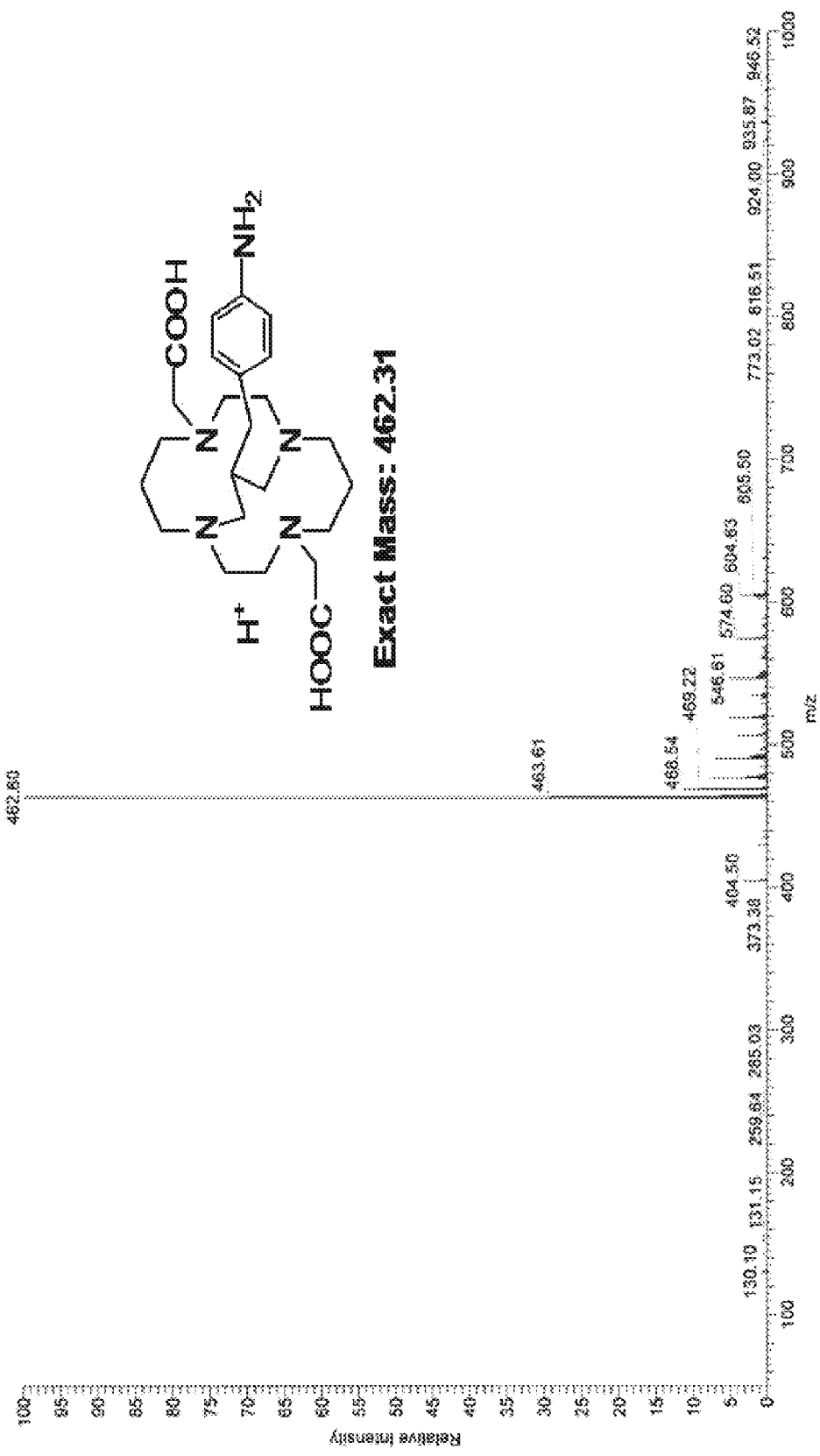

FIG. 58 shows a mass spectrum of the prepared yellow solid 28. It was confirmed that the solid was PCB-TE2A-NH$_2$.

20-c) Synthesis of Cu-PCB-TE2A-NH$_2$ (52)

To a solution of PCB-TE2A-NH$_2$ 28 (102 mg, 0.148 mmol) and Cu(ClO$_4$)$_2$.6H$_2$O (58 mg, 0.155 mmol) in methanol (20 mL) was added 1 M aqueous solution of NaOH (0.887 mmol). The resulting clear blue solution was refluxed for 2 hours, cooled, and filtered through a celite pad. The filtrate was subjected to diethyl ether diffusion. The deposited green crystals 52 were collected and dried (62 mg, 80% yield).

MS (ESI): calculated for $C_{24}H_{37}CuN_5NaO_4$, 545.20 [(M+Na)$^+$]. found: 545.39 [(M+Na)$^+$].

Figure 59:
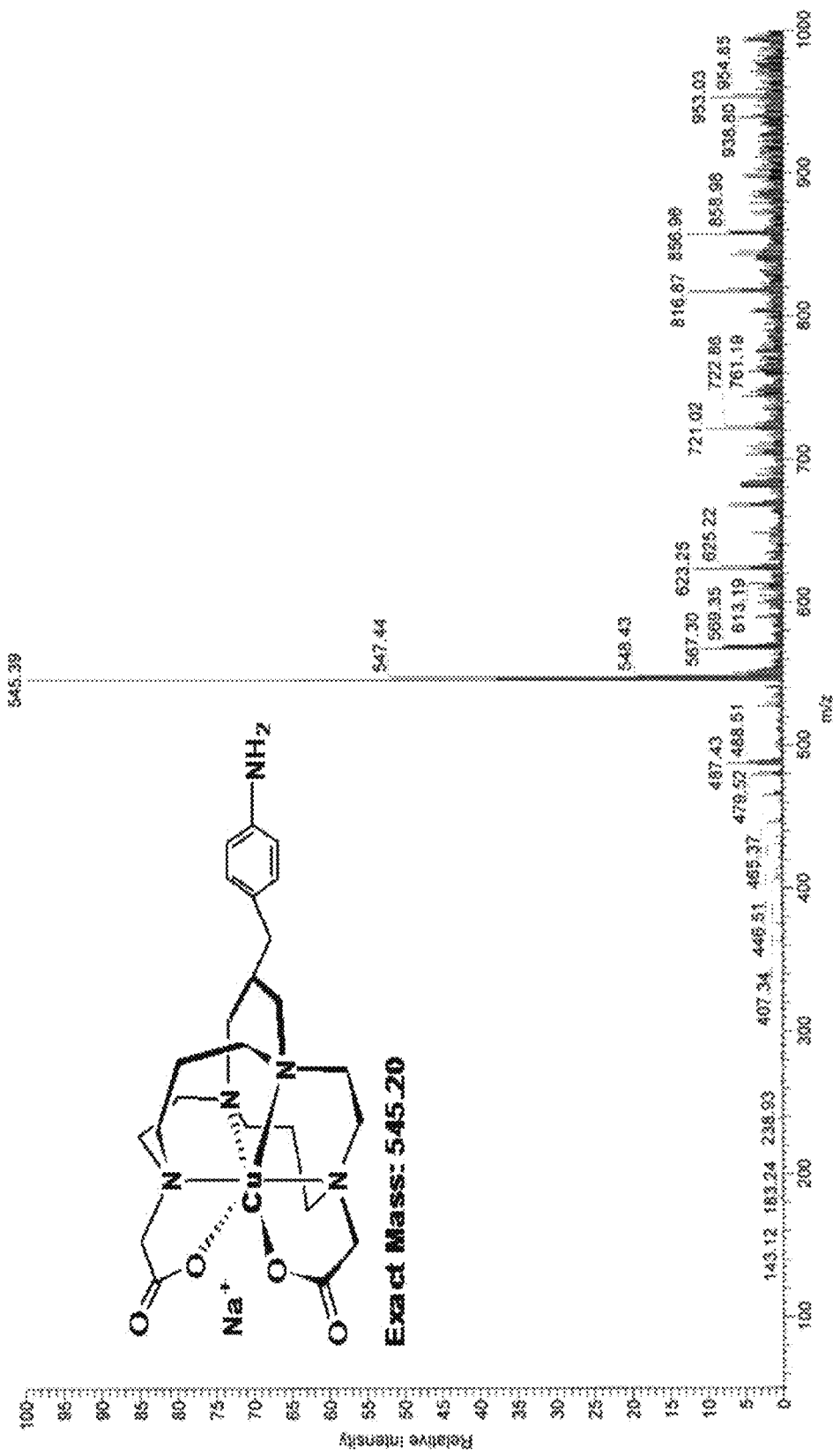

FIG. 59 shows a mass spectrum of the synthesized compound. It was confirmed that the green crystal was Cu-PCB-TE2A-NH$_2$ 52.

Example 21

Conjugation of Cu-PCB-TE2A-NH$_2$ with Trastuzumab 500-fold molar excess of EDC (2.63 mg) and 250-fold molar excess of Cu-PCB-TE2A-NH$_2$ (3.6 mg) 52 in 0.1 M NH$_4$OAc (pH 5.0, 1 mL) were added to trastuzumab (4 mg). The resulting solution was gently agitated at 37° C. for 30 minutes. Then, this solution was placed on Centricon YM-50 and spun down to reduce the volume. PBS (pH 7.2, 3×2 mL) was added to the remaining solution of the Cu-PCB-TE2A-NH$_2$-trastuzumab conjugate 53, followed by centrifugation in order to remove unreacted ligand. The volume of the purified conjugate antibody was brought to 2 mL with PBS and stored at −20° C. The purity of the Cu-PCB-TE2A-NH$_2$-trastuzumab conjugate 53 was determined by size-exclusion HPLC (Bio Silect SEC 250-5 300×7.8 mm; flow rate 1 mL/min, with PBS (pH=7.4) as isocratic mobile phase).

Figure 60:
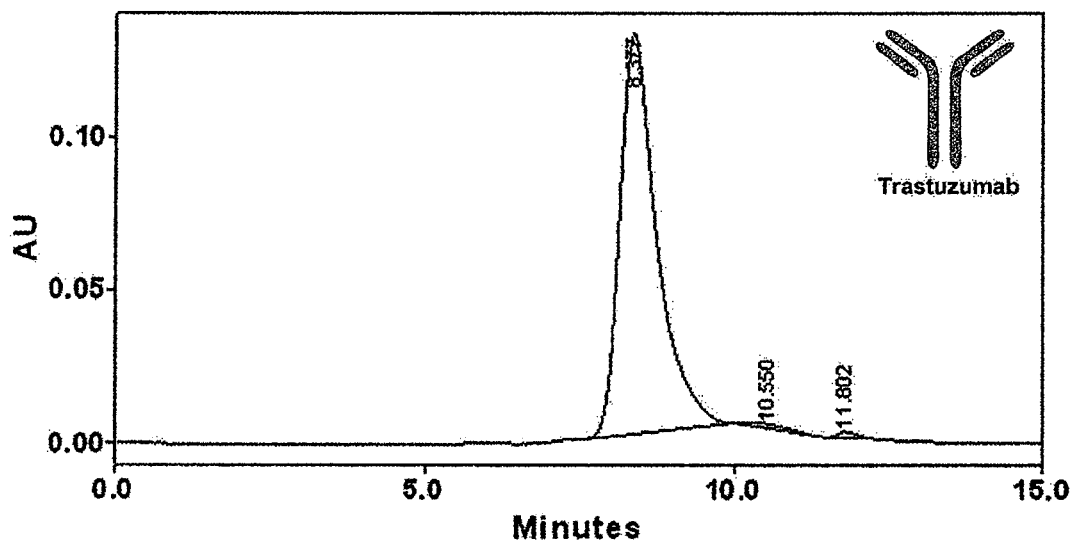
FIGS. 60 to 62 show HPLC chromatograms of trastuzumab and Cu-PCB-TE2A-NH$_2$-trastuzumab and a superposition of the two.
Figure 61:
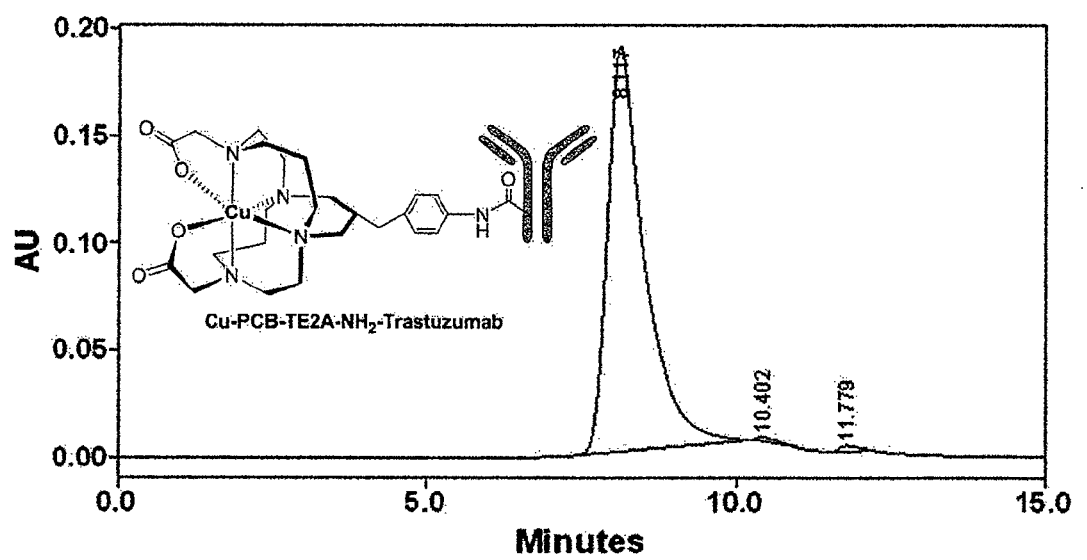
Figure 62:
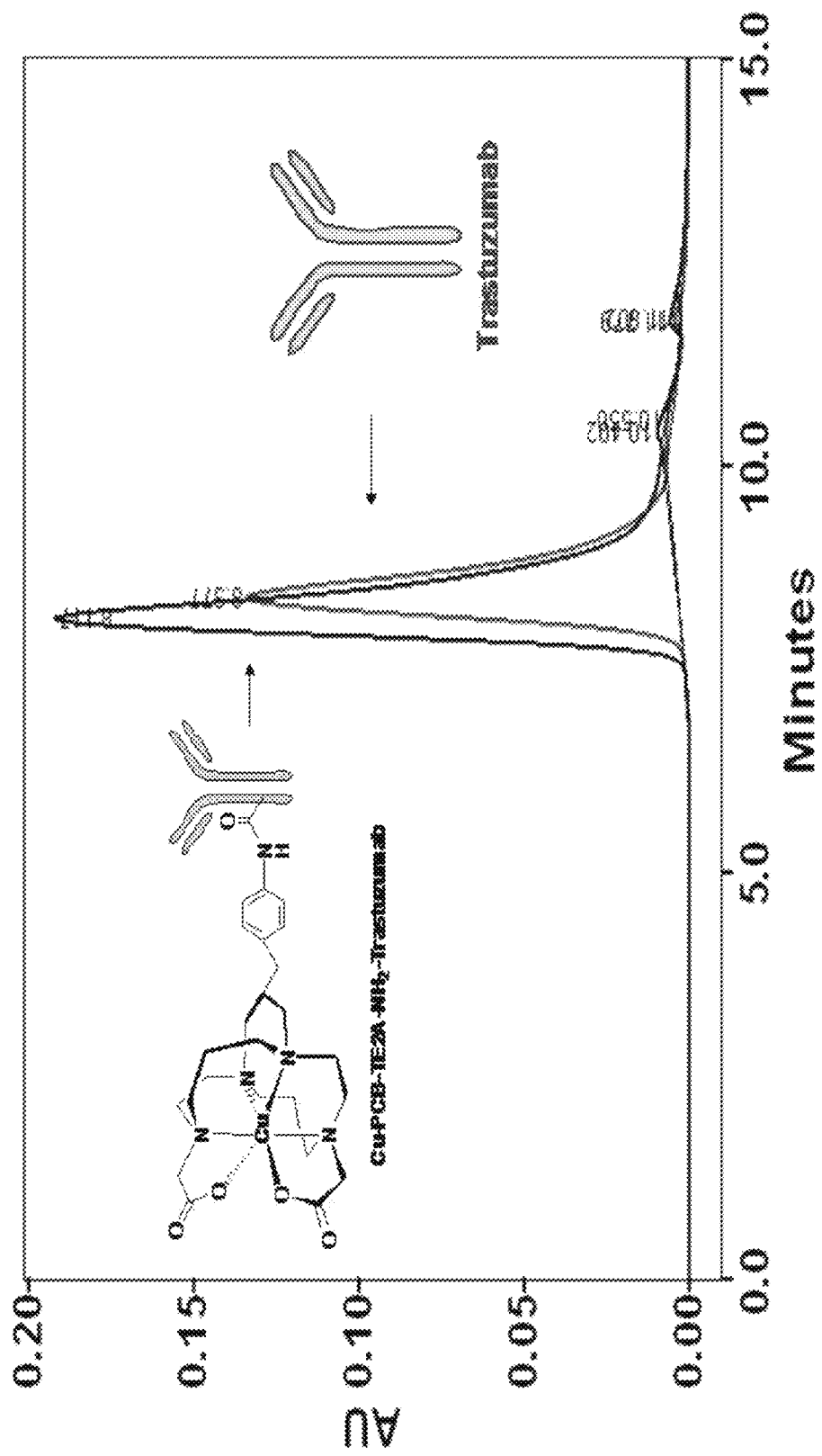

FIG. 60 shows an SE-HPLC chromatogram (UV detector: 220 nm) of trastuzumab before conjugation, FIG. 61 shows an SE-HPLC chromatogram (UV detector: 220 nm) of the Cu-PCB-TE2A-NH$_2$-conjugated trastuzumab, and FIG. 62 compares the chromatogram of the Cu-PCB-TE2A-NH$_2$-conjugated trastuzumab (black) with that of trastuzumab before conjugation (red). The conjugation of trastuzumab with Cu-PCB-TE2A-NH$_2$ was confirmed.

Thus, it was confirmed that, when PCB-TE2A is used to label the antibody with a radionuclide such as $^{64}$Cu, PCB-TE2A may be first labeled with the radionuclide at high yield and then the labeled PCB-TE2A may be conjugated with the antibody at low temperature, differently from the existing method of first attaching PCB-TE2A to the antibody and then labeling the antibody-bound PCB-TE2A with the radionuclide.

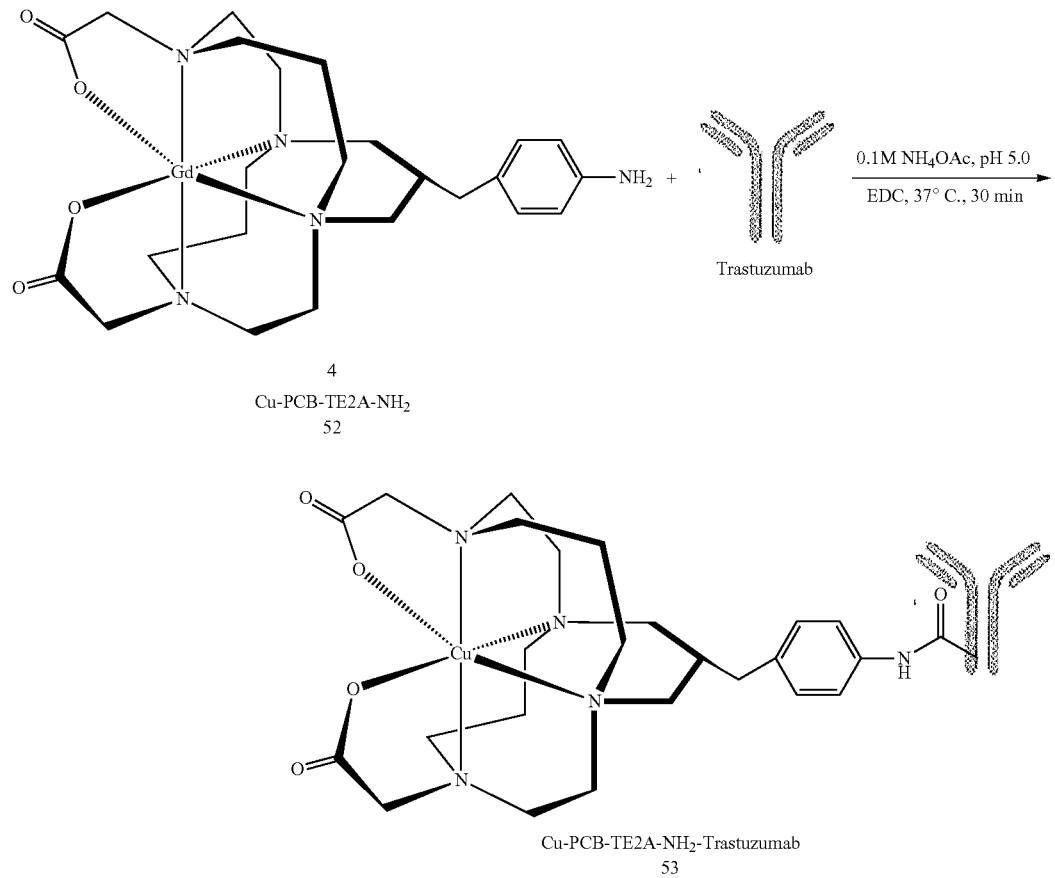

[Scheme 21]

4
Cu-PCB-TE2A-NH$_2$
52

Cu-PCB-TE2A-NH$_2$-Trastuzumab
53

Example 22

Synthesis of 4,11-bis-(carboxymethyl)-16-(4-(bromoacetamido)benzyl)-1,4,8,11-tetraazabicyclo[6.6.3]heptadecane (54)

[Scheme 22]

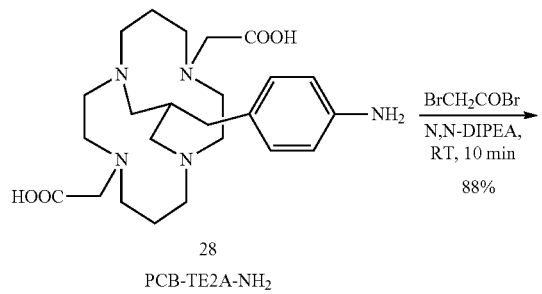

28
PCB-TE2A-NH₂

54
PCB-TE2A-NH-CO-CH₂-Br

Compound 28 (0.101 g, 0.146 mmol) was dissolved in water (15 mL). pH was adjusted to 7-8 using diisopropylethylamine. This solution was added dropwise to a solution of 0.1 mL of bromoacetyl bromide in 15 mL of chloroform. After adjusting pH to 7.0 with diisopropylethylamine, the resulting solution was stirred vigorously for 10 minutes. After the layers were separated, the aqueous phase was extracted with chloroform. After adjusting pH to 7-8 with diisopropylethylamine, the aqueous phase was extracted with chloroform. This procedure was repeated four more times. After adjusting pH to 1.5-1.8 with 3 M HCl, the aqueous phase was extracted twice with equal volume of ethyl ether. The pH was adjusted again with 3 M HCl and the aqueous phase was extracted twice with ethyl ether. This procedure was continued until the pH remained constant. Residual ether was removed from the aqueous solution under reduced pressure. The pH of the solution was adjusted to 4.5 with 3 M NaOH, and the solution was divided into aliquots, and stored at −70° C. (75 mg, 88% yield).

MS (ESI): calculated for $C_{26}H_{41}BrN_5O_5$, 582.23 [(M+H)$^+$]. found: 582.54 [(M+H)$^+$].

Figure 63:
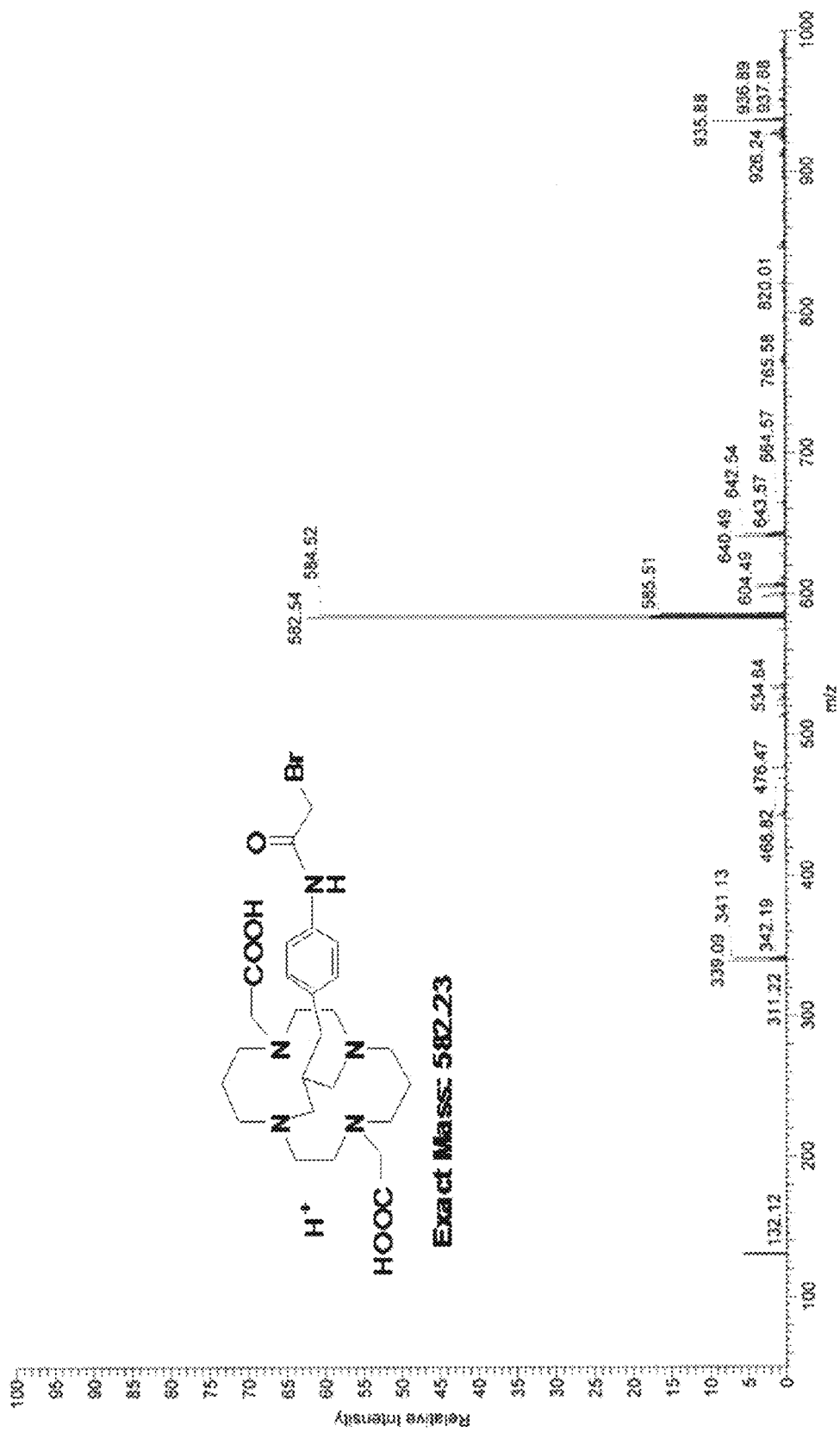

FIG. 63 shows a mass spectrum of the synthesized compound. It was confirmed that the synthesized compound was PCB-TE2A-NH₂—NHCOCH₂Br 54.

Example 23

Synthesis of Ga-PCB-TE2A

[Scheme 23]

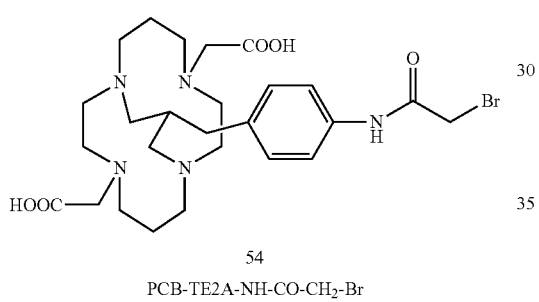

16
PCB-TE2A

55
Ga-PCB-TE2A

A solution of Ga(NO₃)₃ hydrate (38.4 mg, 0.15 mmol) in MeOH (10 mL) was added to an MeOH solution (20 mL) of PCB-TE2A.2CF₃COOH (86.7 mg, 0.148 mmol) 16. Anhydrous sodium acetate (48.6 mg, 0.592 mmol) in MeOH (10 mL) was then added. The reaction mixture was refluxed for 2 days, after which time a white precipitate was isolated by centrifugation. The resulting white precipitate was dried to give the final complex 55 (44 mg, 70%).

MS (ESI): calculated for $C_{17}H_{30}N_4O_4Ga$, 423.15 [(M)$^+$]. found: 422.86 [(M)$^+$].

Figure 64:
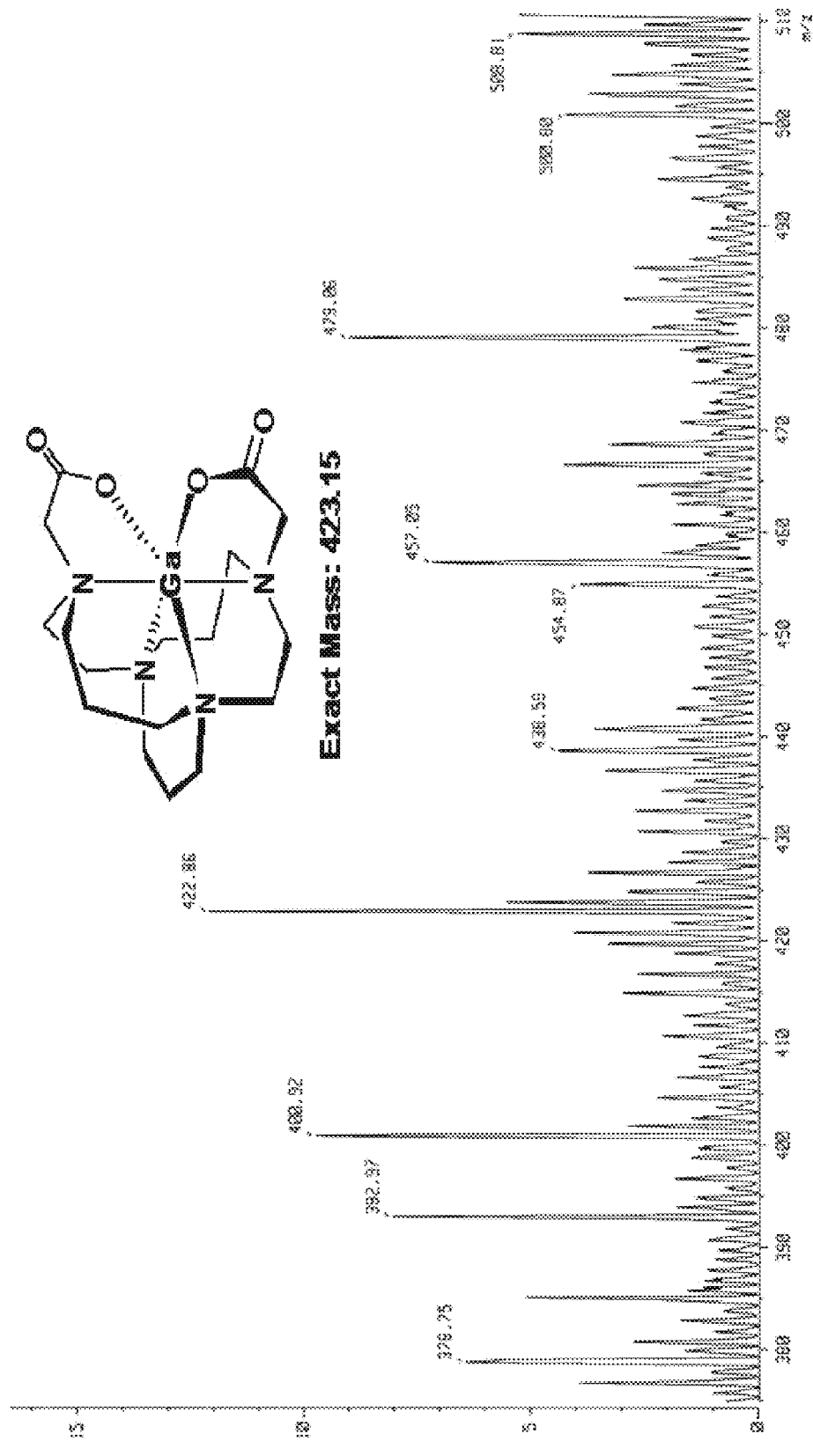

FIG. 64 shows a mass spectrum of the synthesized compound. It was confirmed that the synthesized compound was Ga-PCB-TE2A 55.

Example 24

Synthesis of Ga-PCB-DO2A

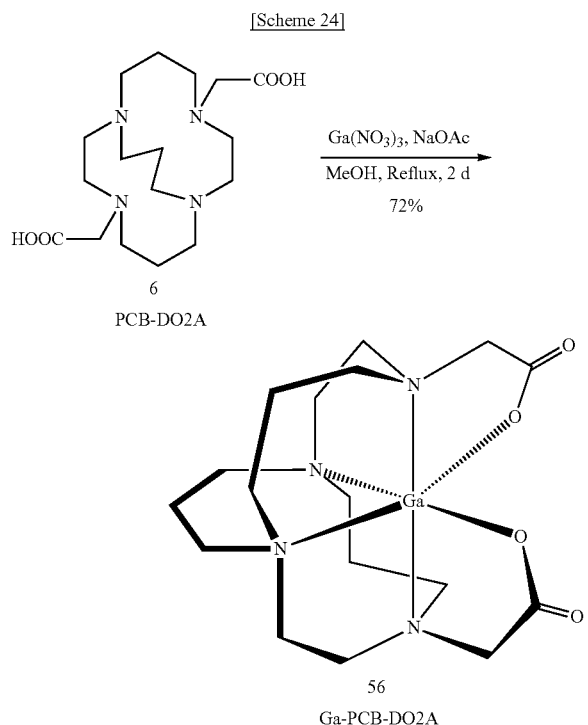

Ga-PCB-DO2A

A solution of Ga(NO$_3$)$_3$ hydrate (88.2 mg, 0.345 mmol) in MeOH (10 mL) was added to a MeOH solution (15 mL) of PCB-DO2A 6 (112 mg, 0.341 mmol). Anhydrous sodium acetate (112 mg, 1.36 mmol) in MeOH (12 mL) was then added. The reaction mixture was refluxed for 2 days, after which time a white precipitate was isolated by centrifugation. The resulting white precipitate was dried to give the final complex 56 (97 mg, 72%).

MS (ESI): calculated for C$_{15}$H$_{26}$N$_4$NaO$_4$Ga, 418.11 [(M+Na)$^+$]. found: 418.33 [(M+Na)$^+$].

Figure 65:

FIG. 65 shows a mass spectrum of the synthesized compound. It was confirmed that the synthesized compound was Ga-PCB-DO2A 56.

Example 25

Synthesis of Gd-PCB-TE2A

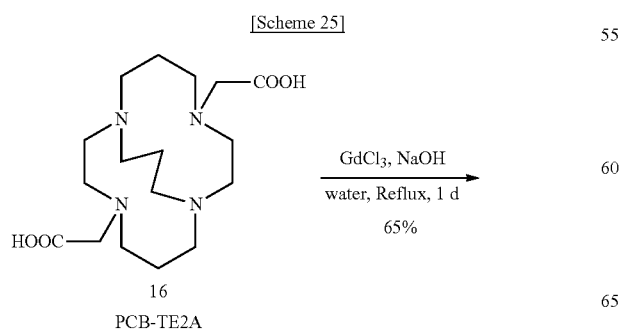

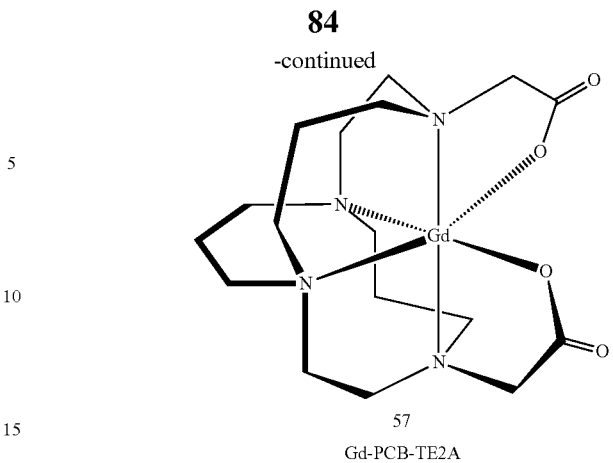

Gd-PCB-TE2A

PCB-TE2A 16 (52 mg, 0.145 mmol) and GdCl$_3$ (40 mg, 0.15 mmol) were dissolved in water (15 mL) and the pH was monitored and kept between 6.0 and 6.5 using 0.1 M NaOH. The reaction mixture was refluxed for 24 hours. The temperature was then allowed to fall to room temperature. The pH of the solution was adjusted to 10, and the resulting precipitate was removed by filtration. The pH of the filtrate was adjusted to 7.4. The filtrate was evaporated in vacuo, yielding 40 mg of a slightly yellow solid 57.

MS (ESI): calculated for C$_{17}$H$_{29}$N$_4$ClO$_4$Gd, 546.12 [(M+Cl–H)$^+$]. found: 545.94 [(M+Cl–H)$^+$].

Figure 66:
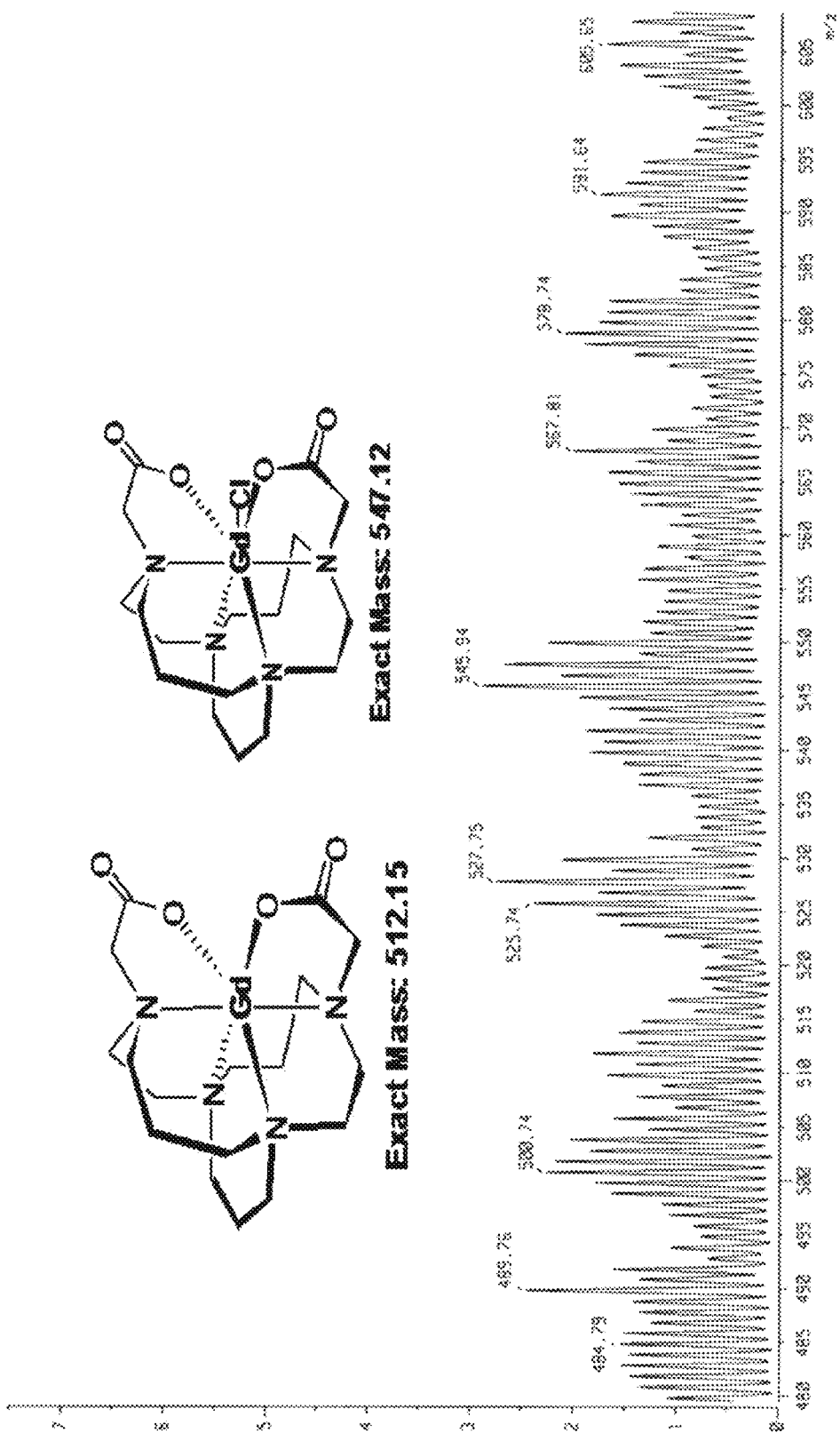

FIG. 66 shows a mass spectrum of the yellow solid 57. It was confirmed that the synthesized compound was Gd-PCB-TE2A 57.

Example 26

Synthesis of Gd-PCB-DO2A

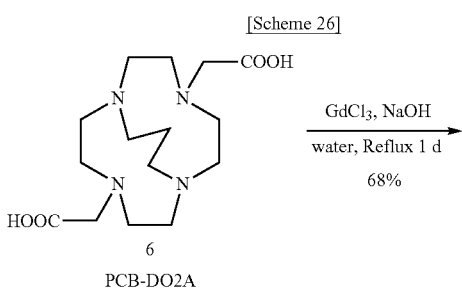

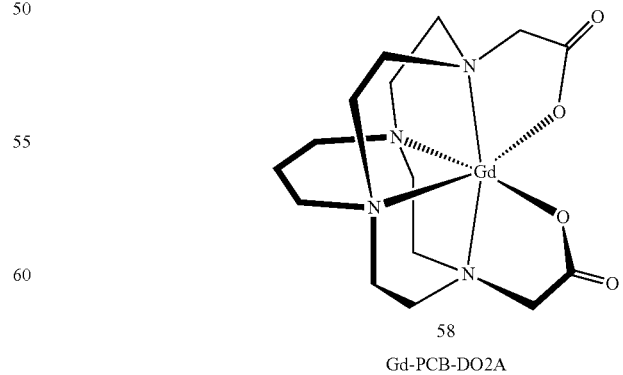

Gd-PCB-DO2A

PCB-DO2A 6 (82 mg, 0.249 mmol) and GdCl$_3$ (66 mg, 0.25 mmol) were dissolved in water (20 mL) and the pH was monitored and kept between 6.0 and 6.5 using 0.1 M NaOH. The reaction mixture was refluxed for 24 hours. The temperature was then allowed to fall to room temperature. The pH of the solution was adjusted to 10, and the resulting precipitate was removed by filtration. The pH of the filtrate was adjusted to 7.4. The filtrate was evaporated in vacuo, yielding 72 mg of an off-white solid 58.

MS (ESI): calculated for $C_{15}H_{26}ClN_4GdNaO_4$, 542.08 [(M+Cl+Na)$^+$]. found: 541.80 [(M+Cl+Na)$^+$].

Figure 67:
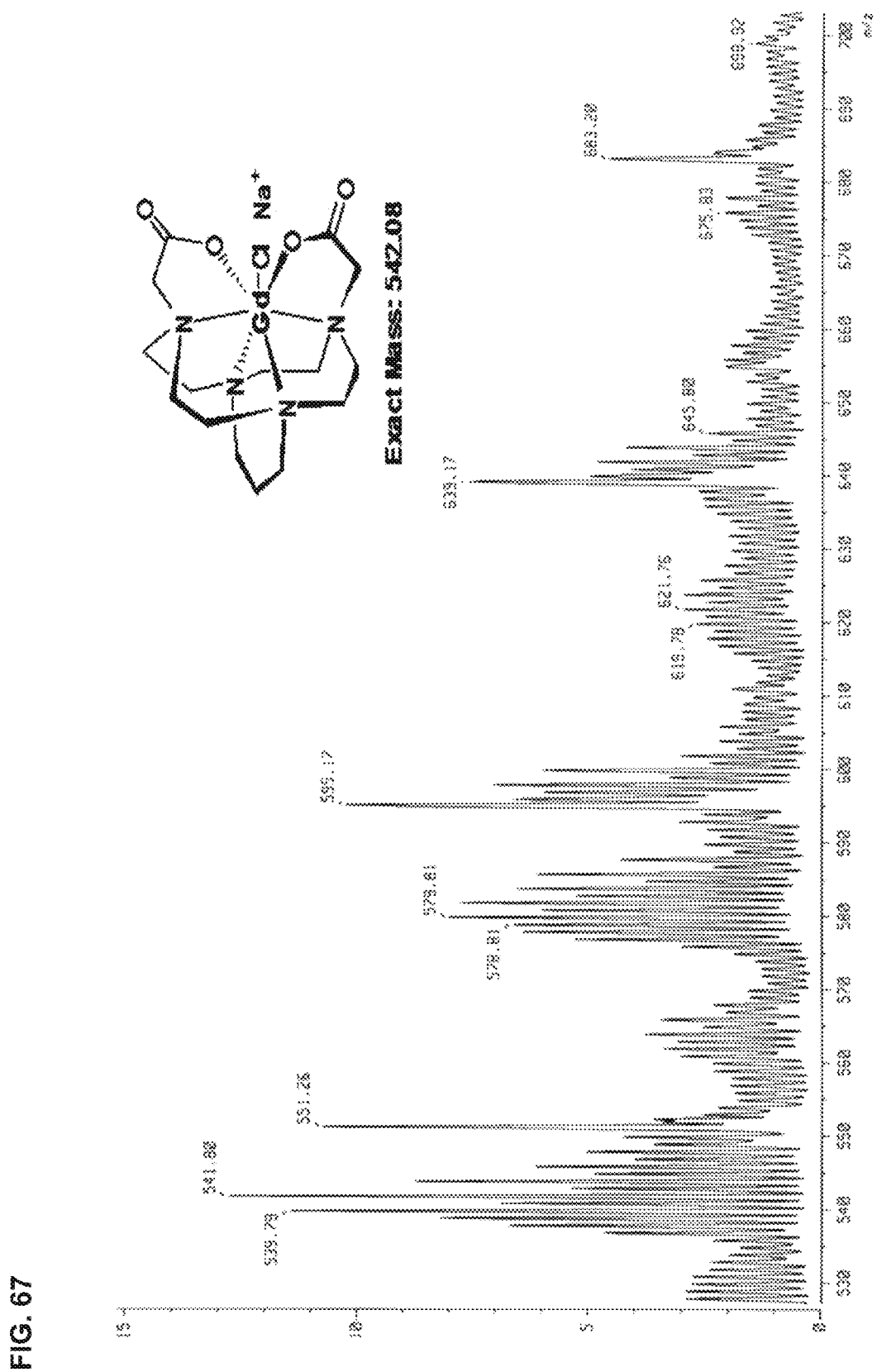

FIG. 67 shows a mass spectrum of the off-white solid 58. It was confirmed that the synthesized compound was Gd-PCB-DO2A 58.

Example 27

Synthesis of Gd-PCB-TE2A-NCS

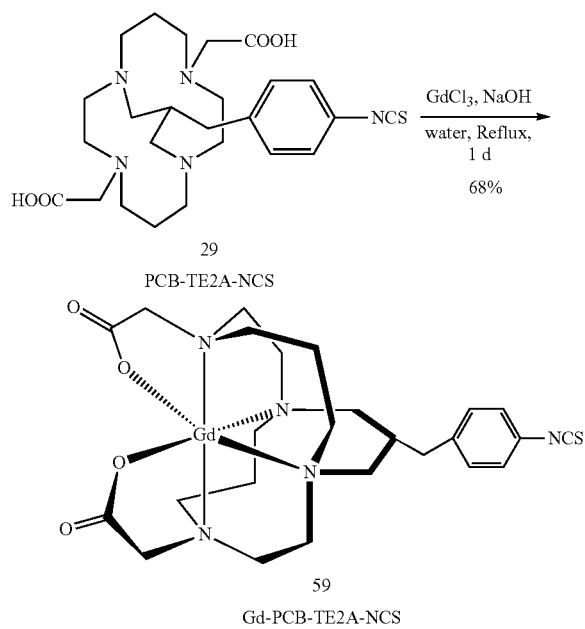

PCB-TE2A-NCS 29 (51 mg, 0.101 mmol) and GdCl$_3$ (28 mg, 0.105 mmol) were dissolved in water (10 mL) and the pH was monitored and kept between 6.0 and 6.5 using 0.1 M NaOH. The reaction mixture was refluxed for 24 hours. The temperature was then allowed to fall to room temperature. The pH of the solution was adjusted to 10, and the resulting precipitate was removed by filtration. The pH of the filtrate was adjusted to 7.4. The filtrate was evaporated in vacuo, yielding 32 mg of a slightly yellow solid 59.

MS (ESI): calculated for $C_{25}H_{36}Cl_2N_5O_4GdS$, 730.80 [(M+2Cl+H)$^+$]. found: 731.00 [(M+2Cl+H)$^+$].

Figure 68:
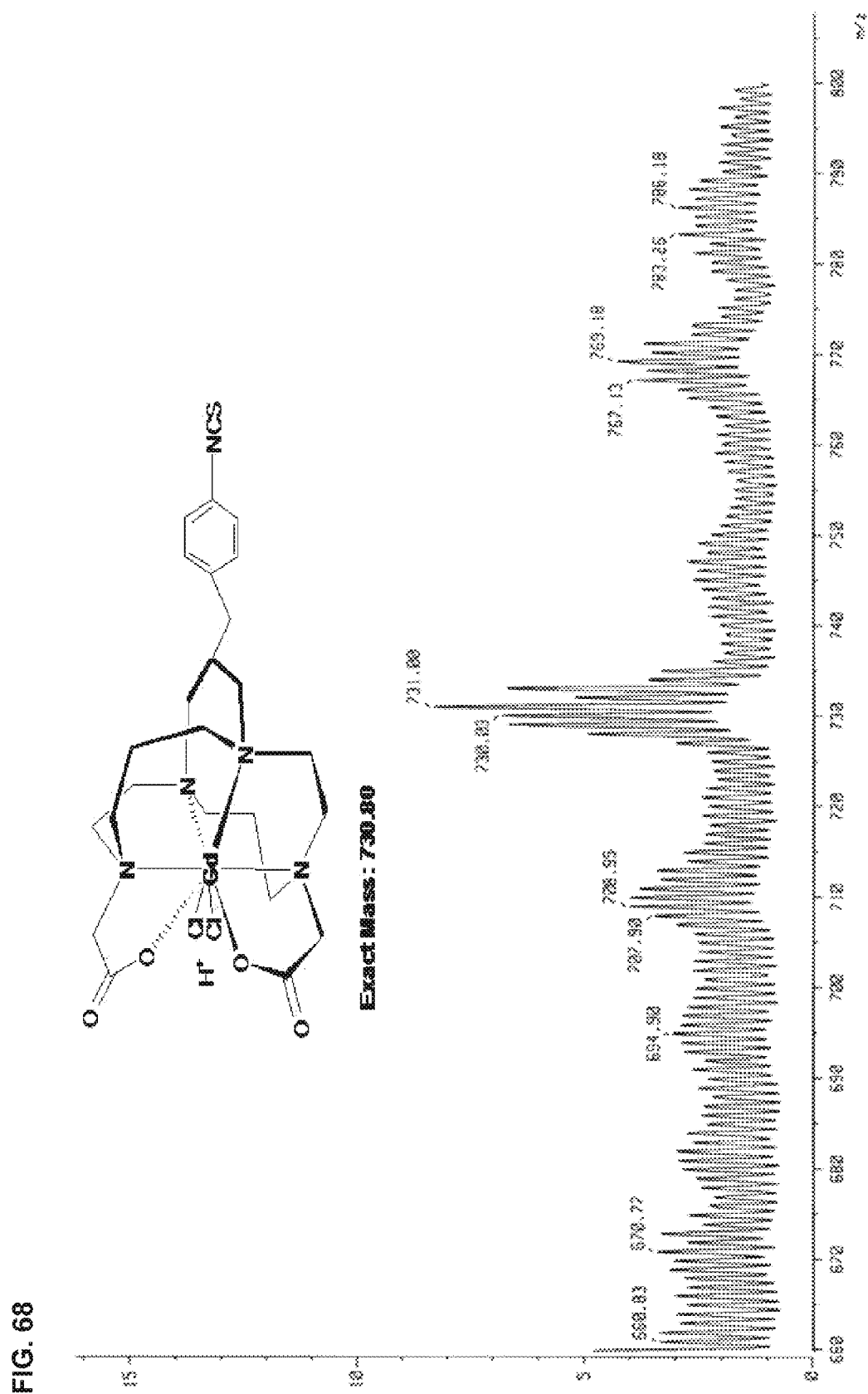

FIG. 68 shows a mass spectrum of the yellow solid 59. It was confirmed that the synthesized compound was Gd-PCB-TE2A-NCS 59.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

INDUSTRIAL APPLICABILITY

The compound of the present disclosure is very useful in diagnostic imaging for use as a contrast agent, since it exhibits excellent in vivo stability, can be labeled at low temperature and is easily conjugated with a biomolecule. Further, it may be used as a therapeutic radiopharmaceutical by conjugating a medical radionuclide with a disease-specific antibody. Further, it may be used as a contrast agent for magnetic resonance imaging (MRI), since it forms a stable complex with a paramagnetic metal such as Gd.

The invention claimed is:
1. A tetraaza macrocyclic compound represented by Chemical Formula 1 or a pharmaceutically acceptable salt thereof:

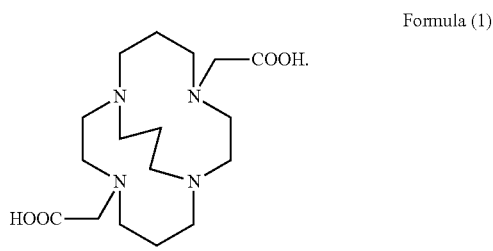 [SMILES: O=C(O)CN1CCCN2CCCN(CCCN(CC(=O)O)CC2)CC1]

Formula (1)

* * * * *